(12) United States Patent
Ahern et al.

(10) Patent No.: US 11,661,600 B2
(45) Date of Patent: May 30, 2023

(54) METHODS OF RESCUING STOP CODONS VIA GENETIC REASSIGNMENT WITH ACE-TRNA

(71) Applicant: UNIVERSITY OF IOWA RESEARCH FOUNDATION, Iowa City, IA (US)

(72) Inventors: Christopher Ahern, Iowa City, IA (US); John D. Lueck, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 16/761,205

(22) PCT Filed: Nov. 2, 2018

(86) PCT No.: PCT/US2018/059065
§ 371 (c)(1),
(2) Date: May 1, 2020

(87) PCT Pub. No.: WO2019/090154
PCT Pub. Date: May 9, 2019

(65) Prior Publication Data
US 2020/0291401 A1    Sep. 17, 2020

Related U.S. Application Data

(60) Provisional application No. 62/580,887, filed on Nov. 2, 2017, provisional application No. 62/687,015, filed on Jun. 19, 2018.

(51) Int. Cl.
| | | |
|---|---|---|
| *C12N 15/113* | (2010.01) | |
| *A61P 43/00* | (2006.01) | |
| *A61K 9/127* | (2006.01) | |
| *A61K 31/7105* | (2006.01) | |

(52) U.S. Cl.
CPC ............ *C12N 15/113* (2013.01); *A61K 9/127* (2013.01); *A61K 31/7105* (2013.01); *A61P 43/00* (2018.01)

(58) Field of Classification Search
CPC ........ C12N 9/78; C12N 15/85; C12N 15/111; C12N 15/115; C12N 2310/20; C12N 2320/31; C12N 2320/34
USPC ...................... 435/6.1, 91.1, 91.31, 455, 458; 514/44 A, 44 R; 536/23.1, 24.5
See application file for complete search history.

(56) References Cited

U.S. PATENT DOCUMENTS

| | | |
|---|---|---|
| 4,687,737 A | 8/1987 | Sharp et al. |
| 5,840,702 A | 11/1998 | Bedwell |
| 6,309,830 B1 | 10/2001 | Panchal et al. |
| 6,964,859 B2 | 11/2005 | Rajbhandary et al. |
| 7,029,665 B2 | 4/2006 | Panchal et al. |
| 8,338,386 B2 | 12/2012 | McLean et al. |
| 10,513,699 B2 | 12/2019 | Short |
| 10,905,778 B2 | 2/2021 | Coller et al. |
| 10,982,209 B2 | 4/2021 | Xia et al. |
| 2005/0014835 A1 | 1/2005 | Arakawa et al. |
| 2009/0298920 A1 | 12/2009 | Dardel et al. |
| 2012/0077186 A1 | 3/2012 | Skach et al. |
| 2012/0117673 A1 | 5/2012 | Ardell |
| 2017/0342422 A1 | 11/2017 | Holzmann et al. |
| 2017/0354672 A1 | 12/2017 | Siegwart et al. |
| 2018/0171321 A1 | 6/2018 | Mureev et al. |
| 2020/0263180 A1 | 8/2020 | Mali et al. |
| 2020/0277607 A1 | 9/2020 | Mali et al. |
| 2020/0407714 A1 | 12/2020 | Ignatova et al. |
| 2021/0023120 A1 | 1/2021 | Siegwart et al. |
| 2021/0163948 A1 | 6/2021 | Mali et al. |
| 2021/0198673 A1 | 7/2021 | Mali et al. |

FOREIGN PATENT DOCUMENTS

| | | |
|---|---|---|
| WO | 1999036519 A1 | 7/1999 |
| WO | 2007070659 A2 | 6/2007 |
| WO | 2017049409 A1 | 3/2017 |
| WO | 2017152809 A1 | 9/2017 |
| WO | 2017201091 A1 | 11/2017 |
| WO | 2018031531 A4 | 4/2018 |
| WO | 2018161032 A1 | 9/2018 |
| WO | 2019090169 A1 | 5/2019 |
| WO | 2020069194 A1 | 4/2020 |
| WO | 2020208169 A1 | 10/2020 |

(Continued)

OTHER PUBLICATIONS

Andersen et al, Trends in Biochemical Sci., vol. 28, No. 8, pp. 434-441 (2003)) (Year: 2003).*

(Continued)

*Primary Examiner* — Jane J Zara
(74) *Attorney, Agent, or Firm* — Viksnins Harris Padys Malen LLP

(57) ABSTRACT

In certain embodiments, the present invention provides a modified transfer RNA (tRNA) comprising a T-arm, a D-arm, and anticodon-arm and an acceptor arm, wherein the T-arm comprises nucleotides that interact with the elongation factor 1 alpha protein, and methods of use thereof. In certain embodiments, the present invention provides a modified transfer RNA (tRNA) comprising a T-arm, a D-arm, and anticodon-arm and an acceptor arm, (a) wherein the anticodon-arm comprises a tri-nucleotide anticodon, wherein the anticodon is 5'-UCA-3' and recognizes TGA stop codons, and wherein the acceptor arm is operably linked to a arginine, tryptophan or glycine; (b) wherein the anticodon-arm comprises a tri-nucleotide anticodon, wherein the anticodon is 5'-UUA-3' and recognizes TAA stop codons, and wherein the acceptor arm is operably linked to a glutamine or, glutamate; or (c) wherein the anticodon-arm comprises a tri-nucleotide anticodon, wherein the anticodon is 5'-CUA-3' and recognizes TAG stop codons, and wherein the acceptor arm is operably linked to a tryptophan, glutamate or glutamine.

24 Claims, 51 Drawing Sheets
Specification includes a Sequence Listing.

(56) References Cited

FOREIGN PATENT DOCUMENTS

| WO | 2021072201 A1 | 4/2021 |
|---|---|---|
| WO | 2021087401 A1 | 5/2021 |
| WO | 2021092064 A1 | 5/2021 |
| WO | 2021113218 A1 | 6/2021 |

OTHER PUBLICATIONS

Bordeira-Carrico et al (European J. Human Genetics, vol. 22, pp. 1085-1092 (2014)) (Year: 2014).*
Lueck et al (bioRxiv20, pp. 1-9 (2016)) (Year: 2016).*
Albers, S , et al., "Repurposing tRNAs for nonsense suppression", Nature Communications 12 (3850), 1-10 (2021).
Andersen, G , et al., "Elongation factors in protein biosynthesis", Trends in Biochemical Sciences 28(8), 434-441 (2003).
Atkinson, J , et al., "Mutations to nonsense codons in human genetic disease: implications for gene therapy by nonsense suppressor tRNAs", Nucleic Acids Research 22(8), 1327-1334 (1994).
Bednarova, A , et al., "Lost in Translation: Defects in Transfer RNA Modifications and Neurological Disorders", Front Mol Neurosci 10(135), 1-8 (2017).
Biddle, W , et al., "Modification of orthogonal tRNAs: unexpected consequences for sense codon reassignment", Nucleic Acids Res 44(21), 10042-10050 (2016).
Bordeira-Carrico, R , et al., "Rescue of wild-type E-cadherin expression from nonsense-mutated cancer cells by a suppressor-tRNA", European Journal of Human Genetics 22, 1085-1092 (2014).
Capone, J , et al., "Amber, ochre and opal suppressor tRNA genes derived from a human serine tRNA gene", The EMBO Journal 4(1), 213-221 (1985).
Dreher , et al., "Quantitative Assessment of EF-1α•GTP Binding to Aminoacyl-tRNAs, Aminoacyl-viral RNA, and tRNA Shows Close Correspondence to the RNA Binding Properties of EF-Tu", Journal of Biochemistry 274(2), 666-672 (1999).
Forster, C , et al., "Discrimination between initiation and elongation of protein biosynthesis in yeast: identity assured by a nucleotide modification in the initiator tRNA", Nucleic Acids Research 21(24), 5679-5683 (1993).
Gatti, R , "SMRT compounds correct nonsense mutations in primary immunodeficiency and other genetic models", Am N Y Acad Sci 1250, 33-40 (2012).
Geiduschek, E , et al., "Transcription by RNA Polymerase III", Annu Rev Biochem 57, 873-914 (1988).
Guy, M , et al., "Identification of the determinants of tRNA function and susceptibility to rapid tRNA decay by high-throughput in vivo analysis", Genes & Development 28, 1721-1732 (2014).
Huang, Q , et al., "In vivo identification of essential nucleotides in tRNA Leu to its functions by using a constructed yeast tRNA Leu knockout strain", Nucleic Acids Research 40(20), 10463-10477 (2012).
Katrekar, D , et al., "In vivo RNA targeting of point mutations via suppressor tRNAs and adenosine deaminases", URL:https://www.biorxiv.org/content/biorxiv/early/2017/10/28/210278.full.pdf, doi:http://dx.doi.org/10.1101/210278, 25 pages (2017).
Keeling, K , et al., "Therapeutics based on stop codon readthrough", Annual Review of Genomics and Human Genetics 15(1), 371-394 (2014).
Klassen , et al., "Collaboration of tRNA modifications and elongation factor eEF1A in decoding and nonsense suppression", Scientific Reports 8(12749), pp. 1-12 (2018).
Kleina, L , et al., "Construction of *Escherichia coil* Amber Suppressor tRNA Genes", J Mol Biol 213, 705-717 (1990).
Koukuntla, R , et al., "U6 promoter-enhanced GlnUAG suppressor tRNA has higher suppression efficacy and can be stably expressed in 293 cells", Journal of Gene Medicine 15, 93-101 (2013).
Lueck, J , et al., "Engineered transfer RNAs for suppression of premature termination codons", Nature Communications 10(822), 1-11 (2019).
Lueck , et al., "Engineered tRNA suppression of a CFTR nonsense mutation", bioRxiv 20, pp. 1-9 (2016).
Olejniczak, M , et al., "Idiosyncratic tuning of tRNAs to achieve uniform ribosome binding", Nature Structural & Molecular Biology 12(9), 788-793 (2005).
Panchal, R , et al., "Partial Functional Correction of Xeroderma Pigmentosum Group A Cells by Suppressor tRNA", Human Gene Therapy 10, 2209-2219 (1999).
Patent Cooperation Treaty, International Searching Authority, Search Report and Written Opinion for PCT/US2018/059065, 12 pages, dated Apr. 15, 2019.
Raftery, L , et al., "Systematic alterations in the anticodon arm make tRNA Glu-Suoc a more efficient suppressor", EMBO Journal 6(5), 1499-1506 (1987).
Saks, M , et al., "Functional consequences of T-stem mutations in *E. coli* tRNAThrUGU in vitro and in vivo", RNA 17(6), 1038-1047 (2011).
Schmid, S , et al., "A Versatile RNA Vector for Delivery of Coding and Noncoding RNAs", J Virol 88(4), 2333-2336 (2014).
Schrader, J , et al., "Tuning the affinity of aminoacyl-tRNA to elongation factor Tu for optimal decoding", PNAS 108(13), 5215-5220 (2011).
Schrader, J , et al., "Understanding the Sequence Specificity of tRNA Binding to Elongation Factor Tu using tRNA Mutagenesis", J Mol Biol 386, 1255-1264 (2009).
Sharp, S , et al., "Structure and transcription of eukaryotic tRNA genes", Crit Rev Biochem 19(2), 107-144 (1985).
Sissler, M , et al., "Arginine aminoacylation identity is context-dependent and ensured by alternate recognition sets in the anticodon loop of accepting tRNA transcripts", The EMBO Journal 15(18), 5069-5076 (1996).
Temple, G , et al., "Construction of a functional human suppressor tRNA gene: an approach to gene therapy for beta-thalassaemia". Nature 296, 537-540 (1982).
Tuorto , et al., "Genome recoding by tRNA modifications", Open Biol 6(12), 1-9 (2016).
Muller, S , et al., "Spliceosomal Peptide P140 for Immunotherapy of Systemic Lupus Erythematosus Results of an Early Phase II Clinical Trial", Arthritis & Rheumatism 58 (12), 3873-3883 (2008).
Singer, M , et al., "Genes and genomes", Moscow, "Mir" vol. 1, pp. 52, Table 1.5.) (1998). [Non-English].
Vasil'eva, I , et al., "Influence of Nucleotide Changes in tRNAPhe on the Acceptor End Positioning in the Complex With Phenylalanyl tRNA Synthetase", Biochemistry 69, 192-203 (2004). [English Abstract].
Russian Office Action for RU Application No. 2020117787, 6 pages, dated Nov. 1, 2022. [English Translation].

* cited by examiner

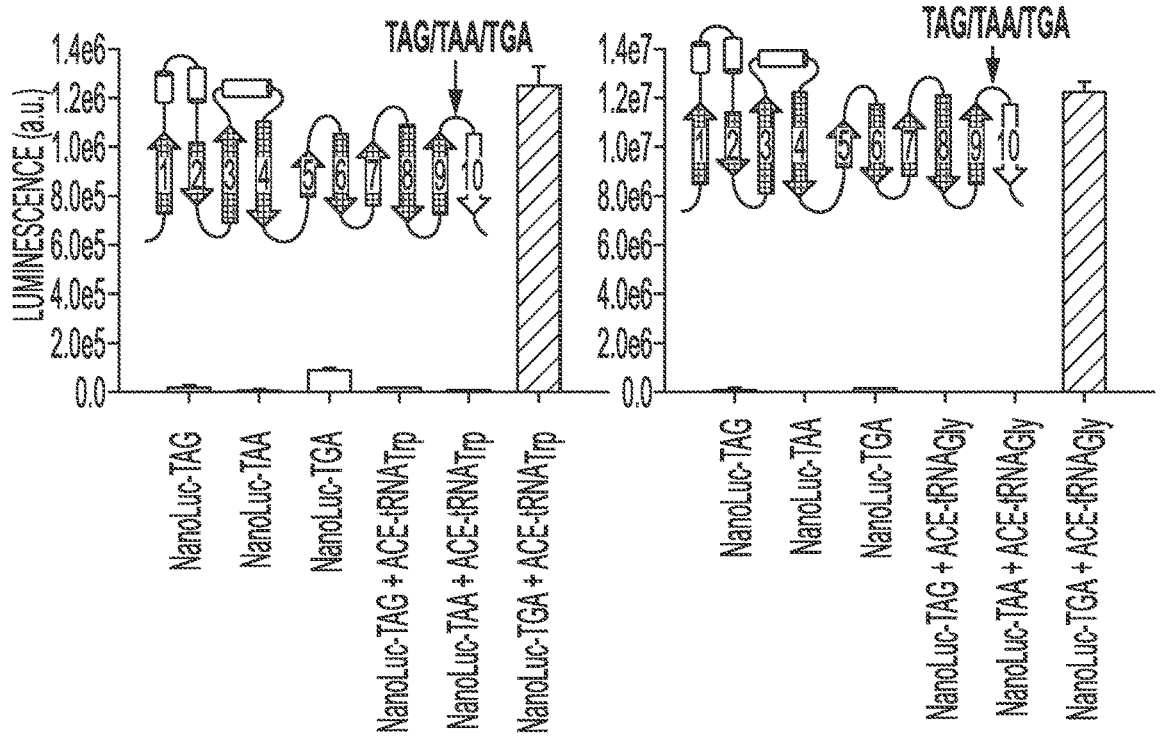
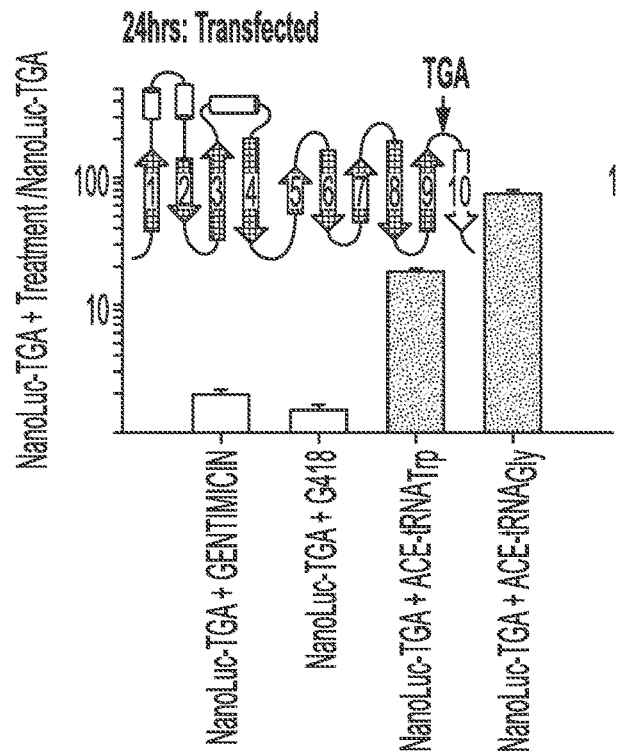
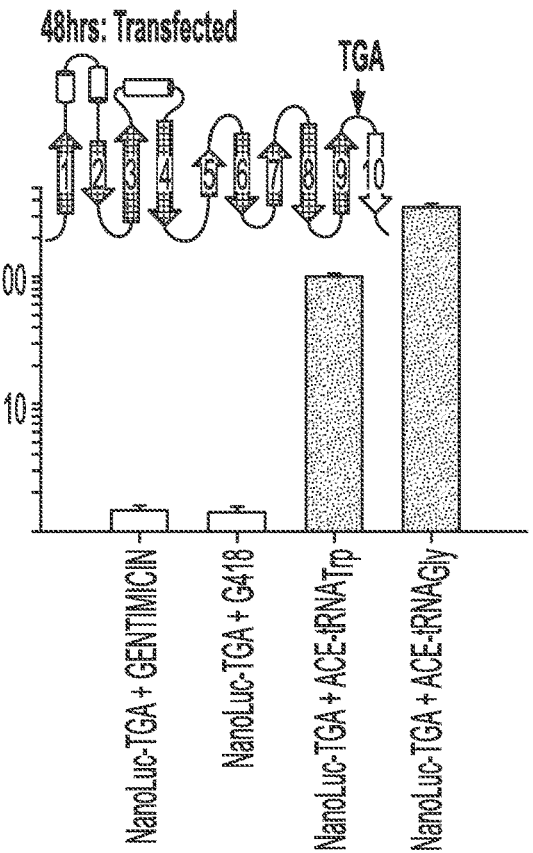
Figure 13A
Figure 13B
Figure 13C
Figure 13D

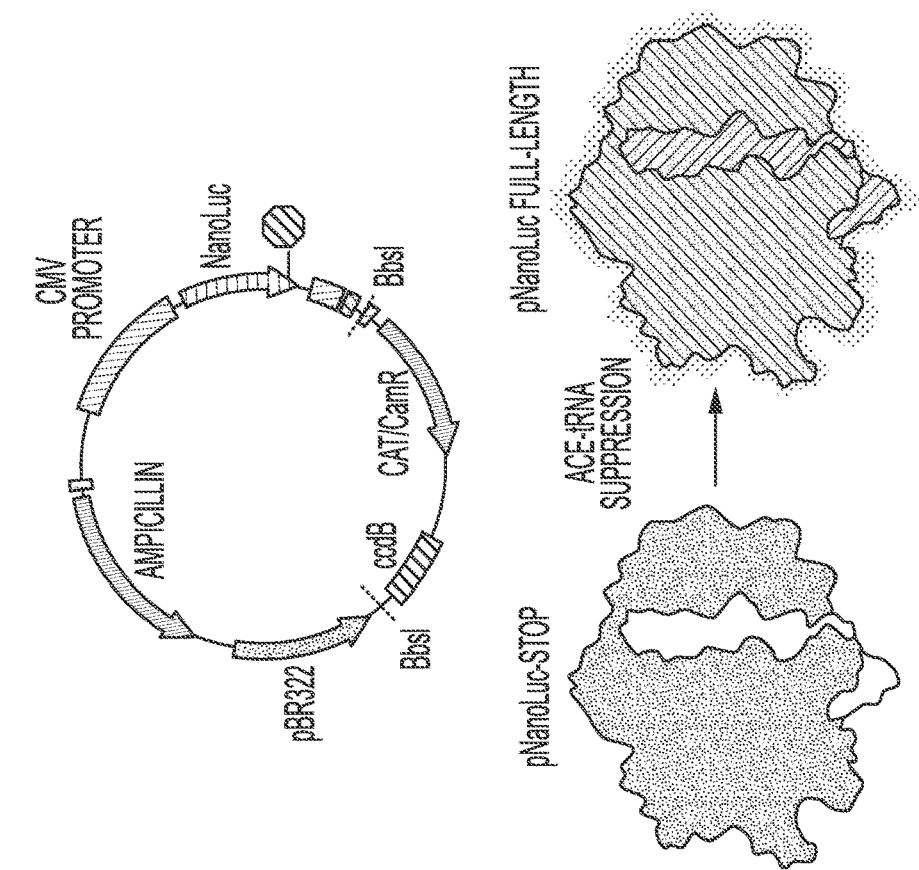
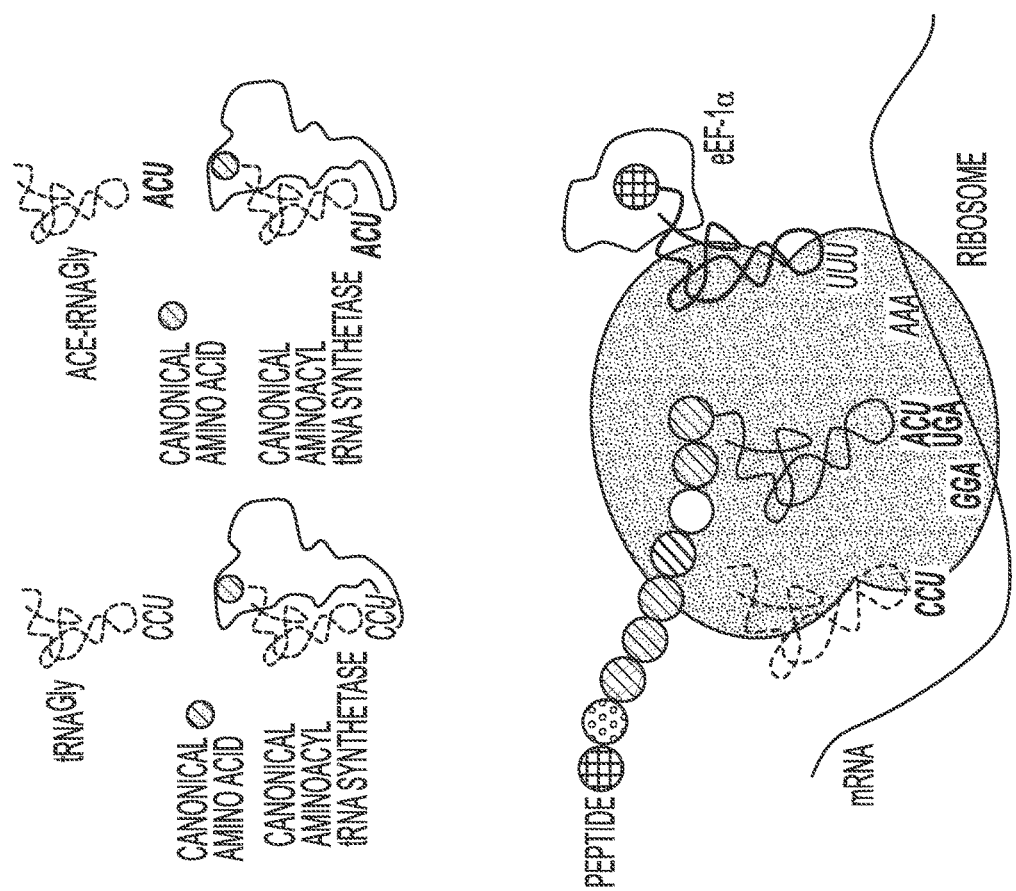
Figure 21A
Figure 21B

| AMINO ACID | | | CODONS | | | | | |
|---|---|---|---|---|---|---|---|---|
| W | Trp | TRYPTOPHAN | TGG | | | | | |
| Y | Tyr | TYROSINE | TAC | TAT | | | | |
| C | Cys | CYSTEINE | TGC | TGT | | | | |
| E | Glu | GLUTAMIC ACID | GAA | GAG | | | | |
| K | Lys | LYSINE | AAA | AAG | | | | |
| Q | Gln | GLUTAMINE | CAA | CAG | | | | |
| S | Ser | SERINE | AGC | AGT | TCA | TCC | TCG | TCT |
| L | Leu | LEUCINE | TTA | TTG | CTA | CTC | CTG | CTT |
| R | Arg | ARGININE | AGA | AGG | CGA | CGC | CGG | CGT |
| G | Gly | GLYCINE | GGA | GGC | GGG | GGT | | |
| F | Phe | PHENYLALANINE | TTC | TTT | | | | |
| D | Asp | ASPARTIC ACID | GAC | GAT | | | | |
| H | His | HISTIDINE | CAC | CAT | | | | |
| N | Asn | ASPARAGINE | AAC | AAT | | | | |
| M | Met | METHIONINE | ATG | | | | | |
| A | Ala | ALANINE | GCA | GCC | GCG | GCT | | |
| P | Pro | PROLINE | CCA | CCC | CCG | CCT | | |
| T | Thr | THREONINE | ACA | ACC | ACG | ACT | | |
| V | Val | VALINE | GTA | GTC | GTG | GTT | | |
| I | Ile | ISOLEUCINE | ATA | ATC | ATT | | | |
| X | STP | STOP CODON | TAA | TAG | TGA | | | |

Figure 25

```
                                      >>>>>>..>>>>.......<<<<.>>>>........
TrpChr17.tRNA39                       -GACCUCGUGGCGCAACGGCAGCGCGUCUGACUucaG-----
TrpChr17.tRNA10                       -GACCUCGUGGCGCAACGGUAGCGCGUCUGACUucaG-----
TrpChr6.tRNA171                       -GGCCUCAUGGUGCAACAGUAGUGUGUCUGACUucaG-----
TrpChr12.tRNA6                        -GACCUCGUGGCGCAAUGGUAGCGCGUCUGACUucaG-----
TrpChr7.tRNA3                         -CGCCUCGUGGCGCAACGGUAGCGCGUCUGACUucaG-----
TrpChr7.tRNA31                        -GACCUCGUGGCGCAACGGUAGCGCGUCUGACUucaG-----

Mus_musculuschr11.tRNA817             -GACCUCGUGGCGCAAUGGUAGCGCGUCUGACUucaG-----
Mus_musculuschr10.tRNA567             -GACCUCGUGGCACAAUGGUAGCACGUCUGACUucaG-----
Saccharomyces_cerevisiaechrVII.tRNA33 -GAAGCGGUGGCUCAAUGGUAGAGCUUCGACUucaAuuaaa
Saccharomyces_cerevisiaechrVII.tRNA33 -GAAGCGGUGGCUCAAUGGUAGCUUCGACUucaA
Pan_troglodyteschr7.tRNA28            -GGCCUCAUGGUGCAACAGUAGUGUGUCUGACUucaG-----
Oryctolagus_cuniculuschrUn0422.tRNA1  -GACCUCGUGGUGCAAUGGUAGCAUGUUUGACUucaA
Oryctolagus_cuniculus_chrUn0563.tRNA1 -GACCUGUGGCGCAAUGGUAGCAUGUUGACUucaA
Oryctolagus_cuniculus_chrUn0062.tRNA12 -GACCUCGUGGCGCAACGGUAGCGCGUCUGACUucaG-----
Rattus_norvegicus_chr13.tRNA4571      -GACCUUGUGGCUCAAUGGUAGCGAUCUGACUucaG-----
Rattus_norvegicus_chr17.tRNA3948      -GACCUUGUGGCGCAACGGUAGCGCGUCUGACUucaG-----
Xenopus_tropicalis_tRNA-trp-cca-10-1  -GACCUCGUGGCGCAACGGUAGCGCGUCUGACUucaG-----
Xenopus_tropicalis_tRNA-trp-cca-11-1  -GACCUCGUGGCGCAACGGCAGCGCGUCUGACUucaC-----
Xenopus_tropicalis_tRNA-trp-cca-12-1  -GACCUCAUGGCGCAACGGUAGCGCGUCUGACUucaG-----
Xenopus_tropicalis_tRNA-trp-cca-13-1  -GACCUCGUGGUGCAACGGUAGCGCGUAUGAUUucaG-----
Xenopus_tropicalis_tRNA-trp-cca-3-1   -GACCUCGUAGCGCAACGGUAGCGCGUCUGACUucaG-----
Xenopus_tropicalis_tRNA-trp-cca-5-1   AGGGUAUAGCCUCAAUUGGCACAGCGUCGGUCUucaA-----
Xenopus_tropicalis_tRNA-trp-cca-6-1   -GACCUCAUGGCGCAACGGUAGCGCGUCUGACUucaG-----
Xenopus_tropicalis_tRNA-trp-cca-7-1   -GACCUCGUGGCGCAACGGUAGCGCGUCUAACUucaG-----
Xenopus_tropicalis_tRNA-trp-cca-8-1   ACGGGAGUAGCUCAGUUGGUAGAGCACCGGUCUucaA-----
Xenopus_tropicalis_tRNA-trp-cca-9-1   -GACCUCGUGGCGCAACGGUAGCGCGUCUGACUucaG-----
D._melanogaster_tRNA-trp-cca-2-1      -GACUCCGUGGCGCAACGGUAGCGCGUCGACUucaG-----
D._melanogaster_tRNA-trp-cca-1-1      -GACUCCGUGGCGCAACGGUAGCGCGUCUGACUucaG-----

TrpChr7.tRNA3-WT                      -GGCCUCGUGGCGCAACGGUAGCGCGUCUGACUccaG-----
TrpChr7.tRNA3-Hirsch-CCA              -GGCCUCGUGGCGCAACGGUAGCACGUCUGACUccaG-----
TrpChr7.tRNA3-Hirsch-G9C-CCA          -GGCCUCGUCGCGCAACGGUAGCGCGUCUGACUccaG-----
TrpChr7.tRNA3-Hirsch-UCA              -GGCCUCGUGGCGCAACGGUAGCACGUCUGACUucaG-----
TrpChr7.tRNA3-G9C-UCA                 -GGCCUCGUCGCGCAACGGUAGCGCGUCUGACUucaG-----
TrpChr7.tRNA3-Hirsch-G9C-UCA          -GGCCUCGUCGCGCAACGGUAGCACGUCUGACUucaG-----
```

Figure 29A

```
                                        ,<<<<<,.....>>>>>.......<<<<<<<<<<<<,
------------------------------------AUCAGAAGGUUGCGUGUUCAAAUCACGUCGGGGUCA
------------------------------------AUCAGAAGGUUGCGUGUUCAAAUCACGUCGGGGUCA
------------------------------------AUCAGAAGGUUGUAUGUUCAAAUCACGUAGGGGUCA
------------------------------------AUCAGAAGGUUGCGUGUUCAAGUCACGUCGGGGUCA
------------------------------------AUCAGAAGGUUGCGUGUUCAAAUCACGUCGGGGUCA
------------------------------------AUCAGAAGCUGCGUGUUCGAAUCACGUCGGGGUCA

------------------------------------AUCAGAAGGUUGCGUGUUCAAAUCACGUCGGGGUCA
------------------------------------AUCAGAAGGUUGCGUGUUCAAAUCACGUCGGGGUCA
ucuuggaaauuccacggaauaagauugcaAUCGAAGGUUGCAGGUUCAAUUCCUGUCGCUUCA
-----------------------------------AUCGAAGGUUGCAGGUUCAAUUCUGUCGCUUCA
------------------------------------AUCAGAAGGUUGUAUGUUCAAAUCACAUAGGGGUCA
------------------------------------AUCAGGAGGUUGUGUGUUCAAGUCACAUCAGGGUCA
------------------------------------AUCAGGAGGUUGUGUGUUCAAGUCACAUCAGGGUCA
------------------------------------AUCAGAAGGCUGCGUGUUCGAAUCACGCCGGGGUCA
------------------------------------AUCAGGAGGUUGCACGUUCAAAUCAUGCCGGGGUCA
------------------------------------AUCAGAAGGUUGCGUGUUCAAAUCACGUCGGGGUCA
------------------------------------AUCAGAAGGUUGCGUAUUCAAAUCACGUCGGGGUCA
------------------------------------AUUAGAAGGUUGCGUGUUCAAAUCACGUCGGGGUCA
------------------------------------AUCAGAAGGUUGCGUGUUCAAAUCACAUCGGGGUCA
------------------------------------AUCAGAAGGUUGCGUGUUCAAAUCACGUCGGGGUCA
------------------------------------AUCAGAAGGUUGCGUGUUCAAAUCACGUCGGGGUCA
------------------------------------AACGAAGGUUGUAGGUUCGAUCCUACUGCCCCUGCCA
------------------------------------AUCAGAAGGUUGCGUGUUCAAAUCACGUCGGGGUCA
------------------------------------AUCAGAAGGUUGCGUGUUCAAAUCACGUCGGGGUCA
------------------------------------AACCGGUGUCGGGAGUUCGAGCCUCUCCUCCCGUG
------------------------------------AUCAGAAGGUUGCAUGUUCAAAUCACGUCGGGGUCA
------------------------------------AUCGGAAGGUUGCGUGUUCAAAUCACGUCGGGGUCA
------------------------------------AUCAGAAGGUUGCGUGUUCAAAUCACGUCGGGGUCA ------------------------------------AUCAGAAGGUUGCGUGUUCAAAUCACGUCGGGGUCA
------------------------------------AUCAGAAGGUUGCGUGUUCAAAUCACGUCGGGGUCA
------------------------------------AUCAGAAGGUUGCGUGUUCAAAUCACGUCGGGGUCA
------------------------------------AUCAGAAGGUUGCGUGUUCAAAUCACGUCGGGGUCA
------------------------------------AUCAGAAGGUUGCGUGUUCAAAUCACGUCGGGGUCA
------------------------------------AUCAGAAGGUUGCGUGUUCAAAUCACGUCGGGGUCA
```

Figure 29A
CONTINUED

MSFNTIIDWNSCTAEQQRQLLMRPAISASESITRTVNDILDNV
KARGDEALREYSAKFDKTTVTALKVSAEEIAAASERLSDELKQ
AMAVAVKNIETFHTAQKLPPVDVETQPGVRCQQVTRPVASVGL
YIPGGSAPLFSTVLMLATPASIAGCKKVVLCSPPPIADEILYA
AQLCGVQDVFNVGGAQAIAALAFGTESVPKVDKIFGPGNAFVT
EAKRQVSQRLDGAAIDMPAGPSEVLVIADSGATPDFVASDLLS
QAEHGPDSQVILLTPAADMARRVAEAVERQLAELPRAETARQA
LNASRLIVTKDLAQCVEISNQYGPEHLIIQTRNARELVDSITS
AGSVFLGDWSPESAGDYASGTNHVLPTYGYTATCSSLGLADFQ
KRMTVQELSKEGFSALASTIETLAAAERLTAHKNAVTLRVNAL
KEQA*HHHHHHHHHSGGSAWSHPQFEK*

Figure 30A

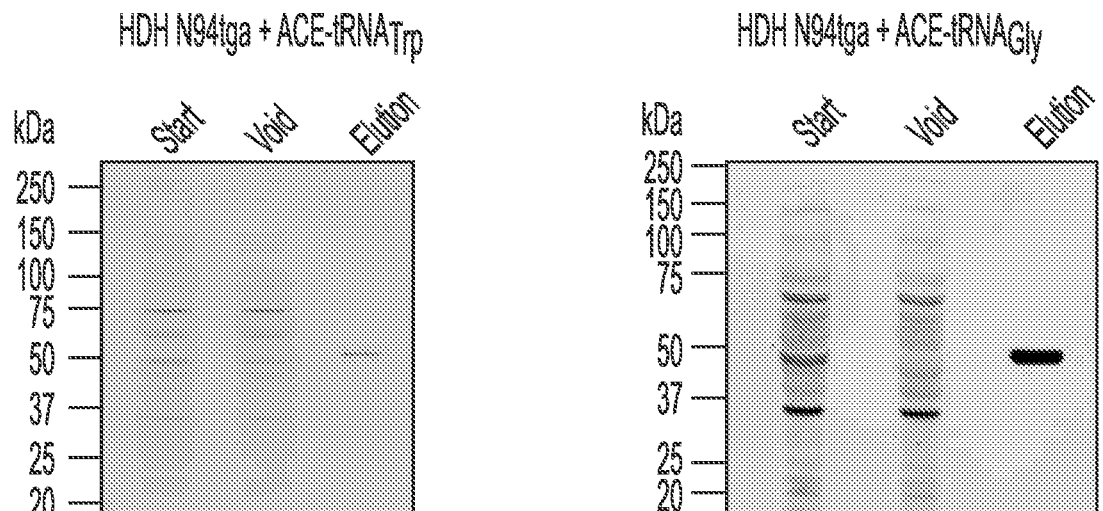

SEQUENCE LISTING

<160> NUMBER OF SEQ ID NOS: 655

<210> SEQ ID NO 1
<211> LENGTH: 72
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1
ggcctcgtgg cgcaacggta gcgcgtctga cttcagatca gaaggttgcg ggttcaaatc      60
ccgtcggggt ca                                                         72

<210> SEQ ID NO 2
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcctcgtgg cgcaacggta gcgcgtctga cttcagatca gaaggttacg ggttcaaatc      60
ccgtcggggt ca                                                         72

<210> SEQ ID NO 3
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcctcgtgg cgcaacggta gcgcgtctga cttcagatca gaaggttccg ggttcaaatc      60
ccggcggggt ca                                                         72

<210> SEQ ID NO 4
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgtcggctct gtggcgcaat ggatagcgca ttggacttca aattcaaagg ttgtgggttc      60
gagtcccacc agagtcg                                                    77

<210> SEQ ID NO 5
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgtcgcccca gtggcctaat ggataaggca ctggccttca aagccaggga ttgtgggttc      60
gagtcccacc tggggtg                                                    77

<210> SEQ ID NO 6
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 6
cgtcggctcc gtggcgcaat ggatagcgca ttggacttca aattcaaagg ttccgggttc    60
gagtcccggc ggagtcg                                                   77

<210> SEQ ID NO 7
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgtcgcccca gtggcctaat ggataaggca ttggccttca aagccaggga ttgtgggttc    60
gagtcccatc tggggtg                                                   77

<210> SEQ ID NO 8
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgtcggctct gtggcgcaat ggatagcgca ttggacttca aattcaaagg ttgtgggttc    60
gaatcccacc agagtcg                                                   77

<210> SEQ ID NO 9
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgtcggctct gtggcgcaat ggatagcgca ttggacttca agctgagcct agtgtggtca    60
ttcaaaggtt gtgggttcga gtcccaccag agtcg                               95

<210> SEQ ID NO 10
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgtcgccccg gtggcctaat ggataaggca ttggccttca aagccaggga ttgtgggttc    60
gagtcccacc cggggta                                                   77

<210> SEQ ID NO 11
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 11
cgtcggctcc gtggcgcaat ggatagcgca ttggacttca agaggctgaa ggcattcaaa    60
ggttccgggt tcgagtcccg gcggagtcg                                       89

<210> SEQ ID NO 12
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgtcggctct gtggcgcaat ggatagcgca ttggacttca agtgacgaat agagcaattc    60
aaaggttgtg ggttcgaatc ccaccagagt cg                                   92

<210> SEQ ID NO 13
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgtcggccgc gtggcctaat ggataaggcg tctgacttca gatcagaaga ttgcaggttc    60
gagtcctgcc gcggtcg                                                    77

<210> SEQ ID NO 14
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgtcgaccgc gtggcctaat ggataaggcg tctgacttca gatcagaaga ttgagggttc    60
gagtcccttc gtggtcg                                                    77

<210> SEQ ID NO 15
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgtcggctct gtggcgcaat ggatagcgca ttggacttca agatagttag agaaattcaa    60
aggttgtggg ttcgagtccc accagagtcg                                      90

<210> SEQ ID NO 16
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 16
cgtcggttcc atggtgtaat ggtgagcact ctggactcta aatccagcga tccgagttcg    60
agtctcggtg aacct                                                     76

<210> SEQ ID NO 17
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgtcggcccc atggtgtaat ggttagcact ctggactcta aatccagcga tccgagttca    60
aatctcggtg ggacct                                                    76

<210> SEQ ID NO 18
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgtcggtccc atggtgtaat ggttagcact ctggactcta aatccagcaa tccgagttcg    60
aatctcggtg ggacct                                                    76

<210> SEQ ID NO 19
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgtcggtccc atggtgtaat ggttagcact ctggactcta aatccagcga tccgagttca    60
aatctcggtg ggacct                                                    76

<210> SEQ ID NO 20
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cgtcggcccc atggtgtaat ggtcagcact ctggactcta aatccagcga tccgagttca    60
aatctcggtg ggaccc                                                    76

<210> SEQ ID NO 21
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 21
cgtcggttcc atggtgtaat ggtaagcact ctggactcta atccagcga tccgagttcg    60 agtctcggtg gaacct                                                   76

<210> SEQ ID NO 22
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgtcggttcc atggtgtaat ggttagcact ctggactcta atccggtaa tccgagttca    60 aatctcggtg gaacct                                                   76

<210> SEQ ID NO 23
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgtcggttcc atggtgtaat ggttagcact ctggactcta atccagcga tccgagttca    60 agtctcggtg gaacct                                                   76

<210> SEQ ID NO 24
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgtcggttcc atggtgtaat ggtaagcact ctggacttta atccagcga tccgagttcg    60 agtctcggtg gaacct                                                   76

<210> SEQ ID NO 25
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cgtcggcccc atggtgtaat ggttagcact ctggacttta atccagcga tccgagttca    60 aatctcggtg ggacct                                                   76

<210> SEQ ID NO 26
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 26
cgtcggttcc atggtgtaat ggtgagcact ctggacttta aatccagcga tccgagttcg    60
agtctcggtg aacct                                                      76

<210> SEQ ID NO 27
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cgtcggttcc atggtgtaat ggttagcact ctggacttta aatccagcga tccgagttca    60
aatctcggtg aacct                                                      76

<210> SEQ ID NO 28
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cgtcggtccc atggtgtaat ggttagcact ctggacttta aatccagcga tccgagttca    60
aatctcggtg ggacct                                                     76

<210> SEQ ID NO 29
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgtcggtccc atggtgtaat ggttagcact ctggacttta aatccagcaa tccgagttcg    60
aatctcggtg ggacct                                                     76

<210> SEQ ID NO 30
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cgtcggttcc atggtgtaat ggttagcact ctggacttta aatccggtaa tccgagttca    60
aatctcggtg aacct                                                      76

<210> SEQ ID NO 31
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 31
cgtcggcccc atggtgtaat ggtcagcact ctggactta aatccagcga tccgagttca    60
aatctcggtg ggaccc    76

<210> SEQ ID NO 32
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgtcggttcc atggtgtaat ggttagcact ctggactta aatccagcga tccgagttca    60
agtctcggtg gaacct    76

<210> SEQ ID NO 33
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgtcgacctc gtggcgcaat ggtagcgcgt ctgactctag atcagaaggt tgcgtgttca    60
agtcacgtcg gggtca    76

<210> SEQ ID NO 34
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cgtcgacctc gtggcgcaac ggtagcgcgt ctgactctag atcagaaggt tgcgtgttca    60
aatcacgtcg gggtca    76

<210> SEQ ID NO 35
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cgtcggcctc gtggcgcaac ggtagcgcgt ctgactctag atcagaaggt tgcgtgttca    60
aatcacgtcg gggtca    76

<210> SEQ ID NO 36
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 36
cgtcgacctc gtggcgcaac ggtagcgcgt ctgactctag atcagaaggc tgcgtgttcg    60
aatcacgtcg gggtca                                                    76

<210> SEQ ID NO 37
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgtcgacctc gtggcgcaac ggcagcgcgt ctgactctag atcagaaggt tgcgtgttca    60
aatcacgtcg gggtca                                                    76

<210> SEQ ID NO 38
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgtctcccac atggtctagc ggttaggatt cctggttcta acccaggcgg cccgggttcg    60
actcccggtg tgggaa                                                    76

<210> SEQ ID NO 39
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgtctcccat atggtctagc ggttaggatt cctggttcta acccaggtgg cccgggttcg    60
actcccggta tgggaa                                                    76

<210> SEQ ID NO 40
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cgtctccctg gtggtctagt ggctaggatt cggcgctcta accgccgcgg cccgggttcg    60
attcccggtc agggaa                                                    76

<210> SEQ ID NO 41
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 41
cgtctccctg gtggtctagt ggttaggatt cggcgctcta accgccgcgg cccgggttcg    60
attcccggtc agggaa                                                    76

<210> SEQ ID NO 42
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgtctccctg gtggtctagt ggctaggatt cggcgctcta accgccgcgg cccgggttcg    60
attcccggcc agggaa                                                    76

<210> SEQ ID NO 43
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cgtctcccac atggtctagc ggttaggatt cctggttcta acccaggcgg cccgggttcg    60
actcccggtg tgggaa                                                    76

<210> SEQ ID NO 44
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgtctcccat atggtctagc ggttaggatt cctggttcta acccaggtgg cccgggttcg    60
actcccggta tgggaa                                                    76

<210> SEQ ID NO 45
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cgtctccctg gtggtctagt ggttaggatt cggcgctcta accgccgcgg cccgggttcg    60
attcccggtc agggaa                                                    76

<210> SEQ ID NO 46
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 46
cgtctccctg gtggtctagt ggttaggatt cggcgctcta accgccgcgg cccgggttcg    60
attcccggtc aggaaa                                                    76

<210> SEQ ID NO 47
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cgtctccctg gtggtctagt ggctaggatt cggcgctcta accgccgcgg cccgggttcg    60
attcccggcc agggaa                                                    76

<210> SEQ ID NO 48
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggcctcgtgg cgcaacggta gcgcgtctga cttcagatca gaaggttgcg tgttcaaatc    60
acgtcggggt ca                                                        72

<210> SEQ ID NO 49
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gacctcgtgg cgcaatggta gcgcgtctga cttcagatca gaaggttgcg tgttcaagtc    60
acgtcggggt ca                                                        72

<210> SEQ ID NO 50
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gacctcgtgg cgcaacggta gcgcgtctga cttcagatca gaaggttgcg tgttcaaatc    60
acgtcggggt ca                                                        72

<210> SEQ ID NO 51
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 51
gacctcgtgg cgcaacggta gcgcgtctga cttcagatca gaaggctgcg tgttcgaatc    60
acgtcggggt ca                                                       72

<210> SEQ ID NO 52
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gacctcgtgg cgcaacggca gcgcgtctga cttcagatca gaaggttgcg tgttcaaatc    60
acgtcggggt ca                                                       72

<210> SEQ ID NO 53
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gcgttggtgg tatagtggtt agcatagctg ccttcaaagc agttgacccg ggttcgattc    60
ccggccaacg ca                                                       72

<210> SEQ ID NO 54
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gcgttggtgg tatagtggtg agcatagctg ccttcaaagc agttgacccg ggttcgattc    60
ccggccaacg ca                                                       72

<210> SEQ ID NO 55
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcgttggtgg tatagtggta agcatagctg ccttcaaagc agttgacccg ggttcgattc    60
ccggccaacg ca                                                       72

<210> SEQ ID NO 56
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 56
ggcctcgtgg cgcaacggta gcgcgtctga cttcagatca gaaggttgcg tgttcaaatc    60
acgtcggggt ca                                                        72

<210> SEQ ID NO 57
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gacctcgtgg cgcaatggta gcgcgtctga cttcagatca gaaggttgcg tgttcaagtc    60
acgtcggggt ca                                                        72

<210> SEQ ID NO 58
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gacctcgtgg cgcaacggta gcgcgtctga cttcagatca gaaggttgcg tgttcaaatc    60
acgtcggggt ca                                                        72

<210> SEQ ID NO 59
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gacctcgtgg cgcaacggta gcgcgtctga cttcagatca gaaggctgcg tgttcgaatc    60
acgtcggggt ca                                                        72

<210> SEQ ID NO 60
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gacctcgtgg cgcaacggca gcgcgtctga cttcagatca gaaggttgcg tgttcaaatc    60
acgtcggggt ca                                                        72

<210> SEQ ID NO 61
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 61
ggcctcatgg tgcaacagta gtgtgtctga cttcagatca gaaggttgta tgttcaaatc    60
acgtaggggt ca                                                       72

<210> SEQ ID NO 62
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggcctcgtgg cgcaacggta gcgcgtctga ctctagatca gaaggttgcg tgttcaaatc    60
acgtcggggt ca                                                       72

<210> SEQ ID NO 63
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gacctcgtgg cgcaatggta gcgcgtctga ctctagatca gaaggttgcg tgttcaagtc    60
acgtcggggt ca                                                       72

<210> SEQ ID NO 64
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gacctcgtgg cgcaacggta gcgcgtctga ctctagatca gaaggttgcg tgttcaaatc    60
acgtcggggt ca                                                       72

<210> SEQ ID NO 65
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gacctcgtgg cgcaacggta gcgcgtctga ctctagatca gaaggctgcg tgttcgaatc    60
acgtcggggt ca                                                       72

<210> SEQ ID NO 66
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 66
gacctcgtgg cgcaacggca gcgcgtctga ctctagatca gaaggttgcg tgttcaaatc      60
acgtcggggt ca                                                         72

<210> SEQ ID NO 67
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggcctcatgg tgcaacagta gtgtgtctga ctctagatca gaaggttgta tgttcaaatc      60
acgtaggggt ca                                                         72

<210> SEQ ID NO 68
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gcattggtgg ttcagtggta gaattctcgc cttcaacgcg ggagacccgg gttcaattcc      60
cggccaatgc a                                                          71

<210> SEQ ID NO 69
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gcgccgctgg tgtagtggta tcatgcaaga tttcaaattc ttgcgacccg ggttcgattc      60
ccgggcggcg ca                                                         72

<210> SEQ ID NO 70
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gcattggtgg ttcaatggta gaattctcgc cttcaacgca ggagacccag gttcgattcc      60
tggccaatgc a                                                          71

<210> SEQ ID NO 71
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 71
gcgttggtgg tttagtggta gaattctcgc cttcaatgcg ggagacccgg gttcaattcc        60
cggccactgc a                                                            71

<210> SEQ ID NO 72
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gccttggtgg tgcagtggta gaattctcgc cttcaacgtg ggagacccgg gttcaattcc        60
cggccaatgc a                                                            71

<210> SEQ ID NO 73
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggtggttcag tggtagaatt ctcgccttca acgcgggaga cccgggttta attcccggtc        60
a                                                                       61

<210> SEQ ID NO 74
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gtggtctagt ggttaggatt cagcgcttca accgccgcag cccgggttcg attcccggtc        60
a                                                                       61

<210> SEQ ID NO 75
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gcgtcagtgg tttagtggtg gaattcctgc cttcaatgca cgagatccgt gttcaactcc        60
tggttggtgc a                                                            71

<210> SEQ ID NO 76
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gcgtcagtgg ttttagtggt ggaattcctg ccttcaatgc acgagatccg tgttcaactc    60
ctggttggtg ca    72

<210> SEQ ID NO 77
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gcgttggcag ttcagtggta gaattctcgc cttcaacccg ggagacctgg attccatttc    60
cggcaaatgc a    71

<210> SEQ ID NO 78
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gcatgggtgg ttcagtggta gaattctcgc cttcaacgcg ggaggcccgg gttcgattcc    60
cggcccatgc a    71

<210> SEQ ID NO 79
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gcattggtgg ttcagtggta gaattctcgc cttcaacgcg ggaggcccgg gttcgattcc    60
cggccaatgc a    71

<210> SEQ ID NO 80
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gcattggtgg ttcagtggta gaattctcgc cttcaacgcg ggaggcccgg gtttgattcc    60
cggccagtgc a    71

<210> SEQ ID NO 81
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 81
gcataggtgg ttcagtggta gaattcttgc cttcaacgca ggaggcccag gtttgattcc    60
tggcccatgc a                                                         71

<210> SEQ ID NO 82
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gcattggtgg ttcagtggta gaattctcgc cttcaatgcg ggcggccggg cttcgattcc    60
tggccaatgc a                                                         71

<210> SEQ ID NO 83
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gcatgggtga ttcagtggta gaattttcac cttcaatgca ggaggtccag gttcatttcc    60
tggcctatgc a                                                         71

<210> SEQ ID NO 84
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gcgttggtgg tatagtggtt agcatagctg ccttcaaagc agttgacccg ggttcgattc    60
ccggccaacg ca                                                        72

<210> SEQ ID NO 85
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gcgttggtgg tatagtggtg agcatagctg ccttcaaagc agttgacccg ggttcgattc    60
ccggccaacg ca                                                        72

<210> SEQ ID NO 86
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 86
gcgttggtgg tatagtggta agcatagctg ccttcaaagc agttgacccg ggttcgattc    60
ccggccaacg ca                                                       72

<210> SEQ ID NO 87
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcgttggtgg tatagtggtg agcatagttg ccttcaaagc agttgacccg ggctcgattc    60
ccgcccaacg ca                                                       72

<210> SEQ ID NO 88
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gcgttggtgg tatagtggtg agcatagttg ccttcaaagc agttgacccg ggctcgattc    60
ccggccaacg ca                                                       72

<210> SEQ ID NO 89
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gggccagtgg cgcaatggat aacgcgtctg acttcagatc agaagattcc aggttcgact    60
cctggctggc tcg                                                      73

<210> SEQ ID NO 90
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gggccagtgg cgcaatggat aacgcgtctg acttcagatc agaagattct aggttcgact    60
cctggctggc tcg                                                      73

<210> SEQ ID NO 91
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 91
ggccgcgtgg cctaatggat aaggcgtctg atttcagatc agaagattga gggttcgagt    60
cccttcgtgg tcg                                                       73

<210> SEQ ID NO 92
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gacccagtgg cctaatggat aaggcatcag ccttcagagc tggggattgt gggttcgagt    60
cccatctggg tcg                                                       73

<210> SEQ ID NO 93
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gccccagtgg cctaatggat aaggcactgg ccttcaaagc cagggattgt gggttcgagt    60
cccacctggg gta                                                       73

<210> SEQ ID NO 94
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gccccagtgg cctaatggat aaggcactgg ccttcaaagc cagggattgt gggttcgagt    60
cccacctggg gtg                                                       73

<210> SEQ ID NO 95
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gccccggtgg cctaatggat aaggcattgg ccttcaaagc cagggattgt gggttcgagt    60
cccacccggg gta                                                       73

<210> SEQ ID NO 96
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 96
gccccagtgg cctaatggat aaggcattgg ccttcaaagc cagggattgt gggttcgagt    60
cccatctggg gtg                                                      73

<210> SEQ ID NO 97
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gccccagtgg cctgatggat aaggtactgg ccttcaaagc cagggattgt gggttcgagt    60
tccacctggg gta                                                      73

<210> SEQ ID NO 98
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggccgcgtgg cctaatggat aaggcgtctg acttcagatc agaagattgc aggttcgagt    60
cctgccgcgg tcg                                                      73

<210> SEQ ID NO 99
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gaccacgtgg cctaatggat aaggcgtctg acttcagatc agaagattga gggttcgaat    60
ccctccgtgg tta                                                      73

<210> SEQ ID NO 100
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gaccgcgtgg cctaatggat aaggcgtctg acttcagatc agaagattga gggttcgagt    60
cccttcgtgg tcg                                                      73

<210> SEQ ID NO 101
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 101
gaccacgtgg cctaatggat aaggcgtctg acttcagatc agaagattga gggttcgaat    60
cccttcgtgg tta                                                      73

<210> SEQ ID NO 102
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gaccacgtgg cctaatggat aaggcgtctg acttcagatc agaagattga gggttcgaat    60
cccttcgtgg ttg                                                      73

<210> SEQ ID NO 103
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggccgtgtgg cctaatggat aaggcgtctg acttcagatc aaaagattgc aggtttgagt    60
tctgccacgg tcg                                                      73

<210> SEQ ID NO 104
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ggctccgtgg cgcaatggat agcgcattgg acttcaagag gctgaaggca ttcaaaggtt    60
ccgggttcga gtcccggcgg agtcg                                         85

<210> SEQ ID NO 105
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ggctccgtgg cgcaatggat agcgcattgg acttcaaatt caaaggttcc gggttcgagt    60
cccggcggag tcg                                                      73

<210> SEQ ID NO 106
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 106
ggctctgtgg cgcaatggat agcgcattgg acttcaagtg acgaatagag caattcaaag    60
gttgtgggtt cgaatcccac cagagtcg                                      88

<210> SEQ ID NO 107
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ggctctgtgg cgcaatggat agcgcattgg acttcaaatt caaaggttgt gggttcgaat    60
cccaccagag tcg                                                      73

<210> SEQ ID NO 108
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ggctctgtgg cgcaatggat agcgcattgg acttcaagct gagcctagtg tggtcattca    60
aaggttgtgg gttcgagtcc caccagagtc g                                  91

<210> SEQ ID NO 109
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggctctgtgg cgcaatggat agcgcattgg acttcaaatt caaaggttgt gggttcgagt    60
cccaccagag tcg                                                      73

<210> SEQ ID NO 110
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ggctctgtgg cgcaatggat agcgcattgg acttcaagat agttagagaa attcaaaggt    60
tgtgggttcg agtcccacca gagtcg                                        86

<210> SEQ ID NO 111
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 111
gtctctgtgg cgcaatggac gagcgcgctg gacttcaaat ccagaggttc cgggttcgag    60
tcccggcaga gatg                                                     74

<210> SEQ ID NO 112
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ggctctgtgg cgcaatggat agcgcattgg acttcaagcc taaatcaaga gattcaaagg    60
ttgcgggttc gagtccctcc agagtcg                                       87

<210> SEQ ID NO 113
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggctctgtgg cgcaatggat agcgcattgg acttcaaatt caaaggttgc gggttcgagt    60
ccctccagag tcg                                                      73

<210> SEQ ID NO 114
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggcagcatag cagagtggtt caggttacag gttcaagatg taaactgagt tcaaatccca    60
gttctgcca                                                           69

<210> SEQ ID NO 115
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tggtgtaata ggtagcacag agaattctag attctcaggg gtaggttcaa ttcctat       57

<210> SEQ ID NO 116
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 116
taggacatgg tgtgataggt agcatggaga attctagatt ctcagggta ggttcaattc    60 ctacagttct ag                                                       72

<210> SEQ ID NO 117
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
taggacgtgg tgtgataggt agcatgggga attctagatt ctcagggtg ggttcaattc    60 ctatagttct ag                                                       72

<210> SEQ ID NO 118
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
taggacgtgg tgtagtaggt agcatggaga atgctaaatt ctcagggta ggttcaattc    60 ctatagttct ag                                                       72

<210> SEQ ID NO 119
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
taggacatgg tgtaataggt agaatggaga attctaaatt ctcagggta ggttcaattc    60 ctatagttct ag                                                       72

<210> SEQ ID NO 120
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
taggatgtgg tgtattaggt agcacagaga attctagatt ctcagggta ggttcgattc    60 ctataattct ac                                                       72

<210> SEQ ID NO 121
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 121
taggacttgg tgtaatgggt agcacagaga attctagatt ctcaggggtg ggttcaattc    60
ctttcgtcct ag                                                       72

<210> SEQ ID NO 122
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tctaggatgt ggtgtgatag gtagcatgga gaattctaga ttctcagggg taggttcaat    60
tcctatattc tagaa                                                    75

<210> SEQ ID NO 123
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
taggacgtgg tgtgataggt agcatggaga attctagatt ctcagggatg ggttcaattc    60
ctatagtcct ag                                                       72

<210> SEQ ID NO 124
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
taggacgtgg tgtgataggt agcacggaga attctagatt ctcagggatg ggttcaattc    60
ctgtagttct ag                                                       72

<210> SEQ ID NO 125
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ggttccatgg tgtaatggtt agcactctgg actctaaatc cagcgatccg agttcaaatc    60
tcggtggaac ct                                                       72

<210> SEQ ID NO 126
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 126
ggttccatgg tgtaatggtg accactttgg actctaaata cagtgatcag agttcaagtc    60
tcactggaac ct                                                        72

<210> SEQ ID NO 127
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ggttccatgg tgtaatggtg agggctttgg actctaacta cagtgatcag agttcaagtc    60
tcagtgggac ct                                                        72

<210> SEQ ID NO 128
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ggttccatgg tgtaatggta agcaccctgg actctaaatc cagcaaccag agttccagtc    60
tcagcgtgga cct                                                       73

<210> SEQ ID NO 129
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ggtagtgtag tctactggtt aaacgcttgg gctctaacat taacgtcctg ggttcaaatc    60
ccagctttgt ca                                                        72

<210> SEQ ID NO 130
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggttccatgg tgtaatggtt agcactctgg actctaaatc cagcgatccg agttcaagtc    60
tcggtggaac ct                                                        72

<210> SEQ ID NO 131
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 131
ggttccatgg tgtaatggtg agcactctgg actctaaatc cagcgatccg agttcgagtc    60
tcggtggaac ct                                                      72

<210> SEQ ID NO 132
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ggttccatgg tgtaatggta agcactctgg actctaaatc cagcgatccg agttcgagtc    60
tcggtggaac ct                                                      72

<210> SEQ ID NO 133
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggttccatgg tgtaatggtt agcactctgg actctaaatc cggtaatccg agttcaaatc    60
tcggtggaac ct                                                      72

<210> SEQ ID NO 134
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ggccccatgg tgtaatggtc agcactctgg actctaaatc cagcgatccg agttcaaatc    60
tcggtgggac cc                                                      72

<210> SEQ ID NO 135
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ggttccatgg tgtaatggta agcactctgg actctaaatc cagccatctg agttcgagtc    60
tctgtggaac ct                                                      72

<210> SEQ ID NO 136
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 136
ggttccatgg tgtaatggtg agcactttgg actctaaata cagtgatcag agttcaagtc    60
tcactgggac ct                                                        72

<210> SEQ ID NO 137
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ggttccatgg gttaatggtg agcaccctgg actctaaatc aagcgatccg agttcaaatc    60
tcggtggtac ct                                                        72

<210> SEQ ID NO 138
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gtttccatgg tgtaatggtg agcactctgg actctaaatc cagaaataca ttcaaagaat    60
taagaaca                                                             68

<210> SEQ ID NO 139
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ggtcccatgg tgtaatggtt agcactctgg actctaaatc cagcgatccg agttcaaatc    60
tcggtgggac ct                                                        72

<210> SEQ ID NO 140
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ggtcccatgg tgtaatggtt agcactctgg actctaaatc cagcaatccg agttcgaatc    60
tcggtgggac ct                                                        72

<210> SEQ ID NO 141
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 141
ggccccatgg tgtaatggtt agcactctgg actctaaatc cagcgatccg agttcaaatc    60
tcggtgggac ct                                                        72

<210> SEQ ID NO 142
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ggtcccatgg tgtaatggtt agcactctgg gctctaaatc cagcaatccg agttcgaatc    60
ttggtgggac ct                                                        72

<210> SEQ ID NO 143
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ggctgtgtac ctcagtgggc aagggtatgg actctaaagc cagactattt gggttcaaat    60
cccagcttgg cct                                                       73

<210> SEQ ID NO 144
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gaccatgtgg cctaagggaa aagacatctc actctaggtc agaagattga gggttcaagt    60
cctttcatgg tca                                                       73

<210> SEQ ID NO 145
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ggtacagtgt taaagggag aaaaattgct gactctaaat acagtagacc taggtttgaa    60
tcctggcttt acca                                                      74

<210> SEQ ID NO 146
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 146
tggtgtaata ggtagcacag agaattttag attctcaggg gtaggttcaa ttcctat      57

<210> SEQ ID NO 147
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
taggacatgg tgtgataggt agcatggaga attttagatt ctcaggggta ggttcaattc   60
ctacagttct ag                                                      72

<210> SEQ ID NO 148
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
taggacgtgg tgtgataggt agcatgggga attttagatt ctcaggggtg ggttcaattc   60
ctatagttct ag                                                      72

<210> SEQ ID NO 149
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
taggacgtgg tgtagtaggt agcatggaga atgttaaatt ctcagggta ggttcaattc    60 ctatagttct ag                                                      72

<210> SEQ ID NO 150
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
taggacatgg tgtaataggt agaatggaga attttaaatt ctcagggta ggttcaattc    60 ctatagttct ag                                                      72

<210> SEQ ID NO 151
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
taggatgtgg tgtattaggt agcacagaga attttagatt ctcaggggta ggttcgattc   60
ctataattct ac                                                      72

```
<210> SEQ ID NO 152
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
taggacttgg tgtaatgggt agcacagaga attttagatt ctcagggtg ggttcaattc      60 ctttcgtcct ag                                                         72

<210> SEQ ID NO 153
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tctaggatgt ggtgtgatag gtagcatgga gaattttaga ttctcagggg taggttcaat    60
tcctatattc tagaa                                                      75

<210> SEQ ID NO 154
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
taggacgtgg tgtgataggt agcatggaga attttagatt ctcaggatg ggttcaattc      60 ctatagtcct ag                                                         72

<210> SEQ ID NO 155
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
taggacgtgg tgtgataggt agcacggaga attttagatt ctcagggatg ggttcaattc    60
ctgtagttct ag                                                         72

<210> SEQ ID NO 156
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ggttccatgg tgtaatggtt agcactctgg actttaaatc cagcgatccg agttcaaatc    60
tcggtggaac ct                                                         72

<210> SEQ ID NO 157
<211> LENGTH: 72
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 157
ggttccatgg tgtaatggtg accactttgg actttaaata cagtgatcag agttcaagtc    60
tcactggaac ct                                                        72

<210> SEQ ID NO 158
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ggttccatgg tgtaatggtg agggctttgg actttaacta cagtgatcag agttcaagtc    60
tcagtgggac ct                                                        72

<210> SEQ ID NO 159
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ggttccatgg tgtaatggta agcaccctgg actttaaatc cagcaaccag agttccagtc    60
tcagcgtgga cct                                                       73

<210> SEQ ID NO 160
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ggtagtgtag tctactggtt aaacgcttgg gctttaacat taacgtcctg ggttcaaatc    60
ccagctttgt ca                                                        72

<210> SEQ ID NO 161
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ggttccatgg tgtaatggtt agcactctgg actttaaatc cagcgatccg agttcaagtc    60
tcggtggaac ct                                                        72

<210> SEQ ID NO 162
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 162
ggttccatgg tgtaatggtg agcactctgg actttaaatc cagcgatccg agttcgagtc    60
tcggtggaac ct                                                        72

<210> SEQ ID NO 163
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggttccatgg tgtaatggta agcactctgg actttaaatc cagcgatccg agttcgagtc    60
tcggtggaac ct                                                        72

<210> SEQ ID NO 164
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ggttccatgg tgtaatggtt agcactctgg actttaaatc cggtaatccg agttcaaatc    60
tcggtggaac ct                                                        72

<210> SEQ ID NO 165
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ggccccatgg tgtaatggtc agcactctgg actttaaatc cagcgatccg agttcaaatc    60
tcggtgggac cc                                                        72

<210> SEQ ID NO 166
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ggttccatgg tgtaatggta agcactctgg actttaaatc cagccatctg agttcgagtc    60
tctgtggaac ct                                                        72

<210> SEQ ID NO 167
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ggttccatgg tgtaatggtg agcactttgg actttaaata cagtgatcag agttcaagtc    60
tcactgggac ct                                                       72

<210> SEQ ID NO 168
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ggttccatgg gttaatggtg agcaccctgg actttaaatc aagcgatccg agttcaaatc    60
tcggtggtac ct                                                       72

<210> SEQ ID NO 169
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gtttccatgg tgtaatggtg agcactctgg actttaaatc cagaaataca ttcaaagaat    60
taagaaca                                                            68

<210> SEQ ID NO 170
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ggtcccatgg tgtaatggtt agcactctgg actttaaatc cagcgatccg agttcaaatc    60
tcggtgggac ct                                                       72

<210> SEQ ID NO 171
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ggtcccatgg tgtaatggtt agcactctgg actttaaatc cagcaatccg agttcgaatc    60
tcggtgggac ct                                                       72

<210> SEQ ID NO 172
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 172
ggccccatgg tgtaatggtt agcactctgg actttaaatc cagcgatccg agttcaaatc    60
tcggtgggac ct                                                       72

<210> SEQ ID NO 173
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ggtcccatgg tgtaatggtt agcactctgg gctttaaatc cagcaatccg agttcgaatc    60
ttggtgggac ct                                                       72

<210> SEQ ID NO 174
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ggctgtgtac ctcagtgggc aagggtatgg actttaaagc cagactattt gggttcaaat    60
cccagcttgg cct                                                      73

<210> SEQ ID NO 175
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gaccatgtgg cctaagggaa aagacatctc actttaggtc agaagattga gggttcaagt    60
cctttcatgg tca                                                      73

<210> SEQ ID NO 176
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ggtacagtgt taaagggag aaaaattgct gactttaaat acagtagacc taggtttgaa     60
tcctggcttt acca                                                     74

<210> SEQ ID NO 177
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 177
tccctggtgg tctagtggtt aggattcggc gctttaaccg ccgcggcccg ggttcgattc    60
ccggtcaggg aa                                                       72

<210> SEQ ID NO 178
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tccctggtgg tctagtggtt aggattcggc gctttaaccg ccgcggcccg ggttcgattc    60
ccggtcagga aa                                                       72

<210> SEQ ID NO 179
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179 ccctggtgg tctagtgctt aggattcggt gctttaaccg ctgctgcctg cgttcgattc    60
ccggtcaggg aa                                                       72

<210> SEQ ID NO 180
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
tccttgatgt ctagtggtta ggatttggtg ctttaactgc agcagcctgg gttcatttct    60
cagtcaggga a                                                        71

<210> SEQ ID NO 181
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tcccatatgg tctagcggtt aggattcctg gttttaaccc aggtggcccg ggttcgactc    60
ccggtatggg aa                                                       72

<210> SEQ ID NO 182
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 182
tccgtggtgg tctagtggct aggattcggc gctttaaccg cctgcagctc gagttcgatt    60
cctggtcagg gaa    73

<210> SEQ ID NO 183
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ccctgtggtc tagtggctaa gactttgtgc tttaattgct gcatcctagg ttcaattccc    60
agtcaggga    69

<210> SEQ ID NO 184
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tcccacatgg tctagcggtt aggattcctg gttttaaccc aggcggcccg ggttcgactc    60
ccggtgtggg aa    72

<210> SEQ ID NO 185
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tccctggtgg tctagtggct aggattcggc gctttaaccg ccgcggcccg ggttcgattc    60
ccggccaggg aa    72

<210> SEQ ID NO 186
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tccctggtgg tctagtggct aggattcggc gctttaaccg ccgcggcccg ggttcgattc    60
ccggtcaggg aa    72

<210> SEQ ID NO 187
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 187
gcgttggtgg tgtagtggtg agcacagctg cctttaaagc agttaacgcg ggttcgattc    60
ccgggtaacg aa    72

<210> SEQ ID NO 188
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tccttggtgg tctagtggct aggattcggt gctttaacct gtgcggcccg ggttcaattc    60
ccgatgaagg aa    72

<210> SEQ ID NO 189
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tgtctggtgg tcaagtggct aggatttggc gctttaactg ccgcggcccg cgttcgattc    60
ccggtcaggg aa    72

<210> SEQ ID NO 190
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tccctggtgg tctagtggct aggattcggc gctttaaccg cctgcagctc gagttcgatt    60
cctggtcagg gaa    73

<210> SEQ ID NO 191
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gcaatggtgg ttcagtggta gaattctcgc ctttaacaca ggagacccgg gttcaattcc    60
tgacccatgt a    71

<210> SEQ ID NO 192
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 192
tccctggtgg tctagtggtt aggattcggc gctctaaccg ccgcggcccg ggttcgattc    60
ccggtcaggg aa                                                       72

<210> SEQ ID NO 193
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tccctggtgg tctagtggtt aggattcggc gctctaaccg ccgcggcccg ggttcgattc    60
ccggtcagga aa                                                       72

<210> SEQ ID NO 194
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
cccctggtgg tctagtgctt aggattcggt gctctaaccg ctgctgcctg cgttcgattc    60
ccggtcaggg aa                                                       72

<210> SEQ ID NO 195
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tccttgatgt ctagtggtta ggatttggtg ctctaactgc agcagcctgg gttcatttct    60
cagtcaggga a                                                        71

<210> SEQ ID NO 196
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tcccatatgg tctagcggtt aggattcctg gttctaaccc aggtggcccg ggttcgactc    60
ccggtatggg aa                                                       72

<210> SEQ ID NO 197
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 197
tccgtggtgg tctagtggct aggattcggc gctctaaccg cctgcagctc gagttcgatt    60
cctggtcagg gaa                                                      73

<210> SEQ ID NO 198
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ccctgtggtc tagtggctaa gactttgtgc tctaattgct gcatcctagg ttcaattccc    60
agtcaggga                                                           69

<210> SEQ ID NO 199
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tcccacatgg tctagcggtt aggattcctg gttctaaccc aggcggcccg ggttcgactc    60
ccggtgtggg aa                                                       72

<210> SEQ ID NO 200
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tccctggtgg tctagtggct aggattcggc gctctaaccg ccgcggcccg ggttcgattc    60
ccggccaggg aa                                                       72

<210> SEQ ID NO 201
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tccctggtgg tctagtggct aggattcggc gctctaaccg ccgcggcccg ggttcgattc    60
ccggtcaggg aa                                                       72

<210> SEQ ID NO 202
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 202
gcgttggtgg tgtagtggtg agcacagctg cctctaaagc agttaacgcg ggttcgattc    60
ccgggtaacg aa                                                       72

<210> SEQ ID NO 203
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tccttggtgg tctagtggct aggattcggt gctctaacct gtgcggcccg ggttcaattc    60
ccgatgaagg aa                                                       72

<210> SEQ ID NO 204
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tgtctggtgg tcaagtggct aggatttggc gctctaactg ccgcggcccg cgttcgattc    60
ccggtcaggg aa                                                       72

<210> SEQ ID NO 205
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tccctggtgg tctagtggct aggattcggc gctctaaccg cctgcagctc gagttcgatt    60
cctggtcagg gaa                                                      73

<210> SEQ ID NO 206
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gcaatggtgg ttcagtggta gaattctcgc ctctactaac acaggagacc cgggttcaat    60
tcctgaccca tgta                                                     74

<210> SEQ ID NO 207
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 207
ccttcaatag ttcagctggt agagcagagg actttagcta cttcctcagt aggagacgtc    60
cttaggttgc tggttcgatt ccagcttgaa gga                                 93

<210> SEQ ID NO 208
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ccttcaatag ttcagctggt agagcagagg actttaggtc cttaggttgc tggttcgatt    60
ccagcttgaa gga                                                       73

<210> SEQ ID NO 209
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ggtaaaatgg ctgagtaagc tttagacttt aaaatctaaa gagagattga gctctctttt    60
tacca                                                                65

<210> SEQ ID NO 210
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ggtaaaatga ctgagtaagc attagacttt aaatctaaag acagaggtca agacctcttt    60
ttacca                                                               66

<210> SEQ ID NO 211
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ggtaaaatgg ctgagtaagc attagacttt aaatctaaag acagaggtca aggcctcttt    60
ttacca                                                               66

<210> SEQ ID NO 212
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ggtaaaatgg ctgagtaagc attagacttt aaatctaaag acagaggtca aggccttttt    60
acca                                                                 64

<210> SEQ ID NO 213
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ccttcgatag ctcagttggt agagcggagg actttagttg gctgtgtcct tagacatcct    60
taggtcgctg gttcgaatcc ggctcgaagg a                                   91

<210> SEQ ID NO 214
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ccttcgatag ctcagttggt agagcggagg actttagatc cttaggtcgc tggttcgaat    60
ccggctcgaa gga                                                       73

<210> SEQ ID NO 215
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gggggtatag ctcagggcta gagcttttg actttagagc aagaggtccc tggttcaaat     60
ccaggttctc cct                                                       73

<210> SEQ ID NO 216
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tatagctcag tggtagagca tttaacttta gatcaagagg tccctggatc aactctgggt    60
g                                                                    61

<210> SEQ ID NO 217
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 217
gtcagtgttg cacaacggtt aagtgaagag gctttaaacc cagactggat gggttcaatt    60
cccatctctg ccg                                                      73

<210> SEQ ID NO 218
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ccttcgatag ctcagttggt agagcggagg actttagtgg atagggcgtg gcaatcctta    60
ggtcgctggt tcgattccgg ctcgaagga                                     89

<210> SEQ ID NO 219
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ccttcgatag ctcagttggt agagcggagg actttagatc cttaggtcgc tggttcgatt    60
ccggctcgaa gga                                                      73

<210> SEQ ID NO 220
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ccttcgatag ctcagttggt agagcggagg actttaggct cattaagcaa ggtatcctta    60
ggtcgctggt tcgaatccgg ctcggagga                                     89

<210> SEQ ID NO 221
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ccttcgatag ctcagttggt agagcggagg actttagatc cttaggtcgc tggttcgaat    60
ccggctcgga gga                                                      73

<210> SEQ ID NO 222
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 222
ccttcgatag ctcagctggt agagcggagg actttagatt gtatagacat ttgcggacat    60
ccttaggtcg ctggttcgat tccagctcga agga    94

<210> SEQ ID NO 223
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ccttcgatag ctcagctggt agagcggagg actttagatc cttaggtcgc tggttcgatt    60
ccagctcgaa gga    73

<210> SEQ ID NO 224
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ccttcgatag ctcagctggt agagcggagg actttagcta cttcctcagc aggagacatc    60
cttaggtcgc tggttcgatt ccggctcgaa gga    93

<210> SEQ ID NO 225
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ccttcgatag ctcagctggt agagcggagg actttagatc cttaggtcgc tggttcgatt    60
ccggctcgaa gga    73

<210> SEQ ID NO 226
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ccttcgatag ctcagctggt agagcggagg actttaggcg cgcgcccgtg gccatcctta    60
ggtcgctggt tcgattccgg ctcgaagga    89

<210> SEQ ID NO 227
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 227
ccttcgatag ctcagctggt agagcggagg actttagatc cttaggtcgc tggttcgatt    60
ccggctcgaa gga                                                       73

<210> SEQ ID NO 228
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ccttcgatag ctcagctggt agagcggagg actttaagcc tgtagaaaca tttgtggaca    60
tccttaggtc gctggttcga ttccggctcg aagga                               95

<210> SEQ ID NO 229
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ccttcgatag ctcagctggt agagcggagg actttagatc cttaggtcgc tggttcgatt    60
ccggctcgaa gga                                                       73

<210> SEQ ID NO 230
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ccttcgatag ctcagctggt agagcggagg actttagatt gtacagacat ttgcggacat    60
ccttaggtcg ctggttcgat tccggctcga agga                                94

<210> SEQ ID NO 231
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ccttcgatag ctcagctggt agagcggagg actttagatc cttaggtcgc tggttcgatt    60
ccggctcgaa gga                                                       73

<210> SEQ ID NO 232
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 232
ccttcgatag ctcagctggt agagcggagg actttagtac ttaatgtgtg gtcatcctta    60
ggtcgctggt tcgattccgg ctcgaagga                                      89

<210> SEQ ID NO 233
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ccttcgatag ctcagctggt agagcggagg actttagatc cttaggtcgc tggttcgatt    60
ccggctcgaa gga                                                       73

<210> SEQ ID NO 234
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ccttcgatag ctcagctggt agagcggagg actttagggg tttgaatgtg gtcatcctta    60
ggtcgctggt tcgaatccgg ctcggagga                                      89

<210> SEQ ID NO 235
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ccttcgatag ctcagctggt agagcggagg actttagatc cttaggtcgc tggttcgaat    60
ccggctcgga gga                                                       73

<210> SEQ ID NO 236
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ccttcgatag ctcagctggt agagcggagg actttagact gcggaaacgt ttgtggacat    60
ccttaggtcg ctggttcaat tccggctcga agga                                94

<210> SEQ ID NO 237
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 237
ccttcgatag ctcagctggt agagcggagg actttagatc cttaggtcgc tggttcaatt    60
ccggctcgaa gga    73

<210> SEQ ID NO 238
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ctttcgatag ctcagttggt agagcggagg actttaggtt cattaaacta aggcatcctt    60
aggtcgctgg ttcgaatccg gctcgaagga    90

<210> SEQ ID NO 239
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ctttcgatag ctcagttggt agagcggagg actttagatc cttaggtcgc tggttcgaat    60
ccggctcgaa gga    73

<210> SEQ ID NO 240
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tcttcaatag ctcagctggt agagcggagg actttaaggt gcacgcccgt ggccattctt    60
aggtgctggt ttgattccga cttggagag    89

<210> SEQ ID NO 241
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
tcttcaatag ctcagctggt agagcggagg actttagatt cttaggtgct ggtttgattc    60
cgacttggag ag    72

<210> SEQ ID NO 242
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 242
ggtaaaatgg ctgagtgaag cattggactt taaatctaaa gacaggggtt aagcctcttt    60
ttacca                                                               66

<210> SEQ ID NO 243
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ggtaaaatgg ctgagcaagc attggacttt aaatctaaag acagatgttg agccatcttt    60
ttagca                                                               66

<210> SEQ ID NO 244
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggtaaaatgg ctgagtgaag cattggactt taaatctaaa gacaggggct aagcctcttt    60
ttacca                                                               66

<210> SEQ ID NO 245
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ggtaaaatgg ctgagcaagc attagacttt aaatctaaag acagaggtta aggcctcttt    60
ttacca                                                               66

<210> SEQ ID NO 246
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ggtaaaatgg ctgagtaagc attagacttt aaatctaaag acagaggtca aggcctcttt    60
tttcct                                                               66

<210> SEQ ID NO 247
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 247
ggtaaaatgg ctgagcaagc attagacttt aaatctgaaa acagaggtca aaggtctctt    60
tttacca                                                              67

<210> SEQ ID NO 248
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ggtaaaatgg ctgagtaagc attagacttt aaatctaaag acagaggtca aggcctcttt    60
ttacca                                                               66

<210> SEQ ID NO 249
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ggtaaaatga ctgaataagc cttagacttt aaatctgaag acagaggtca aggcctcttt    60
ttacca                                                               66

<210> SEQ ID NO 250
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ggtaaaatgg ctgagtaagc attggacttt aaatctaaag acagaggtca agacctcttt    60
ttacca                                                               66

<210> SEQ ID NO 251
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ggtaaaatgg ctgagtaaag cattagactt taaatctaag gacagaggct aaacctcttt    60
ttacca                                                               66

<210> SEQ ID NO 252
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 252
ccttcaatag ttcagctggt agagcagagg actctagcta cttcctcagt aggagacgtc    60
cttaggttgc tggttcgatt ccagcttgaa gga                                 93

<210> SEQ ID NO 253
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ccttcaatag ttcagctggt agagcagagg actctaggtc cttaggttgc tggttcgatt    60
ccagcttgaa gga                                                       73

<210> SEQ ID NO 254
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ggtaaaatgg ctgagtaagc tttagactct aaaatctaaa gagagattga gctctctttt    60
tacca                                                                65

<210> SEQ ID NO 255
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
ggtaaaatga ctgagtaagc attagactct aaatctaaag acagaggtca agacctcttt    60
ttacca                                                               66

<210> SEQ ID NO 256
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ggtaaaatgg ctgagtaagc attagactct aaatctaaag acagaggtca aggcctcttt    60
ttacca                                                               66

<210> SEQ ID NO 257
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 257
ggtaaaatgg ctgagtaagc attagactct aaatctaaag acagaggtca aggccttttt    60
acca                                                                 64

<210> SEQ ID NO 258
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ccttcgatag ctcagttggt agagcggagg actctagttg gctgtgtcct tagacatcct    60
taggtcgctg gttcgaatcc ggctcgaagg a                                   91

<210> SEQ ID NO 259
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
ccttcgatag ctcagttggt agagcggagg actctagatc cttaggtcgc tggttcgaat    60
ccggctcgaa gga                                                       73

<210> SEQ ID NO 260
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gggggtatag ctcagggcta gagcttttg actctaagag caagaggtcc ctggttcaaa    60
tccaggttct ccct                                                      74

<210> SEQ ID NO 261
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tatagctcag tggtagagca tttaactcta gatcaagagg tccctggatc aactctgggt    60
g                                                                    61

<210> SEQ ID NO 262
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gtcagtgttg cacaacggtt aagtgaagag gctctaaacc cagactggat gggttcaatt    60
cccatctctg ccg    73

<210> SEQ ID NO 263
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ccttcgatag ctcagttggt agagcggagg actctagtgg atagggcgtg gcaatcctta    60
ggtcgctggt tcgattccgg ctcgaagga    89

<210> SEQ ID NO 264
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ccttcgatag ctcagttggt agagcggagg actctagatc cttaggtcgc tggttcgatt    60
ccggctcgaa gga    73

<210> SEQ ID NO 265
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ccttcgatag ctcagttggt agagcggagg actctaggct cattaagcaa ggtatcctta    60
ggtcgctggt tcgaatccgg ctcggagga    89

<210> SEQ ID NO 266
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ccttcgatag ctcagttggt agagcggagg actctagatc cttaggtcgc tggttcgaat    60
ccggctcgga gga    73

<210> SEQ ID NO 267
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 267
ccttcgatag ctcagctggt agagcggagg actctagatt gtatagacat ttgcggacat      60
ccttaggtcg ctggttcgat tccagctcga agga                                  94

<210> SEQ ID NO 268
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ccttcgatag ctcagctggt agagcggagg actctagatc cttaggtcgc tggttcgatt      60
ccagctcgaa gga                                                         73

<210> SEQ ID NO 269
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ccttcgatag ctcagctggt agagcggagg actctagcta cttcctcagc aggagacatc      60
cttaggtcgc tggttcgatt ccggctcgaa gga                                   93

<210> SEQ ID NO 270
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ccttcgatag ctcagctggt agagcggagg actctagatc cttaggtcgc tggttcgatt      60
ccggctcgaa gga                                                         73

<210> SEQ ID NO 271
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ccttcgatag ctcagctggt agagcggagg actctaggcg cgcgcccgtg gccatcctta      60
ggtcgctggt tcgattccgg ctcgaagga                                        89

<210> SEQ ID NO 272
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 272
ccttcgatag ctcagctggt agagcggagg actctagatc cttaggtcgc tggttcgatt    60
ccggctcgaa gga                                                       73

<210> SEQ ID NO 273
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
ccttcgatag ctcagctggt agagcggagg actctagcct gtagaaacat tgtggacat    60 ccttaggtcg ctggttcgat tccggctcga agga                                94

<210> SEQ ID NO 274
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ccttcgatag ctcagctggt agagcggagg actctagatc cttaggtcgc tggttcgatt    60
ccggctcgaa gga                                                       73

<210> SEQ ID NO 275
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ccttcgatag ctcagctggt agagcggagg actctagatt gtacagacat tgcggacat    60 ccttaggtcg ctggttcgat tccggctcga agga                                94

<210> SEQ ID NO 276
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
ccttcgatag ctcagctggt agagcggagg actctagatc cttaggtcgc tggttcgatt    60
ccggctcgaa gga                                                       73

<210> SEQ ID NO 277
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 277
ccttcgatag ctcagctggt agagcggagg actctagtac ttaatgtgtg gtcatcctta      60
ggtcgctggt tcgattccgg ctcgaagga                                        89

<210> SEQ ID NO 278
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ccttcgatag ctcagctggt agagcggagg actctagatc cttaggtcgc tggttcgatt      60
ccggctcgaa gga                                                         73

<210> SEQ ID NO 279
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ccttcgatag ctcagctggt agagcggagg actctagggg tttgaatgtg gtcatcctta      60
ggtcgctggt tcgaatccgg ctcggagga                                        89

<210> SEQ ID NO 280
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ccttcgatag ctcagctggt agagcggagg actctagatc cttaggtcgc tggttcgaat      60
ccggctcgga gga                                                         73

<210> SEQ ID NO 281
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ccttcgatag ctcagctggt agagcggagg actctagact gcggaaacgt ttgtggacat      60
ccttaggtcg ctggttcaat tccggctcga agga                                  94

<210> SEQ ID NO 282
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 282
ccttcgatag ctcagctggt agagcggagg actctagatc cttaggtcgc tggttcaatt    60
ccggctcgaa gga    73

<210> SEQ ID NO 283
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ctttcgatag ctcagttggt agagcggagg actctaggtt cattaaacta aggcatcctt    60
aggtcgctgg ttcgaatccg gctcgaagga    90

<210> SEQ ID NO 284
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ctttcgatag ctcagttggt agagcggagg actctagatc cttaggtcgc tggttcgaat    60
ccggctcgaa gga    73

<210> SEQ ID NO 285
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tcttcaatag ctcagctggt agagcggagg actctaggtg cacgcccgtg gccattctta    60
ggtgctggtt tgattccgac ttggagag    88

<210> SEQ ID NO 286
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
tcttcaatag ctcagctggt agagcggagg actctagatt cttaggtgct ggtttgattc    60
cgacttggag ag    72

<210> SEQ ID NO 287
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ggtaaaatgg ctgagtgaag cattggactc taaatctaaa gacaggggtt aagcctcttt    60
ttacca                                                                66

<210> SEQ ID NO 288
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
ggtaaaatgg ctgagcaagc attggactct aaatctaaag acagatgttg agccatcttt    60
ttagca                                                                66

<210> SEQ ID NO 289
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ggtaaaatgg ctgagtgaag cattggactc taaatctaaa gacaggggct aagcctcttt    60
ttacca                                                                66

<210> SEQ ID NO 290
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ggtaaaatgg ctgagcaagc attagactct aaatctaaag acagaggtta aggcctcttt    60
ttacca                                                                66

<210> SEQ ID NO 291
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ggtaaaatgg ctgagtaagc attagactct aaatctaaag acagaggtca aggcctcttt    60
tttcct                                                                66

<210> SEQ ID NO 292
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 292
ggtaaaatgg ctgagcaagc attagactct aaatctgaaa acagaggtca aaggtctctt    60
tttacca                                                              67

<210> SEQ ID NO 293
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ggtaaaatgg ctgagtaagc attagactct aaatctaaag acagaggtca aggcctcttt    60
ttacca                                                               66

<210> SEQ ID NO 294
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
ggtaaaatga ctgaataagc cttagactct aaatctgaag acagaggtca aggcctcttt    60
ttacca                                                               66

<210> SEQ ID NO 295
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
ggtaaaatgg ctgagtaagc attggactct aaatctaaag acagaggtca agacctcttt    60
ttacca                                                               66

<210> SEQ ID NO 296
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
ggtaaaatgg ctgagtaaag cattagactc taaatctaag gacagaggct aaacctcttt    60
ttacca                                                               66

<210> SEQ ID NO 297
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 297
gttaagatgg cagagcctgg taattgcatt aaacttaaaa ttttataatc agaggttcaa    60
ctcctcttct taaca                                                    75

<210> SEQ ID NO 298
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gttaagatgg cagagcccgg caattgcatt agacttaaaa ctttataatc agaggttcaa    60
ctcctctcat taaca                                                    75

<210> SEQ ID NO 299
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ggtagcgtgg ccgagcggtc taaggcgctg gattttagct ccagtctctt cggggggcgtg   60 ggttcaaatc ccaccgctgc ca                                            82

<210> SEQ ID NO 300
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
ggtagcgtgg ccgagtggtc taagacgctg gattttagct ccagtctctt cggggggcgtg   60 ggtttgaatc ccaccgctgc ca                                            82

<210> SEQ ID NO 301
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gggccagtgg ctcaatggat aatgcgtctg actttaaatc agaagattcc agccttgact    60
cctggctggc tca                                                      73

<210> SEQ ID NO 302
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 302
ggtagggtgg ccgagcggtc taaggcactg tattttaact ccagtctctt cagaggcatg      60
ggtttgaatc ccactgctgc ca                                               82

<210> SEQ ID NO 303
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gccgagcggt ctaaggctcc ggattttagc gccggtgtct tcggaggcat gggttcgaat      60
tccac                                                                  65

<210> SEQ ID NO 304
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 304
gtcaggatgg ccgagtggtc taaggcgcca gactttagct aagcttcctc cgcggtgggg      60
attctggtct ccaatggagg cgtgggttcg aatcccactt ctgaca                    106

<210> SEQ ID NO 305
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gtcaggatgg ccgagtggtc taaggcgcca gactttagtt ctggtctcca atggaggcgt      60
gggttcgaat cccacttctg aca                                              83

<210> SEQ ID NO 306
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 306
gtcaggatgg ccgagtggtc taaggcgcca gactttagct tggcttcctc gtgttgagga      60
ttctggtctc caatggaggc gtgggttcga atcccacttc tgaca                     105

<210> SEQ ID NO 307
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 307
gtcaggatgg ccgagtggtc taaggcgcca gactttagtt ctggtctcca atggaggcgt    60
gggttcgaat cccacttctg aca                                             83

<210> SEQ ID NO 308
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 308
gtcaggatgg ccgagtggtc taaggcgcca gactttagct tactgcttcc tgtgttcggg    60
tcttctggtc tccgtatgga ggcgtgggtt cgaatcccac ttctgaca                108

<210> SEQ ID NO 309
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gtcaggatgg ccgagtggtc taaggcgcca gactttagtt ctggtctccg tatggaggcg    60
tgggttcgaa tcccacttct gaca                                            84

<210> SEQ ID NO 310
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 310
gtcaggatgg ccgagtggtc taaggcgcca gactttagtt gctacttccc aggtttgggg    60
cttctggtct ccgcatggag gcgtgggttc gaatcccact tctgaca                 107

<210> SEQ ID NO 311
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gtcaggatgg ccgagtggtc taaggcgcca gactttagtt ctggtctccg catggaggcg    60
tgggttcgaa tcccacttct gaca                                            84

<210> SEQ ID NO 312
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 312
gtcaggatgg ccgagtggtc taaggcgcca gactttaggt aagcaccttg cctgcgggct    60
ttctggtctc cggatggagg cgtgggttcg aatcccactt ctgaca                  106

<210> SEQ ID NO 313
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gtcaggatgg ccgagtggtc taaggcgcca gactttagtt tctggtctcc ggatggaggc    60
gtgggttcga atcccacttc tgaca                                         85

<210> SEQ ID NO 314
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gcctccttag tgcagtaggt agcgcatcag tctttaaatc tgaatggtcc tgagttcaag    60
cctcagaggg ggca                                                     74

<210> SEQ ID NO 315
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gtcaggatgg ccgagcagtc ttaaggcgct gcgttttaat cgcaccctcc gctggaggcg    60
tgggttcgaa tcccactttt gaca                                          84

<210> SEQ ID NO 316
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ggttccatgg tgtaatggtg agcactctgg actttaaatc cagaagtagt gctggaacaa    60

<210> SEQ ID NO 317
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gtcagggtgg ctgagcagtc tgaggggctg cgttttagtc gcagtctgcc ctggaggcgt    60
gggttcgaat cccactcctg aaa                                           83

```
<210> SEQ ID NO 318
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
accaggatgg ccgagtggtt aaggcgttgg actttagatc caatggacat atgtccgcgt    60
gggttcgaac cccactcctg gta                                           83

<210> SEQ ID NO 319
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
accgggatgg ccgagtggtt aaggcgttgg actttagatc caatgggctg gtgcccgcgt    60
gggttcgaac cccactctcg gta                                           83

<210> SEQ ID NO 320
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
accagaatgg ccgagtggtt aaggcgttgg actttagatc caatggattc atatccgcgt    60
gggttcgaac cccacttctg gta                                           83

<210> SEQ ID NO 321
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
accgggatgg ctgagtggtt aaggcgttgg actttagatc caatggacag gtgtccgcgt    60
gggttcgagc cccactcccg gta                                           83

<210> SEQ ID NO 322
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
actcatttgg ctgagtggtt aaggcattgg actttagatc caatggagta gtggctgtgt    60
gggtttaaac cccactactg gta                                           83

<210> SEQ ID NO 323
<211> LENGTH: 69
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 323
gagaaagtca tcgtagttac gaagttggct ttaacccagt tttgggaggt tcaattcctt    60
cctttctct                                                            69

<210> SEQ ID NO 324
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
accaggatgg ccaagtagtt aaaggcactg gactttagag ccaatggaca tatgtctgtg    60
tgggtttgaa ccccactcct ggtg                                           84

<210> SEQ ID NO 325
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ggtagcgtgg ccgagcggtc taaggcgctg gattttagct ccagtctctt cggaggcgtg    60
ggttcgaatc ccaccgctgc ca                                             82

<210> SEQ ID NO 326
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ggtagtgtgg ccgagcggtc taaggcgctg gattttagct ccagtctctt cggggcgtg     60 ggttcgaatc ccaccactgc ca                                             82

<210> SEQ ID NO 327
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ggtagcgtgg ccgagtggtc taaggcgctg gattttagct ccagtcattt cgatggcgtg    60
ggttcgaatc ccaccgctgc ca                                             82

<210> SEQ ID NO 328
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ggtagtgtgg ttgaatggtc taaggcactg aattttagct ccagtctctt tggggacgtg    60
ggtttaaatc ccactgctgc aa                                             82

<210> SEQ ID NO 329
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gttaagatgg cagagcctgg taattgcact aaacttaaaa ttttataatc agaggttcaa    60
ctcctcttct taaca                                                     75

<210> SEQ ID NO 330
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
gttaagatgg cagagcccgg caattgcact agacttaaaa ctttataatc agaggttcaa    60
ctcctctcat taaca                                                     75

<210> SEQ ID NO 331
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
ggtagcgtgg ccgagcggtc taaggcgctg gattctagct ccagtctctt cggggcgtg    60 ggttcaaatc ccaccgctgc ca                                             82

<210> SEQ ID NO 332
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
ggtagcgtgg ccgagtggtc taagacgctg gattctagct ccagtctctt cggggcgtg    60 ggtttgaatc ccaccgctgc ca                                             82

<210> SEQ ID NO 333
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gggccagtgg ctcaatggat aatgcgtctg actctaaatc agaagattcc agccttgact    60
cctggctggc tca                                                      73

<210> SEQ ID NO 334
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ggtagggtgg ccgagcggtc taaggcactg tattctaact ccagtctctt cagaggcatg    60
ggtttgaatc ccactgctgc ca                                            82

<210> SEQ ID NO 335
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gccgagcggt ctaaggctcc ggattctagc gccggtgtct tcggaggcat gggttcgaat    60
tccac                                                               65

<210> SEQ ID NO 336
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 336
gtcaggatgg ccgagtggtc taaggcgcca gactctagct aagcttcctc cgcggtgggg    60
attctggtct ccaatggagg cgtgggttcg aatcccactt ctgaca                  106

<210> SEQ ID NO 337
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
gtcaggatgg ccgagtggtc taaggcgcca gactctagtt ctggtctcca atggaggcgt    60
gggttcgaat cccacttctg aca                                           83

<210> SEQ ID NO 338
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 338
gtcaggatgg ccgagtggtc taaggcgcca gactctagct tggcttcctc gtgttgagga    60
ttctggtctc caatggaggc gtgggttcga atcccacttc tgaca                   105

<210> SEQ ID NO 339
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gtcaggatgg ccgagtggtc taaggcgcca gactctagtt ctggtctcca atggaggcgt    60
gggttcgaat cccacttctg aca                                            83

<210> SEQ ID NO 340
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 340
gtcaggatgg ccgagtggtc taaggcgcca gactctagct tactgcttcc tgtgttcggg    60
tcttctggtc tccgtatgga ggcgtgggtt cgaatcccac ttctgaca                108

<210> SEQ ID NO 341
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gtcaggatgg ccgagtggtc taaggcgcca gactctagtt ctggtctccg tatggaggcg    60
tgggttcgaa tcccacttct gaca                                           84

<210> SEQ ID NO 342
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 342
gtcaggatgg ccgagtggtc taaggcgcca gactctagtt gctacttccc aggtttgggg    60
cttctggtct ccgcatggag gcgtgggttc gaatcccact tctgaca                 107

<210> SEQ ID NO 343
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 343
gtcaggatgg ccgagtggtc taaggcgcca gactctagtt ctggtctccg catggaggcg    60
tgggttcgaa tcccacttct gaca                                           84

<210> SEQ ID NO 344
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 344
gtcaggatgg ccgagtggtc taaggcgcca gactctaggt aagcaccttg cctgcgggct    60
ttctggtctc cggatggagg cgtgggttcg aatcccactt ctgaca                  106

<210> SEQ ID NO 345
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gtcaggatgg ccgagtggtc taaggcgcca gactctagtt tctggtctcc ggatggaggc    60
gtgggttcga atcccacttc tgaca                                          85

<210> SEQ ID NO 346
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
gcctccttag tgcagtaggt agcgcatcag tctctaaatc tgaatggtcc tgagttcaag    60
cctcagaggg ggca                                                      74

<210> SEQ ID NO 347
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gtcaggatgg ccgagcagtc ttaaggcgct gcgttctaat cgcaccctcc gctggaggcg    60
tgggttcgaa tcccactttt gaca                                           84

<210> SEQ ID NO 348
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 348
ggttccatgg tgtaatggtg agcactctgg actctaaatc cagaagtagt gctggaacaa      60

<210> SEQ ID NO 349
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gtcagggtgg ctgagcagtc tgagggctg cgttctagtc gcagtctgcc ctggaggcgt        60
gggttcgaat cccactcctg aaa                                               83

<210> SEQ ID NO 350
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
accaggatgg ccgagtggtt aaggcgttgg actctagatc caatggacat atgtccgcgt       60
gggttcgaac cccactcctg gta                                               83

<210> SEQ ID NO 351
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
accgggatgg ccgagtggtt aaggcgttgg actctagatc caatgggctg gtgcccgcgt       60
gggttcgaac cccactctcg gta                                               83

<210> SEQ ID NO 352
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
accagaatgg ccgagtggtt aaggcgttgg actctagatc caatggattc atatccgcgt      60
gggttcgaac cccacttctg gta                                              83

<210> SEQ ID NO 353
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
accgggatgg ctgagtggtt aaggcgttgg actctagatc caatggacag gtgtccgcgt      60
gggttcgagc cccactcccg gta                                              83
```

```
<210> SEQ ID NO 354
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
actcatttgg ctgagtggtt aaggcattgg actctaagat ccaatggagt agtggctgtg    60
tgggtttaaa ccccactact ggta                                          84

<210> SEQ ID NO 355
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
gagaaagtca tcgtagttac gaagttggct ctaacccagt tttgggaggt tcaattcctt    60
cctttctct                                                           69

<210> SEQ ID NO 356
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
accaggatgg ccaagtagtt aaaggcactg gactctagag ccaatggaca tatgtctgtg    60
tgggtttgaa ccccactcct ggtg                                          84

<210> SEQ ID NO 357
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
ggtagcgtgg ccgagcggtc taaggcgctg gattctagct ccagtctctt cggaggcgtg    60
ggttcgaatc ccaccgctgc ca                                            82

<210> SEQ ID NO 358
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
ggtagtgtgg ccgagcggtc taaggcgctg gattctagct ccagtctctt cggggcgtg     60 ggttcgaatc ccaccactgc ca                                            82

<210> SEQ ID NO 359
<211> LENGTH: 82
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 359
ggtagcgtgg ccgagtggtc taaggcgctg gattctagct ccagtcattt cgatggcgtg      60
ggttcgaatc ccaccgctgc ca                                              82

<210> SEQ ID NO 360
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
ggtagtgtgg ttgaatggtc taaggcactg aattctagct ccagtctctt tggggacgtg      60
ggtttaaatc ccactgctgc aa                                              82

<210> SEQ ID NO 361
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
gagaaggtca cagaggttat gggattggct ctaaaccagt ctgtgggggg ttcgattccc      60
tccttttca                                                             70

<210> SEQ ID NO 362
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gagaaggtca tagaggttat gggattggct ctaaaccagt ctctgggggg ttcgattccc      60
tccttttca                                                             70

<210> SEQ ID NO 363
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
gaaaaagtca tagggttat gaggctggct ctaaaccagc cttaggaggt tcaattcctt      60
ccttttttg                                                             69

<210> SEQ ID NO 364
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 364
ggccggttag ctcagttggt tagagcgtgc tgctctaaat gccagggtcg aggtttcgat    60
ccccgtacgg gcct                                                      74

<210> SEQ ID NO 365
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
gtagtcgtgg ccgagtggtt aaggcgatgg actctaaatc cattggggtt tccccgcgca    60
ggttcgaatc ctgccgacta cg                                             82

<210> SEQ ID NO 366
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
gtagtcgtgg ccgagtggtt aaggcgatgg actctaaatc cattggggtt tcccacgca     60 ggttcgaatc ctgccgacta cg                                             82

<210> SEQ ID NO 367
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
gtagtcgtgg ccgagtggtt aaggtgatgg actctaaaac ccattggggt ctccccgcgc    60
aggttcgaat cctgccgact acg                                            83

<210> SEQ ID NO 368
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
gggtgtatgg ctcaggggta gagaatttga ctctagatca agaggtccct ggttcaaatc    60
caggtgcccc ct                                                        72

<210> SEQ ID NO 369
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 369
agttgtagct gagtggttaa ggcaacgagc tctaaattcg ttggtttctc tctgtgcagg    60
tttgaatcct gctaatta                                                 78

<210> SEQ ID NO 370
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
caagaaattc atagaggtta tgggattggc tctaaaccag tttcaggagg ttcgattcct    60
tcctttttgg                                                          70

<210> SEQ ID NO 371
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
gctgtgatgg ccgagtggtt aaggcgttgg actctaaatc caatggggtc tccccgcgca    60
ggttcgaatc ctgctcacag cg                                            82

<210> SEQ ID NO 372
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
gctgtgatgg ccgagtggtt aaggcgttgg actctaaatc caatggggtc tccccgcgca    60
ggttcaaatc ctgctcacag cg                                            82

<210> SEQ ID NO 373
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
gctgtgatgg ccgagtggtt aaggtgttgg actctaaatc caatgggggt tccccgcgca    60
ggttcaaatc ctgctcacag cg                                            82

<210> SEQ ID NO 374
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 374
gtcacggtgg ccgagtggtt aaggcgttgg actctaaatc caatggggtt tccccgcaca    60
ggttcgaatc ctgttcgtga cg                                            82

<210> SEQ ID NO 375
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gacgaggtgg ccgagtggtt aaggcgatgg actctaaatc cattgtgctc tgcacgcgtg    60
ggttcgaatc ccaccctcgt cg                                            82

<210> SEQ ID NO 376
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gacgaggtgg ccgagtggtt aaggcgatgg actctaaatc cattgtgctc tgcacgcgtg    60
ggttcgaatc ccaccttcgt cg                                            82

<210> SEQ ID NO 377
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
ggccggttag ctcagttggt tagagcgtgc tctaactaat gccagggtcg aggtttcgat    60
ccccgtacgg gcct                                                     74

<210> SEQ ID NO 378
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gacgaggtgg ccgagtggtt aaggcgatgg actctaaatc cattgtgctc tgcacacgtg    60
ggttcgaatc ccatcctcgt cg                                            82

<210> SEQ ID NO 379
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 379
gaggcctggc cgagtggtta aggcgatgga ctctaaatcc attgtgctct gcacgcgtgg    60
gttcgaatcc catcctcg                                                  78

<210> SEQ ID NO 380
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
gcagcgatgg ccgagtggtt aaggcgttgg actctaaatc caatggggtc tccccgcgca    60
ggttcgaacc ctgctcgctg cg                                             82

<210> SEQ ID NO 381
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
gtagtcgtgg ccgagtggtt aaggcgatgg actctaaatc cattggggtt tccccgcgca    60
ggttcgaatc ctgccgacta cg                                             82

<210> SEQ ID NO 382
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
gtagtcgtgg ccgagtggtt aaggcgatgg actctaaatc cattggggtc tccccgcgca    60
ggttcgaatc ctgccgacta cg                                             82

<210> SEQ ID NO 383
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
gtagtcgtgg ccgagtggtt aaggcgatgg actctaaatc cattggggtt tccccgcgca    60
ggttcgaatc ctgtcggcta cg                                             82

<210> SEQ ID NO 384
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 384
gagaaggtca cagaggttat gggattggct tcaaaccagt ctgtgggggg ttcgattccc      60
tcctttttca                                                             70

<210> SEQ ID NO 385
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
gagaaggtca tagaggttat gggattggct tcaaaccagt ctctgggggg ttcgattccc      60
tcctttttca                                                             70

<210> SEQ ID NO 386
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
gaaaaagtca tagggttat gaggctggct tcaaaccagc cttaggaggt tcaattcctt       60
cctttttttg                                                             69

<210> SEQ ID NO 387
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
ggccggttag ctcagttggt tagagcgtgc tgcttcaaat gccagggtcg aggtttcgat      60
ccccgtacgg gcct                                                        74

<210> SEQ ID NO 388
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
gtagtcgtgg ccgagtggtt aaggcgatgg acttcaaatc cattggggtt tccccgcgca      60
ggttcgaatc ctgccgacta cg                                               82

<210> SEQ ID NO 389
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 389
gtagtcgtgg ccgagtggtt aaggcgatgg acttcaaatc cattggggtt tccccacgca    60
ggttcgaatc ctgccgacta cg                                            82

<210> SEQ ID NO 390
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
gtagtcgtgg ccgagtggtt aaggtgatgg acttcaaacc cattggggtc tccccgcgca    60
ggttcgaatc ctgccgacta cg                                            82

<210> SEQ ID NO 391
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
gggtgtatgg ctcaggggta gagaatttga cttcagatca agaggtccct ggttcaaatc    60
caggtgcccc ct                                                       72

<210> SEQ ID NO 392
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
agttgtagct gagtggttaa ggcaacgagc ttcaaattcg ttggtttctc tctgtgcagg    60
tttgaatcct gctaatta                                                 78

<210> SEQ ID NO 393
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
caagaaattc atagaggtta tgggattggc ttcaaaccag tttcaggagg ttcgattcct    60
tcctttttgg                                                          70

<210> SEQ ID NO 394
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
gctgtgatgg ccgagtggtt aaggcgttgg acttcaaatc caatggggtc tccccgcgca    60
ggttcgaatc ctgctcacag cg    82

<210> SEQ ID NO 395
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gctgtgatgg ccgagtggtt aaggcgttgg acttcaaatc caatggggtc tccccgcgca    60
ggttcaaatc ctgctcacag cg    82

<210> SEQ ID NO 396
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
gctgtgatgg ccgagtggtt aaggtgttgg acttcaaatc caatgggggt tccccgcgca    60
ggttcaaatc ctgctcacag cg    82

<210> SEQ ID NO 397
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
gtcacggtgg ccgagtggtt aaggcgttgg acttcaaatc caatggggtt tccccgcaca    60
ggttcgaatc ctgttcgtga cg    82

<210> SEQ ID NO 398
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gacgaggtgg ccgagtggtt aaggcgatgg acttcaaatc cattgtgctc tgcacgcgtg    60
ggttcgaatc ccaccctcgt cg    82

<210> SEQ ID NO 399
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 399
gacgaggtgg ccgagtggtt aaggcgatgg acttcaaatc cattgtgctc tgcacgcgtg    60
ggttcgaatc ccaccttcgt cg    82

<210> SEQ ID NO 400
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
ggccggttag ctcagttggt tagagcgtgc ttcaactaat gccagggtcg aggtttcgat    60
ccccgtacgg gcct    74

<210> SEQ ID NO 401
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
gacgaggtgg ccgagtggtt aaggcgatgg acttcaaatc cattgtgctc tgcacacgtg    60
ggttcgaatc ccatcctcgt cg    82

<210> SEQ ID NO 402
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
gaggcctggc cgagtggtta aggcgatgga cttcaaatcc attgtgctct gcacgcgtgg    60
gttcgaatcc catcctcg    78

<210> SEQ ID NO 403
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
gcagcgatgg ccgagtggtt aaggcgttgg acttcaaatc caatggggtc tccccgcgca    60
ggttcgaacc ctgctcgctg cg    82

<210> SEQ ID NO 404
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
gtagtcgtgg ccgagtggtt aaggcgatgg acttcaaatc cattggggtt tccccgcgca    60
ggttcgaatc ctgccgacta cg                                              82

<210> SEQ ID NO 405
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
gtagtcgtgg ccgagtggtt aaggcgatgg acttcaaatc cattggggtc tccccgcgca    60
ggttcgaatc ctgccgacta cg                                              82

<210> SEQ ID NO 406
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
gtagtcgtgg ccgagtggtt aaggcgatgg acttcaaatc cattggggtt tccccgcgca    60
ggttcgaatc ctgtcggcta cg                                              82

<210> SEQ ID NO 407
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
gcccagctag ctcagtcggt agagcataag actttaaatc tcagggttgt ggattcgtgc    60
cccatgctgg gtg                                                        73

<210> SEQ ID NO 408
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
ctgcagctag ctcagtcggt agagcatgag actttaaatc tcagggtcat gggttcgtgc    60
cccatgttgg g                                                          71

<210> SEQ ID NO 409
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 409
ccagcatgtc tcagtcggta tagtgtgaga ctttaaatct cagggtcgtg ggttcaagcc    60
ccacattggg                                                          70

<210> SEQ ID NO 410
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
gtctagctag atcagttggt agagcataag actttaaatc tcagggtcat gggtttgagc    60
cctacgttgg gcg                                                      73

<210> SEQ ID NO 411
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
gcccagctag ctcagccggt agagcacaag actttaaatc tcagggtcgt gggtttgagc    60
cctgtgttga gca                                                      73

<210> SEQ ID NO 412
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ccgaatagct tagttgatga agcgtgagac tttaaatctc agggtagtgg gttcaagccc    60
cacattgga                                                           69

<210> SEQ ID NO 413
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
gcctggctac ctcagttggt agagcatggg actttaaatc ccagagtcag tgggttcaag    60
cctcacattg agtg                                                     74

<210> SEQ ID NO 414
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 414
gcccggctag ctcagtcggt agagcatgag accttaaatc tcagggtcgt gggttcgagc    60
cccacgttgg gcg                                                       73

<210> SEQ ID NO 415
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
gcccggctag ctcagtcggt agagcatggg actttaaatc tcagggtcgt gggttcgagc    60
cccacgttgg gcg                                                       73

<210> SEQ ID NO 416
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
gcccggctag ctcagtcgat agagcatgag actttaaatc tcagggtcgt gggttcgagc    60
cgcacgttgg gcg                                                       73

<210> SEQ ID NO 417
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
gcccagctag ctcagtcggt agagcatgag actttaaatc tcagggtcat gggtttgagc    60
cccacgtttg gtg                                                       73

<210> SEQ ID NO 418
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
gcctggctag ctcagtcggc aaagcatgag actttaaatc tcagggtcgt gggctcgagc    60
tccatgttgg gcg                                                       73

<210> SEQ ID NO 419
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 419
gcccgactac ctcagtcggt ggagcatggg actttacatc ccagggttgt gggttcgagc    60
cccacattgg gca                                                       73

<210> SEQ ID NO 420
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
ccccggctgg ctcagtcagt agatcatgag actttaaatc tcagggtcgt gggttcacgc    60
cccacactgg gcg                                                       73

<210> SEQ ID NO 421
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
gcgctagtca gtagagcatg agactttaaa tctcagggtc gtgggttcga gccccacatc    60
gggcg                                                                65

<210> SEQ ID NO 422
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
gcctggatag ctcagttggt agagcatcag actttaaatc tgagggtcca gggttcaagt    60
ccctgttcag gca                                                       73

<210> SEQ ID NO 423
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
gccaggatag ttcaggtggt agagcatcag actttaaaac ctgagggttc agggttcaag    60
tctctgtttg ggcg                                                      74

<210> SEQ ID NO 424
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 424
acccagatag ctcagtcagt agagcatcag actttaaatc tgagggtcca aggttcatgt    60 cccttttttgg gtg                                                      73

<210> SEQ ID NO 425
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
acctgggtag cttagttggt agagcattgg actttaaatt tgagggccca ggtttcaagt    60
ccctgtttgg gtg                                                       73

<210> SEQ ID NO 426
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
gcctgggtag ctcagtcggt agagctatca gactttaagc ctgaggattc agggttcaat    60
cccttgctgg ggcg                                                      74

<210> SEQ ID NO 427
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
gatagctcag ttgatagagc atcagacttt aaatctgagg gtccagggtt catgtccctg    60
tt                                                                   62

<210> SEQ ID NO 428
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
gttggggtaa ctcagttggt agagtagcag actttacatc tgagggtcca gggtttaagt    60
ccatgtccag gca                                                       73

<210> SEQ ID NO 429
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 429
gcctggatag ctcagttggt agagcatcag actttaaatc tgagggtcca gggttcaagt     60
ccctgttcag gcg                                                       73

<210> SEQ ID NO 430
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
gcctggatag ctcagtcggt agagcatcag actttaaatc tgagggtcca gggttcaagt     60
ccctgttcag gcg                                                       73

<210> SEQ ID NO 431
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
gcccggatag ctcagtcggt agagcatcag actttaaatc tgagggtccg gggttcaagt     60
ccctgttcgg gcg                                                       73

<210> SEQ ID NO 432
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
gcctgggtag ctcagtcggt agagcatcag actttaaatc tgagggtcca gggttcaagt     60
ccctgtccag gcg                                                       73

<210> SEQ ID NO 433
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
gcctggatag ctcagttggt agaacatcag actttaaatc tgacggtgca gggttcaagt     60
ccctgttcag gcg                                                       73

<210> SEQ ID NO 434
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 434
gcccggagag ctcagtgggt agagcatcag actttaaatc tgagggtcca gggttcaagt    60
cctcgttcgg gca    73

<210> SEQ ID NO 435
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
acctgggtag ctcagtaggt agaacatcag actttaaatc tgagggtcta gggttcaagt    60
ccctgtccag gcg    73

<210> SEQ ID NO 436
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
gcctggatag ctccttcggt agagcatcat cagactttaa atgtgagggt ccagggttca    60
agttcctgtt tgggcg    76

<210> SEQ ID NO 437
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
gcccagctag ctcagtcggt agagcataag actctaaatc tcagggttgt ggattcgtgc    60
cccatgctgg gtg    73

<210> SEQ ID NO 438
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
ctgcagctag ctcagtcggt agagcatgag actctaaatc tcagggtcat gggttcgtgc    60
cccatgttgg g    71

<210> SEQ ID NO 439
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
ccagcatgtc tcagtcggta tagtgtgaga ctctaaatct cagggtcgtg ggttcaagcc    60
ccacattggg                                                          70

<210> SEQ ID NO 440
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
gtctagctag atcagttggt agagcataag actctaaatc tcagggtcat gggtttgagc    60
cctacgttgg gcg                                                      73

<210> SEQ ID NO 441
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
gcccagctag ctcagccggt agagcacaag actctaaatc tcagggtcgt gggtttgagc    60
cctgtgttga gca                                                      73

<210> SEQ ID NO 442
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
ccgaatagct tagttgatga agcgtgagac tctaaatctc agggtagtgg gttcaagccc    60
cacattgga                                                           69

<210> SEQ ID NO 443
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
gcctggctac ctcagttggt agagcatggg actctaaatc ccagagtcag tgggttcaag    60
cctcacattg agtg                                                     74

<210> SEQ ID NO 444
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 444
gcccggctag ctcagtcggt agagcatgag accctaaatc tcagggtcgt gggttcgagc    60
cccacgttgg gcg                                                       73

<210> SEQ ID NO 445
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
gcccggctag ctcagtcggt agagcatggg actctaaatc tcagggtcgt gggttcgagc    60
cccacgttgg gcg                                                       73

<210> SEQ ID NO 446
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
gcccggctag ctcagtcgat agagcatgag actctaaatc tcagggtcgt gggttcgagc    60
cgcacgttgg gcg                                                       73

<210> SEQ ID NO 447
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
gcccagctag ctcagtcggt agagcatgag actctaaatc tcagggtcat gggtttgagc    60
cccacgtttg gtg                                                       73

<210> SEQ ID NO 448
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
gcctggctag ctcagtcggc aaagcatgag actctaaatc tcagggtcgt gggctcgagc    60
tccatgttgg gcg                                                       73

<210> SEQ ID NO 449
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 449
gcccgactac ctcagtcggt ggagcatggg actctacatc ccagggttgt gggttcgagc    60
cccacattgg gca                                                        73

<210> SEQ ID NO 450
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
ccccggctgg ctcagtcagt agatcatgag actctaaatc tcagggtcgt gggttcacgc    60
cccacactgg gcg                                                        73

<210> SEQ ID NO 451
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
gcgctagtca gtagagcatg agactctaaa tctcagggtc gtgggttcga gccccacatc    60
gggcg                                                                 65

<210> SEQ ID NO 452
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
gcctggatag ctcagttggt agagcatcag actctaaatc tgagggtcca gggttcaagt    60
ccctgttcag gca                                                        73

<210> SEQ ID NO 453
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
gccaggatag ttcaggtggt agagcatcag actctaaacc tgagggttca gggttcaagt    60
ctctgtttgg gcg                                                        73

<210> SEQ ID NO 454
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 454
acccagatag ctcagtcagt agagcatcag actctaaatc tgagggtcca aggttcatgt    60 cccttttttgg gtg    73

<210> SEQ ID NO 455
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
acctgggtag cttagttggt agagcattgg actctaaatt tgagggccca ggtttcaagt    60
ccctgtttgg gtg    73

<210> SEQ ID NO 456
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
gcctgggtag ctcagtcggt agagctatca gactctaaag cctgaggatt cagggttcaa    60
tcccttgctg gggcg    75

<210> SEQ ID NO 457
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
gatagctcag ttgatagagc atcagactct aaatctgagg gtccagggtt catgtccctg    60
tt    62

<210> SEQ ID NO 458
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
gttggggtaa ctcagttggt agagtagcag actctacatc tgagggtcca gggtttaagt    60
ccatgtccag gca    73

<210> SEQ ID NO 459
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
gcctggatag ctcagttggt agagcatcag actctaaatc tgagggtcca gggttcaagt    60
ccctgttcag gcg                                                      73

<210> SEQ ID NO 460
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
gcctggatag ctcagtcggt agagcatcag actctaaatc tgagggtcca gggttcaagt    60
ccctgttcag gcg                                                      73

<210> SEQ ID NO 461
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
gcccggatag ctcagtcggt agagcatcag actctaaatc tgagggtccg gggttcaagt    60
ccctgttcgg gcg                                                      73

<210> SEQ ID NO 462
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
gcctgggtag ctcagtcggt agagcatcag actctaaatc tgagggtcca gggttcaagt    60
ccctgtccag gcg                                                      73

<210> SEQ ID NO 463
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
gcctggatag ctcagttggt agaacatcag actctaaatc tgacggtgca gggttcaagt    60
ccctgttcag gcg                                                      73

<210> SEQ ID NO 464
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
gcccggagag ctcagtgggt agagcatcag actctaaatc tgagggtcca gggttcaagt    60
cctcgttcgg gca    73

<210> SEQ ID NO 465
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
acctgggtag ctcagtaggt agaacatcag actctaaatc tgagggtcta gggttcaagt    60
ccctgtccag gcg    73

<210> SEQ ID NO 466
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
gcctggatag ctccttcggt agagcatcat cagactctaa atgtgagggt ccagggttca    60
agttcctgtt tgggcg    76

<210> SEQ ID NO 467
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
ggcagaatgg tgcagcggtt cagcacccag gctcttcagc cagctgttgc ctgggctcaa    60
atcccagctc tgcca    75

<210> SEQ ID NO 468
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 468
ggctgtatag ctcagtggta gagcatttga cttcagaatc ctatactcag gggaaggaga    60
actgggggtt tctcagtggg tcaaaggact tgtagtggta aatcaaaagc aactctataa   120
gctatgtaac aaactttaaa gtcatatgta gctgggttca atcctgtttt ctgcca       176

<210> SEQ ID NO 469
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
ggctgtatag ctcagtggta gagcatttga cttcagcttt aaagtcatat gtagctgggt    60
tcaaatcctg tttctgcca                                                 79

<210> SEQ ID NO 470
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
gggggcatag ctcagtggta gagcatttga cttcagatca agaggtccct ggttcaaatc    60
caggtgcccc ct                                                        72

<210> SEQ ID NO 471
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
gggggtatag ctcaggggta gagcatttga cttcagatca agaggtccct ggttcaaatc    60
caggtgcccc cc                                                        72

<210> SEQ ID NO 472
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
gggggtatag cttagcggta gagcatttga cttcagatca agaggtcccc ggttcaaatc    60
cgggtgcccc ct                                                        72

<210> SEQ ID NO 473
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473 ggggtatag cttaggggta gagcatttga cttcagatca aaaggtccct ggttcaaatc     60
caggtgcccc tt                                                        72

<210> SEQ ID NO 474
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 474
gggggtatag ctcaggggta gagcatttga cttcagatca agaggtcccc agttcaaatc    60
tgggtgcccc ct                                                       72

<210> SEQ ID NO 475
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
gggggtatag ctcaggggta gagcatttga cttcagatca agaagtcccc ggttcaaatc    60
cgggtgcccc ct                                                       72

<210> SEQ ID NO 476
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
gggggtatag ctcaggggta gagcatttga cttcagatca agaggtctct ggttcaaatc    60
caggtgcccc ct                                                       72

<210> SEQ ID NO 477
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
gggggtatag ctcaggggta gagcacttga cttcagatca agaagtcctt ggttcaaatc    60
caggtgcccc ct                                                       72

<210> SEQ ID NO 478
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
ggggatatag ctcaggggta gagcatttga cttcagatca agaggtcccc ggttcaaatc    60
cgggtgcccc cc                                                       72

<210> SEQ ID NO 479
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 479 ggggtatag ttcaggggta gagcatttga cttcagatca agaggtccct ggttcaaatc    60
caggtgcccc ct                                                      72

<210> SEQ ID NO 480
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480 ggggtatag ctcaggggta gagcatttga cttcaaatca agaggtccct gattcaaatc    60
caggtgcccc ct                                                      72

<210> SEQ ID NO 481
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
gggcgtatag ctcaggggta gagcatttga cttcagatca agaggtcccc agttcaaatc   60
tgggtgcccc ct                                                      72

<210> SEQ ID NO 482
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482 ggggtatag ctcacaggta gagcatttga cttcagatca agaggtcccc ggttcaaatc    60
tgggtgcccc ct                                                      72

<210> SEQ ID NO 483
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
gggcgtatag ctcaggggta gagcatttga cttcagatca agaggtcccc agttcaaatc   60
tgggtgccca                                                         70

<210> SEQ ID NO 484
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 484
gggggtatag ctcacaggta gagcatttga cttcagatca agaggtcccc ggttcaaatc    60
cggttactcc ct                                                       72

<210> SEQ ID NO 485
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
gggggtaggg ctcagggata gagcatttga cttcagatca agaggtcccc ggttcgaatc    60
taggtgcccc ct                                                       72

<210> SEQ ID NO 486
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
ggtatatctc aggggcaga gcatttgact tcagatcaag aggtcccgg ttgaaatccg      60 ggtgct                                                              66

<210> SEQ ID NO 487
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
gggggtatag ctcaggggta gagcacttga cttcagatca agaggtccct ggttcaaatc    60
caggtgcccc ct                                                       72

<210> SEQ ID NO 488
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
gggggtatag ctcagtggta gagcatttga cttcagatca agaggtccct ggttcaaatc    60
cgggtgcccc ct                                                       72

<210> SEQ ID NO 489
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 489
gggggtatag ctcagtgggt agagcatttg acttcagatc aagaggtccc cggttcaaat    60
ccgggtgccc cct                                                      73

<210> SEQ ID NO 490
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
gggggtgtag ctcagtggta gagcatttga cttcagatca agaggtccct ggttcaaatc    60
caggtgcccc ct                                                       72

<210> SEQ ID NO 491
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
gggggtatag ctcaggggta gagcatttga cttcagatca agaggtcccc ggttcaaatc    60
cgggtgcccc ct                                                       72

<210> SEQ ID NO 492
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
gggggtatag ctcaggggta gagcatttga cttcagatca agaggtccct ggttcaaatc    60
caggtgcccc ct                                                       72

<210> SEQ ID NO 493
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
gacctcgtgg cgcaatggta gcgcgtctga cttcagatca gaaggttgcg tgttcaaatc    60
acgtcggggt ca                                                       72

<210> SEQ ID NO 494
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 494
gacctcgtgg cacaatggta gcacgtctga cttcagatca gaaggttgcg tgttcaaatc    60
acgtcggggt ca                                                        72

<210> SEQ ID NO 495
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 495
gaagcggtgg ctcaatggta gagctttcga cttcaattaa atcttggaaa ttccacggaa    60
taagattgca atcgaagggt tgcaggttca attcctgtcc gtttca                  106

<210> SEQ ID NO 496
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
gaagcggtgg ctcaatggta gagctttcga cttcaaatcg aagggttgca ggttcaattc    60
ctgtccgttt ca                                                        72

<210> SEQ ID NO 497
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
ggcctcatgg tgcaacagta gtgtgtctga cttcagatca gaaggttgta tgttcaaatc    60
acataggggt ca                                                        72

<210> SEQ ID NO 498
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
gacctcgtgg tgaaatggta gcatgtttga cttcaaatca ggaggttgtg tgttcaagtc    60
acatcagggt ca                                                        72

<210> SEQ ID NO 499
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 499
gaccttgtgg cgcaatggta gcatgtttga cttcaaatca ggaggttgtg tgttcaagtc    60
acatcagggt ca    72

<210> SEQ ID NO 500
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
gacctcgtgg cgcaacggta gcgcgtctga cttcagatca gaaggctgcg tgttcgaatc    60 acgccgggt ca    72

<210> SEQ ID NO 501
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
gaccttgtgg ctcaatggta gcgcatctga cttcagatca ggaggttgca cgttcaaatc    60 atgccgggt ca    72

<210> SEQ ID NO 502
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
gaccttgtgg cgcaacggta gcgcgtctga cttcagatca gaaggttgcg tgttcaaatc    60 acgtcgggt ca    72

<210> SEQ ID NO 503
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
gacctcgtgg cgcaacggta gcgcgtctga cttcagatca gaaggttgcg tattcaaatc    60 acgtcgggt ca    72

<210> SEQ ID NO 504
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
gacctcgtgg cgcaacggca gcgcgtctga cttcacatta gaaggttgcg tgttcaaatc    60
acgtcggggt ca    72

<210> SEQ ID NO 505
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
gacctcatgg cgcaacggta gcgcgtctga cttcagatca gaaggttgcg tgttcaaatc    60
acatcggggt ca    72

<210> SEQ ID NO 506
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
gacctcgtgg tgcaacggta gcgcgtatga tttcagatca gaaggttgcg tgttcaaatc    60
acgtcggggt ca    72

<210> SEQ ID NO 507
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
gacctcgtag cgcaacggta gcgcgtctga cttcagatca gaaggttgcg tgttcaaatc    60
acgtcggggt ca    72

<210> SEQ ID NO 508
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
aggggtatag ctcaattggc agagcgtcgg tcttcaaaac cgaaggttgt aggttcgatt    60
cctactgccc ctgcca    76

<210> SEQ ID NO 509
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
gacctcatgg cgcaacggta gcgcgtctga cttcagatca gaaggttgcg tgttcaaatc    60
acgtcggggt ca    72

<210> SEQ ID NO 510
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
gacctcgtgg cgcaacggta gcgcgtctaa cttcagatca gaaggttgcg tgttcaaatc    60
acgtcggggt ca    72

<210> SEQ ID NO 511
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
acgggagtag ctcagttggt agagcaccgg tcttcaaaac cgggtgtcgg gagttcgagc    60
ctctcctccc gtg    73

<210> SEQ ID NO 512
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
gacctcgtgg cgcaacggta gcgcgtctga cttcagatca gaaggttgca tgttcaaatc    60
acgtcggggt ca    72

<210> SEQ ID NO 513
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
gactccgtgg cgcaacggta gcgcgtccga cttcagatcg gaaggttgcg tgttcaaatc    60
acgtcggggt ca    72

<210> SEQ ID NO 514
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
gactccgtgg cgcaacggta gcgcgtctga cttcagatca gaaggttgcg tgttcaaatc    60
acgtcggggt ca                                                       72

<210> SEQ ID NO 515
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
ggcctcgtgg cgcaacggta gcgcgtctga ctccagatca gaaggttgcg tgttcaaatc    60
acgtcggggt ca                                                       72

<210> SEQ ID NO 516
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
ggcctcgtgg cgcaacggta gcacgtctga ctccagatca gaaggttgcg tgttcaaatc    60
acgtcggggt ca                                                       72

<210> SEQ ID NO 517
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
cggcctcgtg gcgcaacggt agcacgtctg acttcagatc agaaggttgc gtgttcaaat    60
cacgtcgggg tca                                                      73

<210> SEQ ID NO 518
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
ggcctcgtcg cgcaacggta gcgcgtctga ctccagatca gaaggttgcg tgttcaaatc    60
acgtcggggt ca                                                       72

<210> SEQ ID NO 519
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
ggcctcgtcg cgcaacggta gcgcgtctga cttcagatca gaaggttgcg tgttcaaatc    60
acgtcggggt ca    72

<210> SEQ ID NO 520
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
ggcctcgtcg cgcaacggta gcacgtctga ctccagatca gaaggttgcg tgttcaaatc    60
acgtcggggt ca    72

<210> SEQ ID NO 521
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
ggcctcgtcg cgcaacggta gcacgtctga cttcagatca gaaggttgcg tgttcaaatc    60
acgtcggggt ca    72

<210> SEQ ID NO 522

<400> SEQUENCE: 522

000

<210> SEQ ID NO 523
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
gttaagatgg cagagcctgg taattgcatc aaacttaaaa ttttataatc agaggttcaa    60
ctcctcttct taaca    75

<210> SEQ ID NO 524
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
gttaagatgg cagagcccgg caattgcatc agacttaaaa ctttataatc agaggttcaa    60
ctcctctcat taaca    75

<210> SEQ ID NO 525
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
ggtagcgtgg ccgagcggtc taaggcgctg gatttcagct ccagtctctt cggggcgtg      60 ggttcaaatc ccaccgctgc ca                                              82

<210> SEQ ID NO 526
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
ggtagcgtgg ccgagtggtc taagacgctg gatttcagct ccagtctctt cggggcgtg      60 ggtttgaatc ccaccgctgc ca                                              82

<210> SEQ ID NO 527
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
gggccagtgg ctcaatggat aatgcgtctg acttcaaatc agaagattcc agccttgact      60
cctggctggc tca                                                        73

<210> SEQ ID NO 528
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
ggtagggtgg ccgagcggtc taaggcactg tatttcaact ccagtctctt cagaggcatg      60
ggtttgaatc ccactgctgc ca                                              82

<210> SEQ ID NO 529
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
gccgagcggt ctaaggctcc ggatttcagc gccggtgtct tcggaggcat gggttcgaat      60
tccac                                                                 65

<210> SEQ ID NO 530
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 530
gtcaggatgg ccgagtggtc taaggcgcca gacttcagct aagcttcctc cgcggtgggg    60
attctggtct ccaatggagg cgtgggttcg aatcccactt ctgaca                  106

<210> SEQ ID NO 531

<400> SEQUENCE: 531

000

<210> SEQ ID NO 532
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
gtcaggatgg ccgagtggtc taaggcgcca gacttcagtt ctggtctcca atggaggcgt    60
gggttcgaat cccacttctg aca                                           83

<210> SEQ ID NO 533
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 533
gtcaggatgg ccgagtggtc taaggcgcca gacttcagct tggcttcctc gtgttgagga    60
ttctggtctc caatggaggc gtgggttcga atcccacttc tgaca                   105

<210> SEQ ID NO 534
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
gtcaggatgg ccgagtggtc taaggcgcca gacttcagtt ctggtctcca atggaggcgt    60
gggttcgaat cccacttctg aca                                           83

<210> SEQ ID NO 535
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 535
gtcaggatgg ccgagtggtc taaggcgcca gacttcagct tactgcttcc tgtgttcggg    60
tcttctggtc tccgtatgga ggcgtgggtt cgaatcccac ttctgaca                108

<210> SEQ ID NO 536
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
gtcaggatgg ccgagtggtc taaggcgcca gacttcagtt ctggtctccg tatggaggcg    60
tgggttcgaa tcccacttct gaca                                           84

<210> SEQ ID NO 537
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 537
gtcaggatgg ccgagtggtc taaggcgcca gacttcagtt gctacttccc aggtttgggg    60
cttctggtct ccgcatggag gcgtgggttc gaatcccact tctgaca                 107

<210> SEQ ID NO 538
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
gtcaggatgg ccgagtggtc taaggcgcca gacttcagtt ctggtctccg catggaggcg    60
tgggttcgaa tcccacttct gaca                                           84

<210> SEQ ID NO 539
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 539
gtcaggatgg ccgagtggtc taaggcgcca gacttcaggt aagcaccttg cctgcgggct    60
ttctggtctc cggatggagg cgtgggttcg aatcccactt ctgaca                  106

<210> SEQ ID NO 540
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
gtcaggatgg ccgagtggtc taaggcgcca gacttcagtt tctggtctcc ggatggaggc    60
gtgggttcga atcccacttc tgaca                                          85

<210> SEQ ID NO 541
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
gcctccttag tgcagtaggt agcgcatcag tcttcaaatc tgaatggtcc tgagttcaag    60
cctcagaggg ggca    74

<210> SEQ ID NO 542
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
gtcaggatgg ccgagcagtc ttaaggcgct gcgtttcaat cgcaccctcc gctggaggcg    60
tgggttcgaa tcccactttt gaca    84

<210> SEQ ID NO 543
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
ggttccatgg tgtaatggtg agcactctgg acttcaaatc cagaagtagt gctggaacaa    60

<210> SEQ ID NO 544
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
gtcagggtgg ctgagcagtc tgaggggctg cgtttcagtc gcagtctgcc ctggaggcgt    60
gggttcgaat cccactcctg aaa    83

<210> SEQ ID NO 545
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
accaggatgg ccgagtggtt aaggcgttgg acttcagatc caatggacat atgtccgcgt    60
gggttcgaac cccactcctg gta    83

<210> SEQ ID NO 546
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
accgggatgg ccgagtggtt aaggcgttgg acttcagatc caatgggctg gtgcccgcgt    60
gggttcgaac cccactctcg gta    83

<210> SEQ ID NO 547

<400> SEQUENCE: 547

000

<210> SEQ ID NO 548
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
accagaatgg ccgagtggtt aaggcgttgg acttcagatc caatggattc atatccgcgt    60
gggttcgaac cccacttctg gta                                            83

<210> SEQ ID NO 549
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
accgggatgg ctgagtggtt aaggcgttgg acttcagatc caatggacag gtgtccgcgt    60
gggttcgagc cccactcccg gta                                            83

<210> SEQ ID NO 550
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
actcatttgg ctgagtggtt aaggcattgg acttcagatc caatggagta gtggctgtgt    60
gggtttaaac cccactactg gta                                            83

<210> SEQ ID NO 551
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
gagaaagtca tcgtagttac gaagttggct tcaacccagt tttgggaggt tcaattcctt    60
cctttctct                                                            69

<210> SEQ ID NO 552
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
accaggatgg ccaagtagtt aaaggcactg gacttcagag ccaatggaca tatgtctgtg    60
tgggtttgaa ccccactcct ggtg                                          84

<210> SEQ ID NO 553
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
ggtagcgtgg ccgagcggtc taaggcgctg gatttcagct ccagtctctt cggaggcgtg    60
ggttcgaatc ccaccgctgc ca                                            82

<210> SEQ ID NO 554
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
ggtagtgtgg ccgagcggtc taaggcgctg gatttcagct ccagtctctt cggggcgtg    60 ggttcgaatc ccaccactgc ca                                            82

<210> SEQ ID NO 555
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
ggtagcgtgg ccgagtggtc taaggcgctg gatttcagct ccagtcattt cgatggcgtg    60
ggttcgaatc ccaccgctgc ca                                            82

<210> SEQ ID NO 556
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
ggtagtgtgg ttgaatggtc taaggcactg aatttcagct ccagtctctt tggggacgtg    60
ggtttaaatc ccactgctgc aa                                            82

<210> SEQ ID NO 557
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 557
gagaaggtca cagaggttat gggattggct ttaaaccagt ctgtgggggg ttcgattccc    60
tccttttca                                                            70

<210> SEQ ID NO 558
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
gagaaggtca tagaggttat gggattggct ttaaaccagt ctctgggggg ttcgattccc    60
tccttttca                                                            70

<210> SEQ ID NO 559
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
gaaaaagtca tagggttat gaggctggct ttaaaccagc cttaggaggt tcaattcctt     60
ccttttttg                                                            69

<210> SEQ ID NO 560
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
ggccggttag ctcagttggt tagagcgtgc tgctttaaat gccagggtcg aggtttcgat    60
ccccgtacgg gcct                                                      74

<210> SEQ ID NO 561
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
gtagtcgtgg ccgagtggtt aaggcgatgg actttaaatc cattggggtt tccccgcgca    60
ggttcgaatc ctgccgacta cg                                             82

<210> SEQ ID NO 562
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 562
gtagtcgtgg ccgagtggtt aaggcgatgg actttaaatc cattgggggtt tccccacgca    60 ggttcgaatc ctgccgacta cg    82

<210> SEQ ID NO 563
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
gtagtcgtgg ccgagtggtt aaggtgatgg actttaaacc cattggggtc tccccgcgca    60
ggttcgaatc ctgccgacta cg    82

<210> SEQ ID NO 564
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
gggtgtatgg ctcaggggta gagaatttga ctttagatca agaggtccct ggttcaaatc    60
caggtgcccc ct    72

<210> SEQ ID NO 565
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
agttgtagct gagtggttaa ggcaacgagc tttaaattcg ttggtttctc tctgtgcagg    60
tttgaatcct gctaatta    78

<210> SEQ ID NO 566
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
caagaaattc atagaggtta tgggattggc tttaaaccag tttcaggagg ttcgattcct    60
tcctttttgg    70

<210> SEQ ID NO 567
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
gctgtgatgg ccgagtggtt aaggcgttgg actttaaatc caatggggtc tccccgcgca    60
ggttcgaatc ctgctcacag cg    82

<210> SEQ ID NO 568
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
gctgtgatgg ccgagtggtt aaggcgttgg actttaaatc caatggggtc tccccgcgca    60
ggttcaaatc ctgctcacag cg    82

<210> SEQ ID NO 569
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
gctgtgatgg ccgagtggtt aaggtgttgg actttaaatc caatgggggt tccccgcgca    60
ggttcaaatc ctgctcacag cg    82

<210> SEQ ID NO 570
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
gtcacggtgg ccgagtggtt aaggcgttgg actttaaatc caatggggtt tccccgcaca    60
ggttcgaatc ctgttcgtga cg    82

<210> SEQ ID NO 571
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
gacgaggtgg ccgagtggtt aaggcgatgg actttaaatc cattgtgctc tgcacgcgtg    60
ggttcgaatc ccaccctcgt cg    82

<210> SEQ ID NO 572
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
gacgaggtgg ccgagtggtt aaggcgatgg actttaaatc cattgtgctc tgcacgcgtg    60
ggttcgaatc ccaccttcgt cg                                              82

<210> SEQ ID NO 573
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
ggccggttag ctcagttggt tagagcgtgc tttaactaat gccagggtcg aggtttcgat    60
ccccgtacgg gcct                                                       74

<210> SEQ ID NO 574
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
gacgaggtgg ccgagtggtt aaggcgatgg actttaaatc cattgtgctc tgcacacgtg    60
ggttcgaatc ccatcctcgt cg                                              82

<210> SEQ ID NO 575
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
gaggcctggc cgagtggtta aggcgatgga ctttaaatcc attgtgctct gcacgcgtgg    60
gttcgaatcc catcctcg                                                   78

<210> SEQ ID NO 576
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
gcagcgatgg ccgagtggtt aaggcgttgg actttaaatc caatggggtc tccccgcgca    60
ggttcgaacc ctgctcgctg cg                                              82

<210> SEQ ID NO 577
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 577
gtagtcgtgg ccgagtggtt aaggcgatgg actttaaatc cattggggtt tccccgcgca    60
ggttcgaatc ctgccgacta cg                                             82

<210> SEQ ID NO 578
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
gtagtcgtgg ccgagtggtt aaggcgatgg actttaaatc cattggggtc tccccgcgca    60
ggttcgaatc ctgccgacta cg                                             82

<210> SEQ ID NO 579
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
gtagtcgtgg ccgagtggtt aaggcgatgg actttaaatc cattggggtt tccccgcgca    60
ggttcgaatc ctgtcggcta cg                                             82

<210> SEQ ID NO 580
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 580
gcggauuuag cucagddggg agagcgccag acugaayauc uggagguccu gugtucgauc    60
cacagaauuc gcacca                                                    76

<210> SEQ ID NO 581
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 581
gaccucgugg cgcaacgguu agcgcgucug acutcagauc agaaggcugc guguucgaau    60
cacgucgggg uca                                                       73

<210> SEQ ID NO 582
<211> LENGTH: 10
<212> TYPE: PRT
<213> ORGANISM: Escherichia coli
```

-continued

<400> SEQUENCE: 582

Asn Ile Glu Thr Phe His Thr Ala Gln Lys
1               5                   10

<210> SEQ ID NO 583
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Ile Glu Thr Phe His Thr Ala Gln Lys
1               5

<210> SEQ ID NO 584
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Asn Ile Glu Thr Phe His Thr Ala Gln
1               5

<210> SEQ ID NO 585
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Glu Thr Phe His Thr Ala Gln Lys
1               5

<210> SEQ ID NO 586
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Ile Glu Thr Phe His Thr Ala Gln
1               5

<210> SEQ ID NO 587
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (22)..(27)
<223> OTHER INFORMATION: a, c, t, g, unknown or other

```
<400> SEQUENCE: 587
nnnnnngtat tcatcgaaga cnnnnnn                                           27

<210> SEQ ID NO 588
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (22)..(27)
<223> OTHER INFORMATION: a, c, t, g, unknown or other

<400> SEQUENCE: 588
nnnnnngtct tcgatgaata cnnnnnn                                           27

<210> SEQ ID NO 589
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 589
gaccucgugg cgcaacgguu agcgcgucug acutcagauc agaaggcucc ggguucgaau       60
cccggcgggg uca                                                          73

<210> SEQ ID NO 590
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 590

Xaa Ile Glu Thr Phe His Thr Ala Gln Lys
1               5                   10

<210> SEQ ID NO 591
<211> LENGTH: 71
<212> TYPE: RNA
<213> ORGANISM: Homo sapiens

<400> SEQUENCE: 591
gcauuggugg uucaguggua gaauucucgc cuucaacgcg ggagacccgg guucaauucc       60
cggccaaugc a                                                            71

<210> SEQ ID NO 592
<211> LENGTH: 71
<212> TYPE: RNA
<213> ORGANISM: Homo sapiens
```

```
<400> SEQUENCE: 592
gcgccgcugg uguaguggua ucaugcaaga uuucaauucu ugcgacccgg guucgauucc    60
cgggcggcgc a                                                         71

<210> SEQ ID NO 593
<211> LENGTH: 71
<212> TYPE: RNA
<213> ORGANISM: Homo sapiens

<400> SEQUENCE: 593
gcauuggugg uucaauggua gaauucucgc cuucaacgca ggagacccag guucgauucc    60
uggccaaugc a                                                         71

<210> SEQ ID NO 594
<211> LENGTH: 71
<212> TYPE: RNA
<213> ORGANISM: Homo sapiens

<400> SEQUENCE: 594
gcguuggugg uuuaguggua gaauucucgc cuucaaugcg ggagacccgg guucaauucc    60
cggccacugc a                                                         71

<210> SEQ ID NO 595
<211> LENGTH: 71
<212> TYPE: RNA
<213> ORGANISM: Homo sapiens

<400> SEQUENCE: 595
gccuuggugg ugcaguggua gaauucucgc cuucaacgug ggagacccgg guucaauucc    60
cggccaaugc a                                                         71

<210> SEQ ID NO 596
<211> LENGTH: 61
<212> TYPE: RNA
<213> ORGANISM: Homo sapiens

<400> SEQUENCE: 596
ggugguucag ugguagaauu cucgccuuca acgcgggaga cccggguuua auucccgguc    60
a                                                                    61

<210> SEQ ID NO 597
<211> LENGTH: 61
<212> TYPE: RNA
<213> ORGANISM: Homo sapiens

<400> SEQUENCE: 597
guggucuagu gguaggauu cagcgcuuca accgccgcag cccggguucg auucccgguc     60
a                                                                    61

<210> SEQ ID NO 598
<211> LENGTH: 71
<212> TYPE: RNA
<213> ORGANISM: Homo sapiens

<400> SEQUENCE: 598
gcgucagugg uuuaguggug gaauuccugc cuucaaugca cgagauccgu guucaacucc    60
ugguuggugc a                                                         71
```

```
<210> SEQ ID NO 599
<211> LENGTH: 72
<212> TYPE: RNA
<213> ORGANISM: Homo sapiens

<400> SEQUENCE: 599
gcgucagugg uuuuaguggu ggaauuccug ccuucaaugc acgagauccg uguucaacuc    60
cugguuggug ca                                                       72

<210> SEQ ID NO 600
<211> LENGTH: 71
<212> TYPE: RNA
<213> ORGANISM: Homo sapiens

<400> SEQUENCE: 600
gcguuggcag uucagugguua gaauucucgc cuucaacccg ggagaccugg auccauuuc    60 cggcaaaugc a                                                        71

<210> SEQ ID NO 601
<211> LENGTH: 71
<212> TYPE: RNA
<213> ORGANISM: Homo sapiens

<400> SEQUENCE: 601
gcaugggugg uucagguggua gaauucucgc cuucaacgcg ggaggccggg guucgauucc    60
cggcccaugc a                                                        71

<210> SEQ ID NO 602
<211> LENGTH: 71
<212> TYPE: RNA
<213> ORGANISM: Homo sapiens

<400> SEQUENCE: 602 gcauggugg uucagugguua gaauucucgc cuucaacgcg ggaggccggg guucgauucc    60
cggccaaugc a                                                        71

<210> SEQ ID NO 603
<211> LENGTH: 71
<212> TYPE: RNA
<213> ORGANISM: Homo sapiens

<400> SEQUENCE: 603
gcauuggugg uucagguggua gaauucucgc cuucaacgcg ggaggccggg guuugauucc    60
cggccagugc a                                                        71

<210> SEQ ID NO 604
<211> LENGTH: 71
<212> TYPE: RNA
<213> ORGANISM: Homo sapiens

<400> SEQUENCE: 604
gcauaggugg uucagguggua gaauucuugc cuucaacgca ggaggcccag guuugauucc    60
uggcccaugc a                                                        71

<210> SEQ ID NO 605
<211> LENGTH: 71
<212> TYPE: RNA
<213> ORGANISM: Homo sapiens
```

<400> SEQUENCE: 605
gcauuggugg uucaguggua gaauucucgc cuucaaugcg ggcggccggg cuucgauucc    60
uggccaaugc a    71

<210> SEQ ID NO 606
<211> LENGTH: 71
<212> TYPE: RNA
<213> ORGANISM: Homo sapiens

<400> SEQUENCE: 606 gcaugggugaa uucaguggua gaauuuucac cuucaaugca ggagguccag guucauuucc    60
uggccuaugc a    71

<210> SEQ ID NO 607
<211> LENGTH: 72
<212> TYPE: RNA
<213> ORGANISM: Homo sapiens

<400> SEQUENCE: 607
gcguuggugg uauagugguu agcauagcug ccuucaaagc aguugacccg gguucgauuc    60
ccggccaacg ca    72

<210> SEQ ID NO 608
<211> LENGTH: 72
<212> TYPE: RNA
<213> ORGANISM: Homo sapiens

<400> SEQUENCE: 608
gcguuggugg uauaguggug agcauagcug ccuucaaagc aguugacccg gguucgauuc    60
ccggccaacg ca    72

<210> SEQ ID NO 609
<211> LENGTH: 72
<212> TYPE: RNA
<213> ORGANISM: Homo sapiens

<400> SEQUENCE: 609
gcguuggugg uauaguggua agcauagcug ccuucaaagc aguugacccg gguucgauuc    60
ccggccaacg ca    72

<210> SEQ ID NO 610
<211> LENGTH: 72
<212> TYPE: RNA
<213> ORGANISM: Homo sapiens

<400> SEQUENCE: 610
gcguuggugg uauaguggug agcauaguug ccuucaaagc aguugacccg ggcucgauuc    60
ccgcccaacg ca    72

<210> SEQ ID NO 611
<211> LENGTH: 72
<212> TYPE: RNA
<213> ORGANISM: Homo sapiens

<400> SEQUENCE: 611
gcguuggugg uauaguggug agcauaguug ccuucaaagc aguugacccg ggcucgauuc    60
ccggccaacg ca    72

```
<210> SEQ ID NO 612
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
gaccucgugg cgcaacggca gcgcgucuga cuucagauca gaagguugcg uguucaaauc    60
acgucggggu ca                                                       72

<210> SEQ ID NO 613
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
gaccucgugg cgcaacggua gcgcgucuga cuucagauca gaagguugcg uguucaaauc    60
acgucggggu ca                                                       72

<210> SEQ ID NO 614
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
ggccucaugg ugcaacagua guguqucuga cuucagauca gaagguugua uguucaaauc    60
acguaggggu ca                                                       72

<210> SEQ ID NO 615
<211> LENGTH: 72
<212> TYPE: RNA
<213> ORGANISM: Artificial Sequence
<220> FEATURE:
<223> OTHER INFORMATION: Description of Artificial Sequence: Synthetic
      oligoneotide

<400> SEQUENCE: 615
gaccucgugg cgcaauggua gcgcgucuga cuucagauca gaagguugcg uguucaaguc    60
acgucggggu ca                                                       72

<210> SEQ ID NO 616
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
ggccucgugg cgcaacggua gcgcgucuga cuucagauca gaagguugcg uguucaaauc    60
acgucggggu ca                                                       72

<210> SEQ ID NO 617
<211> LENGTH: 72
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 617
gaccucgugg cgcaacggua gcgcgucuga cuucagauca gaaggcugcg uguucgaauc    60
acgucggggu ca                                                       72

<210> SEQ ID NO 618
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
gaccucgugg cgcaauggua gcgcgucuga cuucagauca gaagguugcg uguucaaauc    60
acgucggggu ca                                                       72

<210> SEQ ID NO 619
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
gaccucgugg cacaauggua gcacgucuga cuucagauca gaagguugcg uguucaaauc    60
acgucggggu ca                                                       72

<210> SEQ ID NO 620
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 620
gaagcggugg cucaauggua gagcuuucga cuucaauuaa aucuuggaaa uuccacggaa    60
uaagauugca aucgaagggu ugcagguuca auccugucc guuuca                  106

<210> SEQ ID NO 621
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
gaagcggugg cucaauggua gagcuuucga cuucaaaucg aagguugca gguucaauuc    60 cugucgguuu ca                                                       72

<210> SEQ ID NO 622
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
ggcucuaugg ugcaacagua gugugucuga cuucagauca gaagguugua uguucaaauc    60 acauagggu ca                                                         72

<210> SEQ ID NO 623
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
gaccucgugg ugaaauggua gcauguuuga cuucaaauca ggagguugug uguucaaguc    60
acaucagggu ca                                                        72

<210> SEQ ID NO 624
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
gaccuugugg cgcaauggua gcauguuuga cuucaaauca ggagguugug uguucaaguc    60
acaucagggu ca                                                        72

<210> SEQ ID NO 625
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
gaccucgugg cgcaacggua gcgcgucuga cuucagauca gaaggcugcg uguucgaauc    60
acgccggggu ca                                                        72

<210> SEQ ID NO 626
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
gaccuugugg cucaauggua gcgcaucuga cuucagauca ggagguugca cguucaaauc    60
augccggggu ca                                                        72

<210> SEQ ID NO 627
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 627
gaccuugugg cgcaacggua gcgcgucuga cuucagauca gaagguugcg uguucaaauc    60
acgucggggu ca                                                      72

<210> SEQ ID NO 628
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
gaccucgugg cgcaacggua gcgcgucuga cuucagauca gaagguugcg uauucaaauc    60
acgucggggu ca                                                      72

<210> SEQ ID NO 629
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 629
gaccucgugg cgcaacggca gcgcgucuga cuucacauua gaagguugcg uguucaaauc    60
acgucggggu ca                                                      72

<210> SEQ ID NO 630
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
gaccucaugg cgcaacggua gcgcgucuga cuucagauca gaagguugcg uguucaaauc    60
acaucggggu ca                                                      72

<210> SEQ ID NO 631
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
gaccucgugg ugcaacggua gcgcguauga uuucagauca gaagguugcg uguucaaauc    60
acgucggggu ca                                                      72

<210> SEQ ID NO 632
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 632
gaccucguag cgcaacggua gcgcgucuga cuucagauca gaagguugcg uguucaaauc    60
acgucggggu ca                                                       72

<210> SEQ ID NO 633
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
aggggauaag cucaauuggc agagcgucgg ucuucaaaac cgaagguugu agguucgauu    60
ccuacugccc cugcca                                                   76

<210> SEQ ID NO 634
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
gaccucaugg cgcaacggua gcgcgucuga cuucagauca gaagguugcg uguucaaauc    60
acgucggggu ca                                                       72

<210> SEQ ID NO 635
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
gaccucgugg cgcaacggua gcgcgucuaa cuucagauca gaagguugcg uguucaaauc    60
acgucggggu ca                                                       72

<210> SEQ ID NO 636
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
acgggaguag cucaguuggu agagcaccgg ucuucaaaac cggguqucgg gaguucgagc    60 cucuccuccc gug                                                      73

<210> SEQ ID NO 637
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 637
gaccucgugg cgcaacggua gcgcgucuga cuucagauca gaagguugca uguucaaauc    60
acgucggggu ca    72

<210> SEQ ID NO 638
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
gacuccgugg cgcaacggua gcgcguccga cuucagaucg gaagguugcg uguucaaauc    60
acgucggggu ca    72

<210> SEQ ID NO 639
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
gacuccgugg cgcaacggua gcgcgucuga cuucagauca gaagguugcg uguucaaauc    60
acgucggggu ca    72

<210> SEQ ID NO 640
<211> LENGTH: 72
<212> TYPE: RNA
<213> ORGANISM: Unknown
<220> FEATURE:
<223> OTHER INFORMATION: Description of Unknown:
      TrpChr7.tRNA3-WT sequence

<400> SEQUENCE: 640
ggccucgugg cgcaacggua gcgcgucuga cuccagauca gaagguugcg uguucaaauc    60
acgucggggu ca    72

<210> SEQ ID NO 641
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
ggccucgugg cgcaacggua gcacgucuga cuccagauca gaagguugcg uguucaaauc    60
acgucggggu ca    72

<210> SEQ ID NO 642
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 642
ggccucgucg cgcaacggua gcgcgucuga cuccagauca gaagguugcg uguucaaauc    60
acgucggggu ca    72

<210> SEQ ID NO 643
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
ggccucgugg cgcaacggua gcacgucuga cuucagauca gaagguugcg uguucaaauc    60
acgucggggu ca    72

<210> SEQ ID NO 644
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
ggccucgucg cgcaacggua gcgcgucuga cuucagauca gaagguugcg uguucaaauc    60
acgucggggu ca    72

<210> SEQ ID NO 645
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
ggccucgucg cgcaacggua gcacgucuga cuucagauca gaagguugcg uguucaaauc    60
acgucggggu ca    72

<210> SEQ ID NO 646
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 646

Met Ser Phe Asn Thr Ile Ile Asp Trp Asn Ser Cys Thr Ala Glu Gln
1               5                   10                  15

Gln Arg Gln Leu Leu Met Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
    50                  55                  60

Ala Leu Lys Val Ser Ala Glu Glu Ile Ala Ala Ser Glu Arg Leu
65                  70                  75                  80

Ser Asp Glu Leu Lys Gln Ala Met Ala Val Ala Val Lys Asn Ile Glu
                85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
        115                 120                 125

Leu Tyr Ile Pro Gly Gly Ser Ala Pro Leu Phe Ser Thr Val Leu Met
    130                 135                 140

Leu Ala Thr Pro Ala Ser Ile Ala Gly Cys Lys Lys Val Val Leu Cys
145                 150                 155                 160

Ser Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Ala Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Leu Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Leu Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala His His His His His His Ser Gly Gly Ser Ala Trp
        435                 440                 445

Ser His Pro Gln Phe Glu Lys
    450                 455

<210> SEQ ID NO 647
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 647

His His His His His His His
1               5

<210> SEQ ID NO 648
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Lys Pro Ile Asn Gln Trp Pro Ala Asn Thr His Glu Arg
1               5                   10

<210> SEQ ID NO 649
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
taatacgact cactatagag cgctccggtt tttctgtgct gaacctcagg ggacgccgac      60
acacgtacac gtc                                                        73

<210> SEQ ID NO 650
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
tagtcttcgg                                                            10

<210> SEQ ID NO 651
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
aagaagaccg                                                            10

<210> SEQ ID NO 652
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652 gtccttttt tgctttagtg agggttaatt                                       30

<210> SEQ ID NO 653
<211> LENGTH: 59
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 653
gaattcttcc cgagacgttc caagtcttca tgaagactac aggcgtctcc caggaagct      59

<210> SEQ ID NO 654
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
attatgctga gtgatatccg gagcaccgcg ttgccatcgc gcagactgaa gtctagtctt      60
ccaacgcaca agtttagtgc agccccagtg gt                                   92

<210> SEQ ID NO 655
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
attatgctga gtgatatcgc aaccaccata taccaatcgt atcgaggaag tttcgtaact      60
gggcccaagc taagggccgg ttgcgtggt                                       89
```

METHODS OF RESCUING STOP CODONS VIA GENETIC REASSIGNMENT WITH ACE-TRNA

PRIORITY OF INVENTION

This application claims priority to U.S. Provisional Application No. 62/580,887 that was filed on Nov. 2, 2017, and to U.S. Provisional Application No. 62/687,015 that was filed on Jun. 19, 2018. The entire content of the applications referenced above are hereby incorporated by reference herein.

STATEMENT REGARDING FEDERALLY SPONSORED RESEARCH

This invention was made with government support under R01 GM106569 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 19, 2018, is named 17023_215WO1_SL.txt and is 206,544 bytes in size.

BACKGROUND

DNA molecules carry genetic information in the form of the sequence of the nucleotide bases that make up the DNA polymer. Only four nucleotide bases are utilized in DNA: adenine, guanine, cytosine, and thymine. This information, in the form of codons of three contiguous bases is transcribed into messenger RNA (mRNA), and then translated by transfer RNA (tRNA) and ribosomes to form proteins. Four nucleotide bases are utilized in RNA: adenine, guanine, cytosine, and uracil. The genetic code is the relation between a triplet codon and a particular amino acid. Sixty-four possible codon triplets form the genetic code, where three stop (also called terminating) codons, which provide a signal to the translation machinery (cellular ribosomes) to stop protein production at the particular codon. The other sixty-one triplets in the code correspond to one of the 20 standard amino acid. See FIG. 1.

DNA is translated by ribosomes, causing each amino acid to be linked together one by one to form polypeptides, according to the genetic instructions specifically provided by the DNA. When the ribosome reaches a stop codon, the elongation of the protein terminates. The three stop codons are UAG (amber), UAA (ochre) and UGA (opal). Mutations that occur that change an amino acid-encoding codon to stop codon are called "nonsense mutations." These nonsense mutations can result in a significant truncation/shortening of the polypeptide sequence, and can cause a profound change in genetic phenotype. Thus, even though a gene directing expression may be present, a crucial protein may not be produced because when the ribosome reaches the mutant stop signal, it terminates translation resulting in an unfinished protein.

Transfer RNAs translate mRNA into a protein on a ribosome. Each tRNA contains an "anti-codon" region that hybridizes with a complementary codon on the mRNA. A tRNA that carries its designated amino acid is called a "charged" tRNA. If the tRNA is one of the 61 amino-acid-associated (i.e., not a stop-signal-associated) tRNAs, it will normally attach its amino acid to the growing peptide. The structural gene of tRNA is about 72-90 nucleotides long and folds into a cloverleaf structure. tRNAs are transcribed by RNA polymerase III and contain their own intragenic split promoters that become a part of the mature tRNA coding sequence (Sharp S. J., Schaack J., Coolen L., Burke D. J. and Soll D., "Structure and transcription of eukaryotic tRNA genes", Crit. Rev. Biochem, 19:107-144 (1985); Geiduschek E. O., and Tocchini-Valentini, "Transcription by RNA polymerase III, Annu. Rev. Biochem. 57:873-914 (1988)).

"Nonsense suppressors" are alleles of tRNA genes that contain an altered anticodon, such that instead of triggering a "stop" signal, they insert an amino acid in response to a termination codon. For example, an ochre mutation results in the creation of a UAA codon in an mRNA. An ochre suppressor gene produces tRNA with an AUU anticodon that inserts an amino acid at the UAA site, which permits the continued translation of the mRNA despite the presence of a codon that would normally trigger a stop in translation.

A number of nonsense suppressor tRNA alleles have been identified in prokaryotes and eukaryotes such as yeast and *C. elegans*. The different suppressor tRNAs vary in their suppression efficiency. In *E. coli* and other systems, the amber suppressors are relatively more efficient, ochre suppressors are less efficient while opal are the least, this suggests that the amber codons are used infrequently to terminate protein synthesis, while ochre and opal codons are more frequently used as natural termination signals.

Unwanted errors in the DNA blueprint can cause disease. For example, the occurrence of an unexpected "stop" signal in the middle of the protein, rather than at the end of the blueprint, results in the production of a truncated or shortened protein that has an altered function, or no function at all. Many human diseases, such as cystic fibrosis, muscular dystrophy, β-thalassemia and Liddle's syndrome result from unwanted stop signals in DNA reading frames for proteins that are important for proper lung, blood, muscle or kidney function, respectively.

Accordingly, there is a need to provide novel modified nonsense suppressor tRNAs that are stabilized as compared to corresponding unmodified nonsense suppressor tRNAs, and nonsense suppressor tRNAs that have an increased activity to suppress termination of genes associated with cystic fibrosis.

SUMMARY

In certain embodiments, the present invention provides a modified transfer RNA (tRNA) comprising a T-arm, a D-arm, an anticodon arm and an acceptor arm, wherein the T-arm comprises a T-stem having nucleotides that interact with Elongation Factor 1-alpha 1 (EF1alpha). EF1alpha recruits aminoacyl-tRNA to the ribosome and protects the tRNA from being deacylated. Rational nucleotide replacement results in a tuned tRNA: EF1α interaction that enhances tRNA delivery to the ribosome and protection from deacylation.

In certain embodiments, the present invention provides a modified transfer RNA (tRNA) of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55, wherein the thymidines are replaced with uracils.

In certain embodiments, the present invention provides a modified transfer RNA (tRNA) of any one of SEQ ID NO: 1-538, wherein the thymidines are replaced with uracils.

In certain embodiments, the modified tRNA is any one of SEQ ID NOs: 56-60, 62-66, 84-86, 90-111, 113, 128-143, 147-149, 153-156, 161-174, 176, 178, 181, 184-186, 192, 196-197, 199-201, 205, 213-240, 246, 255-256, 258-285, 299, 305-312, 314, 318-332, 335-344, 346, 350-354, 357-360, 362, 365-370, 372-383, 388-390, 392, 394-401, 403-407, 414-416, 418, 422, 425, 428-433, 437, 444-445, 452, 455, 459-463, 470, 472-474, 476, 487-492, 525, 530-539, 545-550, 553-555, 561-563, and 567-579, wherein the thymidines are replaced with uracils.

In certain embodiments, the present invention provides a modified transfer RNA (tRNA) comprising a T-stem, a D-stem, an anticodon-loop and an acceptor stem, wherein (a) wherein the anticodon-arm comprises a tri-nucleotide anticodon, wherein the anticodon is 5'-UCA-3' and recognizes TGA stop codons, and wherein the acceptor arm is operably linked to a arginine, tryptophan or glycine; (b) wherein the anticodon-arm comprises a tri-nucleotide anticodon, wherein the anticodon is 5'-UUA-3' and recognizes TAA stop codons, and wherein the acceptor arm is operably linked to a glutamine or, glutamate; or (c) wherein the anticodon-arm comprises a tri-nucleotide anticodon, wherein the anticodon is 5'-CUA-3' and recognizes TAG stop codons, and wherein the acceptor arm is operably linked to a tryptophan, glutamate or glutamine. In certain embodiments, the T-arm comprises rationally altered nucleotide sequences that tune the interaction with the EF1α, enhancing its suppression activity and thereby increasing its therapeutic potential. tRNAs with tuned interaction with the EF1alpha have enhanced nonsense suppression and provide enhanced therapeutic properties.

In certain embodiments, the present invention provides an oligonucleotide sequence that encodes the modified tRNA as described above, wherein the oligonucleotide has a total length of less than 150 nucleotides. In certain embodiments, the oligonucleotide is DNA.

In certain embodiments, the present invention provides an oligonucleotide comprising a first oligonucleotide sequence and a second oligonucleotide sequence, wherein the first and second oligonucleotide sequences independently encode a modified tRNA as described above, wherein the first and second oligonucleotides independently have a total length of less than 150 nucleotides, and wherein the two sequences are in tandem.

In certain embodiments, the present invention provides an expression cassette comprising a promoter and a nucleic acid encoding the modified tRNA or oligonucleotides as described above.

In certain embodiments, the present invention provides a vector comprising the oligonucleotide or the expression cassette described above.

In certain embodiments, the vector is a viral or plasmid vector.

In certain embodiments, the present invention provides a composition comprising a modified tRNA, an oligonucleotide, or a vector described above, and a pharmaceutically acceptable carrier.

In certain embodiments, the carrier is a liposome.

In certain embodiments, the invention provides a cell comprising the vector described above.

The present invention provides a method of treating a stop-codon-associated genetic disease, comprising administering the modified tRNA composition described above to a patient in need thereof.

In certain embodiments, the genetic disease associated with a premature stop codon is cystic fibrosis, muscular dystrophy, β-thalassemia or Liddle's syndrome.

In certain embodiments, the present invention provides a method of restoring translation to a nucleotide sequence that includes a nonsense mutation in a cell, comprising introducing to the cell the composition described above.

In certain embodiments, the present invention provides a method of identifying anti-codon edited (ACE) tRNAs by high-throughput cloning and screening using suppression of a nonsense codon in luciferase enzymes including NanoLuc.

BRIEF DESCRIPTION OF DRAWINGS

FIG. 2 discloses SEQ ID NO: 580.

FIG. 3 discloses SEQ ID NO: 581.

FIG. 6A. Schematic of the Anti-Codon Edited (ACE) Trp tRNA and cherry-TGA-eGFP-HA construct. FIG. 6B. Rescue of the cherry TGA eGFP-HA construct by ACE tryptophan tRNA #4.

FIG. 10A) Co-expression of model protein histidinol dehydrogenase (HDH)-His-Strep N94-TGA and ACE-tRNA$_{Trp}$ (left) and ACE-tRNA$_{Gly}$ (right) results in full-length HDH protein (asterisks) that is detectable by silver stain following affinity purification. FIG. 10B) Spectra of WT HDH (top), HDH-N94+ACE-tRNA$_{Gly}$ (middle), and HDH-N94+ACE-tRNA$_{Trp}$ (bottom). Spectra highlight amino acid mass differences at position N94 that match specifically with Glycine (−57 Da) and Tryptophan (+72 Da), indicating insertion of ACE-tRNA cognate amino acids. FIG. 10B discloses SEQ ID NOS 582-585, 584, 583 and 586, respectively, in order of appearance.

FIG. 11 discloses SEQ ID NOS 587-588, respectively, in order of appearance.

FIG. 12A. Trpchr17.tRNA 39 was systematically mutagenized within the t-stem region. FIG. 12A discloses SEQ ID NO: 581. These efforts identified ACE tRNA TS-10 52-62 G-C, (FIG. 12B) and cross-hatched bar in plot, which displays ~250% increased biological activity. FIG. 12B discloses SEQ ID NO: 589.

FIGS. 13A-13F. ACE-tRNAs are selective for nonsense codons and more efficient than aminoglycoside nonsense suppression. FIG. 13A) ACE-tRNA$_{Trp}$#5 and FIG. 13B) ACE-tRNA$_{Gly}$#16 were cloned into NanoLuc reporter plasmids containing TGA, TAA or TAG nonsense codons. Nonsense suppression was only measured in NanoLuc-TGA constructs following transfection. FIG. 13C & FIG. 13D) Suppression of NanoLuc-TGA by addition of gentimicin (40 uM) and G418 (150 uM) and co-transfection with ACE-tRNA$_{Trp}$#5 and ACE-tRNA$_{Gly}$#16, was measured at FIG. 13C) 24 and FIG. 13D) 48 hrs in HEK293 cells. FIG. 13E & FIG. 13F) HEK293 cells stably expressing NanoLuc-TGA were treated with gentimicin (40 uM) and G418 (150 uM) and transfected with ACE-tRNA$_{Trp}$#5 and ACE-tRNA$_{Gly}$#16. Nonsense suppression was measured at FIG. 13E) 24 and FIG. 13F) 48 hrs post treatment.

FIG. 20A) CFTR cRNA with G542X or W1282X cystic fibrosis causing nonsense mutations was co-injected in Xenopus oocytes with serial dilutions of pre-folded ACE-tRNAGly and ACE-tRNATrp, respectively. Two-electrode voltage-clamp recordings of CFTR Cl-current were performed after 36 hrs. Current-voltage relationships illustrate that increasing amounts of FIG. 20B) ACE-tRNATrp and FIG. 20C) ACE-tRNAGly pre-folded RNA results in increased CFTR function (measured CFTR Cl-currents) with WT CFTR achieved in ACE-tRNAGly experiments. FIG. 20D) Dose response of G542X ACE-tRNAGly (filled circles) and W1282X ACE-tRNATrp (open squares) rescue (CFTR Cl-currents elicited at +40 mV were normalized to WT CFTR Cl-currents at +40 mV). The dose dependence of ACE-tRNAGly (EC50=~20 ng; Hill coefficient ~1.4) shows clear saturation at WT CFTR levels, while ACE-tRNATrp is right shifted (EC50=~94 ng; Hill coefficient 1.24).

FIGS. 21A-21B. A nonsense mutation suppression screen to identify candidate anticodon edited tRNAs (ACE-tRNAs). FIG. 21A, Schematic illustrates requisite interactions of ACE-tRNAs with translational machinery. Following delivery, ACE-tRNAs are recognized by an endogenous aminoacyl-tRNA synthetase and charged (aminoacylated) with their cognate amino acid. The aminoacylated ACE-tRNA is recognized by the endogenous elongation factor 1-alpha, which protects the ACE-tRNA from being de-acylated and delivers the aminoacyl ACE-tRNA to the ribosome for suppression of a premature termination codon, in this instance UGA. FIG. 21B, Individual ACE-tRNAs were cloned into the High Throughput Cloning Nonsense Reporter plasmid using Golden Gate paired with CcdB negative selection. The all-in-one plasmid contains the NLuc luciferase reporter with either a UGA, UAG or UAA PTC at p.162 between the enzymatic large bit and requisite C-terminal small bit.

FIG. 23A, Tryptic fragment of histidinol dehydrogenase (HDH), where "X" indicates suppressed PTC codon. MS/MS spectra of the tryptic fragment with masses of indicated y and b ions for WT (top), N94G (middle) and N94W (bottom) HDH. b9 ion mass is shifted by the predicted mass of −57 Da and +72 Da from the WT asparagine, indicating the encoding of cognate amino acids glycine and tryptophan by ACE-tRNA$^{Gly}$ and ACE-tRNA$^{Trp}$, respectively. FIG. 23A discloses SEQ ID NOS 590, 583-585, 584, 583 and 586, respectively, in order of appearance. FIG. 23B, ACE-TGA-tRNA$^{Gly}$ (Glychr19.t2) selectively suppresses the UGA stop codon in transiently transfected HEK293 cells. FIG. 23C) ACE-tRNA$^{Gly}$ transfection outperforms both gentamicin (40 uM) and G418 (140 uM) following a 48 hr incubation in Hek293 cells stably expressing NLuc-UGA.

FIG. 24A, Ribosome footprint densities on 3'UTRs are plotted as log 2-fold change for reads of treated cells versus control (puc57GG empty vector) as described in the materials and methods. Transcripts were grouped by their endogenous TAA, TAG, and TGA stop codons. Each point represents the mean of two replicates for a transcript. Error bars show Mean±SD of the log 2-fold changes. FIG. 24B, The average log 2-fold change of normalized ribosome footprint occupancy was plotted for each nucleotide from −50 to +50 nt surrounding stop codons of transcriptome (18,101 sequences). The cartoon illustrates the ~15 nt offset from the 5' end of ribosome footprint to the first base position of stop codon in the ribosome A-site.

FIG. 25. Codon usage for common PTC. Cross-hatching indicates the most common codons and corresponding amino acid type that can be converted to stop codons via nucleotide substitution. Engineered tRNA have been developed for each type.

FIG. 27 discloses SEQ ID NOS 591-611, respectively, in order of appearance.

FIGS. 29A-29C. Analysis of ACE-tRNA$^{Trp}$ sequences from multiple species and suppressor tRNA mutations. FIGS. 29A-29B. Sequence alignment. FIG. 29A discloses SEQ ID NOS 612-645, respectively, in order of appearance. FIG. 29C. NLuc-UGA+ACE-tRNA$^{Trp}$/NLuc-UGA.

FIGS. 30A-30C. Histidinol dehydrogenase (HDH) His (8)-streptactin expression construct ("His(8)" disclosed as SEQ ID NO: 647) allows for efficient one-step isolation of protein from HEK293 cells. FIG. 30A) Protein sequence of HDH expression construct. Underlined sequence indicates coverage by mass spectrometry. The bold, underlined asparagine (amino acid position 94) is the residue mutated to a TGA PTC for determining ACE-tRNA fidelity. The dual affinity tag is indicated in bold italics. FIG. 30A discloses SEQ ID NO: 646. Silver stain of HDH protein following PTC suppression with FIG. 30B) Trpchr17.trna39 and FIG. 30C) Glychr19.trna2.

FIG. 32A) Raw and FIG. 32B) normalized luminescence measured 24 hrs following addition of gentamicin (40 uM), G418 (150 uM) and transfection with Trpchr17.trna39 and Glychr19.trna2 in HEK293 cells stably expressing PTC reporter Nluc-UGA. FIG. 32C) Raw and FIG. 32D) normalized luminescence measured 24 hrs following addition of gentamicin (40 uM), G418 (150 uM) and co-transfection with Trpchr17.trna39 and Glychr19.trna2 in HEK293 cells.

DETAILED DESCRIPTION OF THE INVENTION

Figures 1, 2:
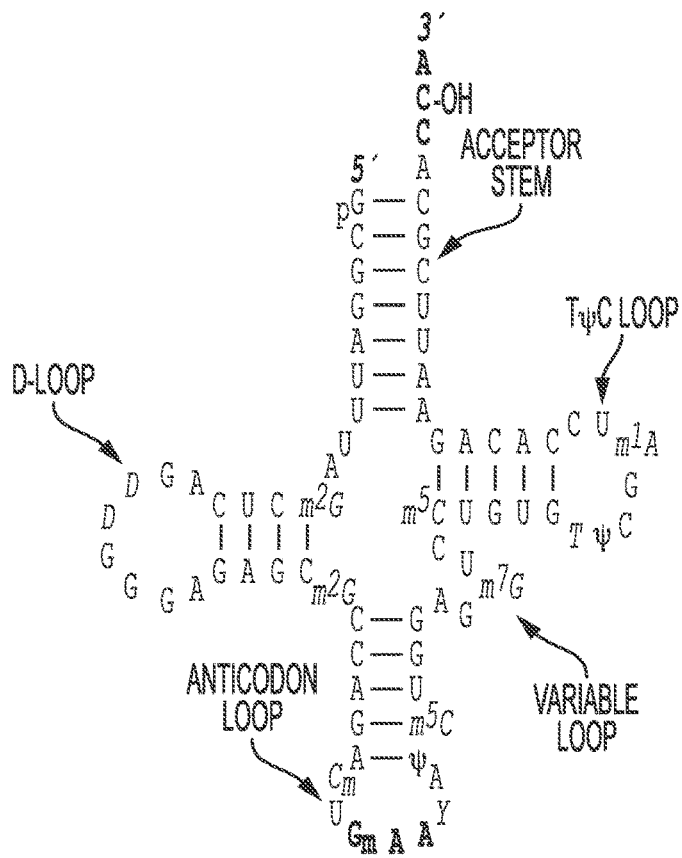
FIG. 1. Table of the Genetic Code.
FIG. 2. tRNAs have a general four-arm structure comprising a T-arm, a D-arm, an anticodon-arm, and an acceptor arm. These arms are also referred to as 'loops' throughout.

Over the years, researchers have identified hundreds of unique point mutations that resulted in nonsense codons being established in human genes. These types of mutations result, for example, in muscular dystrophy, xeroderma pigmentosum, cystic fibrosis, hemophilia, anemia, hypothyroidism, p53 squamal cell carcinoma, p53 hepatocellular carcinoma, p53 ovarian carcinoma, esophageal carcinoma, osteocarcinoma, ovarian carcinoma, esophageal carcinoma, hepatocellular carcinoma, breast cancer, hepatocellular carcinoma, fibrous histiocytoma, ovarian carcinoma, SRY sex reversal, triosephosphate isomerase-anemia, diabetes and rickets. The BRACA-1 and BRACA-2 genes associated with breast cancer also have similar mutations.

The nucleotide sequences encoding several hundred human tRNAs are known and generally available to those of skill in the art through sources such as Genbank. The structure of tRNAs is highly conserved and tRNAs are often functional across species. Thus, bacterial or other eukaryotic tRNA sequences are also potential sources for the oligonucleotides for the stabilized tRNAs of the invention. The determination of whether a particular tRNA sequence is functional in a desired mammalian cell can be ascertained through routine experimentation. Further additional potential tRNA sequences that are not yet known can be modified as described herein in order to be stabilized through routine experimentation.

tRNA genes have strong promoters that are active in all cell types. The promoters for eukaryotic tRNA genes are contained within the structural sequences encoding the tRNA molecule itself. Although there are elements that regulate transcriptional activity within the 5' upstream region, the length of an active transcriptional unit may be considerably less than 500 base pairs and thus accommodation within a delivery vector is straightforward. Once they have been transcribed and processed, tRNAs have low rates of degradation. Finally, gene therapy with a nonsense suppressor maintains the endogenous physiological controls over the target gene that contains the nonsense codon.

Nonsense Mutations

Transfer RNA (tRNA) is a type of RNA molecule that functions in the decoding of a messenger RNA (mRNA) sequence into a protein. tRNAs function at specific sites in the ribosome during translation, which synthesizes a protein from an mRNA molecule. Nonsense mutations, also called Premature Termination Codons (PTCs), make up ~10-15% of the single base pair mutations that cause human disease, and cystic fibrosis follows suit. (Peltz et al., Annu Rev Med., 64:407-25, 2013). In general, nonsense mutations have more serious ramifications than missense mutations because of the almost complete loss of gene expression and activity and with the possibility of dominant negative effects of truncated products. PTCs result in premature translation termination and accelerated mRNA transcript decay through the Nonsense Mediated Decay (NMD) pathway.

The current studies show that the specific site within an RNA transcript to which a tRNA delivers its amino acid can be changed through molecular editing of the anti-codon sequence within the tRNA. This approach allowed for a premature termination codon (PTC) to be effectively and therapeutically reverted back into the originally lost amino acid. Anticodon-edited tRNA (ACE-tRNA) form a new class of biological therapeutics.

Engineered tRNAs allow for "re-editing" of a disease-causing nonsense codon to a specific amino acid. These engineered tRNAs target only one type of stop codon, such as TGA over TAC or TAA. The small size of these tRNA molecules makes them amenable to ready expression, as the tRNA+the promoter is only ~300 bp. Briefly, an oligonucleotide is synthesized that comprises the structural component of a tRNA gene functional in human cells. The sequence of this oligonucleotide is designed based upon the known sequence with substitutions made in the anticodon region of the tRNA causing the specific tRNA to recognize a nonsense or other specific mutation.

Several small molecule screens have been performed to suppress nonsense stop codons through interactions with the ribosome, the most outstanding molecules being G418, Gentamicin and PTC124. PTC124 or Ataluren has recently been relieved from Phase 3 clinical trials as use for a cystic fibrosis therapeutic. Ataluren and aminoglycosides promote read-through of each of the three nonsense codons by putting in a near cognate amino acid that turn a nonsense mutation into a missense mutation. (Roy et al., PNAS 2016 Nov. 1; 113(44):12508-12513)

Anticodon-Edited tRNA (ACE-tRNA)

tRNAs have a general four-arm structure comprising a T-arm, a D-arm, an anticodon-arm, and an acceptor arm (FIG. 2).

The T-arm is made up of a "T-stem" and a "TΨPC loop." In certain embodiments, the T-stem is modified to increase the stability of the tRNA. In certain embodiments, the ACE-tRNA has a modified T-stem that increases the biological activity to suppress stop sites relative to the endogenous T-stem sequence.

The present invention in one embodiment includes compositions comprising stabilized tRNAs, which can be used with higher effectiveness in order to treat a wide variety of nonsense mutation-associated diseases. The following sequences in Tables 1-8 are written as DNA, but as RNA (transcribed DNA) the "T:thymidine" is "U:uracil." Therefore, tRNAs transcribed from the following sequences all contain uracils in place of the thymidines.

In certain embodiments, the tRNA has the following sequences (wherein the thymidines are replaced with uracils):

TS-36:
(SEQ ID NO: 1)
GGCCTCGTGGCGCAACGGTAGCGCGTCTGACTtCAGATCAGAAGGtT

GCGgGTTCAAATCcCGTCGGGGTCA

TS-37:
(SEQ ID NO: 2)
GGCCTCGTGGCGCAACGGTAGCGCGTCTGACTtCAGATCAGAAGGtT aCGgGTTCAAATCcCGTCGGGGTCA

TS-38:
(SEQ ID NO: 3)
GGCCTCGTGGCGCAACGGTAGCGCGTCTGACTtCAGATCAGAAGGtT cCGgGTTCAAATCcCGgCGGGGTCA

TABLE 1

| Ranking | Identifier | Sequence | SEQ ID NO. |
|---|---|---|---|
| #1 | ArgTGAchr9.trna6/ nointron | CGTCGGCTCTGTGGCGCAATGGATAGCGCATTGGACTTC AAATTCAAAGGTTGTGGGTTCGAGTCCCACCAGAGTCG | 4 |
| #2 | ArgTGAchr17.trna19 | CGTCGCCCCAGTGGCCTAATGGATAAGGCACTGGCCTTC AAAGCCAGGGATTGTGGGTTCGAGTCCCACCTGGGGTG | 5 |
| #3 | ArgTGAchr1.trna10/ nointron | CGTCGGCTCCGTGGCGCAATGGATAGCGCATTGGACTTC AAATTCAAAGGTTCCGGGTTCGAGTCCCGGCGGAGTCG | 6 |
| #4 | ArgTGAchr7.trna5 | CGTCGCCCCAGTGGCCTAATGGATAAGGCATTGGCCTTC AAAGCCAGGGATTGTGGGTTCGAGTCCCATCTGGGGTG | 7 |
| #4 | ArgTGAchr17.trna3/ nointron | CGTCGGCTCTGTGGCGCAATGGATAGCGCATTGGACTTC AAATTCAAAGGTTGTGGGTTCGAATCCCACCAGAGTCG | 8 |
| #5 | ArgTGAchr9.trna6/ withintron | CGTCGGCTCTGTGGCGCAATGGATAGCGCATTGGACTTC AAGCTGAGCCTAGTGTGGTCATTCAAAGGTTGTGGGTTC GAGTCCCACCAGAGTCG | 9 |
| #5 | ArgTGAchr16.trna3 | CGTCGCCCCGGTGGCCTAATGGATAAGGCATTGGCCTTC AAAGCCAGGGATTGTGGGTTCGAGTCCCACCCGGGGTA | 10 |
| #6 | ArgTGAchr1.trna10/ withintron | CGTCGGCTCCGTGGCGCAATGGATAGCGCATTGGACTTC AAGAGGCTGAAGGCATTCAAAGGTTCCGGGTTCGAGTCC CGGCGGAGTCG | 11 |
| #7 | ArgTGAchr17.trna3/ withinron | CGTCGGCTCTGTGGCGCAATGGATAGCGCATTGGACTTC AAGTGACGAATAGAGCAATTCAAAGGTTGTGGGTTCGAA TCCCACCAGAGTCG | 12 |
|  | ArgTGAchr15.trna4 | CGTCGGCCGCGTGGCCTAATGGATAAGGCGTCTGACTTC AGATCAGAAGATTGCAGGTTCGAGTCCTGCCGCGGTCG | 13 |
|  | ArgTGAchr17.trna17 | CGTCGACCGCGTGGCCTAATGGATAAGGCGTCTGACTTC AGATCAGAAGATTGAGGGTTCGAGTCCCTTCGTGGTCG | 14 |
|  | ArgTGAchr11.trna3/ withintron | CGTCGGCTCTGTGGCGCAATGGATAGCGCATTGGACTTC AAGATAGTTAGAGAAATTCAAAGGTTGTGGGTTCGAGTC CCACCAGAGTCG | 15 |

TABLE 2

| Ranking | Identifier | Sequence | SEQ ID NO. |
|---|---|---|---|
| #1 | GlnTAGchr1. trna17 | CGTCGGTTCCATGGTGTAATG GTgAGCACTCTGGACTctaAA TCCAGCGaTCCGAGTTCGAGT CTCGGTGGAACCT | 16 |
| #2 | GlnTAGchr6. trna175 | CGTCGGCCCCATGGTGTAATG GTtAGCACTCTGGACTctaAA TCCAGCGaTCCGAGTTCAAAT CTCGGTGGGACCT | 17 |
| #3 | GlnTAGchr6. trna63 | CGTCGGTCCCATGGTGTAATG GTtAGCACTCTGGACTctaAA TCCAGCAaTCCGAGTTCGAAT CTCGGTGGGACCT | 18 |

TABLE 2-continued

| Ranking | Identifier | Sequence | SEQ ID NO. |
|---|---|---|---|
| #4 | GlnTAGchr17.trna14 | CGTCGGTCCCATGGTGTAATG GTtAGCACTCTGGACTctaAA TCCAGCGaTCCGAGTTCAAAT CTCGGTGGACCT | 19 |
| #5 | GlnTAGchr6.trna132 | CGTCGGCCCCATGGTGTAATG GTcAGCACTCTGGACTctaAA TCCAGCGaTCCGAGTTCAAAT CTCGGTGGACCC | 20 |
|  | GlnTAGchr1.trna101 | CGTCGGTTCCATGGTGTAATG GTaAGCACTCTGGACTctaAA TCCAGCGaTCCGAGTTCGAGT CTCGGTGGAACCT | 21 |
|  | GlnTAGchr6.trna42 | CGTCGGTTCCATGGTGTAATG GTtAGCACTCTGGACTctaAA TCCGGTAaTCCGAGTTCAAAT CTCGGTGGAACCT | 22 |
|  | GlnTAGchr6.trna147 | CGTCGGTTCCATGGTGTAATG GTtAGCACTCTGGACTctaAA TCCAGCGaTCCGAGTTCAAGT CTCGGTGGAACCT | 23 |

TABLE 3

| Ranking | Identifier | Sequence | SEQ ID NO. |
|---|---|---|---|
| #1 | GlnTAAchr1.trna101 | CGTCGGTTCCATGGTGTAATG GTaAGCACTCTGGACTtaAA TCCAGCGaTCCGAGTTCGAGT CTCGGTGGAACCT | 24 |
| #2 | GlnTAAchr6.trna175 | CGTCGGCCCCATGGTGTAATG GTtAGCACTCTGGACTtaAA TCCAGCGaTCCGAGTTCAAAT CTCGGTGGAACCT | 25 |
| #3 | GlnTAAchr1.trna17 | CGTCGGTTCCATGGTGTAATG GTgAGCACTCTGGACTtaAA TCCAGCGaTCCGAGTTCGAGT CTCGGTGGAACCT | 26 |
| #4 | GlnTAAchr6.trna1 | CGTCGGTTCCATGGTGTAATG GTtAGCACTCTGGACTtaAA TCCAGCGaTCCGAGTTCAAAT CTCGGTGGAACCT | 27 |
| #5 | GlnTAAchr17.trna14 | CGTCGGTCCCATGGTGTAATG GTtAGCACTCTGGACTtaAA TCCAGCGaTCCGAGTTCAAAT CTCGGTGGACCT | 28 |
| #5.2 | GlnTAAchr6.trna63 | CGTCGGTCCCATGGTGTAATG GTtAGCACTCTGGACTtaAA TCCAGCAaTCCGAGTTCAAT CTCGGTGGACCT | 29 |
|  | GlnTAAchr6.trna42 | CGTCGGTTCCATGGTGTAATG GTtAGCACTCTGGACTtaAA TCCGGTAaTCCGAGTTCAAAT CTCGGTGGAACCT | 30 |
|  | GlnTAAchr6.trna132 | CGTCGGCCCCATGGTGTAATG GTcAGCACTCTGGACTtaAA TCCAGCGaTCCGAGTTCAAAT CTCGGTGGACCC | 31 |
|  | GlnTAAchr6.trna147 | CGTCGGTTCCATGGTGTAATG GTtAGCACTCTGGACTtaAA TCCAGCGaTCCGAGTTCAAGT CTCGGTGGAACCT | 32 |

TABLE 4

| Ranking | Identifier | Sequence | SEQ ID NO. |
|---|---|---|---|
| #1 | TrpTAGchr17.trna10 | CGTCGACCTCGTGGCGCAATG GTAGCGCGTCTGACTctAGAT CAGAAGGtTGCGTGTTCAAGT CACGTCGGGGTCA | 33 |
| #2 | TrpTAGchr6.trna171 | CGTCGACCTCGTGGCGCAACG GTAGCGCGTCTGACTctAGAT CAGAAGGtTGCGTGTTCAAAT CACGTCGGGGTCA | 34 |
| #3 | TrpTAGchr17.trna39 | CGTCGGCCTCGTGGCGCAACG GTAGCGCGTCTGACTctAGAT CAGAAGGtTGCGTGTTCAAAT CACGTCGGGGTCA | 35 |
| #4 | TrpTAGchr12.trna6 | CGTCGACCTCGTGGCGCAACG GTAGCGCGTCTGACTctAGAT CAGAAGGcTGCGTGTTCGAAT CACGTCGGGGTCA | 36 |
|  | TrpTAGchr7.trna3 | CGTCGACCTCGTGGCGCAACG GCAGCGCGTCTGACTctAGAT CAGAAGGtTGCGTGTTCAAAT CACGTCGGGGTCA | 37 |

TABLE 5

| Ranking | Identifier | Sequence | SEQ ID NO. |
|---|---|---|---|
| #1 | GluTAGchr13.trna2 | CGTCTCCCACATGGTCTAGCG GTtAGGATTCCTGGTTctaAC CCAGGCGGCCCGGGTTCGACT CCCGGTGTGGGAA | 38 |
| #2 | GluTAGchr2.trna18 | CGTCTCCCATATGGTCTAGCG GTtAGGATTCCTGGTTctaAC CCAGGTGGCCCGGGTTCGACT CCCGGTATGGGAA | 39 |
| #3 | GluTAGchr1.trna123 | CGTCTCCCTGGTGGTCTAGTG GCtAGGATTCGGCGCTctaAC CGCCGCGGCCCGGGTTCGATT CCCGGTCAGGGAA | 40 |
| #4 | GluTAGchr1.trna106 | CGTCTCCCTGGTGGTCTAGTG GTtAGGATTCGGCGCTctaAC CGCCGCGGCCCGGGTTCGATT CCCGGTCAGGGAA | 41 |
|  | GluTAGchr1.trna5 | CGTCTCCCTGGTGGTCTAGTG GCtAGGATTCGGCGCTctaAC CGCCGCGGCCCGGGTTCGATT CCCGGCCAGGGAA | 42 |

TABLE 6

| Ranking | Identifier | Sequence | SEQ ID NO. |
|---|---|---|---|
|  | GluTAAchr13.trna2 | CGTCTCCCACATGGTCTAGCG GTtAGGATTCCTGGTTctaAC CCAGGCGGCCCGGGTTCGACT CCCGGTGTGGGAA | 43 |
|  | GluTAAchr2.trna18 | CGTCTCCCATATGGTCTAGCG GTtAGGATTCCTGGTTctaAC CCAGGTGGCCCGGGTTCGACT CCCGGTATGGGAA | 44 |

TABLE 6-continued

| Ranking | Identifier | Sequence | SEQ ID NO. |
|---|---|---|---|
| | GluTAAchr1.trna106 | CGTCTCCCTGGTGGTCTAGTGGTtAGGATTCGGCGCTctaACCGCCGCGGCCCGGGTTCGATTCCCGGTCAGGGAA | 45 |
| | GluTAAchr1.trna55 | CGTCTCCCTGGTGGTCTAGTGGTtAGGATTCGGCGCTctaACCGCCGCGGCCCGGGTTCGATTCCCGGTCAGGAAA | 46 |
| | GluTAAchr1.trna5 | CGTCTCCCTGGTGGTCTAGTGGCtAGGATTCGGCGCTctaACCGCCGCGGCCCGGGTTCGATTCCCGGCCAGGGAA | 47 |

TABLE 7

| Ranking | Identifier | Sequence | SEQ ID NO. |
|---|---|---|---|
| #1 | TrpTGAchr17.trna39 | GGCCTCGTGGCGCAACGGTAGCGCGTCTGACTtCAGATCAGAAGGtTGCGTGTTCAAATCACGTCGGGGTCA | 48 |
| #2 | TrpTGAchr17.trna10 | GACCTCGTGGCGCAATGGTAGCGCGTCTGACTtCAGATCAGAAGGtTGCGTGTTCAAGTCACGTCGGGGTCA | 49 |
| #3 | TrpTGAchr6.trna171 | GACCTCGTGGCGCAACGGTAGCGCGTCTGACTtCAGATCAGAAGGtTGCGTGTTCAAATCACGTCGGGGTCA | 50 |
| | TrpTGAchr12.trna6 | GACCTCGTGGCGCAACGGTAGCGCGTCTGACTtCAGATCAGAAGGcTGCGTGTTCGAATCACGTCGGGGTCA | 51 |
| | TrpTGAchr7.trna3 | GACCTCGTGGCGCAACGGCAGCGCGTCTGACTtCAGATCAGAAGGtTGCGTGTTCAAATCACGTCGGGGTCA | 52 |

TABLE 8

| Ranking | Identifier | Sequence | SEQ ID NO. |
|---|---|---|---|
| #1 | GlyTGAchr19.trna2 | GCGTTGGTGGTATAGTGGTtAGCATAGCTGCCTTCaAAGCAGTTGaCCCGGGTTCGATTCCCGGCCAACGCA | 53 |
| #2 | GlyTGAchr1.trna107 | GCGTTGGTGGTATAGTGGTgAGCATAGCTGCCTTCaAAGCAGTTGaCCCGGGTTCGATTCCCGGCCAACGCA | 54 |
| #3 | GlyTGAchr17.trna9 | GCGTTGGTGGTATAGTGGTaAGCATAGCTGCCTTCaAAGCAGTTGaCCCGGGTTCGATTCCCGGCCAACGCA | 55 |

Figure 3:
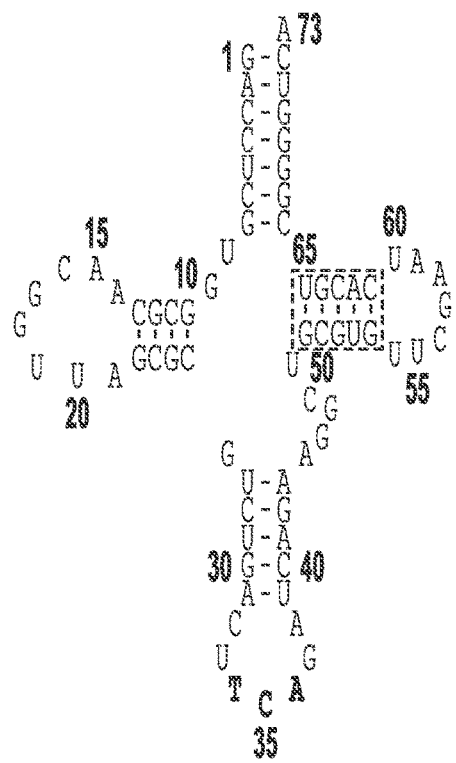
FIG. 3. ACE-tRNA for nonsense suppression (*H. sapiens* tRNA$^{Trp}_{TGA}$).

In one embodiment, the ACE-tRNA for nonsense suppression is as depicted in FIG. 3 (*H. sapiens* tRNA$^{Trp}_{TGA}$).

According to the invention, human UAA, UAG, and UGA suppressor tRNAs have been designed. The screen has identified codon edited tRNA for the repair of Trp-TGA, Trp-TAG, Arg-TGA, Gln-TAG, Gln-TA, Glu-TAG, Glu-TAA. The tRNAs are approximately 100 nucleotides in length and can be introduced to cells to suppress nonsense codons mutations where the wild-type amino acid should be present. The oligonucleotides can be introduced directly to recipient cells or can be ligated in tandem to increase efficacy of the oligonucleotide.

Expression Cassettes and Vectors

In certain embodiments, the ACT-tRNA is encoded by an expression cassette. In yet another embodiment, the suppressor tRNA of the invention may be introduced to the cells using standard conventional genetic engineering techniques through use of vectors. Because of the internal promoter sequences of tRNA encoding sequences, the tRNA sequence need not be included in a separate transcription unit, although one may be provided.

In one embodiment of the present invention, the nucleotide expression system of the invention is included within an appropriate gene transfer vehicle which is then used to transduce cells to express the suppressor tRNA. The gene delivery vehicle can be any delivery vehicle known in the art, and can include naked DNA that is facilitated by a receptor and/or lipid mediated transfection, as well as any of a number of vectors. Such vectors include but are not limited to eukaryotic vectors, prokaryotic vectors (such as for example bacterial vectors) and viral vectors including, but not limited to, retroviral vectors, adenoviral vectors, adeno-associated viral vectors, lentivirus vectors (human and other including porcine), Herpes virus vectors, Epstein-Barr viral vectors, SV40 virus vectors, pox virus vectors, and pseudo-typed viral vectors.

Figure 4:
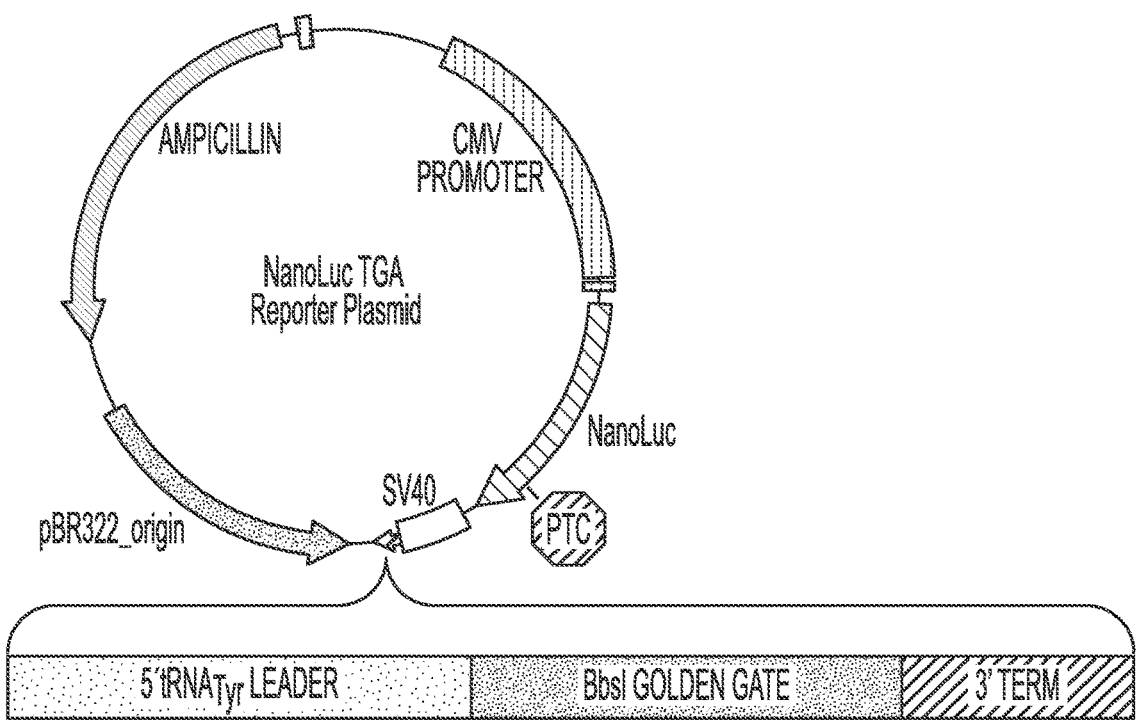
FIG. 4. Anti-codon edited (ACE)-tRNA encoded in a vector used to identify functional ACE tRNA sequences. This vector sequence includes a Nanoluciferase reporter system. The depicted vector was used to identify ACE tRNA with TGA suppression. TAA and TAG variants were used for the appropriate tRNA screens (see FIGS. 14 through 17).
Figure 5:
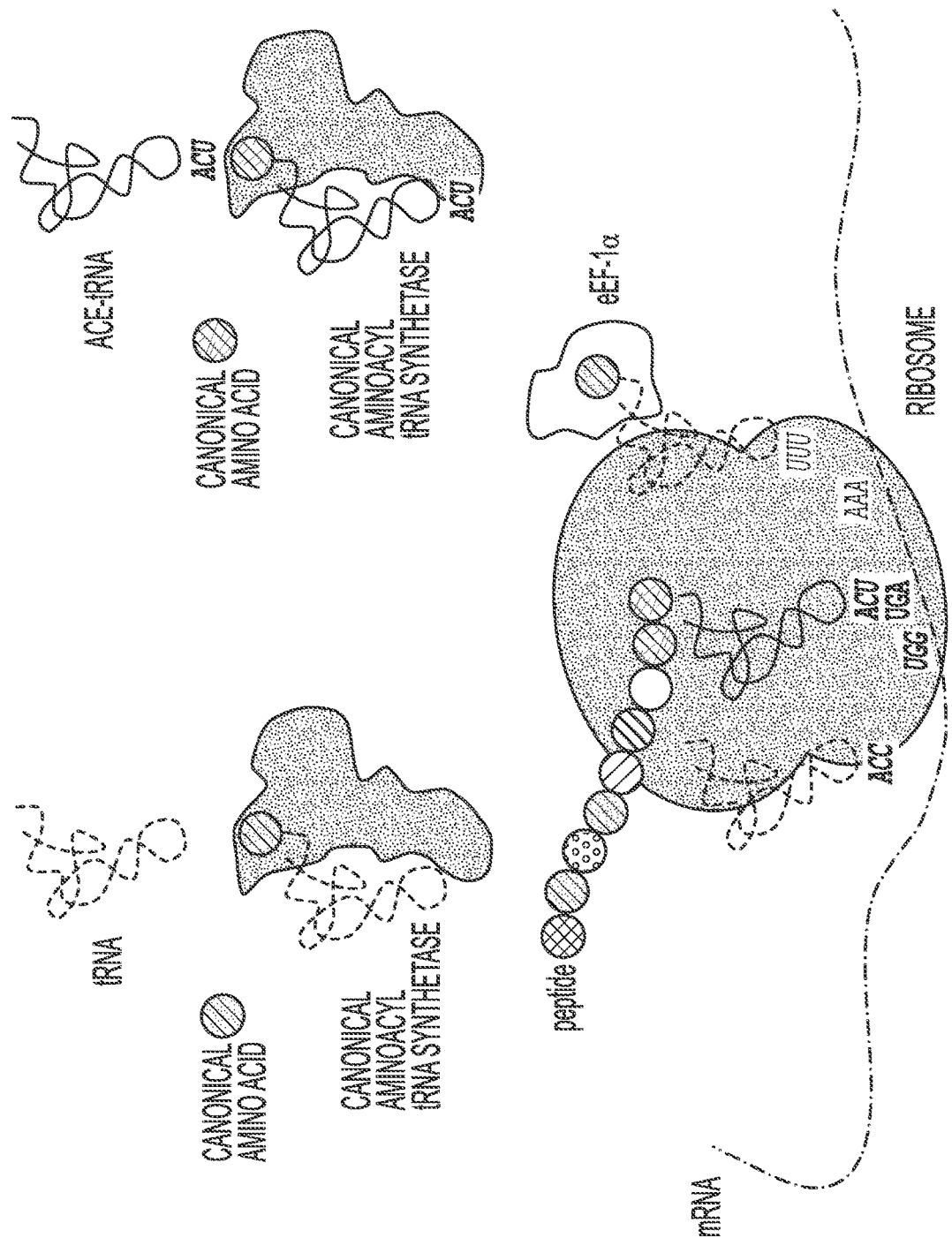
FIG. 5. Schematic of the rescue of proteins and ion channels with stop codons via suppressor tRNA.

In certain embodiments, the ACT-tRNA (PTC) is encoded in a vector. FIG. 4. In certain embodiments, the viral vector is a retroviral or adenoviral vector. Examples of retroviral vectors that may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus.

Retroviruses; Retroviral Vectors

The term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules that encode the structural proteins and enzymes needed to produce new viral particles. At each end of the provirus are structures called "long terminal repeats" or "LTRs." The LTR contains numerous regulatory signals including transcriptional control elements, polyadenylation signals and sequences needed for replication and integration of the viral genome. There are several genera included within the family Retroviridae, including Cisternavirus A, Oncovirus A, Oncovirus B, Oncovirus C, Oncovirus D, Lentivirus, and Spumavirus. Some of the retroviruses are oncogenic (i.e., tumorigenic), while others are not. The oncoviruses induce sarcomas, leukemias, lymphomas, and mammary carcinomas in susceptible species. Retroviruses infect a wide variety of species, and may be transmitted both horizontally and vertically. They are integrated into the host DNA, and are capable of transmitting sequences of host DNA from cell to cell. This has led to the development of retroviruses as vectors for various purposes including gene therapy.

Retroviruses, including human foamy virus (HFV) and human immunodeficiency virus (HIV) have gained much recent attention, as their target cells are not limited to dividing cells and their restricted host cell tropism can be readily expanded via pseudotyping with vesicular stomatitis virus G (VSV-G) envelope glycoproteins (See e.g., J. C. Burns et al., Proc. Natl. Acad. Sci. USA 90:8033-8037 [1993]; A. M. L. Lever, Gene Therapy. 3:470-471 [1996]; and D. Russell and A. D. Miller, J. Virol., 70:217-222 [1996]).

Vector systems generally have a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (D. Markowitz et al., J. Virol., 62:1120 [1988]). In one embodiment of the present invention, an FIV system employing a three-plasmid transfection production method in 293T cells was used (Johnston et al., J Virol. 1999 73:4991-5000). Replication incompetent virus was successfully produced.

The vector DNA is introduced into the packaging cell by any of a variety of techniques (e.g., calcium phosphate coprecipitation, lipofection, electroporation). The viral proteins produced by the packaging cell mediate the insertion of the vector sequences in the form of RNA into viral particles, which are shed into the culture supernatant.

For cells that are naturally dividing, or are stimulated to divide by growth factors, simple retroviruses like murine leukemia virus (MLV) vectors are suitable delivery systems. A major limitation in the use of many commonly used retroviral vectors in gene transfer, however, is that many of the vectors are restricted to dividing cells. If a non-dividing cell is the target cell, then a lentivirus, which is capable of infecting non-dividing cells, may be used.

As used herein, the term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, that causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells).

Lentiviruses including HIV, SIV, FIV and equine infectious anemia virus (EIAV) depend on several viral regulatory genes in addition to the simple structural gag-pol-env genes for efficient intracellular replication. Thus, lentiviruses use more complex strategies than classical retroviruses for gene regulation and viral replication, with the packaging signals apparently spreading across the entire viral genome. These additional genes display a web of regulatory functions during the lentiviral life cycle. For example, upon HIV-1 infection, transcription is up-regulated by the expression of Tat through interaction with an RNA target (TAR) in the LTR. Expression of the full-length and spliced mRNAs is then regulated by the function of Rev, which interacts with RNA elements present in the gag region and in the env region (RRE) (S. Schwartz et al., J. Virol., 66:150-159 [1992]). Nuclear export of gag-pol and env mRNAs is dependent on the Rev function. In addition to these two essential regulatory genes, a list of accessory genes, including vif, vpr, vpx, vpu, and nef, are also present in the viral genome and their effects on efficient virus production and infectivity have been demonstrated, although they are not absolutely required for virus replication (K. and F. Wong-Staal, Microbiol. Rev., 55:193-205 (1991]; R. A. Subbramanian and E. A. Cohen, J. Virol. 68:6831-6835 [1994]; and D. Trono, Cell 82:189-192 [1995]). A detailed description of the structure of an exemplary lentivirus, HIV-1, is given in U.S. Pat. No. 6,531,123.

A "source" or "original" retrovirus is a wild-type retrovirus from which a pseudotyped retrovirus is derived, or is used as a starting point, during construction of the packaging or transgene vector, for the preparation of one or more of the genetic elements of the vector. The genetic element may be employed unchanged, or it may be mutated (but not beyond the point where it lacks a statistically significant sequence similarity to the original element). A vector may have more than one source retrovirus, and the different source retroviruses may be, e.g., MLV, FIV, HIV-1 and HIV-2, or HIV and SIV. The term "genetic element" includes but is not limited to a gene.

A cognate retrovirus is the wild-type retrovirus with which the vector in question has the greatest percentage sequence identity at the nucleic acid level. Normally, this will be the same as the source retrovirus. However, if a source retrovirus is extensively mutated, it is conceivable that the vector will then more closely resemble some other retrovirus. It is not necessary that the cognate retrovirus be the physical starting point for the construction; one may choose to synthesize a genetic element, especially a mutant element, directly, rather than to first obtain the original element and then modify it. The term "cognate" may similarly be applied to a protein, gene, or genetic element (e.g., splice donor site or packaging signal). When referring to a cognate protein, percentage sequence identities are determined at the amino acid level.

The term "cognate" retrovirus may be difficult to interpret in the extreme case, i.e., if all retroviral genetic elements have been replaced with surrogate non-lentiviral genetic elements. In this case, the source retrovirus strain mentioned previously is arbitrarily considered to be the cognate retrovirus.

The term "replication" as used herein in reference to a virus or vector, refers not to the normal replication of proviral DNA in a chromosome as a consequence of cell reproduction, or the autonomous replication of a plasmid DNA as a result of the presence of a functional origin of replication. Instead "replication" refers to the completion of a complete viral life cycle, wherein infectious viral particles containing viral RNA enter a cell, the RNA is reverse transcribed into DNA, the DNA integrates into the host chromosome as a provirus, the infected cell produces virion proteins and assembles them with full length viral genomic RNA into new, equally infectious particles.

The term "replication-competent" refers to a wild-type virus or mutant virus that is capable of replication, such that replication of the virus in an infected cell result in the production of infectious virions that, after infecting another, previously uninfected cell, causes the latter cell to likewise produce such infectious virions. The present invention contemplates the use of replication-defective virus.

As used herein, the term "attenuated virus" refers to any virus (e.g., an attenuated lentivirus) that has been modified so that its pathogenicity in the intended subject is substantially reduced. The virus may be attenuated to the point it is nonpathogenic from a clinical standpoint, i.e., that subjects exposed to the virus do not exhibit a statistically significant increased level of pathology relative to control subjects.

The present invention contemplates the preparation and use of a modified retrovirus. In some embodiments, the retrovirus is an mutant of murine leukemia virus, human immunodefciency virus type 1, human immunodeficiency virus type 2, feline immunodeficiency virus, simian immunodeficiency virus, visna-maedi, caprine arthritis-encephalitis virus, equine infectious anemia virus, and bovine immune deficiency virus, or a virus comprised of portions of more than one retroviral species (e.g., a hybrid, comprised of portions of MLV, FIV, HIV-1 and HIV-2, or HIV-1 and/or SIV).

A reference virus is a virus whose genome is used in describing the components of a mutant virus. For example, a particular genetic element of the mutant virus may be said to differ from the cognate element of the reference virus by various substitutions, deletions or insertions. It is not necessary that the mutant virus actually be derived from the reference virus.

The preferred reference FIV sequence is found in Talbott et al., Proc Natl Acad Sci USA. 1989 86:5743-7; Genbank access #NC_001482. In certain embodiments, a three-plasmid transient transfection method can be used to produce replication incompetent pseudotyped retroviruses (e.g., FIV). General methods are described in Wang et al., J Clin Invest. 1999 104:R55-62 and Johnston et al., J Virol. 1999 73:4991-5000.

Retroviral Vector System

The present invention contemplates a retroviral gene amplification and transfer system comprising a transgene vector, one or more compatible packaging vectors, an envelope vector, and a suitable host cell. The vectors used may be derived from a retrovirus (e.g., a lentivirus). Retrovirus vectors allow (1) transfection of the packaging vectors and envelope vectors into the host cell to form a packaging cell line that produces essentially packaging-vector-RNA-free viral particles, (2) transfection of the transgene vector into the packaging cell line, (3) the packaging of the transgene vector RNA by the packaging cell line into infectious viral particles, and (4) the administration of the particles to target cells so that such cells are transduced and subsequently express a transgene.

Either the particles are administered directly to the subject, in vivo, or the subject's cells are removed, infected in vitro with the particles, and returned to the body of the subject.

The packaging vectors and transgene vectors of the present invention will generate replication-incompetent viruses. The vectors chosen for incorporation into a given vector system of the present invention are such that it is not possible, without further mutation of the packaging vector(s) or transgene vector, for the cotransfected cells to generate a replication-competent virus by homologous recombination of the packaging vector(s) and transgene vector alone. The envelope protein used in the present system can be a retroviral envelope, a synthetic or chimeric envelope, or the envelope from a non-retroviral enveloped virus (e.g., baculovirus).

Packaging Signal

As used herein, the term "packaging signal" or "packaging sequence" refers to sequences located within the retroviral genome or a vector that are required for, or at least facilitate, insertion of the viral or vector RNA into the viral capsid or particle. The packaging signals in an RNA identify that RNA as one that is to be packaged into a virion. The term "packaging signal" is also used for convenience to refer to a vector DNA sequence that is transcribed into a functional packaging signal. Certain packaging signals may be part of a gene, but are recognized in the form of RNA, rather than as a peptide moiety of the encoded protein.

The key distinction between a packaging vector and a transgene vector is that in the packaging vector, the major packaging signal is inactivated, and, in the transgene vector, the major packaging sign al is functional. Ideally, in the packaging vector, all packaging signals would be inactivated, and, in the transgene vector, all packaging signals would be functional. However, countervailing considerations, such as maximizing viral titer, or inhibiting homologous recombination, may lend such constructs less desirable.

Packaging System; Packaging Vectors; Packaging Cell Line

A packaging system is a vector, or a plurality of vectors, which collectively provide in expressible form all of the genetic information required to produce a virion that can encapsidate suitable RNA, transport it from the virion-producing cell, transmit it to a target cell, and, in the target cell, cause the RNA to be reverse transcribed and integrated into the host genome in a such a manner that a transgene incorporated into the aforementioned RNA can be expressed. However, the packaging system must be substantially incapable of packaging itself. Rather, it packages a separate transgene vector.

In the present invention, the packaging vector will provide functional equivalents of the gag and pol genes (a "GP" vector). The env gene(s) will be provided by the envelope vector. In theory, a three vector system ("G", "P", and "E" vectors) is possible if one is willing to construct distinct gag and pol genes on separate vectors, and operably link them to different regulatable promoters (or one to a regulatable and the other to a constitutive promoter) such that their relative levels of expression can be adjusted appropriately.

A packaging cell line is a suitable host cell transfected by a packaging system that, under achievable conditions, produces viral particles. As used herein, the term "packaging cell lines" is typically used in reference to cell lines that express viral structural proteins (e.g., gag, pol and env), but do not contain a packaging signal. For example, a cell line has been genetically engineered to carry at one chromosomal site within its genome, a 5'-LTR-gag-pol-3'-LTR fragment that lacks a functional psi$^+$ sequence (designated as Δ-psi), and a 5'-LTR-env-3'-LTR fragment that is also Δ-psi located at another chromosomal site. While both of these segments are transcribed constitutively, because the psi region is missing and the viral RNA molecules produced are less than full-size, empty viral particles are formed.

If a host cell is transfected by the packaging vector(s) alone, it produces substantially only viral particles without the full-length packaging vector. In one example, less than 10% of the viral particles produced by the packaging cell contain full length packaging vector-derived RNA. However, since the packaging vector lacks a functional primer-binding site, even if these particles infect a new cell, the packaging vector RNA will not be reverse transcribed back into DNA and therefore the new cell will not produce virion. Thus, by itself, the packaging vector is a replication-incompetent virus.

In some embodiments, the packaging cell and/or cell line contains a transgene vector. The packaging cell line will package the transgene vector into infectious particles. Such a cell line is referred to herein as a "transgenic virion production cell line."

It is contemplated that packaging may be inducible, as well as non-inducible. In inducible packaging cells and packaging cell lines, retroviral particles are produced in response to at least one inducer. In non-inducible packaging cell lines and packaging cells, no inducer is required in order for retroviral particle production to occur.

The packaging vectors necessarily differ from wild-type, replication-competent retroviral genomes by virtue of the inactivation of at least one packaging signal of the cognate wild-type genome. More than one packaging signal may be inactivated. In one example, only the retroviral genes provided by the packaging vector are those encoding structural, or essential regulatory, proteins.

Transgene Vectors

A transgene vector is an expression vector that bears an expressible non-retroviral gene of interest and includes at least one functional retroviral packaging signal, so that, after the transgene vector is transfected into a packaging cell line, the transgene vector is transcribed into RNA, and this RNA is packaged into an infectious viral particle. These particles, in turn, infect target cells, their RNA is reverse transcribed into DNA, and the DNA is incorporated into the host cell genome as a proviral element, thereby transmitting the gene of interest to the target cells.

As used herein, the term "transduction" refers to the delivery of a gene(s) using a viral or retroviral vector by means of infection rather than by transfection. In certain embodiments, retroviral vectors are transduced. Thus, a "transduced gene" is a gene that has been introduced into the cell via retroviral or vector infection and provirus integration. In certain embodiments, viral vectors (e.g., "transgene vectors") transduce genes into "target cells" or host cells. The, present invention encompasses transgene vectors that are suitable for use in the present invention that are linked to any gene of interest (or a "marker gene" or "reporter gene," used to indicate infection or expression of a gene).

As used herein, the term "long-term transduction" refers to vectors that are capable of remaining transduced in host or target cells for time periods that are longer than those observed with other vectors. For example, the present invention provides retroviral vectors that are capable of remaining transduced for at least 120 days, at least one year, or for the life of the subject or the necessary time course of treatment. The duration of expression is a function of the choice of promoter and the target cell type, more so than the choice of vector.

The term "stable transduction" or "stably transduced" refers to the introduction and integration of foreign DNA into the genome of the transducted cell. The term "stable transductant" refers to a cell that has stably integrated foreign DNA into the genomic DNA.

The term "transient transduction" or "transiently transduced" refers to the introduction of foreign DNA into a cell where the foreign DNA fails to integrate into the genome of the transducted cell. The foreign DNA persists in the nucleus of the transducted cell for several days. During this time the foreign DNA is subject to the regulatory controls that govern the expression of endogenous genes in the chromosomes. The term "transient transductant" refers to cells that have taken up foreign DNA but have failed to integrate this DNA.

In some embodiments, the target and/or host cells of the present invention are "non-dividing" cells. These cells include cells such as neuronal cells that do not normally divide. However, it is not intended that the present invention be limited to non-dividing cells (including, but not limited to muscle cells, white blood cells, spleen cells, liver cells, eye cells, epithelial cells).

In some embodiments, the vector and the vector progeny are capable of transducing a plurality of target cells so as to achieve vector titers of at least $10^5$ cfu/ml. The multiplicity of infection (MOI) may be at least one (i.e., one hit on average per cell), or even at least two.

Expression Cassettes and Vectors

The present invention also provides an expression cassette comprising a sequence encoding ACE-tRNA.

In certain embodiments, the expression cassette further contains a promoter. In certain embodiments, the promoter is a regulatable promoter. In certain embodiments, the promoter is a constitutive promoter. In certain embodiments, the promoter is a PGK, CMV, RSV, H1 or U6 promoter (Pol II and Pol III promoters).

The present invention provides a vector containing the expression cassette described above. In certain embodiments, the vector is a viral vector. In certain embodiments, the viral vector is an adenoviral, lentiviral, adeno-associated viral (AAV), poliovirus, HSV, or murine Maloney-based viral vector.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

Adeno Associated Virus (AAV)

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats that can fold into hairpin structures and serve as the origin of viral DNA replication. Physically, the parvovirus virion is non-enveloped and its icosohedral capsid is approximately 20 nm in diameter.

To date, numerous serologically distinct AAVs have been identified, and more than a dozen have been isolated from humans or primates. The genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Furthermore, two of the Rep proteins have been associated with the preferential integration of AAV genomes into a region of the q arm of human chromosome 19. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs, which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV virion is a non-enveloped, icosohedral particle approximately 25 nm in diameter, consisting of three related proteins referred to as VP1, VP2 and VP3. The right ORF encodes the capsid proteins VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles. An AAV particle is a viral particle comprising an AAV capsid protein. An AAV capsid polypeptide can encode the entire VP1, VP2 and VP3 polypeptide. The particle can be a particle comprising AAV2 and other AAV capsid proteins (i.e., a chimeric protein, such as AAV1 and AAV2). Variations in the amino acid sequence of the AAV2 capsid protein are contemplated herein, as long as the resulting viral particle comprises the AAV2 capsid remains antigenically or immunologically distinct from AAV1, as can be routinely determined by standard methods. Specifically, for example, ELISA and Western blots can be used to determine whether a viral particle is antigenically or immunologically distinct from AAV1. Furthermore, the AAV2 viral particle preferably retains tissue tropism distinct from AAV1.

An AAV2 particle is a viral particle comprising an AAV2 capsid protein. An AAV2 capsid polypeptide encoding the entire VP1, VP2, and VP3 polypeptide can overall have at least about 63% homology (or identity) to the polypeptide having the amino acid sequence encoded by nucleotides set forth in NC_001401 (nucleotide sequence encoding AAV2 capsid protein). The capsid protein can have about 70% homology, about 75% homology, 80% homology, 85% homology, 90% homology, 95% homology, 98% homology, 99% homology, or even 100% homology to the protein encoded by the nucleotide sequence set forth in NC_001401. The capsid protein can have about 70% identity, about 75% identity, 80% identity, 85% identity, 90% identity, 95% identity, 98% identity, 99% identity, or even 100% identity to the protein encoded by the nucleotide sequence set forth in NC_001401. The particle can be a particle comprising another AAV and AAV2 capsid protein, i.e., a chimeric protein. Variations in the amino acid sequence of the AAV2 capsid protein are contemplated herein, as long as the resulting viral particle comprising the AAV2 capsid remains antigenically or immunologically distinct from AAV4, as can be routinely determined by standard methods. Specifically, for example, ELISA and Western blots can be used to determine whether a viral particle is antigenically or immunologically distinct from AAV 1. Furthermore, the AAV2 viral particle preferably retains tissue tropism distinction from AAV 1, such as that exemplified in the examples herein, though an AAV2 chimeric particle comprising at least one AAV2 coat protein may have a different tissue tropism from that of an AAV2 particle consisting only of AAV2 coat proteins.

In certain embodiments, the invention further provides an AAV2 particle containing, i.e., encapsidating, a vector comprising a pair of AAV2 inverted terminal repeats. The nucleotide sequence of AAV2 ITRs is known in the art. Furthermore, the particle can be a particle comprising both AAV1 and AAV2 capsid protein, i.e., a chimeric protein. Moreover, the particle can be a particle encapsidating a vector comprising a pair of AAV inverted terminal repeats from other AAVs (e.g., AAV1-AAV9 and AAVrh10). The vector encapsidated in the particle can further comprise an exogenous nucleic acid inserted between the inverted terminal repeats.

The following features of AAV have made it an attractive vector for gene transfer. AAV vectors have been shown in vitro to stably integrate into the cellular genome; possess a broad host range; transduce both dividing and non-dividing cells in vitro and in vivo and maintain high levels of expression of the transduced genes. Viral particles are heat stable, resistant to solvents, detergents, changes in pH, temperature, and can be concentrated on CsCl gradients or by other means. The present invention provides methods of administering AAV particles, recombinant AAV vectors, and recombinant AAV virions. For example, an AAV2 particle is a viral particle comprising an AAV2 capsid protein, or an AAV1 particle is a viral particle comprising an AAV1 capsid protein. A recombinant AAV2 vector is a nucleic acid construct that comprises at least one unique nucleic acid of AAV2. A recombinant AAV2 virion is a particle containing a recombinant AAV2 vector. To be considered within the term "AAV2 ITRs" the nucleotide sequence must retain one or both features described herein that distinguish the AAV2 ITR from the AAV1 ITR: (1) three (rather than four as in AAV1) "GAGC" repeats and (2) in the AAV2 ITR Rep binding site the fourth nucleotide in the first two "GAGC" repeats is a C rather than a T.

The promoter to drive expression of the sequence encoding the tRNA to be delivered can be any desired promoter, selected by known considerations, such as the level of expression of a nucleic acid functionally linked to the promoter and the cell type in which the vector is to be used. Promoters can be an exogenous or an endogenous promoter. Promoters can include, for example, known strong promoters such as SV40 or the inducible metallothionein promoter, or an AAV promoter, such as an AAV p5 promoter. Additional examples of promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc. Additional examples include regulated promoters.

The AAV vector can further comprise an exogenous (heterologous) nucleic acid functionally linked to the promoter. By "heterologous nucleic acid" is meant that any heterologous or exogenous nucleic acid can be inserted into the vector for transfer into a cell, tissue or organism. The nucleic acid can encode a tRNA, for example. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer. The nucleic acid can encode more than one gene product, limited only by the size of nucleic acid that can be packaged.

An AAV1 particle is a viral particle comprising an AAV1 capsid protein. Variations in the amino acid sequence of the AAV1 capsid protein are contemplated herein, as long as the resulting viral particle comprising the AAV1 capsid remains antigenically or immunologically distinct from other AAV capsids, as can be routinely determined by standard methods. Specifically, for example, ELISA and Western blots can be used to determine whether a viral particle is antigenically or immunologically distinct from other AAV serotypes.

The term "polypeptide" as used herein refers to a polymer of amino acids and includes full-length proteins and fragments thereof. Thus, "protein" and "polypeptide" are often used interchangeably herein.

The present method provides a method of delivering a nucleic acid to a cell comprising administering to the cell an AAV particle containing a vector comprising the nucleic acid inserted between a pair of AAV inverted terminal repeats, thereby delivering the nucleic acid to the cell. Administration to the cell can be accomplished by any means, including simply contacting the particle, optionally contained in a desired liquid such as tissue culture medium, or a buffered saline solution, with the cells. The particle can be allowed to remain in contact with the cells for any desired length of time, and typically, the particle is administered and allowed to remain indefinitely. For such in vitro methods, the virus can be administered to the cell by standard viral transduction methods, as known in the art and as exemplified herein. Titers of virus to administer can vary, particularly depending upon the cell type, but will be typical of that used for AAV transduction in general. Additionally the titers used to transduce the particular cells in the present examples can be utilized. The cells can include any desired cell in humans as well as other large (non-rodent) mammals, such as primates, horse, sheep, goat, pig, and dog.

The present invention further provides a method of delivering a nucleic acid to a cell in a subject comprising administering to the subject an AAV particle comprising the nucleic acid inserted between a pair of AAV inverted terminal repeats, thereby delivering the nucleic acid to a cell in the subject.

Certain embodiments of the present disclosure provide a cell comprising a viral vector as described herein.

AAV Vectors

In one embodiment, a viral vector of the disclosure is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV, which is identified by, and distinguished from other AAVs based on capsid protein reactivity with defined antisera, e.g., there are eight known serotypes of primate AAVs, AAV-1 to AAV-9 and AAVrh10. For example, serotype AAV2 is used to refer to an AAV, which contains capsid proteins encoded from the cap gene of AAV2 and a genome containing 5' and 3' ITR sequences from the same AAV2 serotype. As used herein, for example, rAAV1 may be used to refer an AAV having both capsid proteins and 5'-3' ITRs from the same serotype or it may refer to an AAV having capsid proteins from one serotype and 5'-3' ITRs from a different AAV serotype, e.g., capsid from AAV serotype 2 and ITRs from AAV serotype 5. For each example illustrated herein, the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from AAV2. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from non-viral genes, such as the murine metallothionein gene, will also find use herein. Such promoter sequences are commercially available from, e.g., Stratagene (San Diego, Calif.).

In one embodiment, both heterologous promoters and other control elements, such as tissue-specific and inducible promoters, enhancers and the like, will be of particular use. Examples of heterologous promoters include the CMV promoter. Examples of inducible promoters include DNA responsive elements for ecdysone, tetracycline, hypoxia and aufin.

In one embodiment, the AAV expression vector that harbors the DNA molecule of interest bounded by AAV ITRs, can be constructed by directly inserting the selected sequence(s) into an AAV genome, which has had the major AAV open reading frames ("ORFs"), excised therefrom. Other portions of the AAV genome can also be deleted, so long as sufficient portions of the ITRs remain to allow for replication and packaging functions. Such constructs can be designed using techniques well known in the art.

Alternatively, AAV ITRs can be excised from the viral genome or from an AAV vector containing the same and fused 5' and 3' of a selected nucleic acid construct that is present in another vector using standard ligation techniques. For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs.

Additionally, chimeric genes can be produced synthetically to include AAV ITR sequences arranged 5' and 3' of one or more selected nucleic acid sequences. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. See, e.g., Sambrook et al. (1989) Molecular Cloning, a laboratory manual, Cold Spring Harbor Laboratories, New York. Particularly suitable transfection methods include calcium phosphate co-precipitation, direct micro-injection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell that has been transfected. Thus, a "host cell" as used herein generally refers to a cell that has been transfected with an exogenous DNA sequence. Cells from the stable human cell line, 293 (readily available through, e.g., the American Type Culture Collection under Accession Number ATCC CRL1573) can be used in the practice of the present disclosure. Particularly, the human cell line 293 is a human embryonic kidney cell line that has been transformed with adenovirus type-5 DNA fragments, and expresses the adenoviral E1a and E1b genes. The 293 cell line is readily transfected, and provides a particularly convenient platform in which to produce rAAV virions.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome that encodes the capsid proteins VP1, VP2, and VP3, or functional homologues thereof. These Cap expression products supply the packaging functions, which are collectively required for packaging the viral genome.

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 that encode both Rep and Cap expression products. A number of other vectors have been described that encode Rep and/or Cap expression products.

Methods of delivery of viral vectors include injecting the AAV into the subject. Generally, rAAV virions may be introduced into cells using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, pharmaceutical compositions will comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

It should be understood that more than one transgene could be expressed by the delivered viral vector. Alternatively, separate vectors, each expressing one or more different transgenes, can also be delivered to the subject as described herein. Furthermore, it is also intended that the viral vectors delivered by the methods of the present disclosure be combined with other suitable compositions and therapies.

As is apparent to those skilled in the art in view of the teachings of this specification, an effective amount of viral vector that must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

In certain embodiments, the rAAV is administered at a dose of about 0.3-2 ml of $1\times10^5$-$1\times10^{16}$ vg/ml. In certain embodiments, the rAAV is administered at a dose of about 1-3 ml of $1\times10^7$-$1\times10^{14}$ vg/ml. In certain embodiments, the rAAV is administered at a dose of about 1-2 ml of $1\times10^8$-$1\times10^{13}$ vg/ml.

Formulations containing the rAAV particles will contain an effective amount of the rAAV particles in a vehicle, the effective amount being readily determined by one skilled in the art. The rAAV particles may typically range from about 1% to about 95% (w/w) of the composition, or even higher or lower if appropriate. The quantity to be administered depends upon factors such as the age, weight and physical condition of the animal or the human subject considered for treatment. Effective dosages can be established by one of ordinary skill in the art through routine trials establishing dose response curves. The subject is treated by administration of the rAAV particles in one or more doses. Multiple doses may be administered as is required to maintain adequate enzyme activity.

Vehicles including water, aqueous saline, artificial CSF, or other known substances can be employed with the subject invention. To prepare a formulation, the purified composition can be isolated, lyophilized and stabilized. The composition may then be adjusted to an appropriate concentration, optionally combined with an anti-inflammatory agent, and packaged for use.

The present invention provides a method of increasing the level of a target protein in a cell by introducing a protein, or nucleic acid molecule encoding a protein described above into a cell in an amount sufficient to increase the level of the target protein in the cell. In certain embodiments, the accumulation of target protein is increased by at least 10%. The accumulation of target protein is increased by at least 10%, 20%, 30%, 40%, 50%, 60%, 70%, 80%, 90% 95%, or 99%. 39

Nucleic Acids Encoding Therapeutic Agents

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides.

A "nucleic acid fragment" is a portion of a given nucleic acid molecule. The term "substantial identity" of polynucleotide sequences means that a polynucleotide comprises a sequence that has at least 70%, 71%, 72%, 73%, 74%, 75%, 76%, 77%, 78%, or 79%, or at least 80%, 81%, 82%, 83%, 84%, 85%, 86%, 87%, 88%, or 89%, or at least 90%, 91%, 92%, 93%, or 94%, or even at least 95%, 96%, 97%, 98%, or 99% sequence identity, compared to a reference sequence using one of the alignment programs described using standard parameters.

Methods for Introducing Genetic Material into Cells

The exogenous genetic material (e.g., a DNA encoding one or more therapeutic ACE-tRNAs) is introduced into the cell in vivo by genetic transfer methods, such as transfection or transduction, to provide a genetically modified cell. Various expression vectors (i.e., vehicles for facilitating delivery of exogenous genetic material into a target cell) are known to one of ordinary skill in the art.

As used herein, "transfection of cells" refers to the acquisition by a cell of new genetic material by incorporation of added DNA. Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-facilitated microparticle bombardment. Strontium phosphate DNA co-precipitation is another possible transfection method.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced cell. A cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion, an "enhancer" is simply any non-translated DNA sequence that works contiguous with the coding sequence (in cis) to change the basal transcription level dictated by the promoter. The exogenous genetic material may introduced into the cell genome immediately downstream from the promoter so that the promoter and coding sequence are operatively linked so as to permit transcription of the coding sequence. A retroviral expression vector may include an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes that encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eucaryotic cells. These include the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector may include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

Disease Conditions and Methods of Treatment

The present invention in one embodiment includes compositions and methods for treating cystic fibrosis by reversing the effects of mutations present that are associated with nonsense mutations through introduction of the synthetic oligonucleotide suppressor tRNAs of the invention.

Certain embodiments of the present disclosure provide a method of treating a disease in a mammal comprising administering a protein or vector encoding a therapeutic agent (e.g., a modified and/or stabilized ACE-tRNA) as described herein to the mammal. In certain embodiments, the mammal is human.

Certain embodiments of the present disclosure provide a use of a therapeutic agent or vector encoding a therapeutic agent as described herein to prepare a medicament useful for treating disease in a mammal. In certain embodiments, the disease is cystic fibrosis.

The present disclosure also provides a mammalian cell containing a vector described herein. The cell may be human.

Certain aspects of the disclosure relate to polynucleotides, polypeptides, vectors, and genetically engineered cells (modified in vivo), and the use of them. In particular, the disclosure relates to a method for gene therapy that is capable of both systemic delivery of a therapeutically effective dose of the therapeutic agent.

According to one aspect, a cell expression system for expressing a therapeutic agent in a mammalian recipient is provided. The expression system (also referred to herein as a "genetically modified cell") comprises a cell and an expression vector for expressing the therapeutic agent. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector.

The expression vector further includes a promoter for controlling transcription of the heterologous gene. The promoter may be an inducible promoter (described herein). The expression system is suitable for administration to the mammalian recipient. The expression system may comprise a plurality of non-immortalized genetically modified cells, each cell containing at least one recombinant gene encoding at least one therapeutic agent.

The cell expression system is formed in vivo. According to yet another aspect, a method for treating a mammalian recipient in vivo is provided. The method includes introducing an expression vector for expressing a heterologous gene product into a cell of the patient in situ, such as via intravenous administration. To form the expression system in vivo, an expression vector for expressing the therapeutic agent is introduced in vivo into the mammalian recipient i.v.

According to yet another aspect, a method for treating a mammalian recipient in vivo is provided. The method includes introducing the target therapeutic agent into the patient in vivo.

The expression vector for expressing the heterologous gene may include an inducible promoter for controlling transcription of the heterologous gene product. Accordingly, delivery of the therapeutic agent in situ is controlled by exposing the cell in situ to conditions, which induce transcription of the heterologous gene.

The present disclosure provides methods of treating a disease in a mammal by administering an expression vector to a cell or patient. For the gene therapy methods, a person having ordinary skill in the art of molecular biology and gene therapy would be able to determine, without undue experimentation, the appropriate dosages and routes of administration of the expression vector used in the novel methods of the present disclosure.

According to one embodiment, the cells are transformed or otherwise genetically modified in vivo. The cells from the mammalian recipient are transformed (i.e., transduced or transfected) in vivo with a vector containing exogenous genetic material for expressing a heterologous (e.g., recombinant) gene encoding a therapeutic agent and the therapeutic agent is delivered in situ.

As used herein, "exogenous genetic material" refers to a nucleic acid or an oligonucleotide, either natural or synthetic, that is not naturally found in the cells; or if it is naturally found in the cells, it is not transcribed or expressed at biologically significant levels by the cells. Thus, "exogenous genetic material" includes, for example, a non-naturally occurring nucleic acid that can be transcribed into a tRNA.

The above-disclosed therapeutic agents and conditions amenable to gene therapy are merely illustrative and are not intended to limit the scope of the instant disclosure. The selection of a suitable therapeutic agent for treating a known condition is deemed to be within the scope of one of ordinary skill of the art without undue experimentation.

In certain embodiments, the therapy has potential use for the treatment/management of diseases that are caused by Premature Termination Codons (PTCs), including, but not limited to, cystic fibrosis, muscular dystrophy, β-thalassemia and Liddle's syndrome. This therapy is advantageous in that it provides improved stop codon suppression specificity. The therapeutic ACE-tRNAs of the present invention target a specific stop-codon, TGA for instance, thus reducing off-target effects at stop-codons unrelated to disease. The present therapy is also advantageous in that it provides amino-acid specificity. The expressed tRNA is engineered to specifically replace the amino acid that was lost via insertion of the disease stop codon, thus negating any spurious effects on protein stability, folding and trafficking.

In certain embodiments, the present system is modular, and thus can be "personalized" to every possible disease PTC. For instance, there are nine individual tryptophan tRNAs in the human genome that are recognized by the Trp synthetase, all of which suppress the mRNA UGG codon. Thus, each of these nine Trp tRNA provides an opportunity for codon re-editing tolerance (UGG UGA). Additionally, given their proximity to stop codons in the genetic code, the mutation of arginine codons to PTC nonsense codons are common in disease. There are over thirty Arg tRNA that could be tested for codon editing tolerance and suppression efficacy.

A further advantage of the present invention is that it provides facile expression and cell specific delivery, because the entire system (tRNA+promoter sequence) is compact.

Dosages, Formulations and Routes of Administration of the Agents of the Invention The agents of the invention are administered so as to result in a reduction in at least one symptom associated with a genetic disease (e.g., cystic fibrosis). The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems that are well known to the art.

The present invention envisions treating genetic disease (e.g., cystic fibrosis) by the administration of an agent, e.g., ACE-tRNA, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well-known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0 and water.

Definitions

Disease state: For the purposes of the present invention, a "disease state" or "disease phenotype" is a characteristic of a mammalian cell that results from a stop codon within the coding region of a gene inside the cell (e.g., that results from a nonsense mutation). For example, an increasing number of human genetic diseases are thought to be caused by nonsense mutations (see, for example, Atkinson et al., Nuc. Acids Res. 22:1327, 1994). To give but a few examples, β-thalessemia, Duchenne muscular dystrophy, xeroderma pigmentosum, Fanconi's anemia, and cystic fibrosis can all be caused by nonsense mutations in identified genes.

Endogenous tRNA synthetase: A tRNA synthetase is considered to be "endogenous" to a cell if it is present in the cell into which a tRNA is introduced according to the present invention. As will be the apparent to those of ordinary skill in the art, a tRNA synthetase may be considered to be endogenous for these purposes whether it is naturally found in cells of the relevant type, or whether the particular cell at issue has been engineered or otherwise manipulated by the hand of man to contain or express it.

Suppressor tRNA: A "suppressor tRNA" is one whose anti-codon is complementary with a codon that would otherwise terminate translation, so that detectable read-through occurs under the conditions of the experiment. Standard termination codons are amber (UAG), ochre (UAA), and opal (UGA) codons. However, non-standard termination codons (e.g., 4-nucleotide codons) have also been employed in the literature (see, for example, Moore et al., J. Mol. Biol. 298:195, 2000; Hohsaka et al., J. Am. Chem. Soc. 121:12194, 1999).

The invention is now illustrated by the following non-limiting Examples.

EXAMPLE 1

The genetic code uses four nucleotides that in turn form triplet codons, which form the basis for DNA to protein translation. There are 64 codons in total, 61 of which are used to encode amino acids, and three (TAG, TGA and TAA) of which encode protein termination "stop" or "nonsense" codons.

Five to ten percent of cystic fibrosis cases are caused by "nonsense" mutations that lead to premature truncation of the cystic fibrosis transmembrane conductance regulator (CFTR) protein. An example of this "class 1" mutation is p.Trp1282X, a premature termination codon (PTC) which causes a loss of CFTR function and severe cystic fibrosis phenotypes. Some compounds, such as ataluren, promote stop read-through of disease producing nonsense mutations but have been only modestly successful as therapeutics due to a number of caveats, including poor stop-codon specificity and unexpectedly low efficiency of codon skipping in vivo. However, the widespread use of these compounds and the discovery that endogenous stop-codon read-through is common in metazoans, suggests that assisted suppression could be viable if delivered to a subset of cell types, i.e., airway epithelium. Yet, when therapeutically assisted stop-codon read-through is successful, the nonselective incorporation of an amino acid at the location of the nonsense codon has the potential to affect protein folding, trafficking and function (as is the case with CFTR 1282X); and thus, requires additional therapeutic intervention. Thus, there is an acute unmet need to understand the nature of disease PTCs and potentially therapeutic suppressors and generally, more effective treatments of PTC diseases.

This Example characterizes anticodon edited (ACE) Trp-tRNA for the rescue of CFTR p.Trp1282X channels. Such tRNAs are engineered to 'suppress' the disease-causing TGA stop codon and incorporate the original amino acid, Trp at p.Trp1282X CFTR, in effect, genetically reconstructing the wild-type CFTR protein. Data demonstrate that this general approach (nonsense suppression) produces robust rescue of transcripts that carry in-frame stop codons, through either transient transfection of a tRNA and its cognate synthetase in adherent cells, or their virus-based delivery to more native airway cell-types, such as A549 airway cells. This approach offers a number of significant benefits over existing strategies: 1) Improved codon specificity—the expressed tRNA may be directed towards a specific stop-codon, thus reducing off-target effects at stop-codons unrelated to disease. 2) Amino-acid specificity—the expressed tRNA and/or synthetase can be engineered to replace the amino acid that was lost via insertion of the disease stop codon, thus negating any spurious effects on CFTR stability, folding and trafficking. 3) Tunability—the system can be theoretically personalized for each type of tRNA and PTC mutation. 4) Facile expression—the entire system is compact (<1 kb) and can be easily packaged and expressed transiently or via nanoparticle delivery of tRNA. 5) Proof of principle for a general strategy—in-frame stop codons are a major cause of human disease and few treatment options exist; the experiments performed here on p.Trp1282X are expected to lead to insights into the mechanisms of other CFTR nonsense codons.

Data shows that ACE-tRNA stop-codon suppressor tRNA are efficient at "rescuing" transcripts which contain introduced stop-sites (FIGS. 6A and 6B) suggesting that such tRNA have the potential to interfere with nonsense mediated decay (NMD) as the major biological hurdle in the therapeutic rescue of disease stop sites. Thus opening the possibility for the use of suppressor tRNA to gain more molecular insights into NMD in disease.

Results

Figures 6A, 6B, 7:
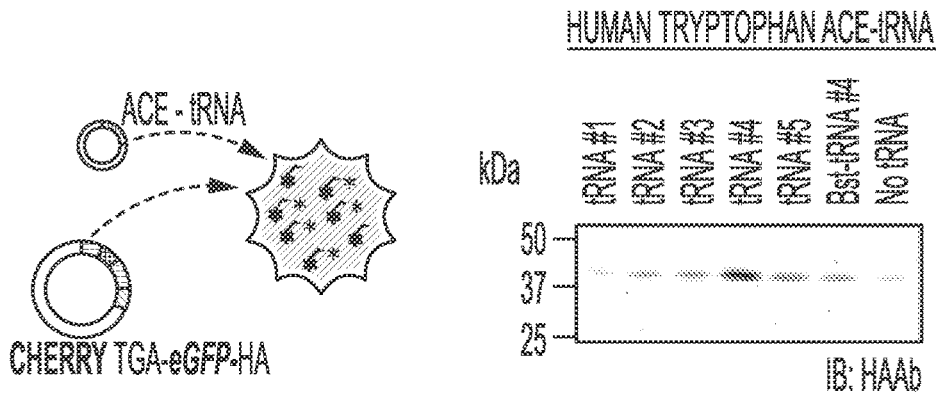
FIGS. 6A and 6B. Nonsense codon rescue with human ACE-tRNA.
FIG. 7. Nonsense codon rationale and prevalence observed in human disease. The twenty natural amino acids codons ranked as to their contribution to human disease, with dark cross-hatched codons being most prevalent (TGG, TAC, TAT, TCA, and TTA) and stippled codons being least prevalent. All cross-hatched codon sequences require a single nucleotide mutation to convert to a stop codon from the intended amino acid. Right panel, the most common disease causative nonsense codons within the cystic fibrosis transmembrane conductance regulator (CFTR). Herein, novel tRNA sequences have been discovered for the repair of the indicated mutation.

We questioned if it might be possible to express eukaryotic tRNA that had been anticodon edited to suppress stop sites, TGA for instance, and not its designated codon. This was tested in five human tryptophan tRNA on a test construct consisting of a fluorescent protein (cherry) in frame with eGFP sequence that are separated by a linker containing a TGA site. To indicate the production of the full-length protein an HA epitope was added to the C-terminus of the eGFP reading frame. This test system is useful because visual appearance of the cherry signal indicates plasmid delivery and expression and in combination with the eGFP rescue shows TGA suppression. Data in FIGS. 6A and 6B show western blot data using this test construct to assay the ability of five anticodon edited Trp tRNA human to suppress the TGA stop site in the short linker between cherry and eGFP reading frames. Of these constructs, the candidates 1, 2, 3 & 5 show modest activity in this regard. This may be due to structural intolerance to the mutation or the possibility that altering the anticodon, even just by a single base, disrupted the ability of the Trp synthetase to recognize and/or acylate the tRNA with tryptophan. However, number 4 of these test tRNA (tRNA #4) shows significant suppression activity of the TGA site, producing a full-length cherry-eGFP-HA protein (FIG. 6B). Further, no read-through was seen in the absence of co-expressed tRNA, last lane, FIG. 6B.

Methods

The Trp tRNA were examined for codon editing tolerance (TGG→TGA) and their ability to suppress a targeted TGA test site in a transiently transfected tandem-fluorophore (mCherry-TGA-GFP) and CFTR Trp1282X. Initial screening of 5/9 Trp tRNA discovered an anticodon edited Trp-tRNA that was transiently transfected in HEK cells and has 'stand alone' functionality to rescue a cherry-TGA-eGFP-HA test construct, FIG. 6B. The selective presence of the HA epitope indicates successful rescue, as well as confocal examination of both cherry and eGFP fluorescence at the single cell level (not shown). This result provides proof of principle data that a) some ACE-tRNA can tolerate anticodon editing b) that these tRNA retain the ability to be acylated with Trp by endogenous tryptophan synthetases, and c) these tRNA can suppress TGA sites embedded within open protein reading frames.

The remaining four Trp-tRNA are functionally examined for tolerance of anticodon editing from TAA to TGA suppressors. These anticodon edited tRNA are tested for their ability to rescue the cherry-TGA-eGFPHA clone. Biochemical (western blot) data are obtained for cherry and eGFP signals as well as HA epitopes. Here, cherry expression serves as the positive transfection control. Confocal imaging verifies cherry and eGFP fluorescence at the single cell level.

The fidelity of endogenous Trp synthetases to charge ACE—Trp tRNA with the tryptophan amino acid is determined by mass spectroscopic analysis of tryptic fragments of purified rescued cherry-Trp-eGFPHAprotein. Predicted mass for the tryptic fragment generated from the linker between the cherry and eGFP reading frames is: KPINQW-PANTHER (SEQ ID NO: 648) with a predicted mass of 1590.8135; bold W indicates incorporation site, FIG. 10. Thus, this represents the first example of a nonsense codon repair and replacement with the wild-type amino acid and therefore is a significant advance over existing approaches, such as the therapeutic Ataluran. The later example, the compound promotes read-through of the nonsense codon with the incorrect amino acid, thus the discovery and identification of new tRNA sequences that provide stringent repair is significant.

Rescue of transiently transfected CFTR 1282X channels by ACE-tRNA identified above are assessed by standard biochemical methods for full maturation of the B and C glycosylated CFTR bands 20. Thus, the channel has been repaired with the wildtype amino acid, is fully functional and successfully trafficked to the plasma membrane.

The next step is to functionally characterize CFTR Trp1282X channels rescued with ACE-tRNA systems identified above using electrophysiological (single cell patch clamp and Ussing chamber) and biochemical approaches. The efficacy of expressed tRNA to diminish nonsense-mediated decay (NMD) of 1282X mRNA would be assessed with quantitative rtPCR. Reprogramed human airway cells are used to test expressed codon edited Trp-tRNA rescue of native 1282X CFTR channels.

It is demonstrated that anticodon editing is tolerated in an identified human Trp tRNA and this 75-base pair transfer RNA is capable of suppressing an in-frame TGA codon within a test construct. These experiments extrapolate this discovery to characterize the ability of this ACE-tRNA to interact with CFTR 1282TGA mRNA and produce functional CFTR channels in model cells (FRT and A549) as well as p. 1282X human reprogrammed airway cells.

Biochemical determination of rescue levels in transiently expressed CFTR 1282X channels as well as those in reprogrammed airway cells. Antibody M3A7 is used to recognize the rescued (epitope is aa 1370-1380) and to detect all CFTR, rescued and non-rescued, antibody binding to the N-terminus like MM13-4 (epitope aa 25-36), available through EMD Millipore. Alternatively, L12B4 (epitope aa 386-412, EMD Millipore) or 660 (epitope aa 576-585) are available through Cystic Fibrosis Foundation Therapeutics.

Surface functionality is examined through electrophysiological approaches, patch-clamp and Ussing chamber recording. 1282X mRNA stability and abundance is assayed by quantitative rtPCR of RNA extracts from transiently expressing cells and reprogrammed airway cells.

Bioinformatic analysis of RNA transcriptome data from human airway cells identifies abundance, context and identity of TGA codon containing transcripts. The top 10 expressing transcripts using TGA for their normal stop sites are followed up at the level of individual transcript with protein biochemistry before and after ACE-tRNA expression. Biochemical and immunohistological probes of cellular apoptosis are also used to examine the impact of ACE-tRNA in cell death.

Figure 9:
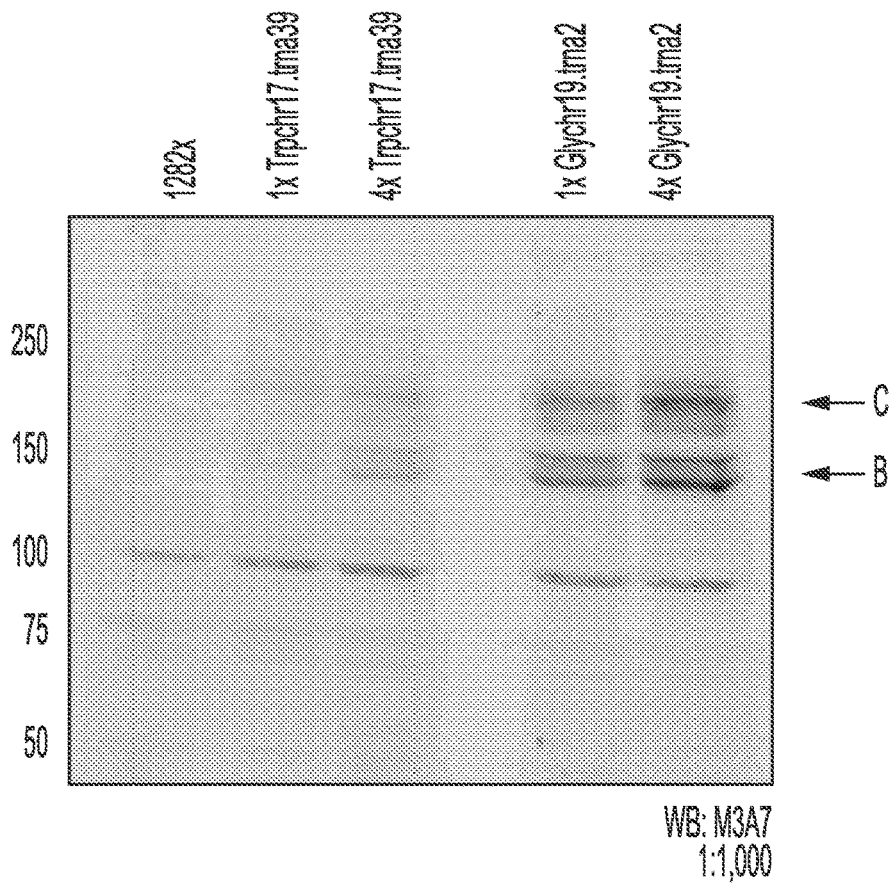
FIG. 9. CFTR 1282x rescue with Trpchr17.trna39 and Glychr19.trna2 ACE-tRNAs. Biochemical western blot data of CFTR W1282X channels co-expressed in HEK cells with the indicated tRNA. Expression vectors containing four copies of the indicated tRNA display higher rescue of the CFTR protein. "C" band indicates rescue of the fully mature, glycosylated CFTR protein. Antibody used was M3A7 from Cystic Fibrosis Therapeutics at a 1:1000 dilution.

In conclusion, the data show that ion channel genes with in-frame stop sites are amenable to this type of "rescue" (FIG. 9) and components of the system can be expressed virally in airway cells. Further, a highly simplified form of this idea, an ACE-tRNA of human origin, demonstrates the "stand alone" ability to rescue in-frame CFTR TGA codons in mammalian cell lines (FIG. 9). This approach has many advantages over existing stop-codon strategies and merits closer examination in terms of the ability of ACE-tRNA to 1) abrogate nonsense mediated decay 2) function in lung cell preparations and 3) to specifically rescue CFTR 1282X.

EXAMPLE 2

Several different nonsense mutations cause CF, thus underlying roughly 10% of all CF disease. FIG. 7. These cases are concentrated into ten specific genetic lesions: E60X, R75X, G542X, R553X, Q890X, Y1092X, R1158X, R1162X and W1282X. We propose that it should be feasible, with the right approach, to screen existing human tRNA sequences for modification and tolerance to anti-codon editing. To this end, roughly 144 ACE-tRNAs were candidates to test for those that could be used to promote the repair of the disease causative nonsense codon and the expression of the full-length protein. Specifically, using the scheme described in FIG. 11, tRNA libraries were generated to identify novel tRNA sequences that encode for ACE tRNA with the ability to repair the top CF causative nonsense mutations. Specifically, 10 ng of annealed oligos encoding the ACE-tRNAs were combined with 50 ng of NanoLuc reporter plasmid, 1 ul 10× CutSmart Buffer (NEB), 1 ul T4 ligase (NEB), 10 mM ATP and 1 ul BbsI (NEB) and cycled in a thermocycler as described in FIG. 11. 1 ul of the reaction was transformed into competent *E. coli* and the transformants were plated on ampicillin agar plates. One transformant was picked per plate was picked, grown in 1 ml of LB under ampicillin selection, miniprepped and sequence verified.

Figure 8:
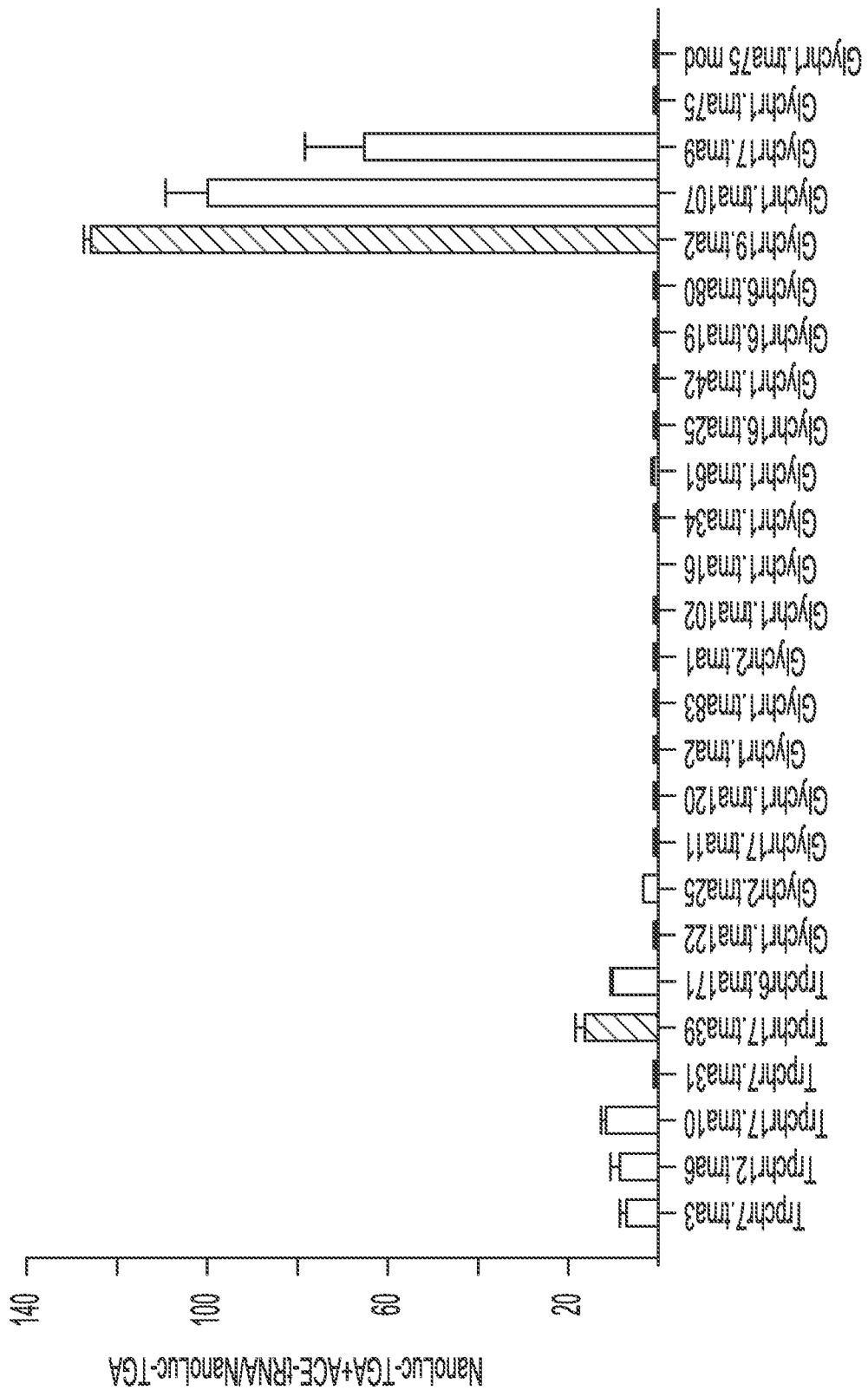
FIG. 8. Identification of tRNA sequences for the repair of tryptophan-TGA and glycine-TGA. Left axis indicates fold above background for luciferase activity. A majority tRNA with mutant anti-codon loops lack rescue activity.

Screening studies were first performed to identify the best ACE-tRNA Candidates from tryptophan and glycine. 125 ng of sequence verified miniprep cDNA of NanoLuc reporter plasmid with ACE-tRNA was transfected into HEK cells using calcium phosphate. HEK cells were plated in 96 well plates at $4 \times 10^4$ the day prior. 24 hrs after transfection the media was replaced with 20 ul of PBS and 15 ul of NanoGlo reagent (Promega) was added. Plates were read on a SpectraMax i3 (Molecular Devices). Data are of replicates of 3 or greater. FIG. 8. The data show that most tRNA demonstrate poor codon editing tolerance. However, clear high-performing tRNA emerge from the screen, with identification of ACE-Trp and ACE-Gly tRNA which demonstrate rescue of nonsense codon containing protein of 20-fold to 130-fold over background.

To assess is these novel tRNA could rescue CFTR channels harboring nonsense codons, they were co-expressed in mammalian HEK cells with a CFTR W1282X cDNA plasmid. The cellular preparations were analyzed by standard biochemical approaches via Western blot assessment of CFTR protein. This method is highly advantageous for this purpose because the CFTR protein displays a multi-banded pattern that is well-established. Specifically, the "B" and "C" bands represent the full-length and fully mature, post-translationally proceeded CFTR protein at the cell surface, respectively. In this case, both rescue with Trpchr17.trna39 and Glychr19.trna2 ACT-tRNAs produce robust populations of 'B' and 'C' CFTR immunopositive (antibody MA37) bands, indicating the promotion by said tRNA of the full-length, successfully trafficked ion channel protein. FIG. 9.

EXAMPLE 3

Figure 10A:
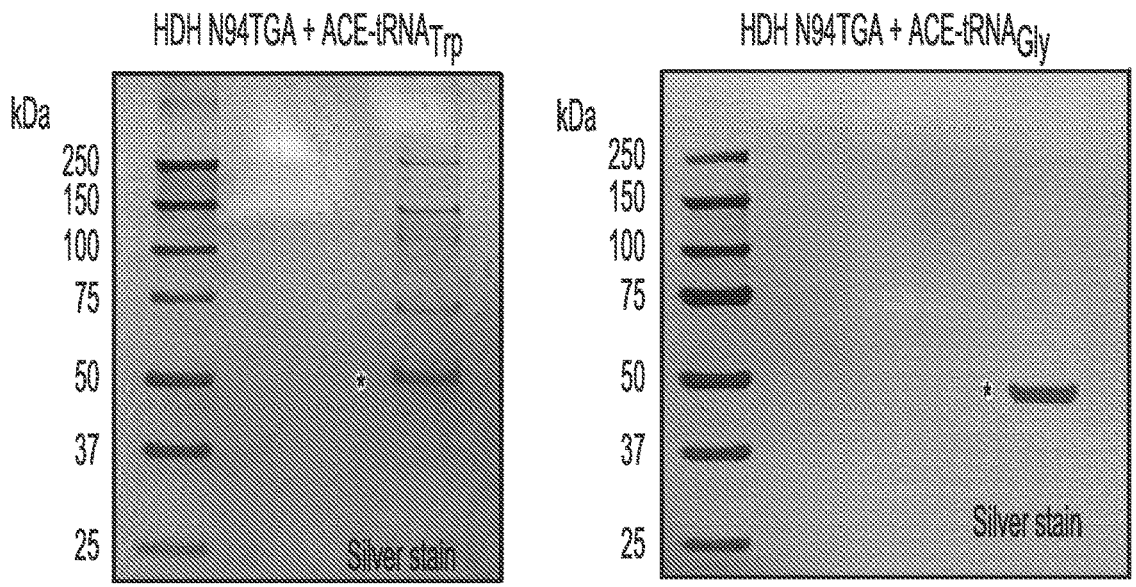
FIGS. 10A and 10B. Expression of ACE-tRNA$_{Trp}$ and ACE-tRNA$_{Gly}$ results in specific incorporation of cognate amino acids into nonsense codons.
Figure 10B:
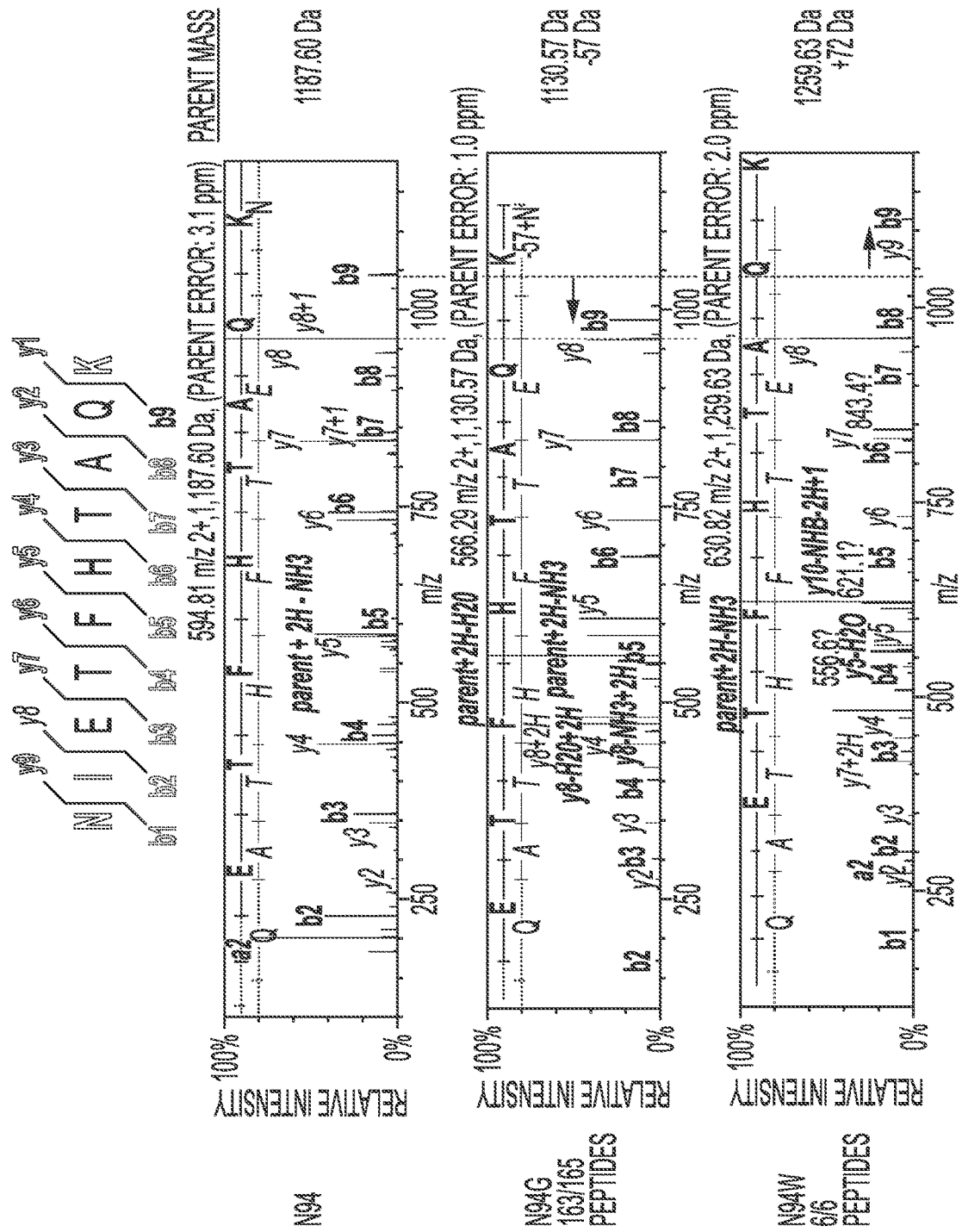
Figure 12A:
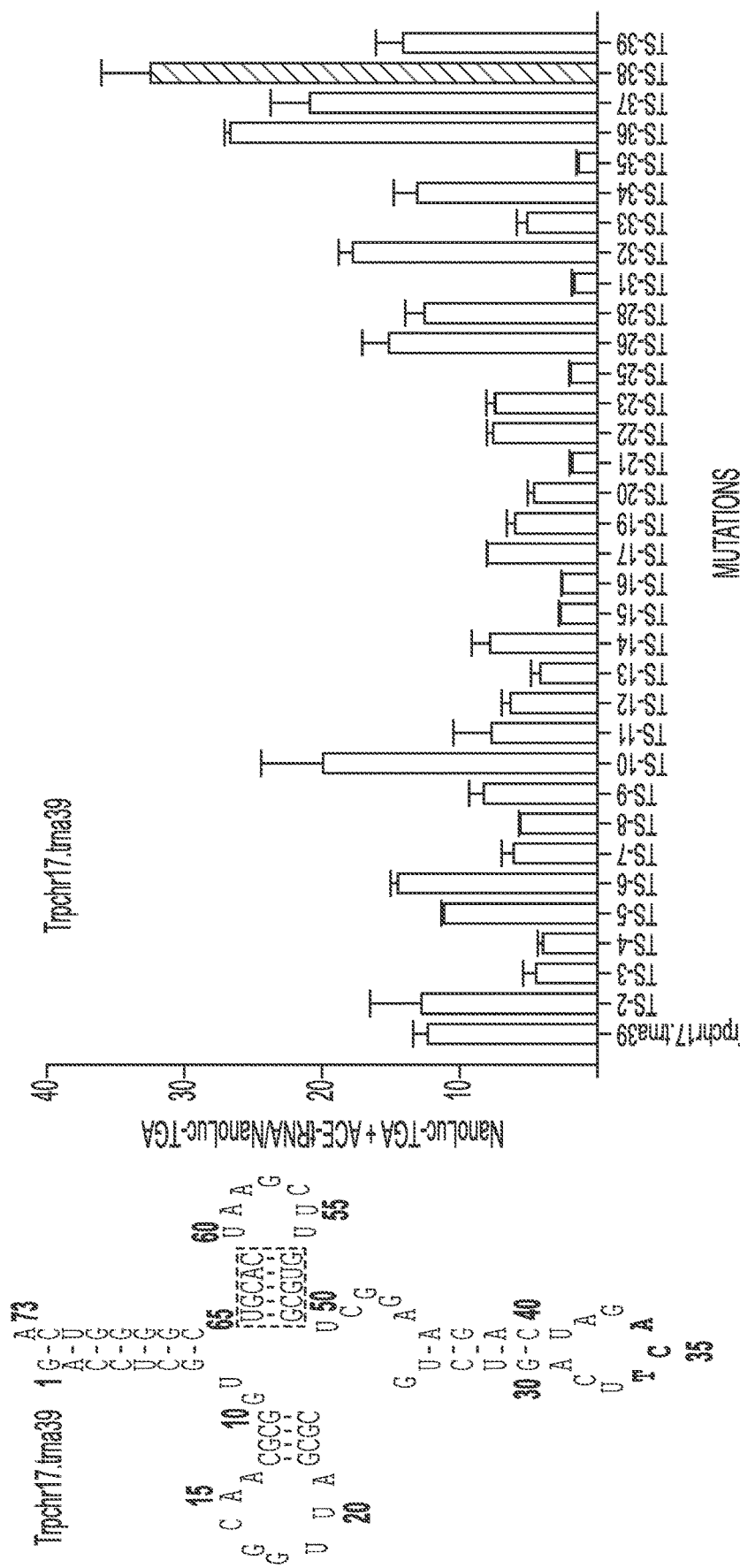
FIGS. 12A-12B. Targeted mutations of nucleotides within the t-stem region further enhance ACE-tRNA rescue function.
Figure 12B:
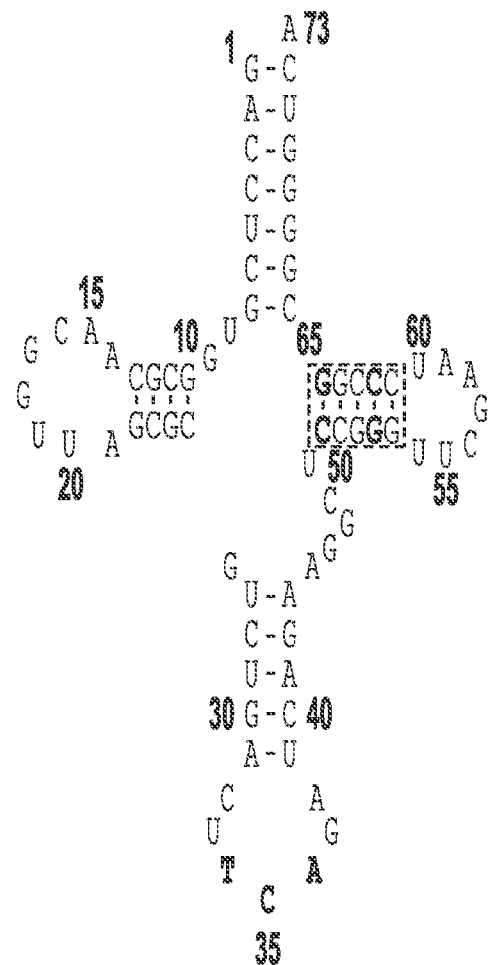

T-stem modification significantly improves nonsense suppression. FIG. 10. Herein we propose an additional modification of the tRNA to further enable their function for the purpose of suppression of nonsense codons and the promotion of protein expression. The hypothesis is based on the possibility that rationally introduced mutations within the tRNA 't-stem' loop, shown in FIG. 10, will yield a tRNA molecule that is more stable and functionally more potent for nonsense codon suppression. To this end, single and double mutations were directly engineered into the t-stem loop of tRNA Trpchr17.trna39—an ACE-tRNA identified with activity for the rescue of tryptophan TGA nonsense codons. Thirty-eight tRNA t-stem variants were thus generated and screened in HEK cells transiently transfected with the nonsense rescue reporter construct shown in FIG. 4. 24 hours post-transfection, cells were assayed for luciferase activity, shown in FIG. 10. The data show strong variation and identify novel tRNA sequences with varied t-stem loop sequences with enhanced suppression activity. Notably, one such mutant, TS-38 52-62 G-C enhances the suppression ability of Trpchr17.trna39 by roughly 250% (FIG. 12). We thus propose this is a generalizable modification, that is, of new tRNA sequences identified, by example 1 and 2, can be made better (for their ability to rescue nonsense codons) through further rationale modifications. Such approaches aid in the therapeutic utility of ACE-tRNA directed to tissue types with low abundance target RNA or where tRNA delivery may be limiting.

EXAMPLE 4

Figure 11:
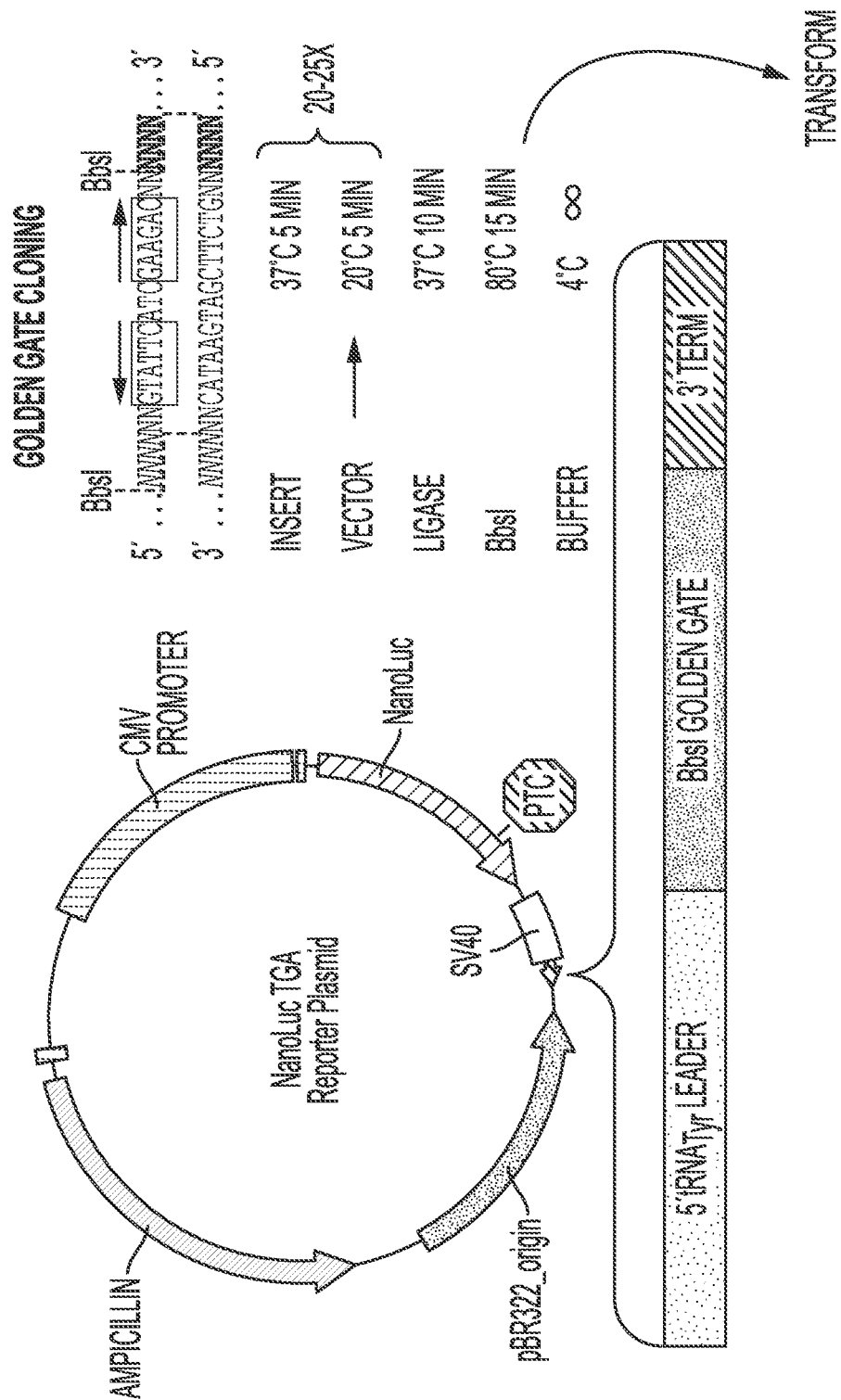
FIG. 11. Cloning workflow for the construction of tRNA libraries.

In order to enable the identification of the nucleotide composition and functional ability to suppress nonsense codons by new types of tRNA, an All-In-One Plasmid With A One Pot Cloning Reaction was invented for High Throughput Cloning FIG. 11. This approach enables the facile investigation of ACE-tRNA activity via luciferase activity in a standard 96 well format. Briefly, synthetic nucleotide sequences encoding for tRNA are ligated into the NanoLuc Reporter plasmid, with an example of the TGA nonsense reporter plasmid variant shown in FIG. 11. TAA (Opal) and TAG (amber) stop codon rescue vectors have been successfully designed and implemented in FIGS. 16-19. The benefits are the approach is that DNA oligos encoding for tRNA libraries can be ligated in the NanoLuc reporter plasmid with the presence of the restriction enzyme and ligase with the reaction pushed to nearly 100% incorporation of tRNA insert (FIG. 11)-thus the 'one-pot' designation. The reaction is transformed into *E. coli*, with the resultant cDNA purified by standard methods. Another benefit of the invented method is that the tRNA and reporter gen are within the single expression cassette, therefore lowering biological variability and improving data quality obtaining in resulting screens of tRNA suppression activity. The purified cDNA plasmids are then screened in high-throughput 96 well format for their ability to repair nonsense codons by inferred luciferase activity. The approach is suitable for the high-throughput screening of hundreds to thousands of tRNA for novel therapeutic activity.

Figure 13E:
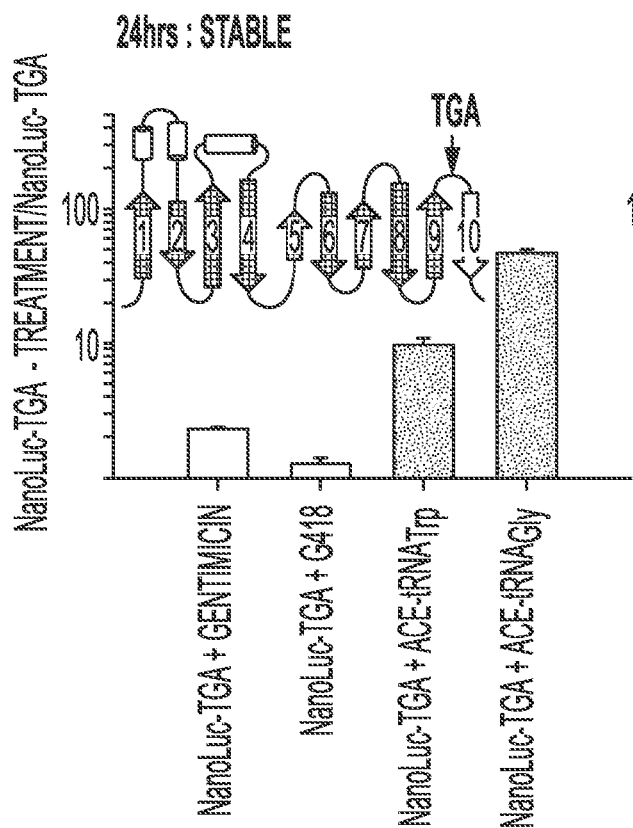
Figure 13F:
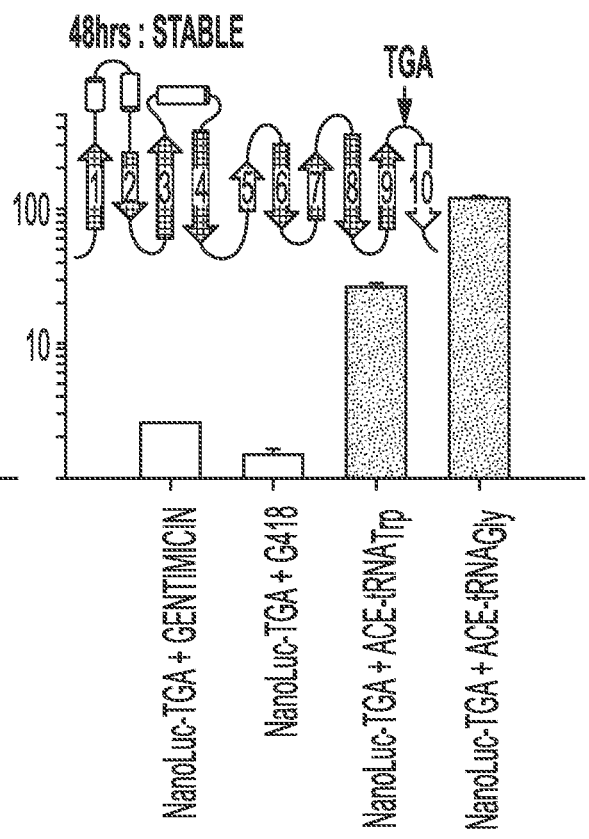
Figure 14:
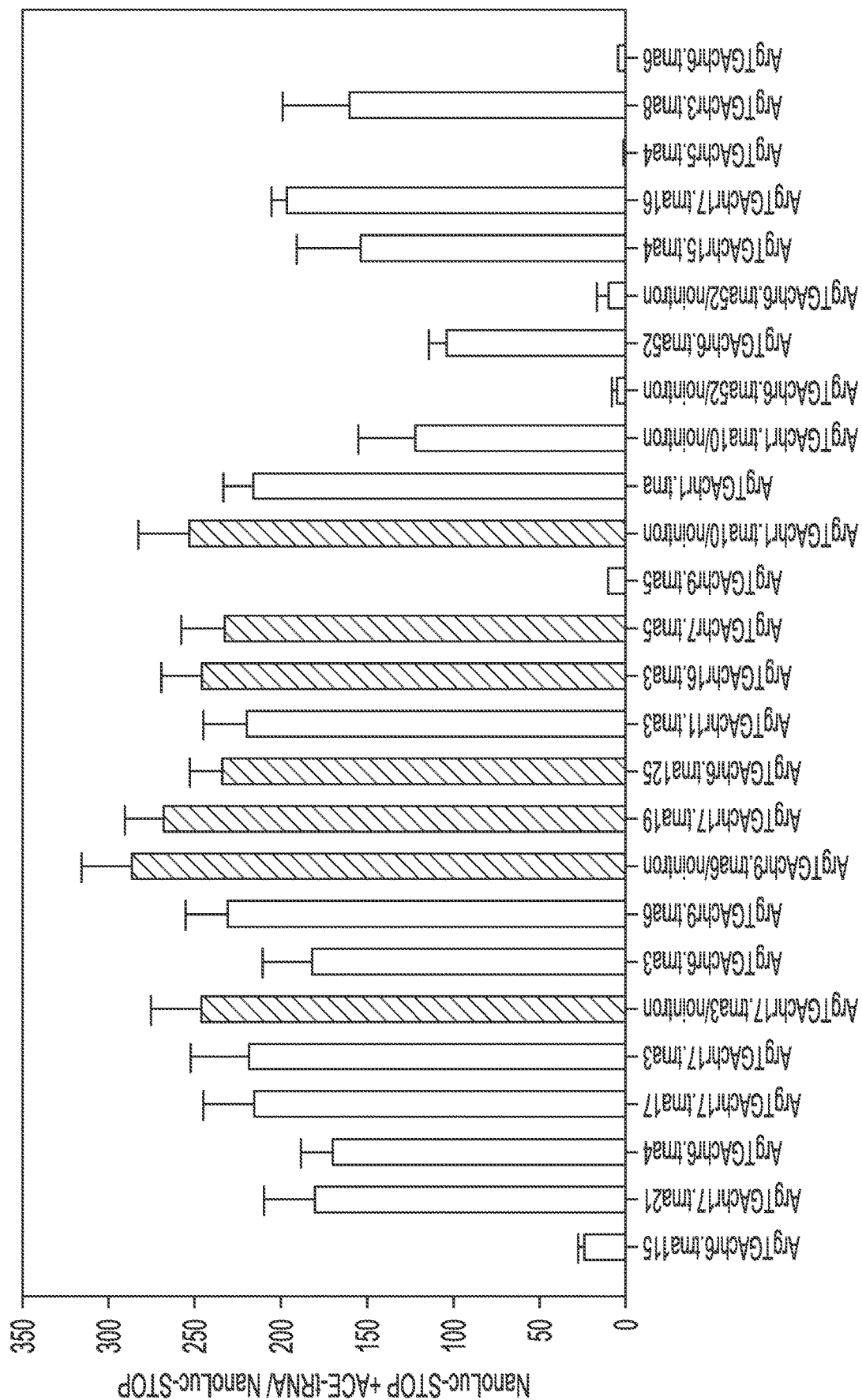
FIG. 14. ACE-tRNA-Arg-TGA. Identification of ACE-tRNA for repair of arginine-TGA nonsense codons.
Figure 15:
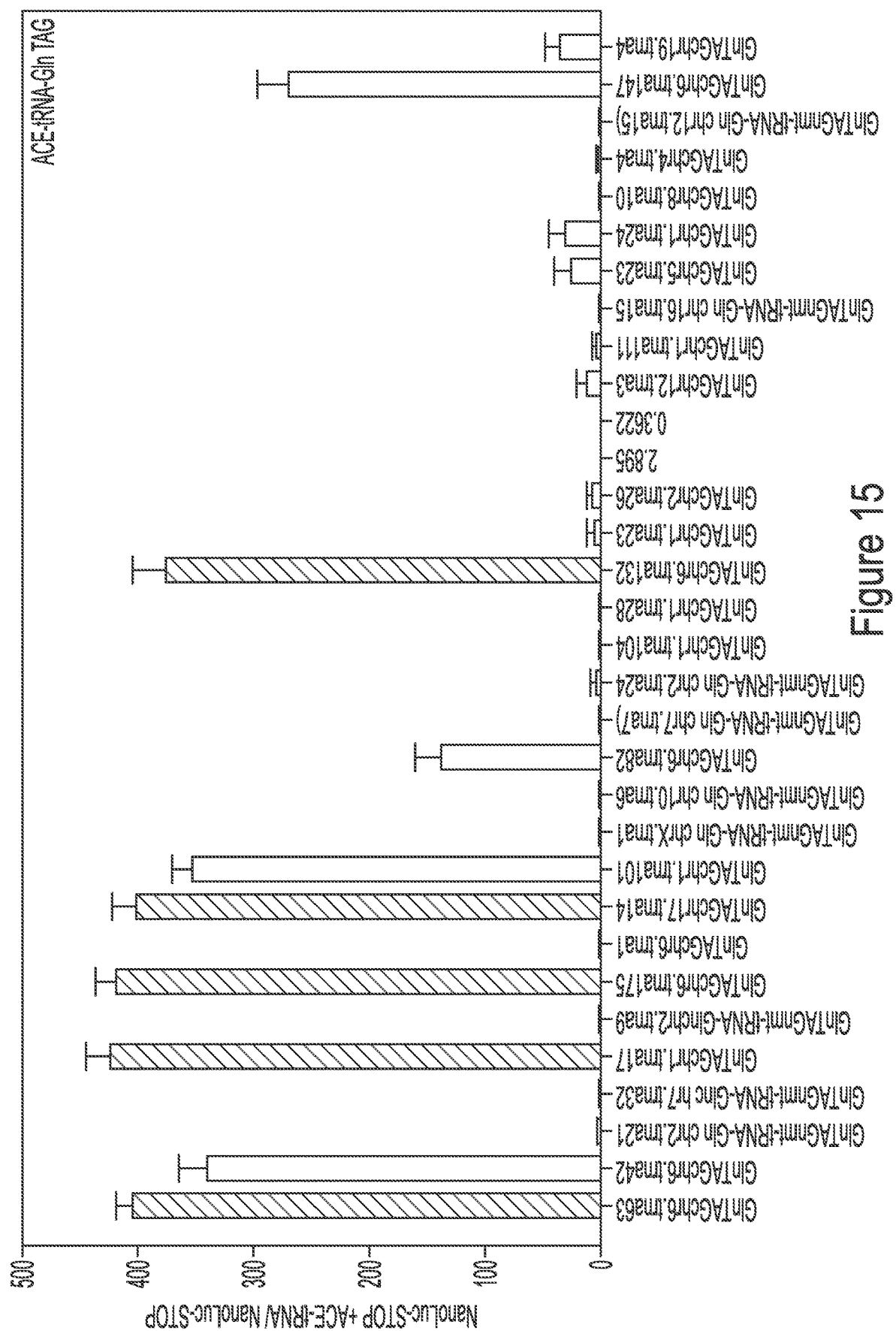
FIG. 15. ACE-tRNA-Gln TAG. Identification of ACE-tRNA for repair of glutamine TAG nonsense codons.
Figure 16:
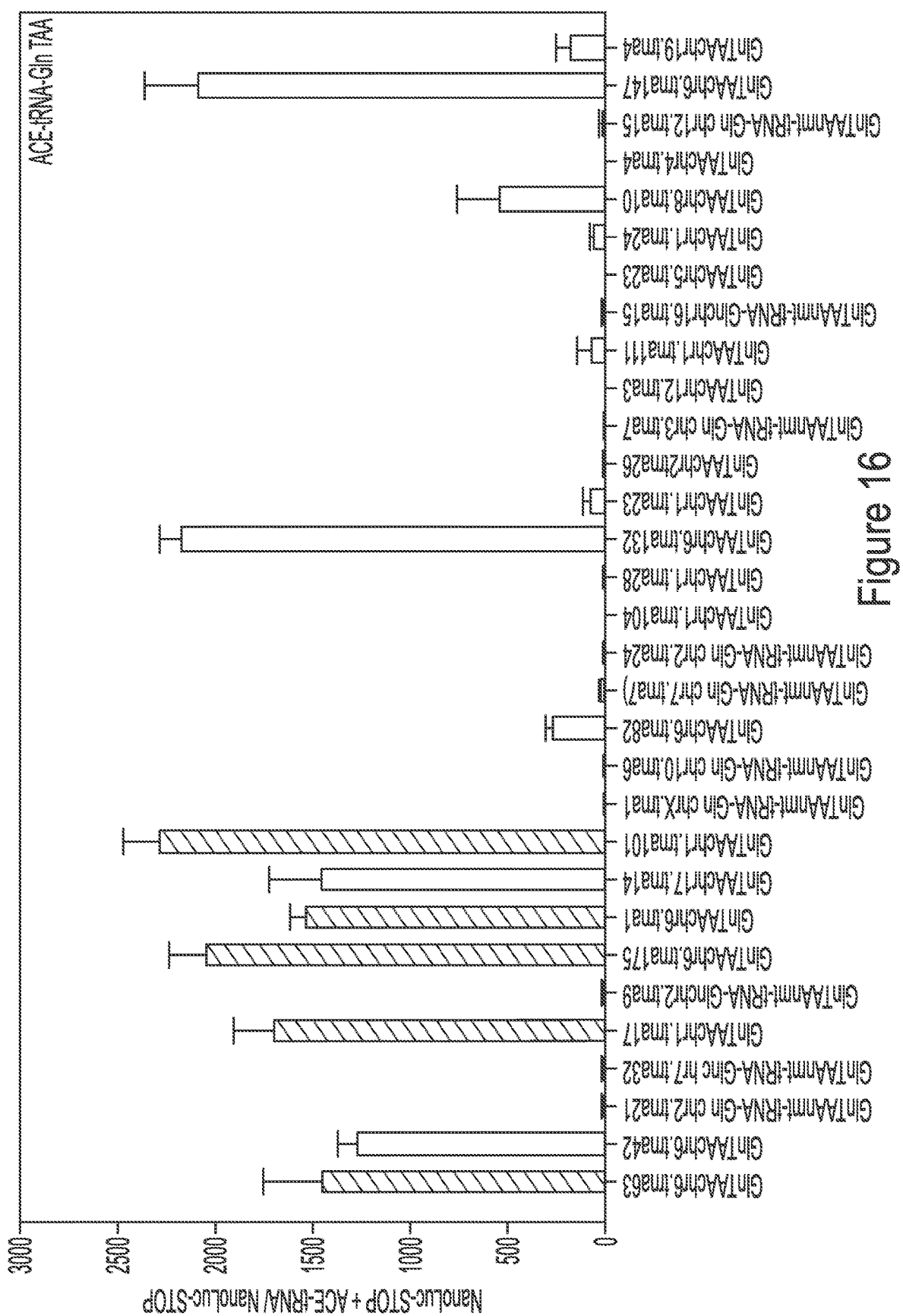
FIG. 16. ACE-tRNA-Gln TAA Identification of ACE-tRNA for repair of glutamine TAA nonsense codons.
Figure 17:
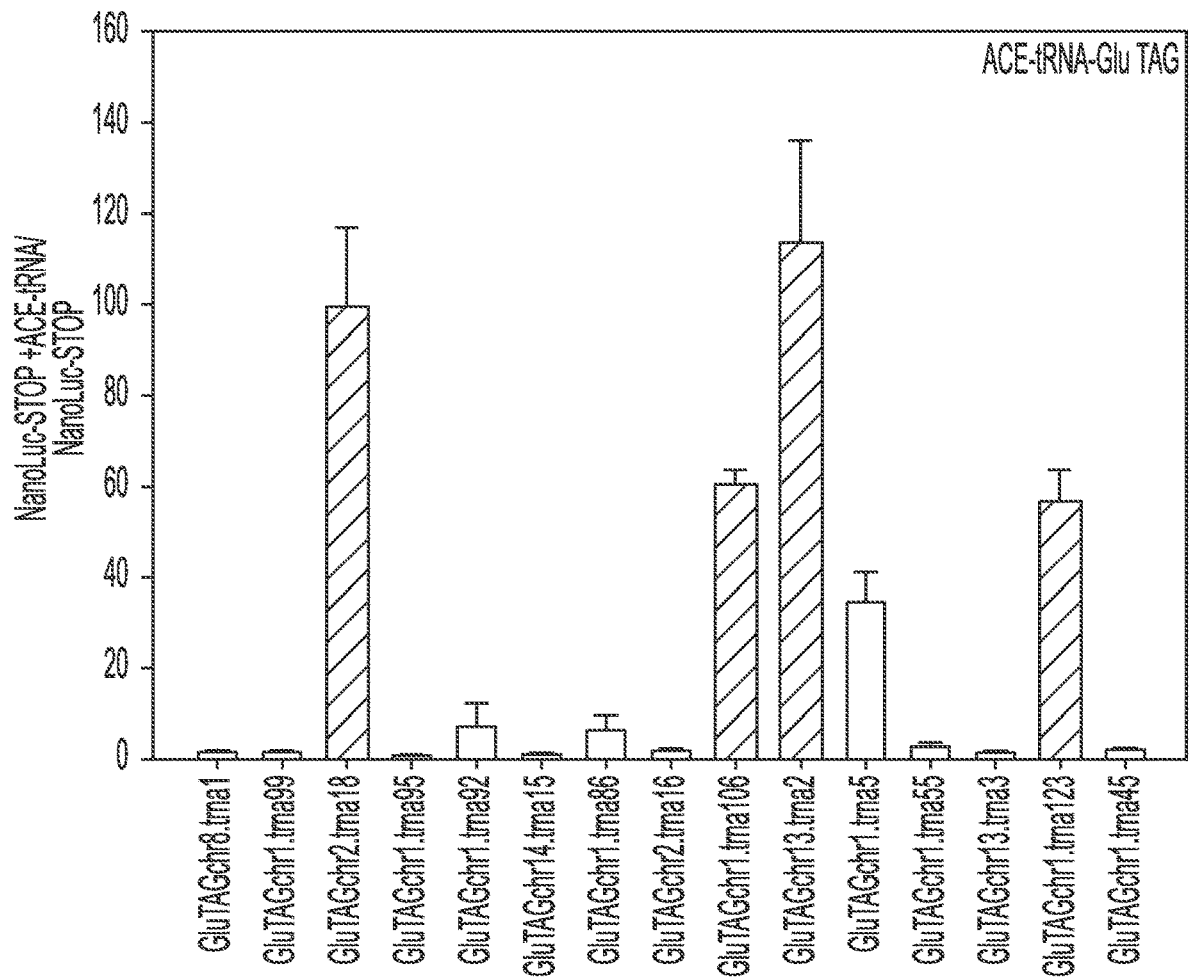
FIG. 17. ACE-tRNA-Glu TAG Identification of ACE-tRNA for repair of glutamate-TAG nonsense codons.
Figure 18:
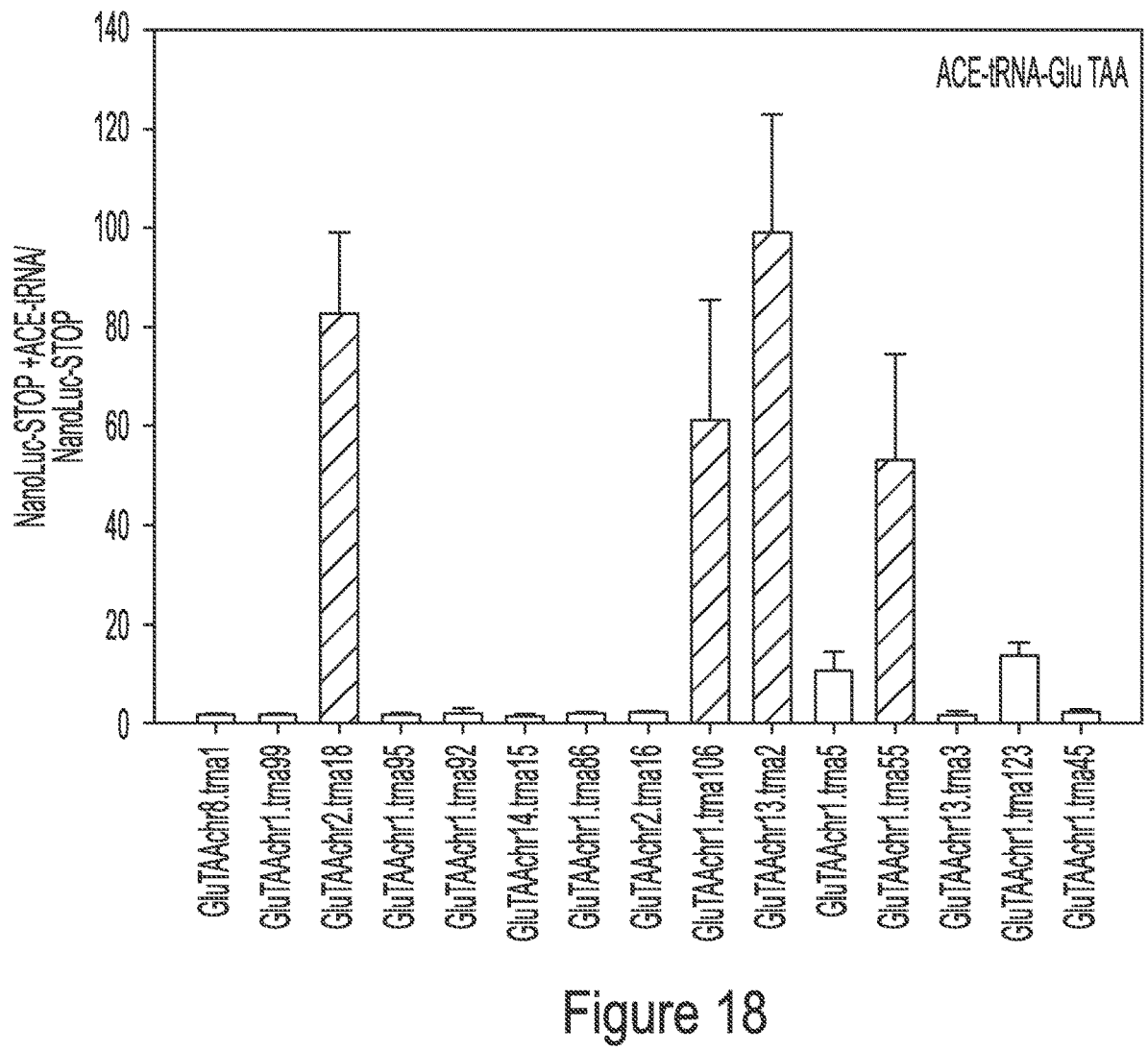
FIG. 18. ACE-tRNA-Gln TAA Identification of ACE-tRNA for repair of glutamate TAA nonsense codons.
Figure 19:
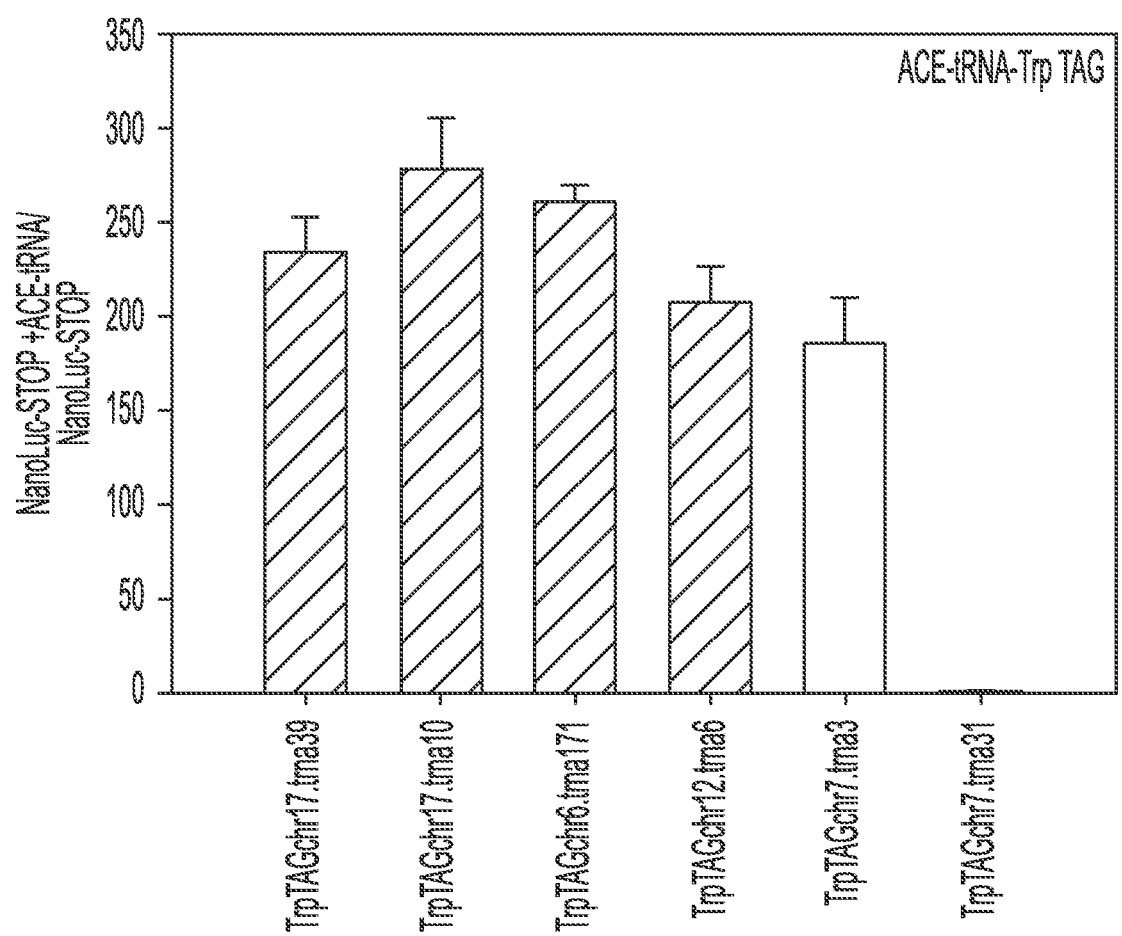
FIG. 19. ACE-tRNA-Trp TAG Identification of ACE tRNA for the repair of tryptophan TAG nonsense codons.
Figure 20A:
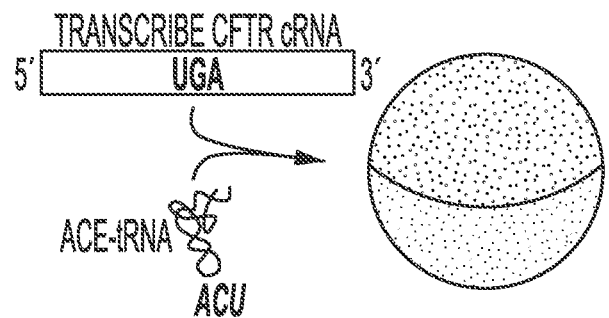
FIGS. 20A-20D. Delivery of ACE-tRNA as small RNA supports robust suppression of G542X and W1282X nonsense mutations.
Figure 20B:
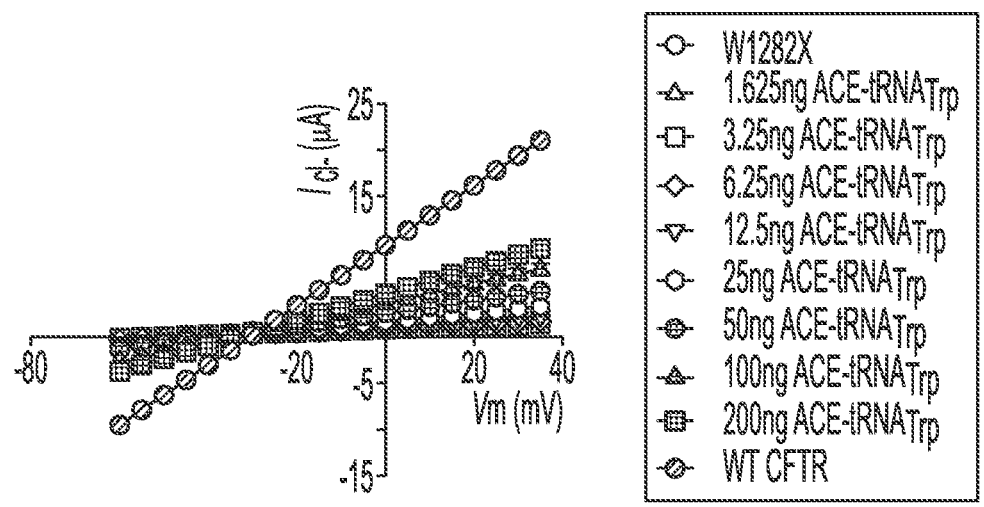
Figure 20C:
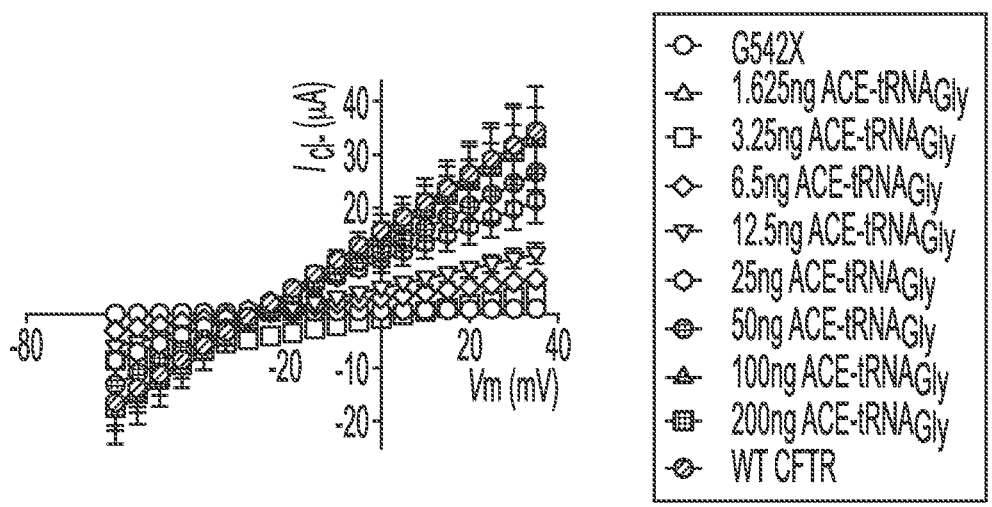
Figure 20D:
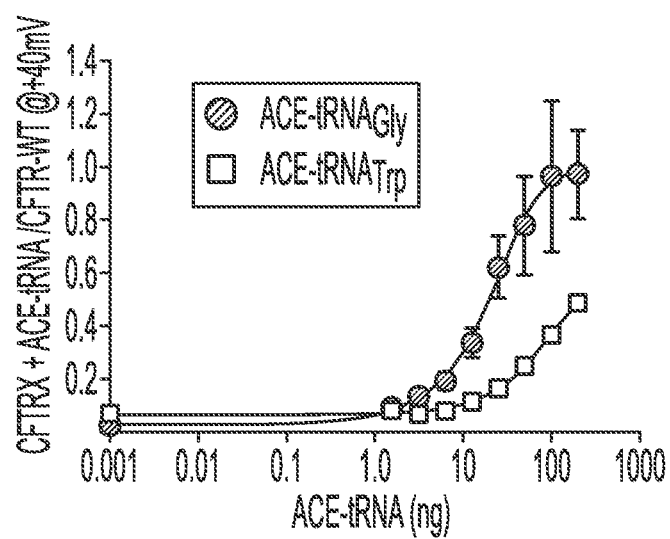

The 'one-pot' cloning and expression system described in FIG. 11 has been used successfully to identify unique tRNA sequences for the repair of Tryptophan and Glycine ACE-tRNA (FIG. 13), ACE-tRNA-Arg (FIG. 14), ACE-tRNA-Gln TAG (FIG. 15), ACE-tRNA-Gln TAA (FIG. 16), ACE-tRNA-Glu TAG (FIG. 17), ACE-tRNA-Gln TAA (FIG. 18) and ACE-tRNA-Trp TAG (FIG. 19). FIGS. 20A-20D show that delivery of ACE-tRNA as small RNA supports robust suppression of G542X and W1282X nonsense mutations.

EXAMPLE 5

Engineered transfer RNAs for suppression of premature termination codons ABSTRACT Premature termination codons (PTCs) are responsible for 10-15% of all inherited disease. PTC suppression during translation offers a promising approach to treat a variety of genetic disorders, yet small molecules that promote PTC read-through have yielded mixed performance in clinical trials. A high-throughput, cell-based assay is presented to identify anticodon engineered transfer RNAs (ACE-tRNA) that can effectively suppress in-frame PTCs and faithfully encode their cognate amino acid. In total, ACE-tRNA were identified with a high degree of suppression activity targeting the most common human disease-causing nonsense codons. Genome-wide transcriptome ribosome profiling of cells expressing ACE-tRNA at levels which repair PTC indicate that there are limited interactions with translation termination codons. These ACE-tRNAs display high suppression potency in mammalian cells, *Xenopus* oocytes and mice in vivo, producing PTC repair in multiple genes, including disease causing mutations within the cystic fibrosis transmembrane conductance regulator (CFTR).

Introduction

Premature termination codons (PTCs) arise from single nucleotide mutations that convert a canonical triplet nucleotide codon into one of three stop codons, e.g., TAG, TGA, or TAA. PTCs are often more deleterious than missense mutations because they result in the loss of protein expression. Additionally, mRNA abundance is reduced through nonsense-mediated decay (NMD) and in some cases, truncated proteins may have a dominant negative function[1-3]. Therefore, it is not surprising that PTCs are associated with many severe disease phenotypes, including cystic fibrosis[4], Duchenne muscular dystrophy, spinal muscular atrophy[5], infantile neuronal ceroid lipofuscinosis[6], β-thalessemia cystinosis[8], X-linked nephrogenic diabetes insipidus[9], Hurler syndrome[10], Usher syndrome[11], and polycystic kidney disease. Additionally, nonsense mutations occur within the tumor suppressor genes p53 and ATM[12], further implicating their role in disease. Amino acid codons most vulnerable to PTC conversion are those with a single nucleotide substitution from a stop codon: tryptophan, tyrosine, cysteine, glutamic acid, lysine, glutamine, serine, leucine, arginine, and glycine (FIG. 25). As such, PTCs represent a unique constellation of diseases which afflict over 30 million people worldwide, accounting for 10-15% of all genetic diseases[13].

Small molecules, such as aminoglycosides[14], dipeptides[15], and oxadiazoles[16], promote the "read-through" or "suppression" of nonsense mutations. These compounds are effective in model organisms[17, 18], mammalian cell lines[19] and some animal disease models 16, 20. However, this approach results in the encoding of a near-cognate amino acid[21], effectively generating a missense mutation at the PTC, which itself may have deleterious effects on protein folding, trafficking, and function. Furthermore, aminoglycosides are oto- and nephrotoxic[22], and the first-in-class oxadiazole, Ataluren, displayed unexpectedly low efficacy in patient populations (ACT DMD Phase 3 clinical trial, NCT01826487; ACT CF, NCT02139306), thus limiting their utility as PTC therapeutics. Recent and ongoing advances in CRISPR/Cas9-mediated genome editing provides potentially a permanent solution for diseases resulting from nonsense mutations. However, aspects of this technology impart hurdles for its rapid use as a therapeutic[23, 24]. This is not limited to the requirement of "precision" or "personalized" diagnostics for each mutation based on the context of each patient's genetic variability.

A PTC repair approach was identified that displays the versatility of small molecules and the precision of gene editing. tRNAs were investigated to fulfill these criteria, whereby their anticodons have been engineered via mutagenesis to recognize and suppress UGA, UAA or UAG PTC codons. In order to be effective, the anticodon edited tRNAs, aka ACE-tRNAs, should still be recognized by the endogenous translation cellular machinery, including the aminoacyl-tRNA synthetase for charging the ACE-tRNA with their cognate amino acid and the eukaryotic elongation factor 1α (eEF-1α) for delivery of the charged tRNA to the ribosome, FIG. 21A. Such suppressor tRNAs have been shown, in a limited manner, to rescue in frame stop codons associated with β-thalassemia[25], xeroderma pigmentosum[26] and a transgenic PTC reporter gene[27].

Here it is shown that an anti-codon editing approach is generalizable to multiple tRNA gene families, indicating that many annotated tRNA are biologically viable. Further, it is demonstrate that anti-codon edited suppressor tRNA encode their cognate amino acid, lack significant interactions with termination stop codons and are efficacious in vivo to suppress PTC. In total, the data support the possibility that such engineered tRNA satisfy the broad requirement for coverage of disease-causing PTCs and thus represent a promising new class of RNA therapeutic agent.

Results

Figure 22:
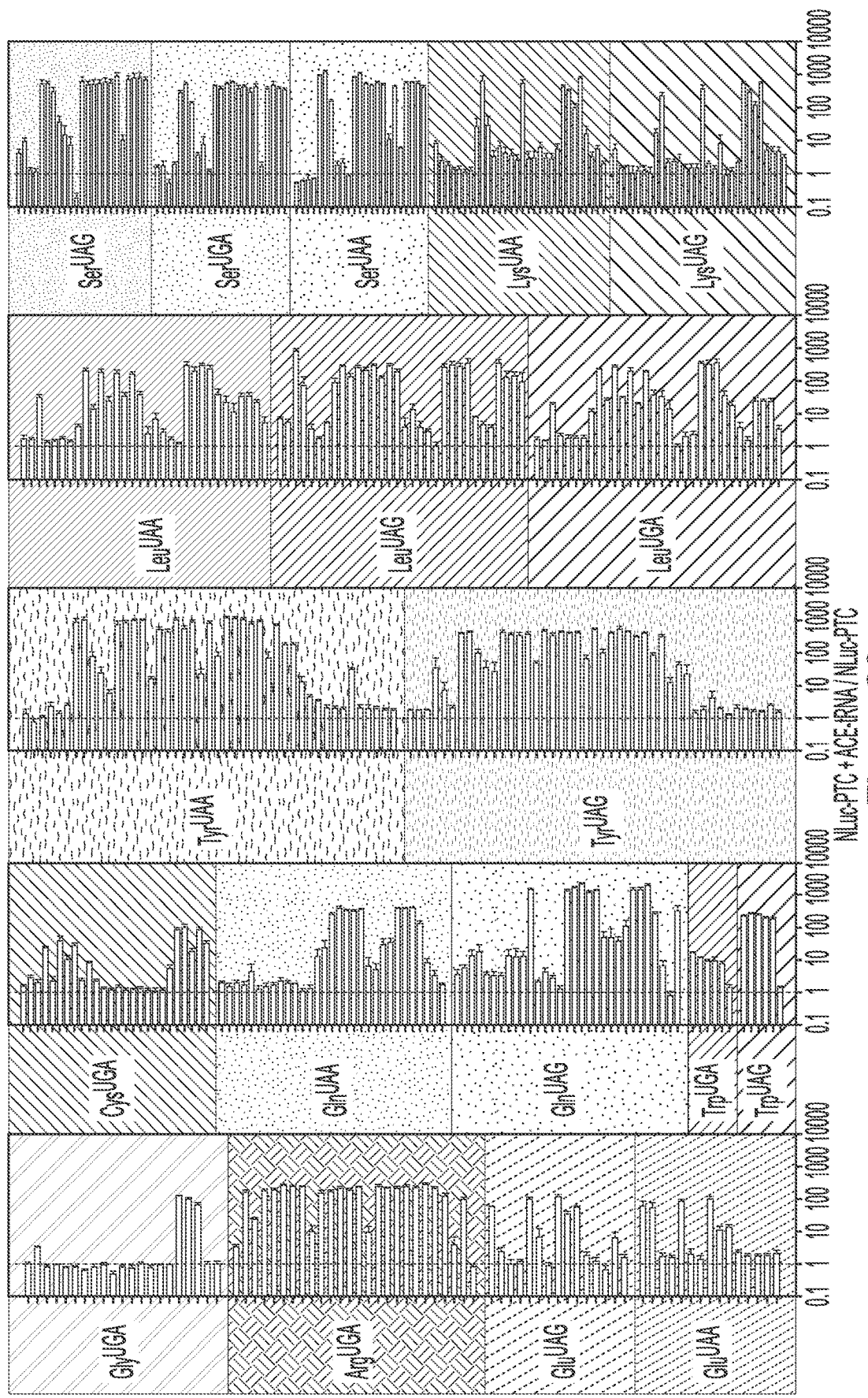
FIG. 22 Screens of ACE-tRNA gene families with the high throughput cloning nonsense mutation reporter platform. The indicated anticodon edited PTC sequences were tested for each ACE-tRNA family that is one nucleotide away from the endogenous anticodon sequence, FIG. 25. Multiple high performing suppressor tRNA were identified for each class. Data are shown in Log 10 scale in terms of normalized NLuc luminescence. Each tRNA dataset were obtained in triplicates and are displayed at SEM, with the corresponding ANOVA statistical analysis in Table 2. Coded identities and corresponding tRNA sequences are shown in FIG. 26 and Table 9, respectively.

The rationale of this study is rooted in the observation that there are multiple tRNA genes with unique sequences (isodecoders) for a given cognate amino acid (isoacceptors), leading to >400 tRNAs annotated in the human genome (http:lowelab.ucsc.edu/GtRNAdb/)[28, 29]. First, tRNA genes were examined to identify individual ACE-tRNAs that retain suppression efficacy of PTCs in mammalian cells. In order to maximize sequence coverage, an all-in-one cDNA plasmid was generated that supports both high-throughput cloning (HTC) of ACE-tRNAs and quantitative measurement of PTC suppression using luminescence following delivery to mammalian cells, FIG. 21B. ACE-tRNA sequences were cloned as DNA oligos into the HTC plasmid using Golden Gate cloning[30] paired with ccdB negative selection[31]. This strategy produced ~100% cloning efficiency. ACE-tRNA suppression efficiency was read out from a split NanoLuc luciferase (NLuc) NanoBiT platform whereby the PTC of interest (UGA, UAA, or UAG) was introduced in-frame at the junction between the large bit and small bit domains, FIG. 21B, using a 96-well format and normalized to background obtained in NLuc-PTC expressing cells. Twenty-one glycine ACE-tRNAs were first evaluated for suppression of the UGA PTC, FIG. 22, top left, column 1

Figure 27:
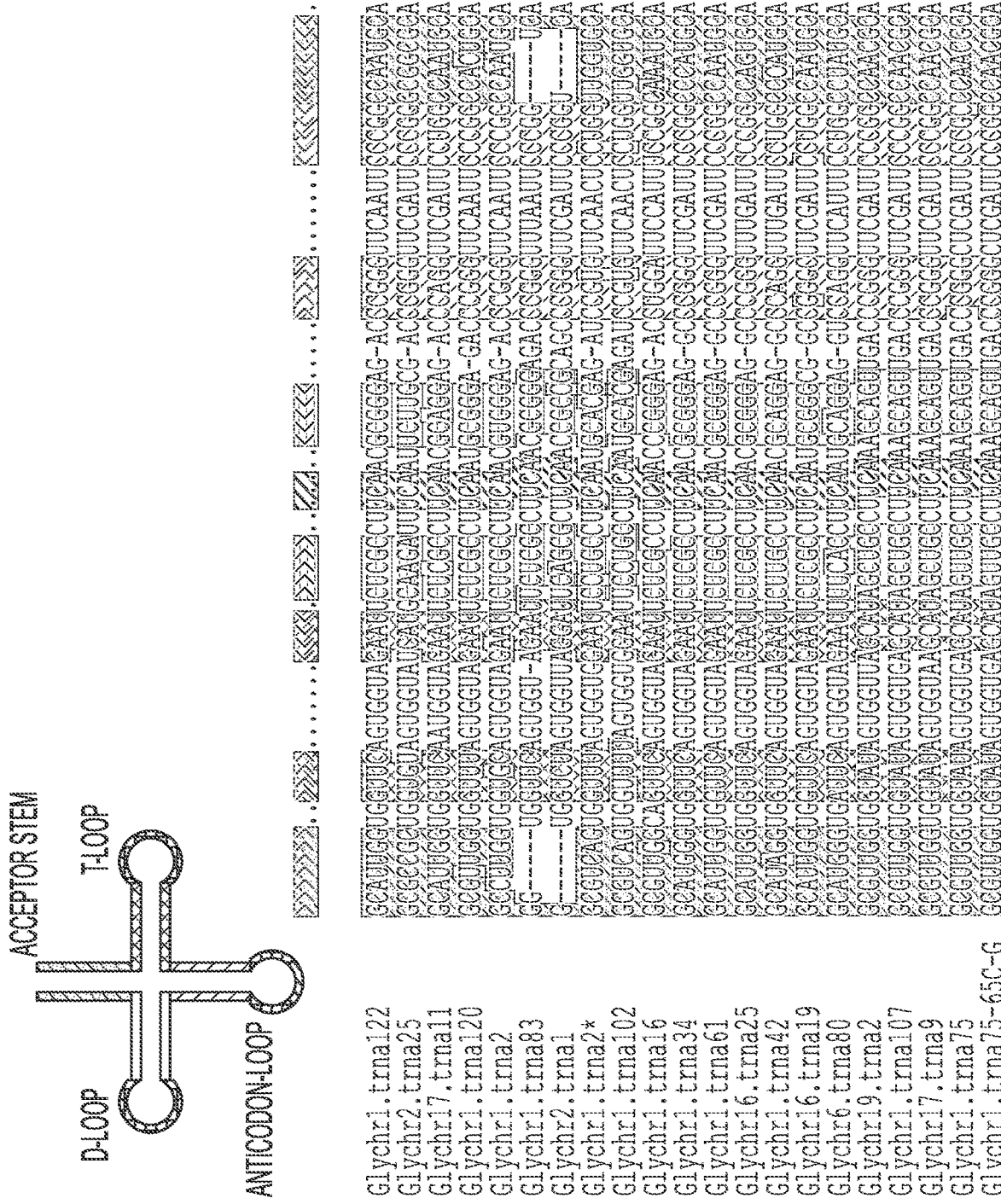
FIG. 27. Alignment of Glycine tRNA sequences. 21 tRNAGly human sequences demonstrate high sequence homology amongst tRNA clades. Pattern in tRNA image corresponds to patterned boxes in sequences.

(violet). A majority of the ACE-tRNA$^{Gly}$ sequences failed to suppress the UGA NLuc PTC, however, three Gly-tRNA$^{UGA}$ were identified with high suppression yields (~100-fold over background). Given the high sequence conservation among the Gly-tRNAs screened for anti-codon tolerance (FIG. 27), it would be difficult to predict de novo which tRNA would be most amenable to anticodon-editing.

Next, performed screens were performed on codon-edited tRNA for the each of the possible single nucleotide mutations which could produce a disease-causing PTCs: Arg-tRNA$^{UGA}$, Gln-tRNA$^{UAA}$, Gln-tRNA$^{UAG}$ Trp-tRNA$^{UGA}$, Trp-tRNA$^{UAG}$, Glu-tRNA$^{UAA}$, Glu-tRNA$^{UAG}$, Cys-tRNA$^{UGA}$, Tyr-tRNA$^{UAG}$, Tyr-tRNA$^{UAA}$, Ser-tRNAUAG, Leu-tRNA$^{UAG}$, Leu-tRNA$^{UAA}$, Lys-tRNA$^{UAG}$, Lys-tRNA$^{UGA}$ and Ser-tRNA$^{UAG}$. The enzymatic activity of NLuc was not significantly influenced by the introduced amino acid (FIG. 28), therefore owing the difference in NLuc luminescence to ACE-tRNA suppression ability. The screen identified multiple ACE-tRNAs for each of the amino acids and stop codon type, with suppression coverage for all three stop codons, FIG. 22. Many of these ACE-tRNAs exhibited strong activity with >100-fold PTC suppression over background, which is significantly higher than the aminoglycosides used in this study. Interestingly, some ACE-tRNAs displayed a clear preference for a particular anticodon editing, possibly reflecting altered aminoacyl-tRNA synthetase binding to the tRNA anticodon isoacceptor sequences[33]. For instance, tryptophan conversion to UAG suppression yielded rescue that was ten times higher than that of UGA editing of the same ACE-tRNA$^{Trp}$. Yet the opposite was true for glutamine, where a clear preference was shown for UAA over UAG. Notably, in each case, multiple high performing suppressors were identified, and this was especially evident with Arg$^{UGA}$, a PTC which plays an outsized role in human disease; where twenty efficient ACE-Arg$^{UGA}$ suppressors were identified. In other cases, such as ACE-tRNA$^{Glu}$, of those which exhibited function, the suppression efficiency was roughly equal for UAA and UAG. And a similar pattern was found in ACE-tRNA$^{Lys}$ where encoding via UAG or UGA suppression were strongly mirrored. For Gln-tRNA$^{UAA}$, the suppression activity resulted in suppression signals >2,000-fold over background. Of the ACE-tRNAs identified in the screen, the tryptophan tRNA gene family displayed the weakest suppression activity for UGA PTCs. With only 6 unique human ACE-tRNA$^{Trp}$ sequences available to screen, the UGA suppressing ACE-tRNA$^{Trp}$ library was expanded using tRNA from a range of species. UGA anticodon-editing tolerance was tested for tryptophan tRNA genes with unique sequences from yeast, fly, mouse, rat, rabbit, and frog; in addition to a miscoding A9C tRNA$^{Trp}$ and bacterial Hirsh Trp suppressor[34-36], FIG. 29A-29B. This effort was unsuccessful in identifying ACE-tRNA$^{Trp}$ UGA PTC suppression activity that exceeded that of the human ACE Trp tRNA, FIG. 29C. Overall, the tRNA screens identified multiple engineered tRNAs (for each amino acid and stop codon type) that displayed potent suppression, thus bearing general tolerance to anticodon editing.

Figure 23A:
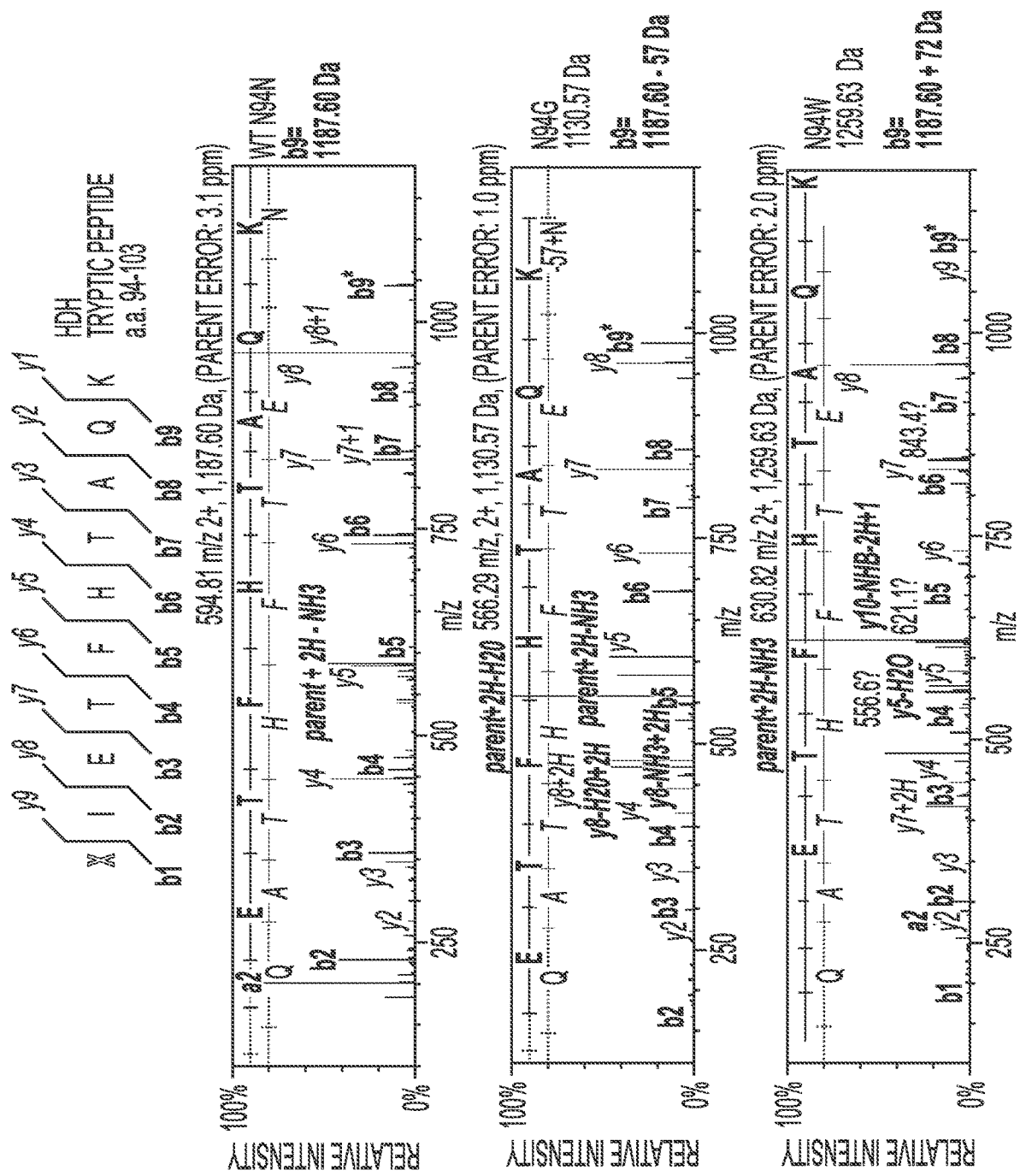
FIGS. 23A-23C Cognate Encoding and High-Fidelity Suppression by Engineered tRNA.
Figure 23B:
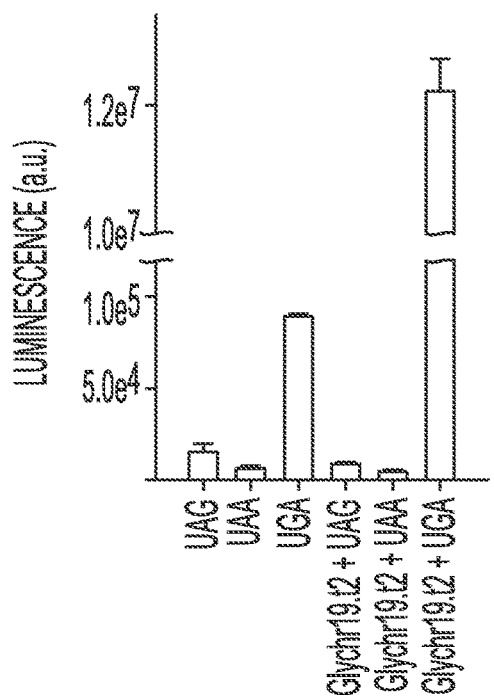
Figure 23C:
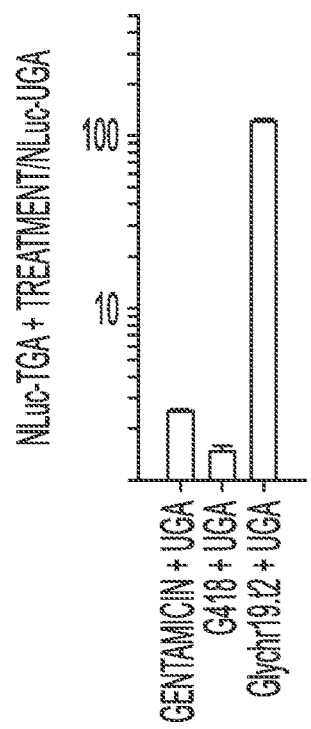
Figure 28:
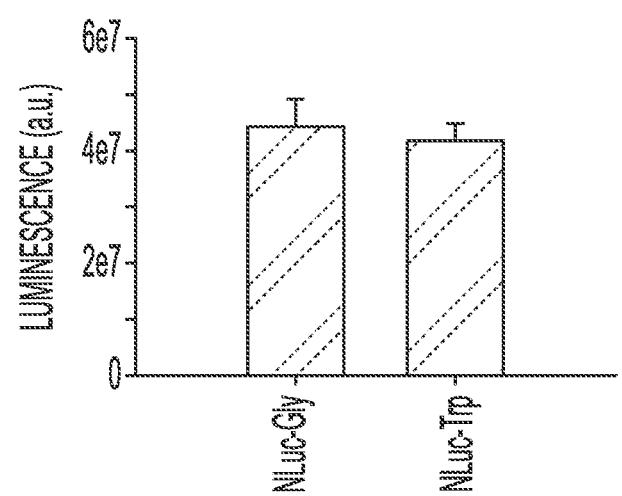
FIG. 28. Side-chain identity at p.162 in Nanoluciferase does not affect activity. Total luminescence activity is indicated for each mutation at site.
Figure 29B:
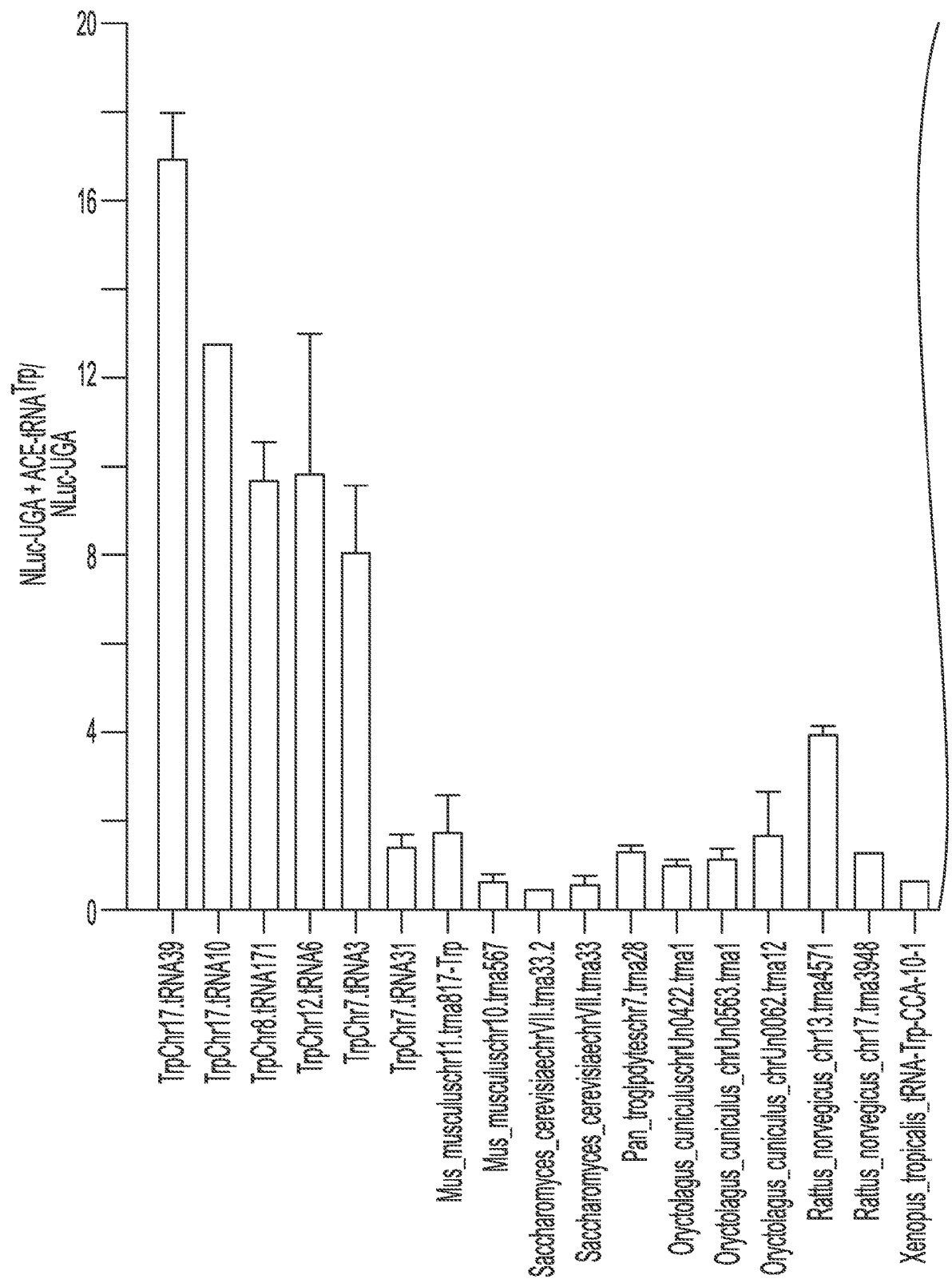
Figure 29B:
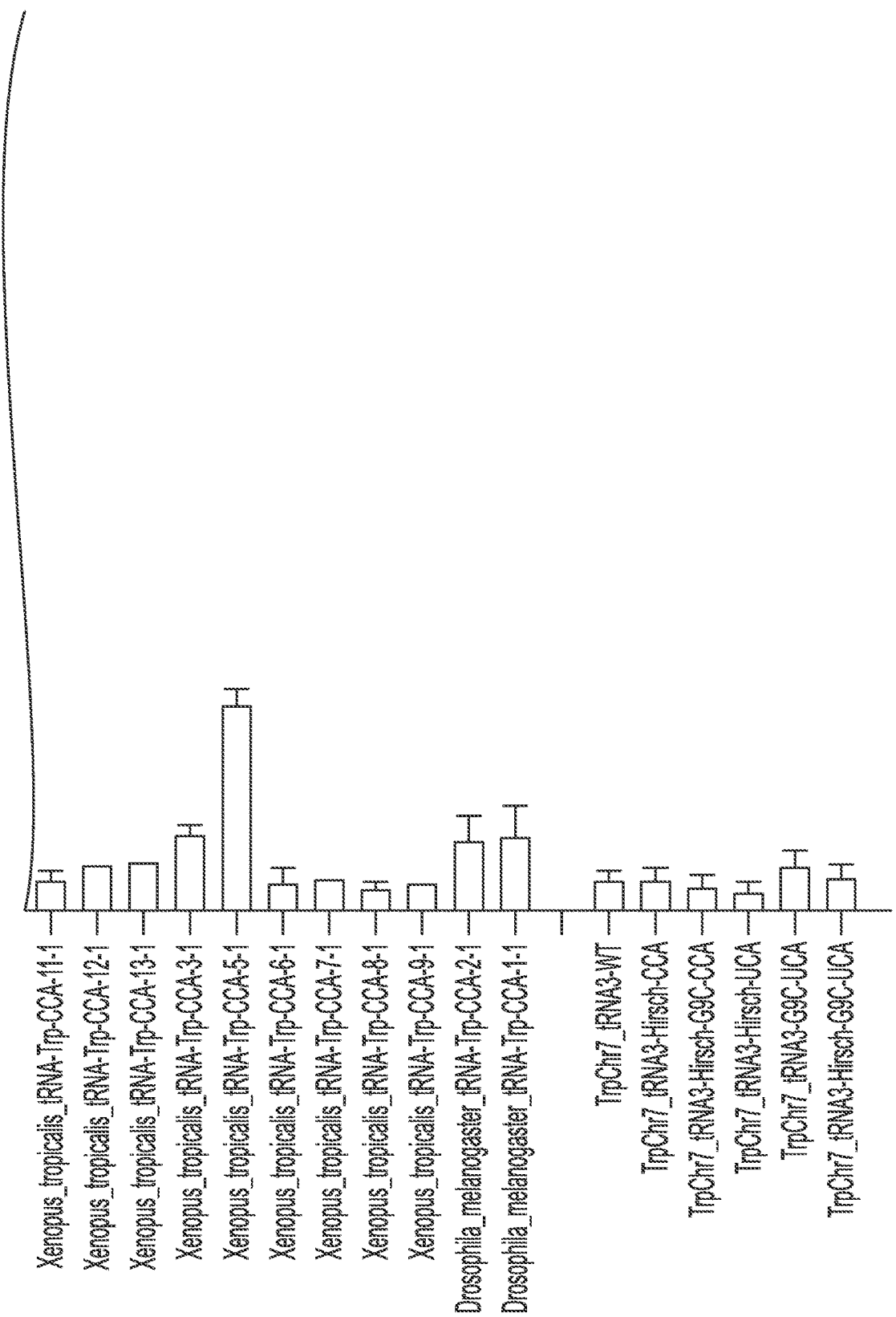
Figure 31:
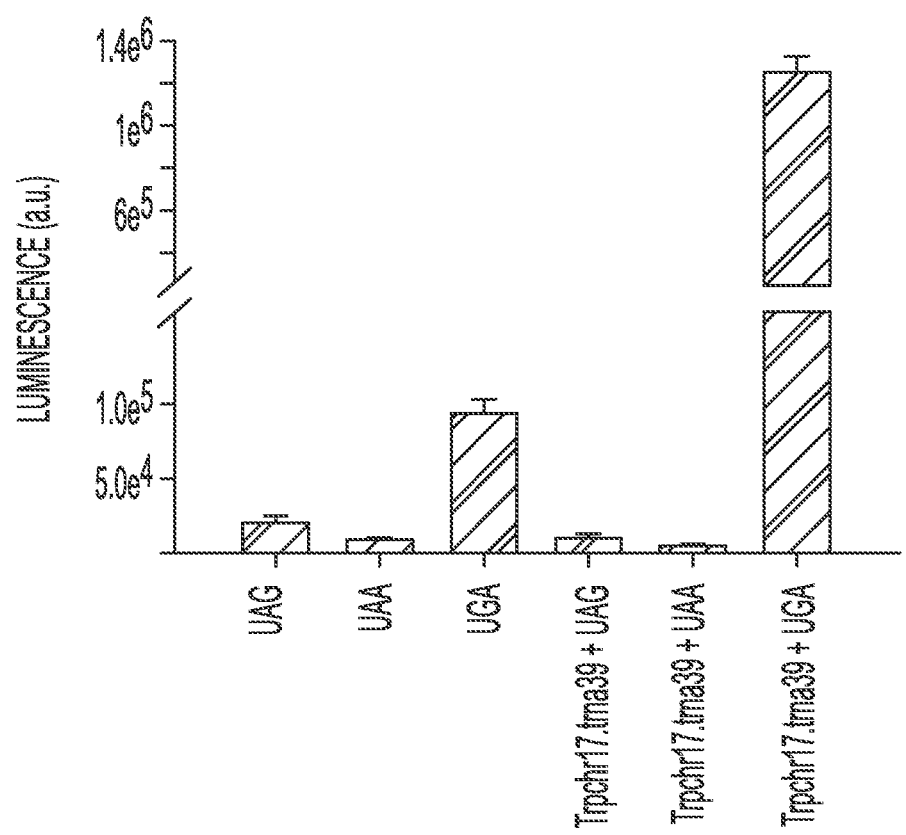
FIG. 31. Stop codon specificity is maintained for ACE-tRNA$^{Trp}$. Suppression activity 36for tRNA Trp$^{TGA}$ Trpchr17.trna39, the top performing Trp$^{TGA}$ suppressor tRNA, FIG. 22. This tRNA was co-expressed with the indicated pNano-STOP plasmid.
Figure 32A:
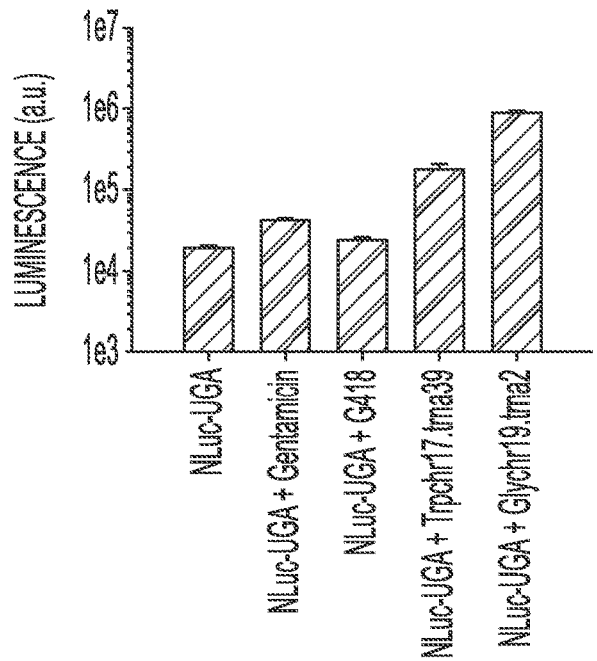
FIGS. 32A-32D. ACE-tRNAs are more efficient than aminoglycoside PTC suppression.
Figure 32B:
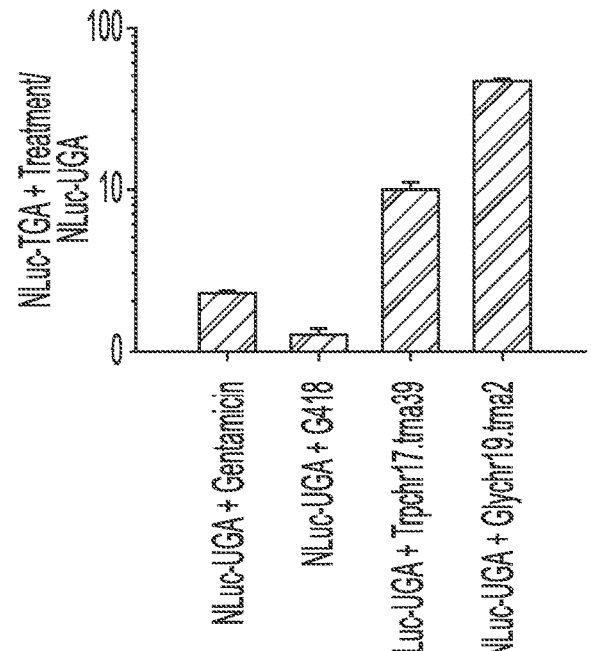
Figure 32C:
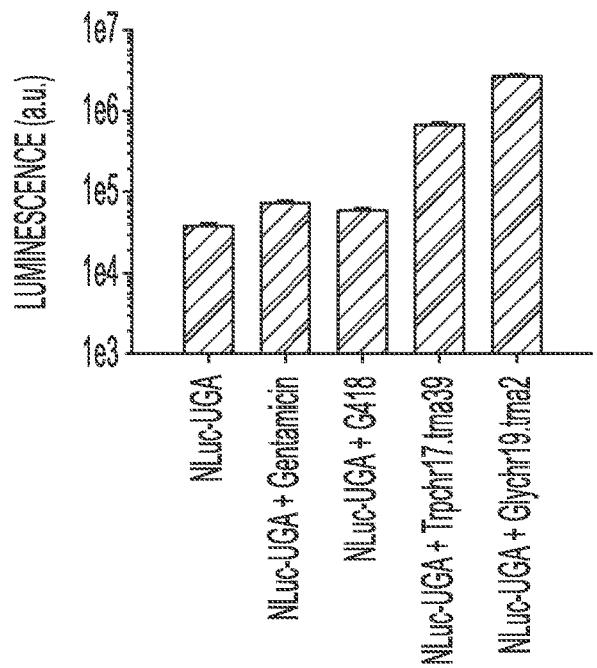
Figure 32D:
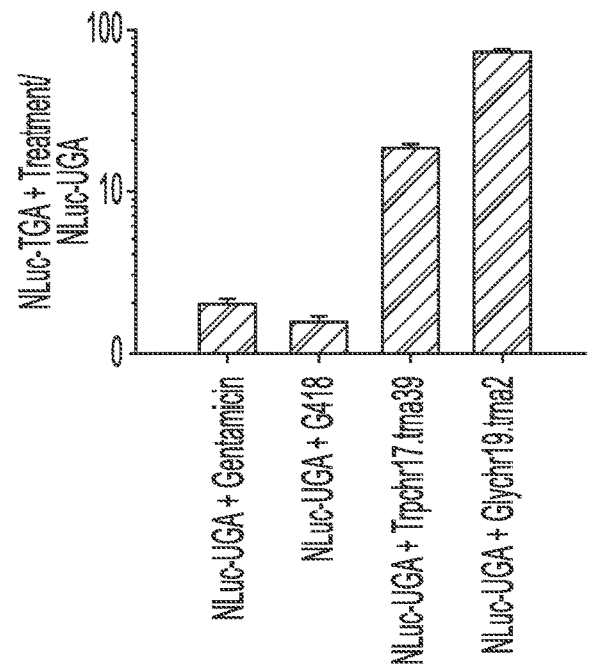
Figure 33:
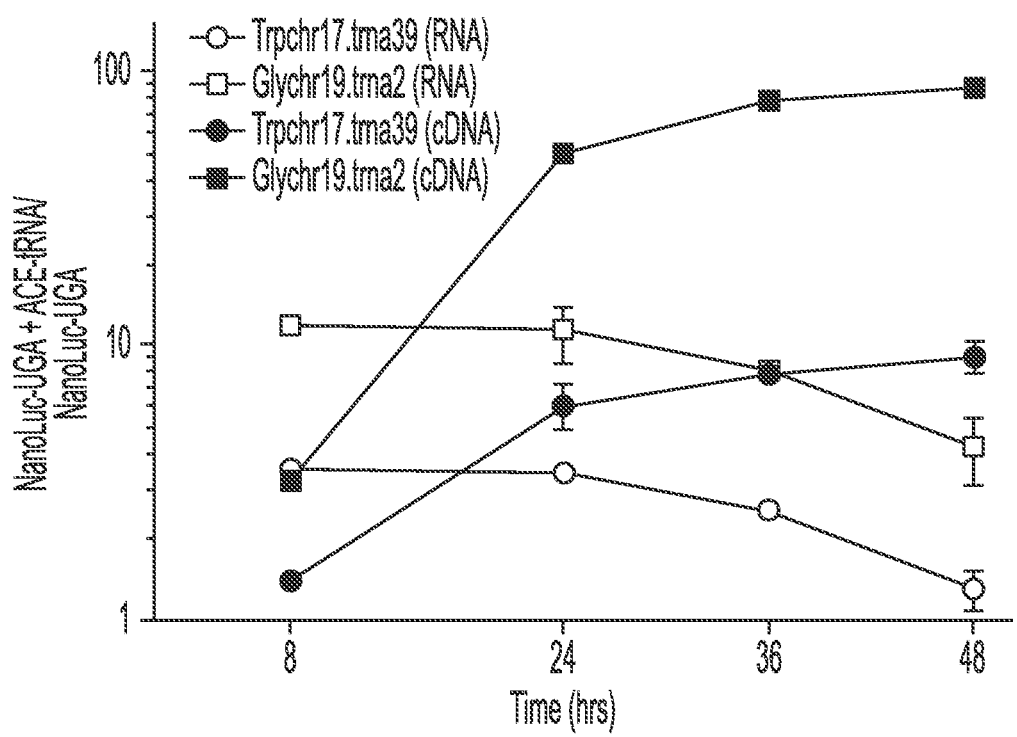
FIG. 33. Comparison of time courses of ACE-tRNA activity following delivery as RNA or cDNA. ACE-tRNAs were delivered to HEK293 cells that stably express pNano-Luc-UGA, however only 5 µl of the reaction mix was added to the cells to reduce the effect of transfection reagents on cell viability. ACE-tRNA delivered as RNA (open symbols), was more rapid in rescuing expression of the PTC reporter than cDNA constructs (close circles). However, ACE-tRNA activity continued to rise over the 48 hours when expressed from cDNA and decreased as an RNA deliverable.

Next it was established whether ACE-tRNAs identified in the screen were functionalized at the expense of aminoacylation stringency by the cognate aminoacyl-tRNA synthetase. To this end, mass spectrometry was used to examine PTC suppression in a model soluble protein, histidinol dehydrogenase (HDH), FIG. 23A. A TGA codon was introduced at asparagine 94 (N94) (FIGS. 30A-C) and co-expressed in HEK293 cells in tandem with plasmids encoding Glychr19.trna2 or Trpchr17.trna39 ACE-tRNAs, the top performing glycine and tryptophan ACE-tRNA$^{UGA}$, respectively. The resulting full-length, suppressed, HDH proteins were purified via a Strep-Tactin® C-terminal affinity tag and analyzed by mass spectrometry, FIG. 23A (FIG. 28). Subsequent searches of the data identified the modification of Asn to Trp (+72 Da) for Trp chr17.trna39 and (−57 Da) for Glychr19.trna2, thus confirming the faithful encoding of the cognate amino acid for each ACE-tRNA type. Importantly, in each case >98% of the peptide identified at the HDH p.N94X site had the encoded cognate tryptophan and glycine. Further, both ACE-tRNAs retained selectivity for the UGA stop codon, over UAA and UAG, FIG. 23B (ACE-tRNA$^{Gly}$) and FIG. 31 (ACE-tRNA$^{Trp}$). Lastly, when transiently expressed, the ACE-tRNA$^{Gly}$ outperformed the conventional small molecule suppressors gentamicin (40 µM) and G418 (140 µM) in their ability to suppress NLuc-UGA stably expressed in HEK293 cells, FIG. 23C. The same was true even for ACE-tRNA$^{Trp}$, which had a lower suppression efficiency yet exceeded PTC rescue compared to G418, FIG. 33A-D.

Figure 24A:
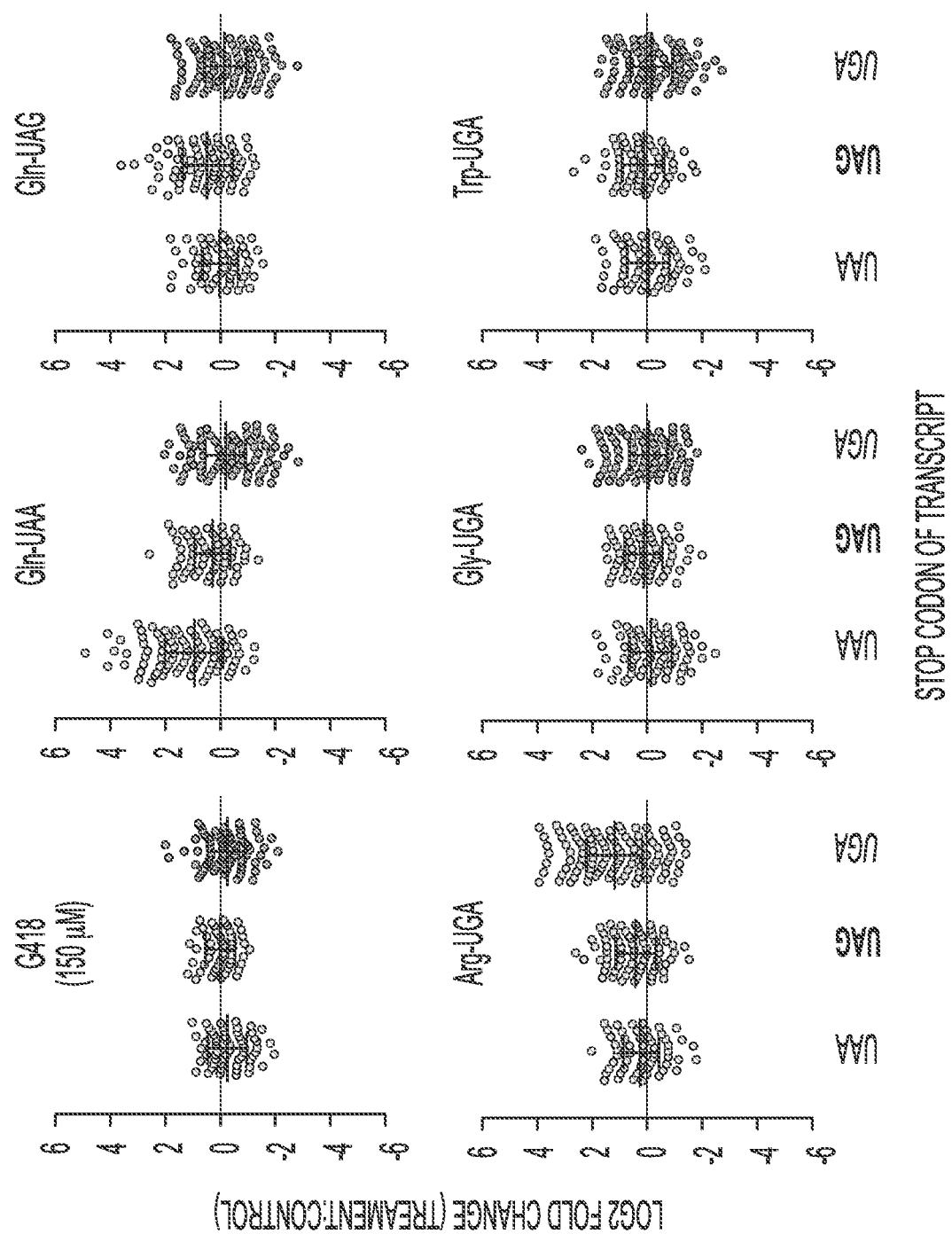
FIGS. 24A-24B. Ribosome profiling of ACE-tRNA on transcriptome-wide 3'UTRs.

The question was raised whether ACE-tRNAs that show efficacious suppression of premature stop codons may also induce global readthrough of native stop codons. To address this potential "off target" suppression, a transcriptome-wide quantitative profile of actively engaged ribosomes on all cellular transcripts was obtained by generating libraries of ribosome footprints from HEK293 cells expressing exogenous ACE-tRNAs or a control mock plasmid (puc57GG). Streptomycin was removed from the growth media to prevent readthrough artifacts. For comparison, the ribosome footprint library was also generated from cells in the presence or absence of G418 (150 µM, 48 h). FIG. 24A shows ribosome footprint densities of G418 and five ACE-tRNAs compared against controls (log 2-fold change) on 3'UTR regions. Only transcripts with a minimum threshold of 5 RPKM in the coding sequence and 0.5 RPKM in the 3'UTR in two replicate libraries were included for the quantitation comparison (254 transcripts in G418 and 495-748 transcripts in ACE-tRNAs). In this system, G418 had no observable effect on transcriptome-wide 3'UTR ribosome density for any of the three endogenous stop codon groups. ACE-tRNAs examined here had no detectable change of 3'UTR ribosome density with the exception of ACE-tRNA Gln-UAA and Arg-UGA which induced approximately a 2-fold increase in 3'UTR ribosome density for the cognate stop codon complimentary to the ACE-tRNA anticodon. Understanding the biological significance of 2-fold readthrough of protein stops will require further study, but this effect is substantially lower compared to the 100- to 1000-fold suppression of PTC for the same ACE-tRNA.

Figure 24B:
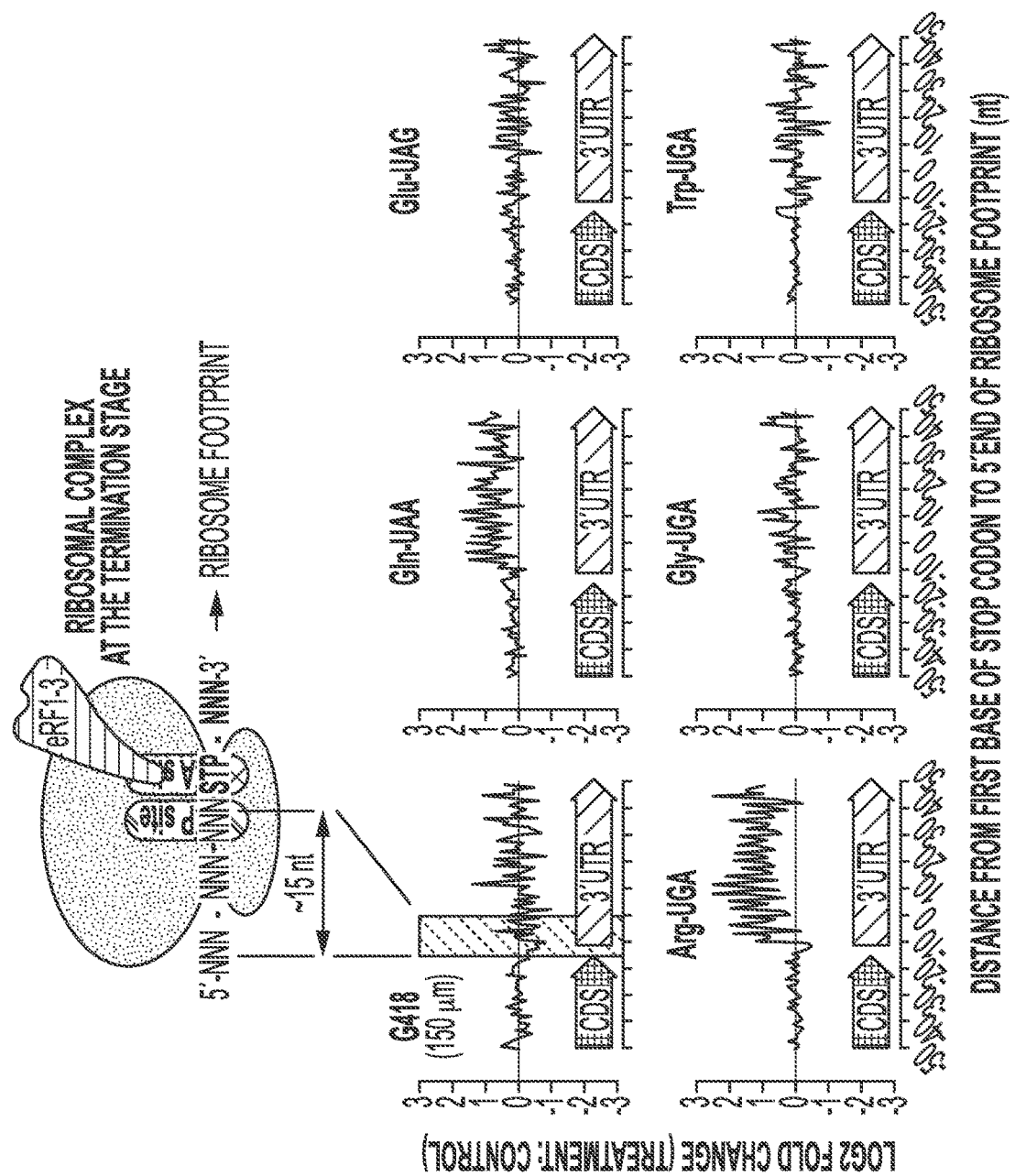

Multiple in-frame stop codons are frequently found at the end of genes[37-39] and may cause a minor difference in overall 3'UTR ribosome density for ACE-tRNA and G418 treatment. Ribosome occupancy was examined at each nucleotide in the 3'UTR within a 60 nt region downstream of the stop codons. FIG. 24B demonstrates the ribosome occupancy surrounding native stop codons for each nucleotide within the region from −35 to +65 nt relative to the first nucleotide of stop codon. Reads were normalized per total million-mapped reads, compared against control cells, and reported as a log 2-fold change as in panel A. More than 5,200 transcripts were mapped to at least 1 footprint in the region of interest. ACE-tRNA Gln-UAA and Arg-UGA showed not only notable increased ribosome occupancy in the early region but also characteristic 3-nt periodicity, indicating that the ribosomes were not randomly distributed but followed codon-by-codon movement. ACE-tRNAs for UGA-Trp, UGA-Gly and UAG-Glu, or G418, consistently showed no observable change of ribosome occupancy even in the early region of 3'UTR. Taken together, the ribosome profiling data argue that efficiency of native stop codon suppression by ACE-tRNAs is generally low, and markedly less than the level of PTC suppression.

Discussion

PTCs cause a multitude of human diseases and there are no established therapeutic options for their therapeutic management. The high-throughput cloning and identification, characterization and functional analysis of anticodon-edited tRNA that display efficacious PTC reversion in eukaryotic cells and mouse skeletal muscle is reported herein. Notably, the screen identifies ACE-tRNA, in total, with the ability to repair a vast majority of known human disease-causing PTC. The engineered tRNA faithfully encode their cognate amino acid, thus abrogating spurious effects on downstream protein stability, folding, and trafficking, and consequently negating the need for tandem therapies involving protein folding or trafficking agents. When transfected as cDNA, ACE-tRNAs rescued multiple full-length proteins via PTC suppression; a NLuc luciferase reporter, a model protein HDH, and two disease nonsense mutations in CFTR. Potent and stable in vivo PTC suppression in mouse skeletal muscle was displayed by an ACE-tRNA$^{Arg}$ cDNA, suggesting a particularly high level of cellular tolerance for ACE-tRNA activity. The identification of an active ACE-tRNA for arginine in muscle is relevant for the treatment of dystrophinopathies caused by nonsense mutations. Following suit with most genetic diseases, greater than 10 percent of dystrophinopathies are caused by nonsense mutations[43], where CGA→TGA mutations are most prevalent[43]. Efficient suppression was also achieved with ACE-tRNAs delivered as synthetic RNA transcripts, thus enabling the development of nanoparticle formulations. Future studies will be needed to assess ideal tRNA delivery strategies for each tissue and disease type, where efforts will likely benefit from rapidly expanding technologies for nucleic acid delivery.

Agents that suppress PTCs have the potential to also produce readthrough of native stop codons. The RNA profiling data presented herein suggest this is, generally, not the case in the cells and for the codon-edited tRNA that were tested. While detectable readthrough was found with Arg-tRNA$^{UGA}$ and Gln-tRNA$^{UAA}$, no significant effect on global translation termination was measured with Glu$_{UAG}$, UGA-Gly-tRNA$^{UGA}$ and Trp-tRNA$^{UGA}$. This behavior did not obviously segregate with stop codon type, or the intrinsic PTC suppression activity of the tRNA. One potential reason that ACE-tRNA ineffectually promote readthrough at real stop codons may be due to the contextual sequence landscapes near translation terminations[44]. This possibility is supported by the finding that the composition of termination complexes at PTCs differ from those at native stops[45, 46]. However, in cases where lower level readthrough occurs, there are multiple cellular mechanisms in place to limit both normal stop read-through and damaging effects thereof. Multiple in-frame stop codons are frequently found at the end of genes[37-39] and specialized ubiquitin ligases[47] and ribosome associated pathways[48] are known to identify and degrade proteins with erroneous translation termination. Nonetheless, despite the limited impact seen here in mammalian cells, similar ribosomal profiling experiments should be performed in the desired cell or tissue type for ACE-tRNA delivery and expression.

Previous studies have shown that the surrounding mRNA sequence influences inherent stop codon suppression efficacy of aminoglycosides and Ataluren PTC[49-52], and ACE-tRNA may be similarly affected. Further, while gene addition strategies to replace a PTC containing gene, via viral or non-viral delivery, have achieved short term benefit in some settings, it may be difficult to regulate transgene expression levels. In contrast, the abundance of protein rescue via ACE-tRNA suppression is coupled to native cellular RNA levels, and thus upper levels of expression will be intrinsically regulated. The biological purpose remains unknown for a majority of the variable isoacceptor tRNA sequences in the human genome, and almost half these genes have been speculated to be transcriptionally silent pseudogenes[53], however the data here suggest many annotated tRNA are viable. Consistent with this possibility, a suppression approach has been used to identify functional isodecoder tRNAs within Ser and Leu isoacceptor families[54]. The data presented here further demonstrate that the majority of tRNA gene sequences support viable activity when removed from the genomic context, further deepening the mystery for the biological need for a plurality of tRNA, and codon usage. Thus, the high-throughput suppression strategy described here will be useful to identify new types of tRNA sequences with unique suppression properties, and such studies have the potential to produce new RNA reagents as well as advance the molecular understanding tRNA expression and suppression.

Materials and Methods

Nonsense Reporter HTC Plasmid

The parent plasmid used was pcDNA3.1(+). The cDNA encoding pNLuc was Gibson Assembled (New England Biolabs, USA) into restriction sites HindIII and XhoI. A glycine (codon gga), tryptophan (tgc), amber (tag), opal (tga) and ochre (taa), were added to amino acid position 160 during cDNA pcr. The pcDNA3.1(+) polyA sequence was replaced for one with no BbsI restriction sites using pcr based Gibson Assembly. The high throughput ACE-tRNA Golden Gate cloning site was generated by first inserting the 5' leader sequence of the human tRNA$^{Tyr}$ gene (bold) with a T7 promoter sequence upstream (italics)

(*TAATACGACTCACTATAG*AGCGCTCCGGTTTTTCTGTGCTGAACCTC AGGGGACGCCGACACACGTACACGTC (SEQ ID NO: 649))

(Ye et al., 2008) followed by two BbsI restriction sites (bold italics) (TA*GTCTTC* GG (SEQ ID NO: 650) (ccdB cassette) AA*GAAGAC* CG (SEQ ID NO: 651)) and 3' termination sequence (bold) followed by a reverse T3 primer sequence (italics)

(GTCCTTTTTTTG*CTTTAGTGAGGGTTAATT* (SEQ ID NO: 652)).

Figure 26:
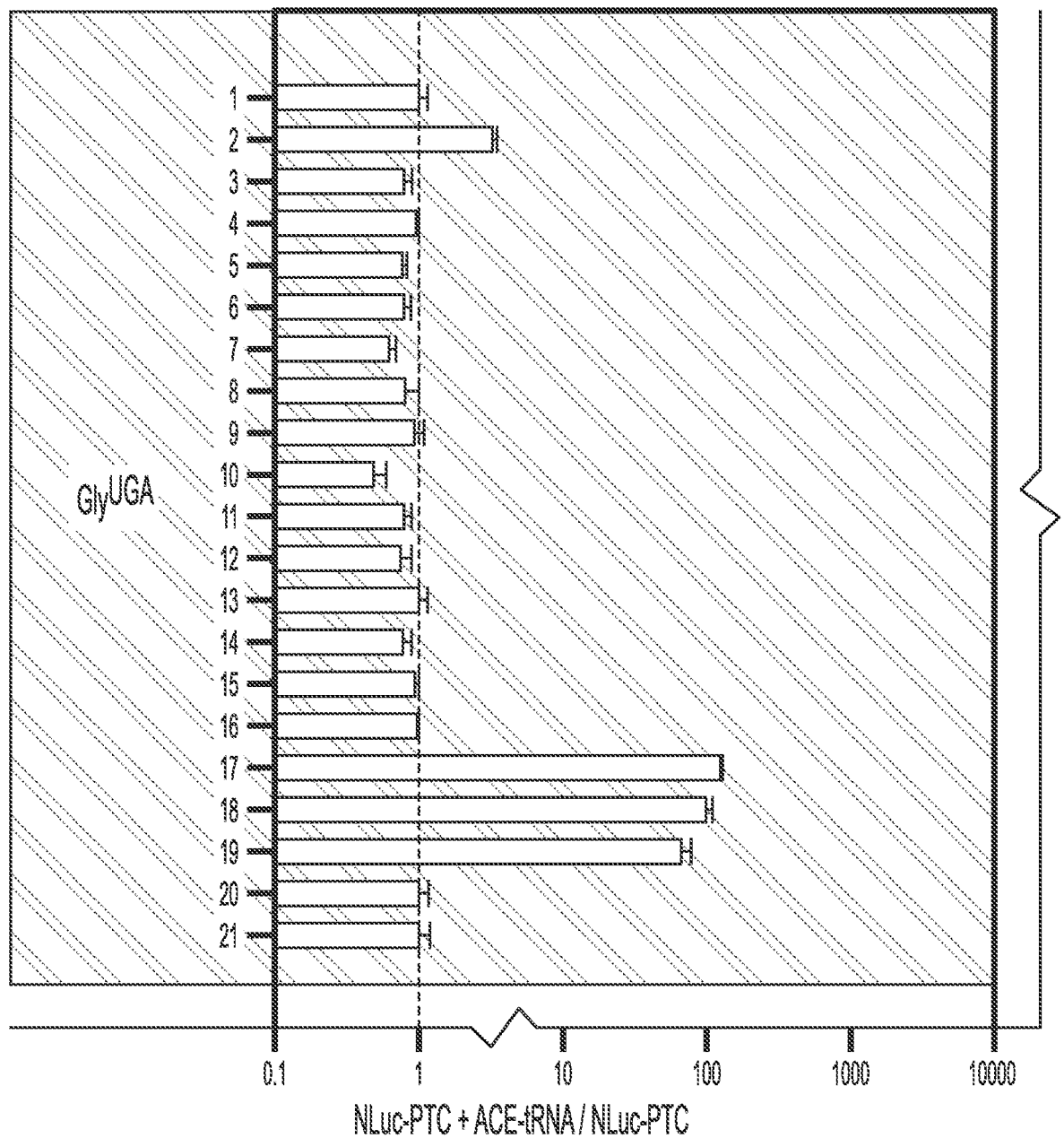
FIG. 26. Number referenced ACE-tRNA activity plot.
Figure 26:
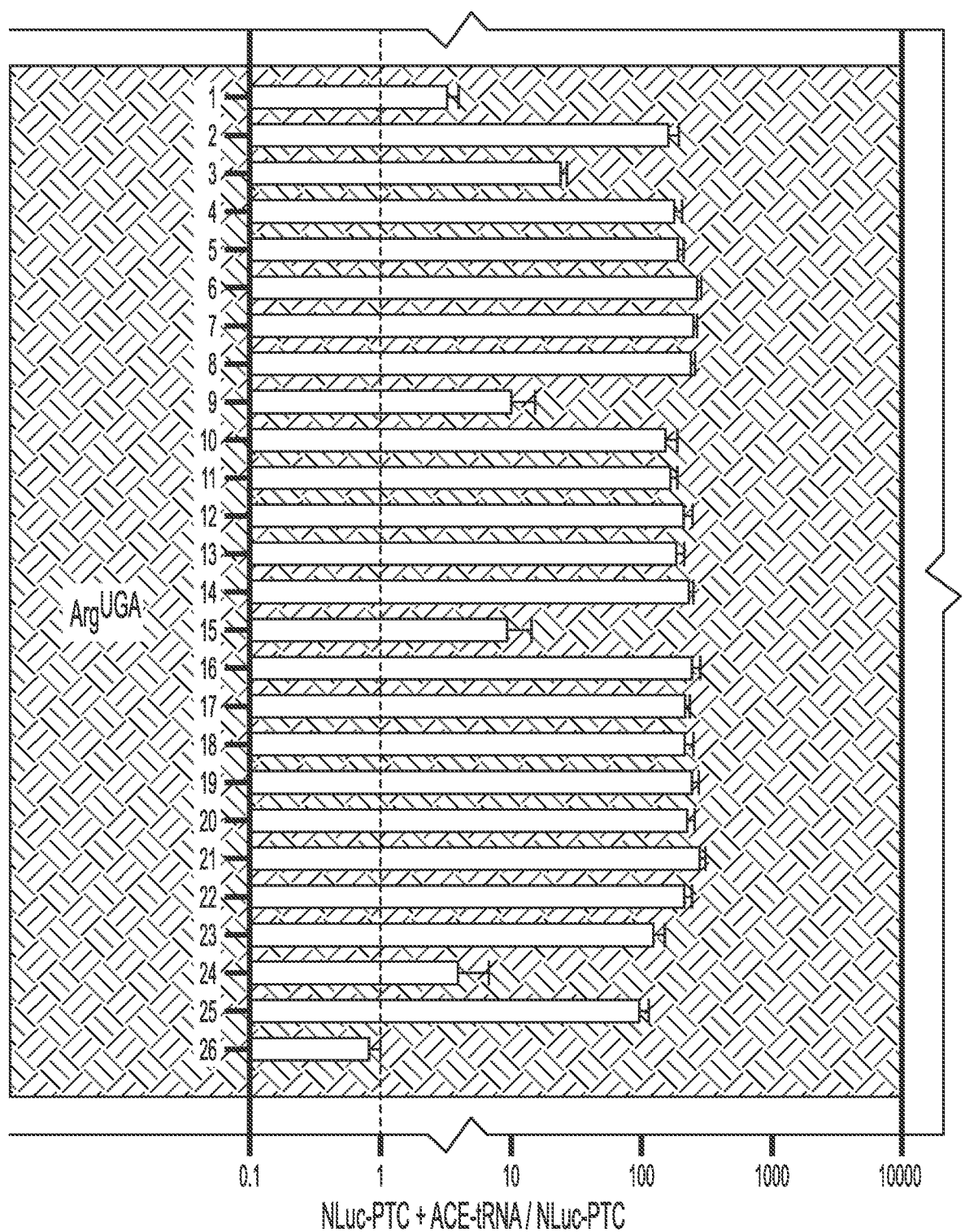
Figure 26:
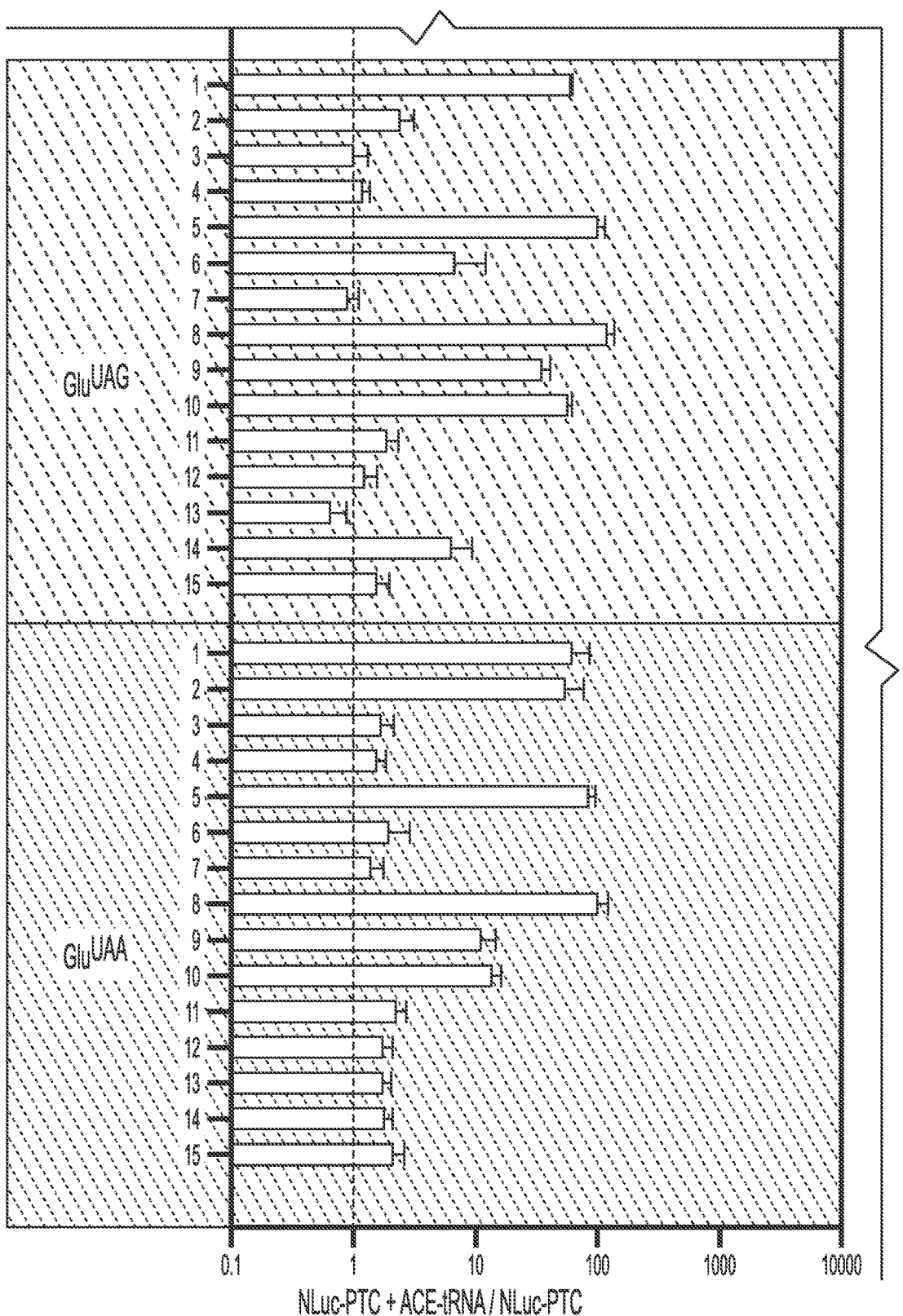
Figure 26:
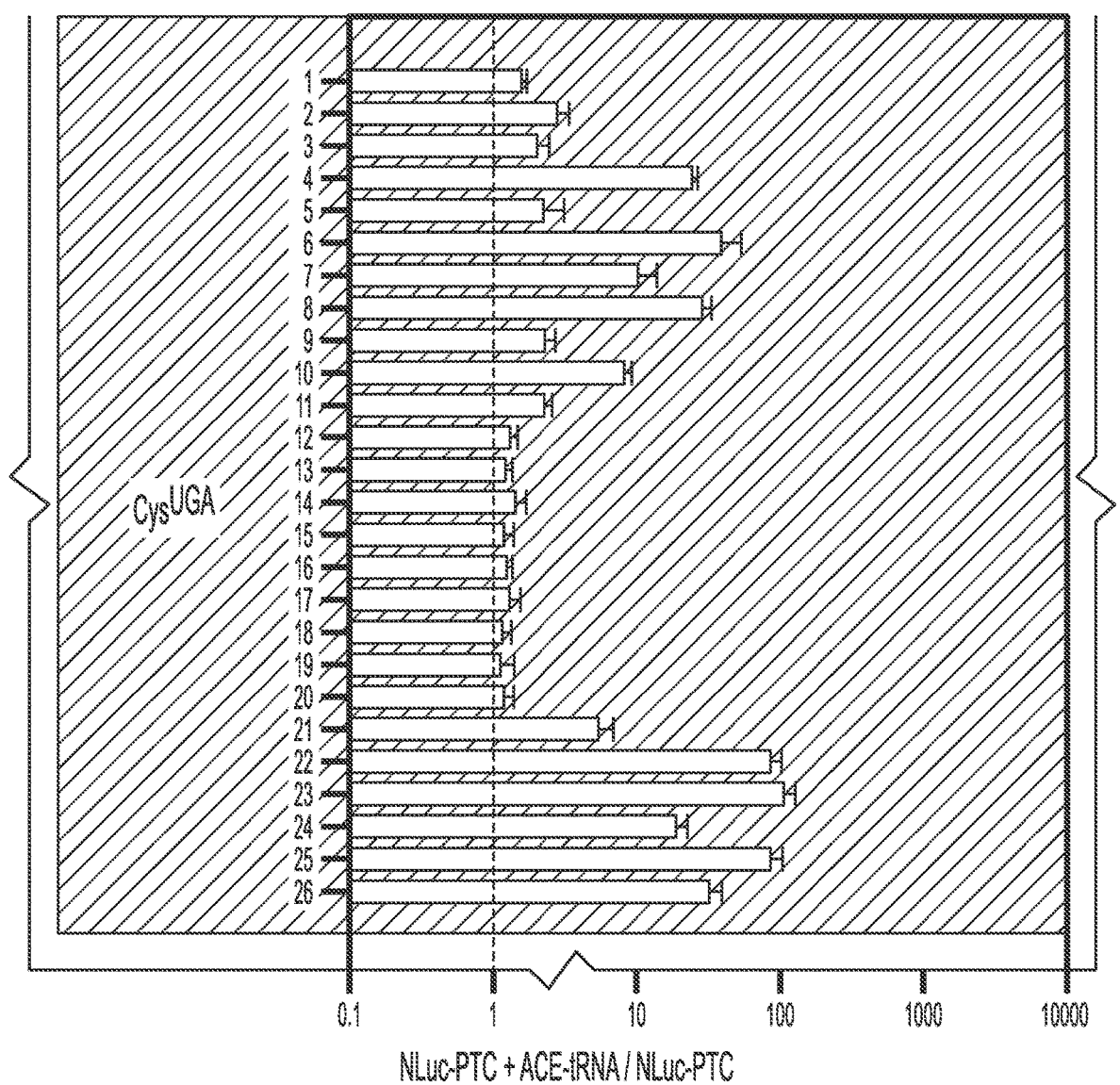
Figure 26:
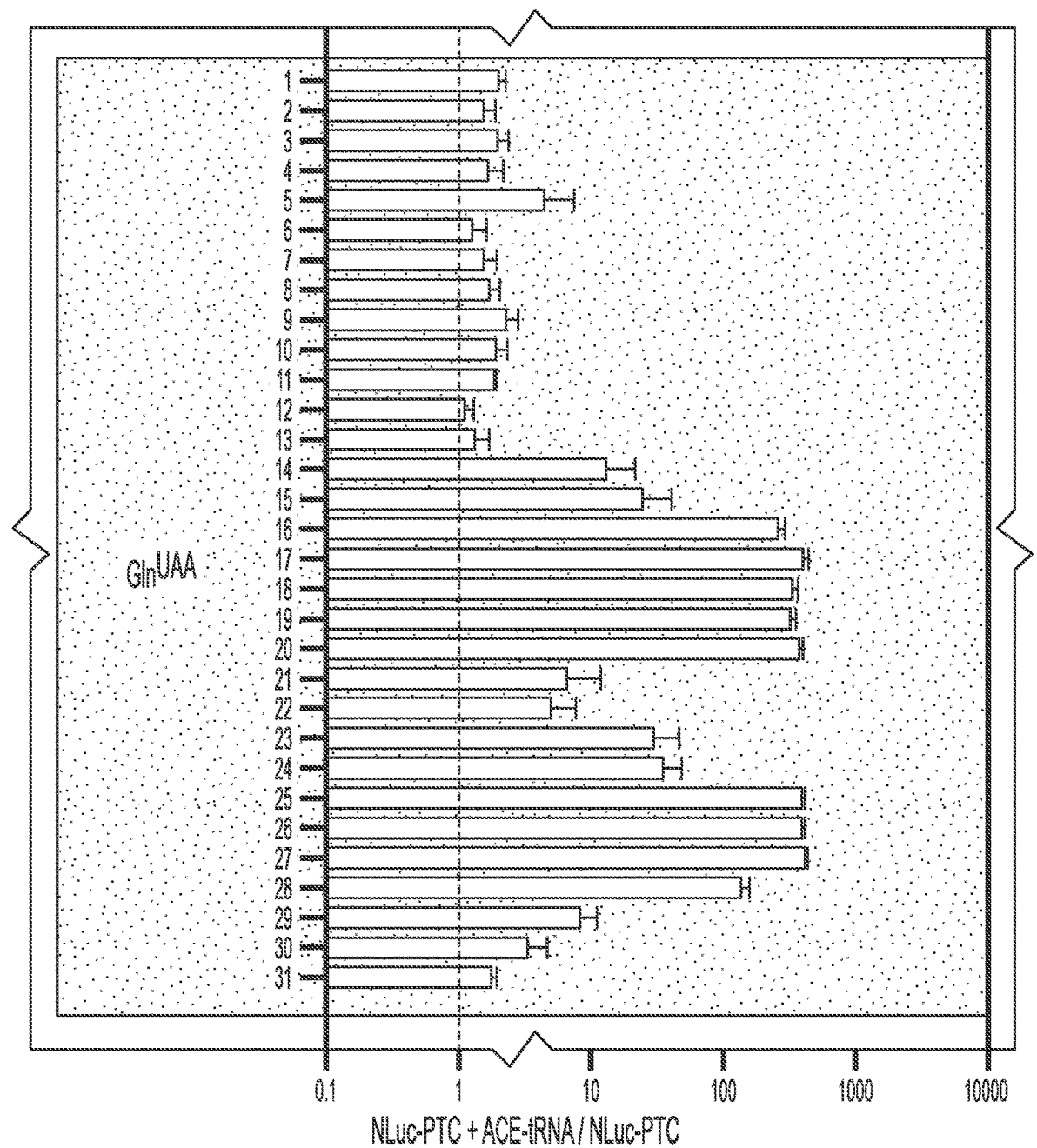
Figure 26:
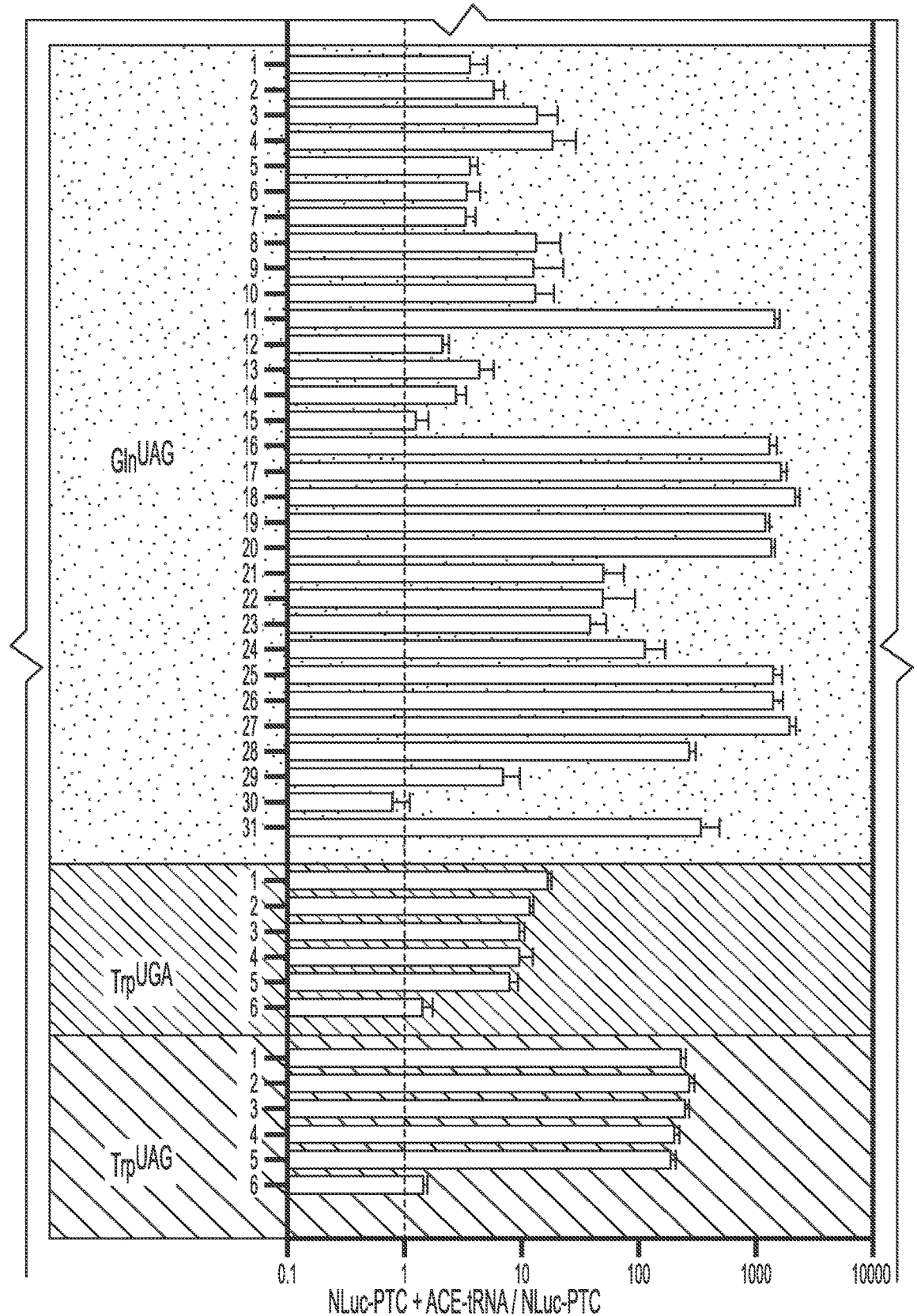
Figure 26:
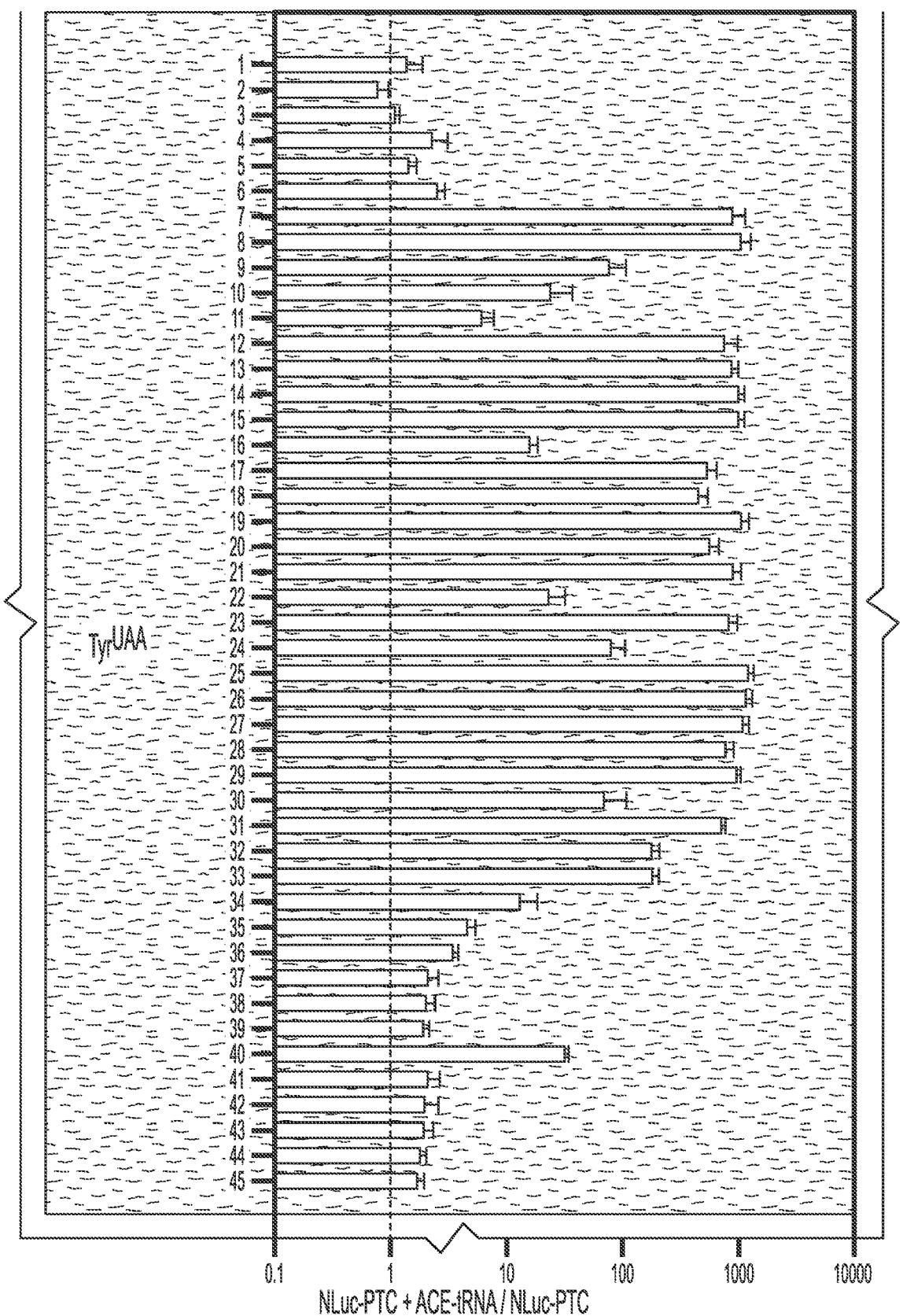
Figure 26:
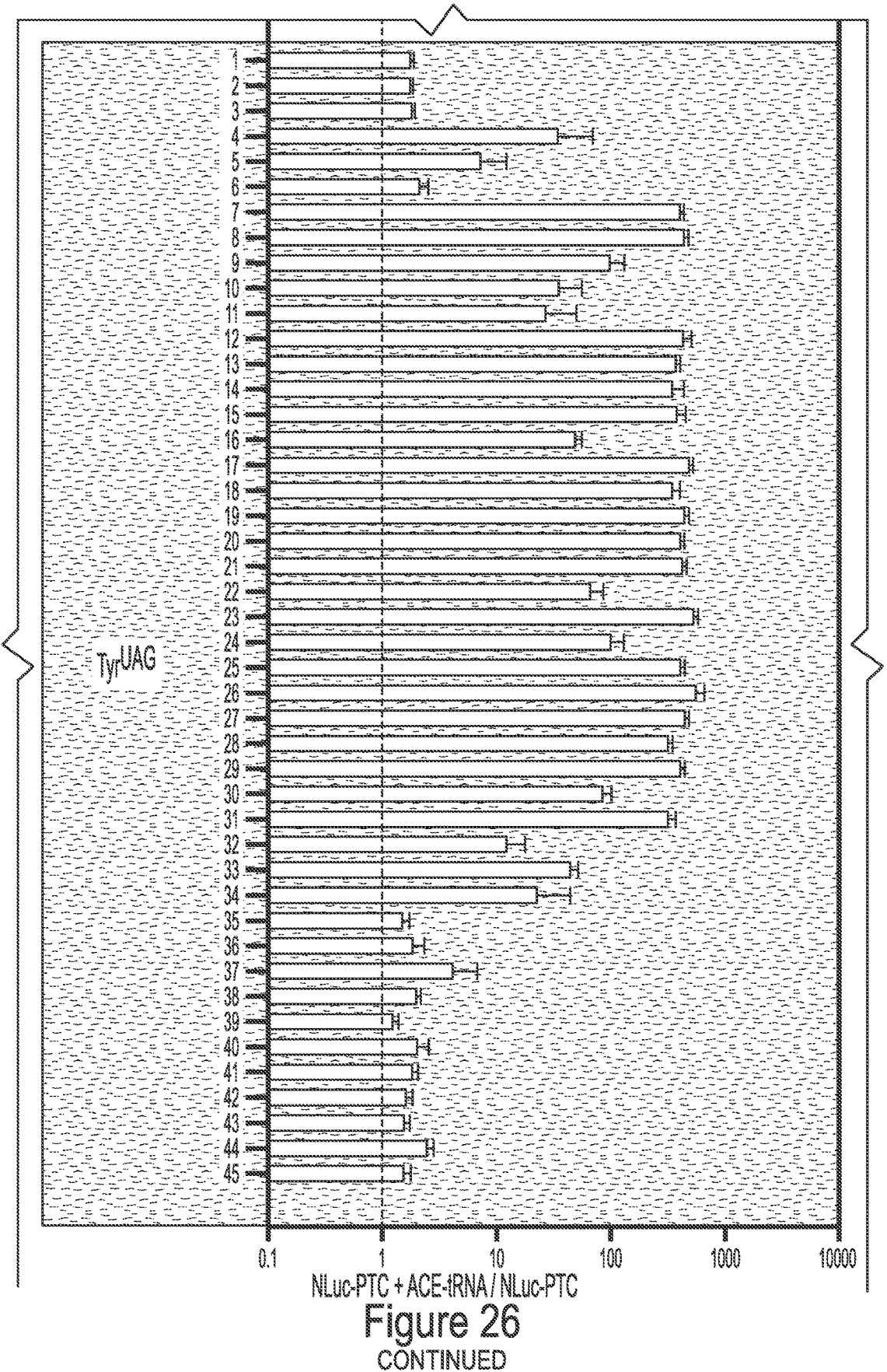
Figure 26:
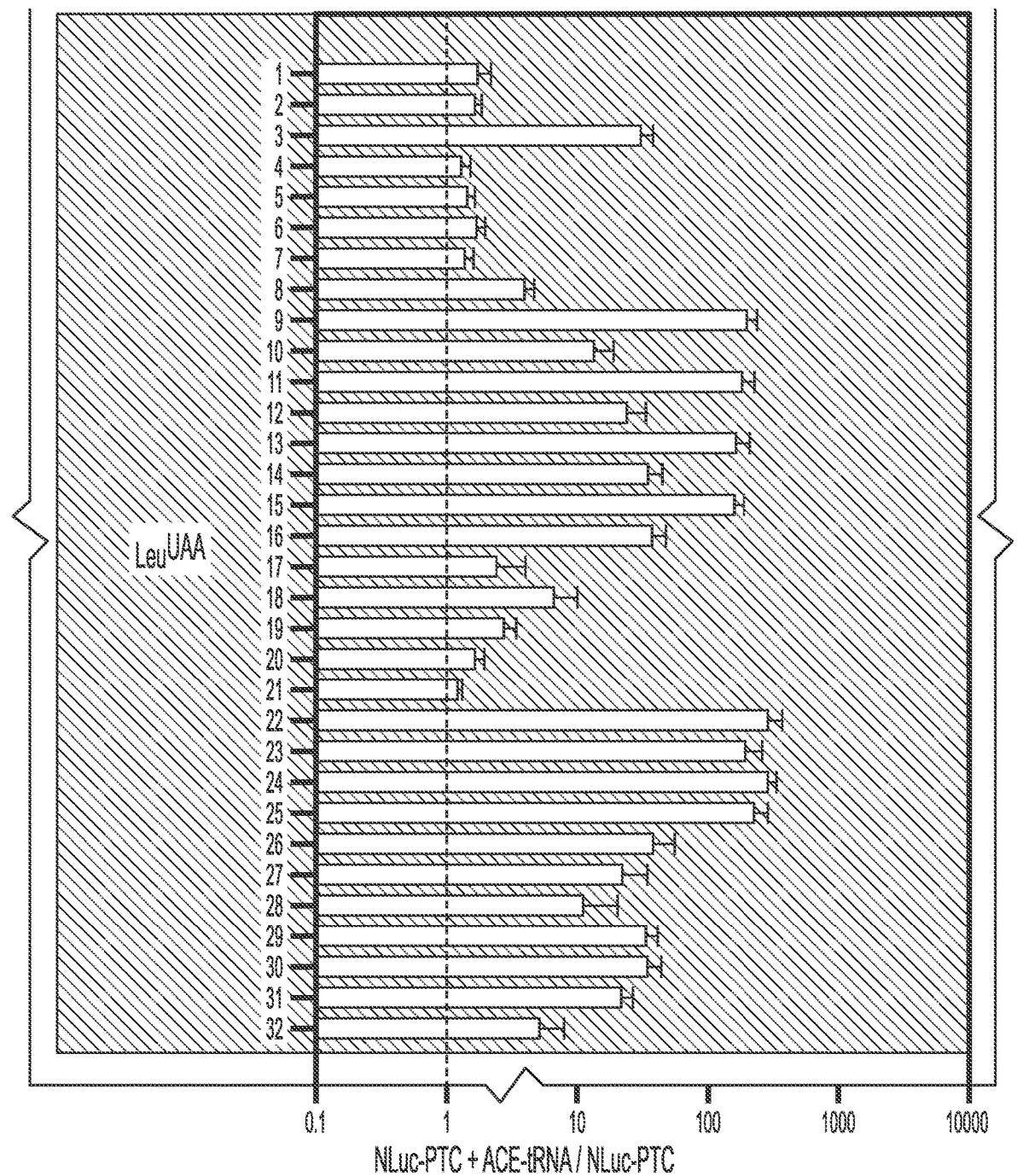
Figure 26:
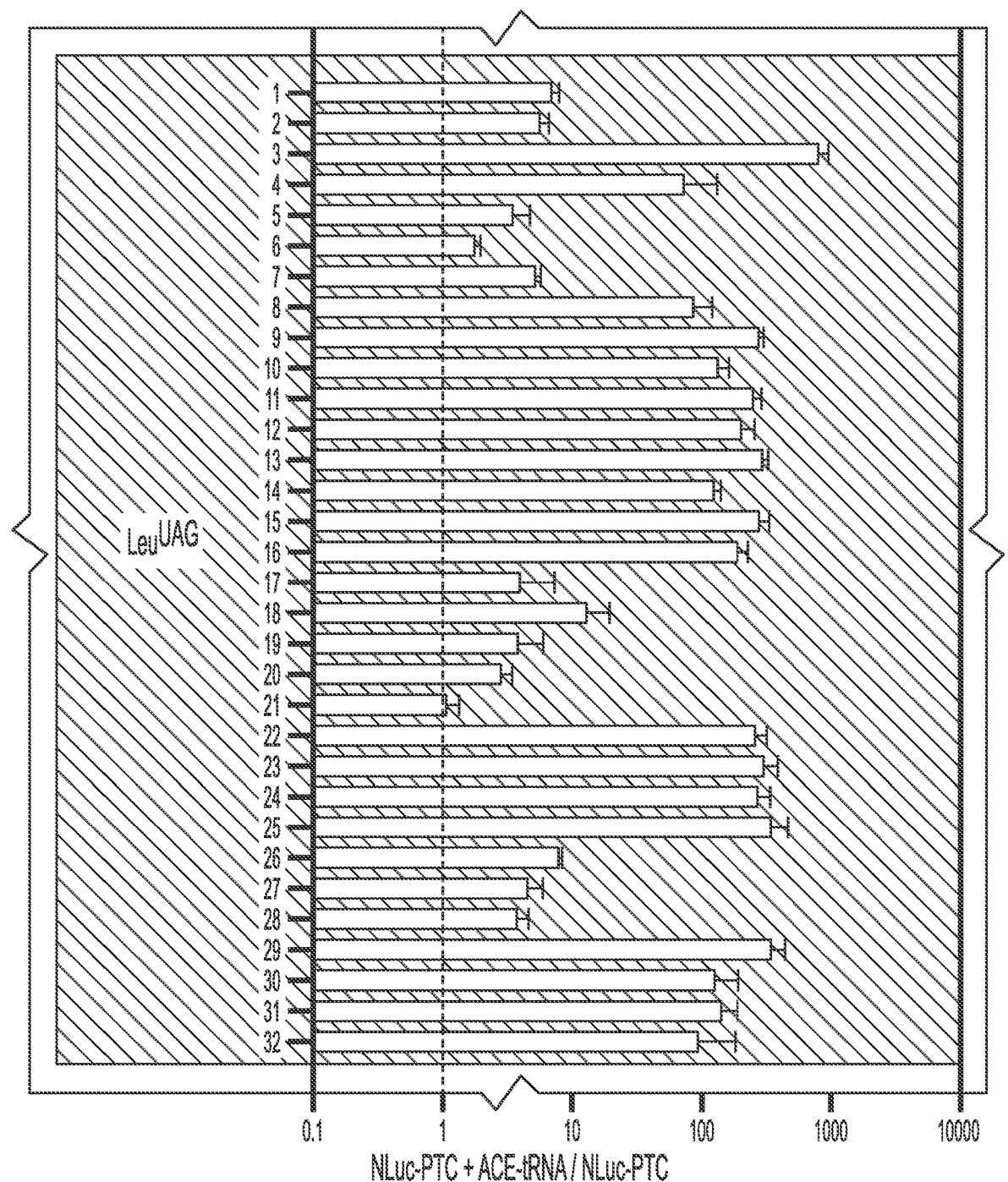
Figure 26:
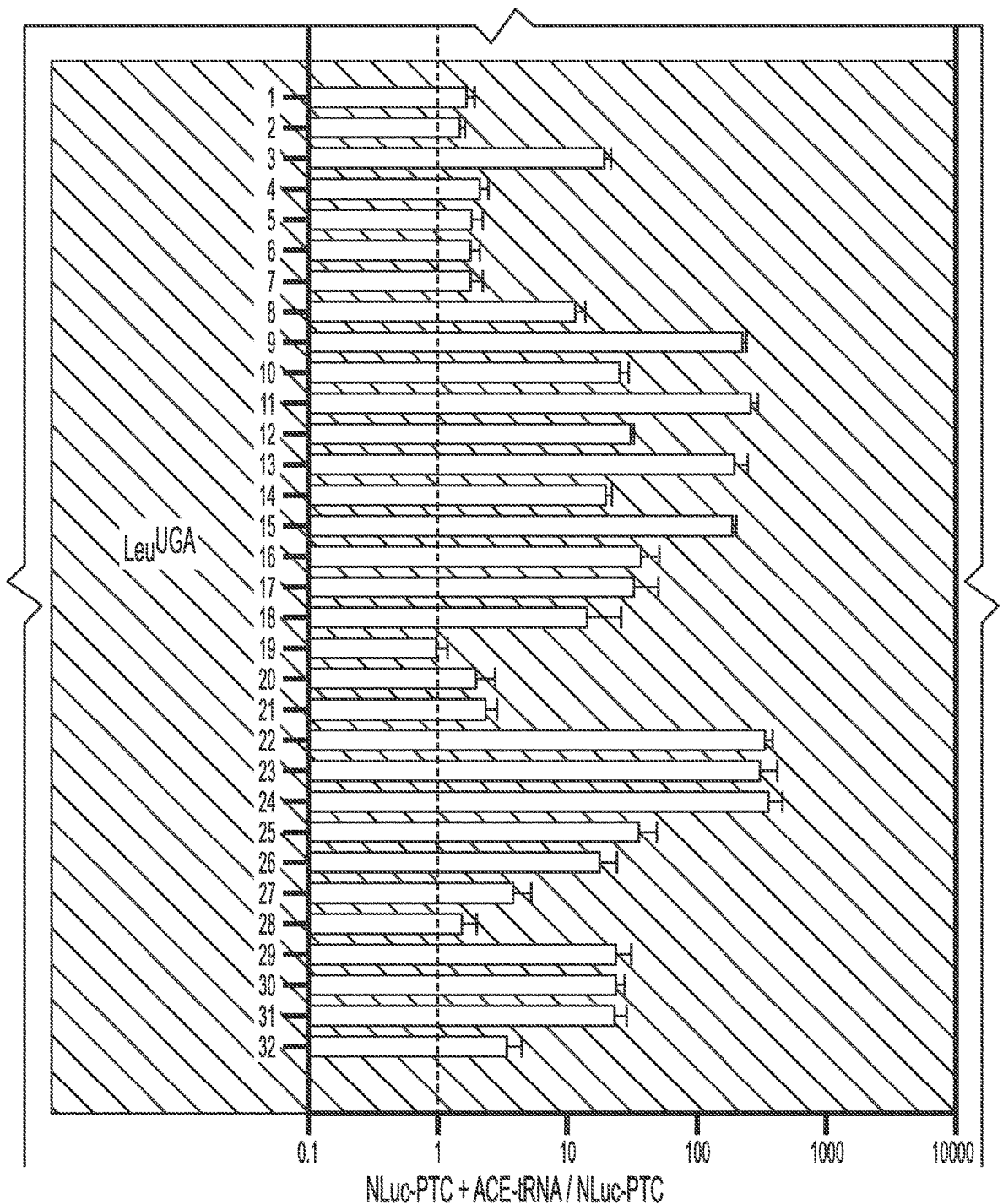
Figure 26:
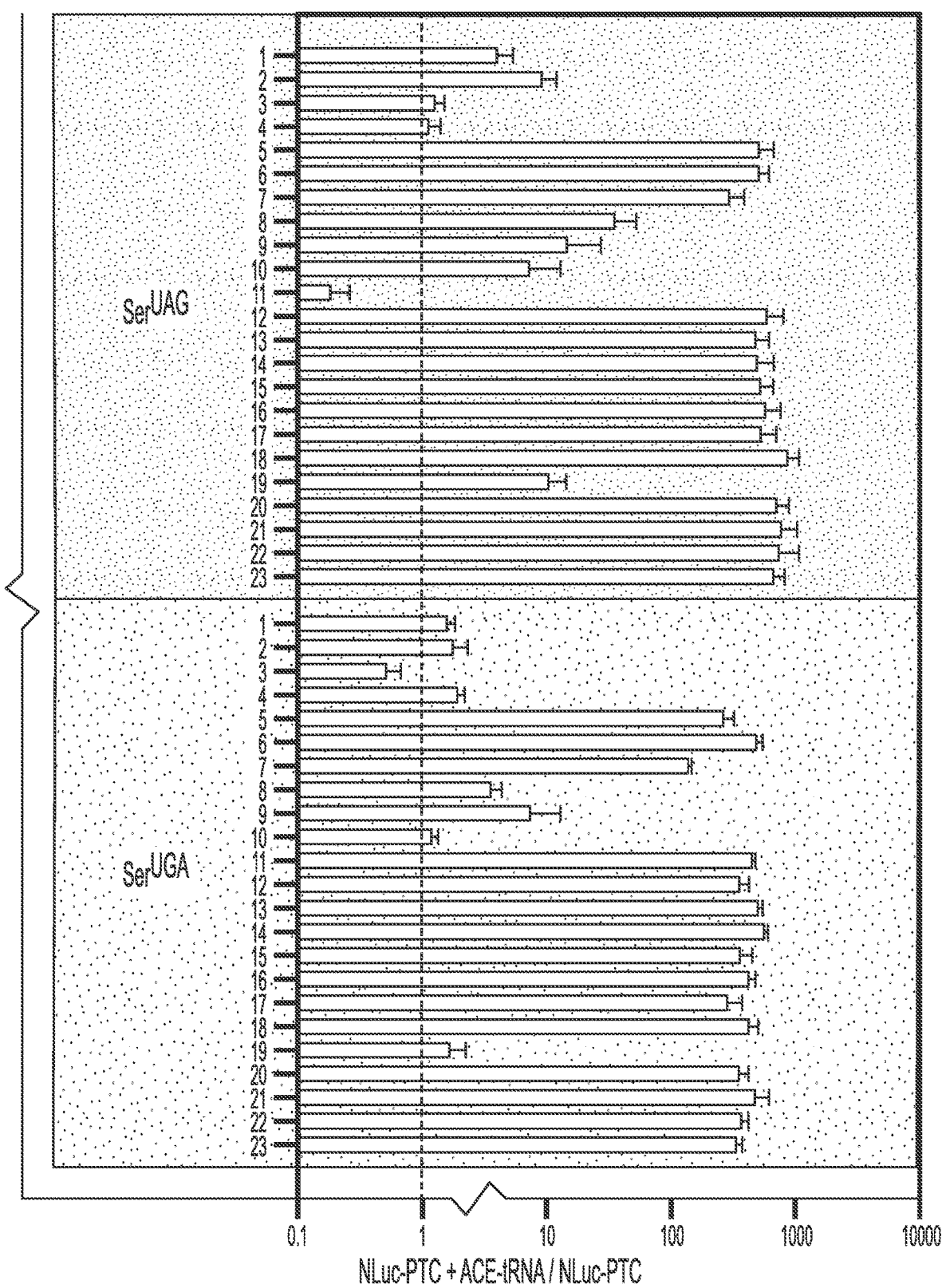
Figure 26:
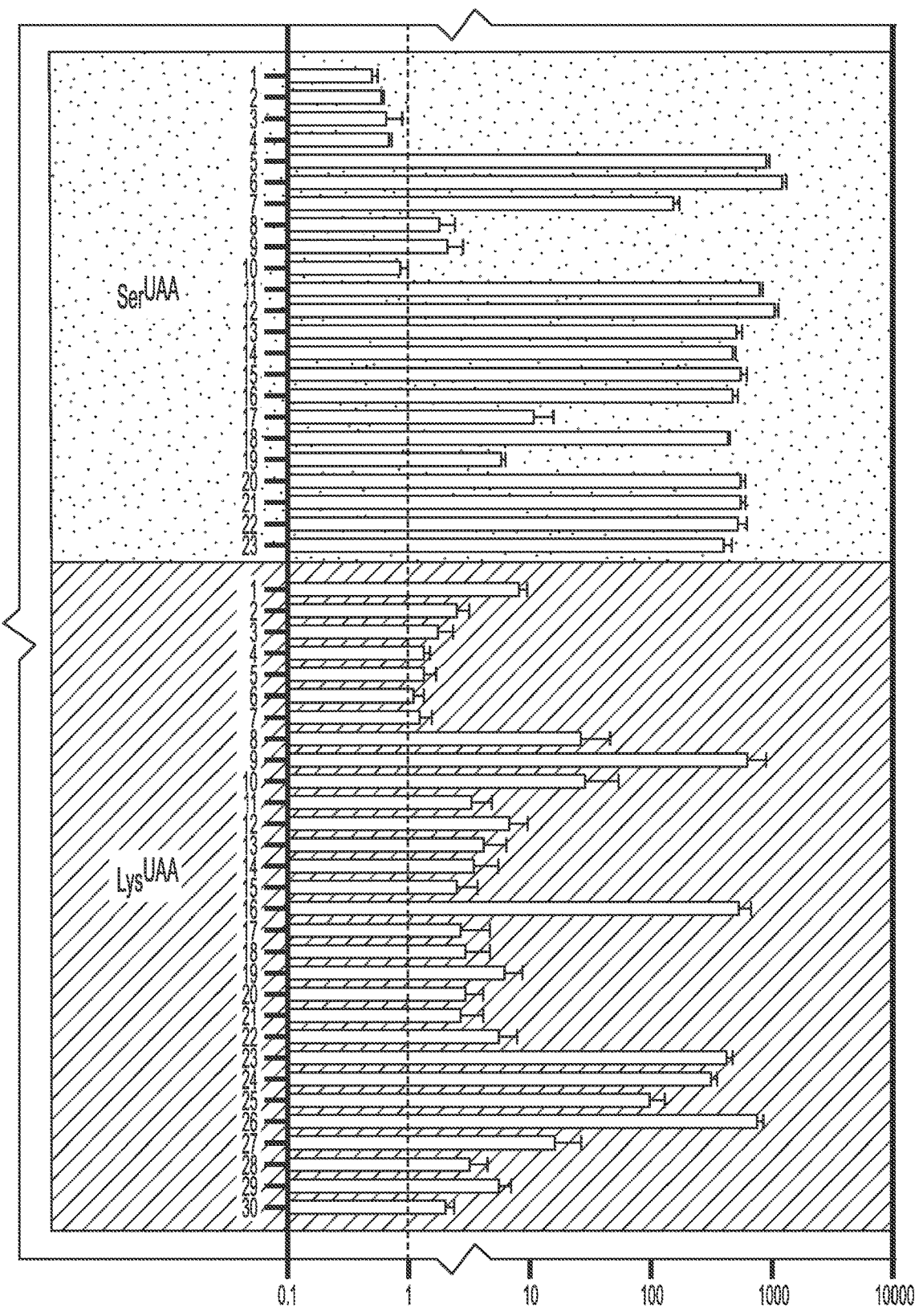
Figure 26:
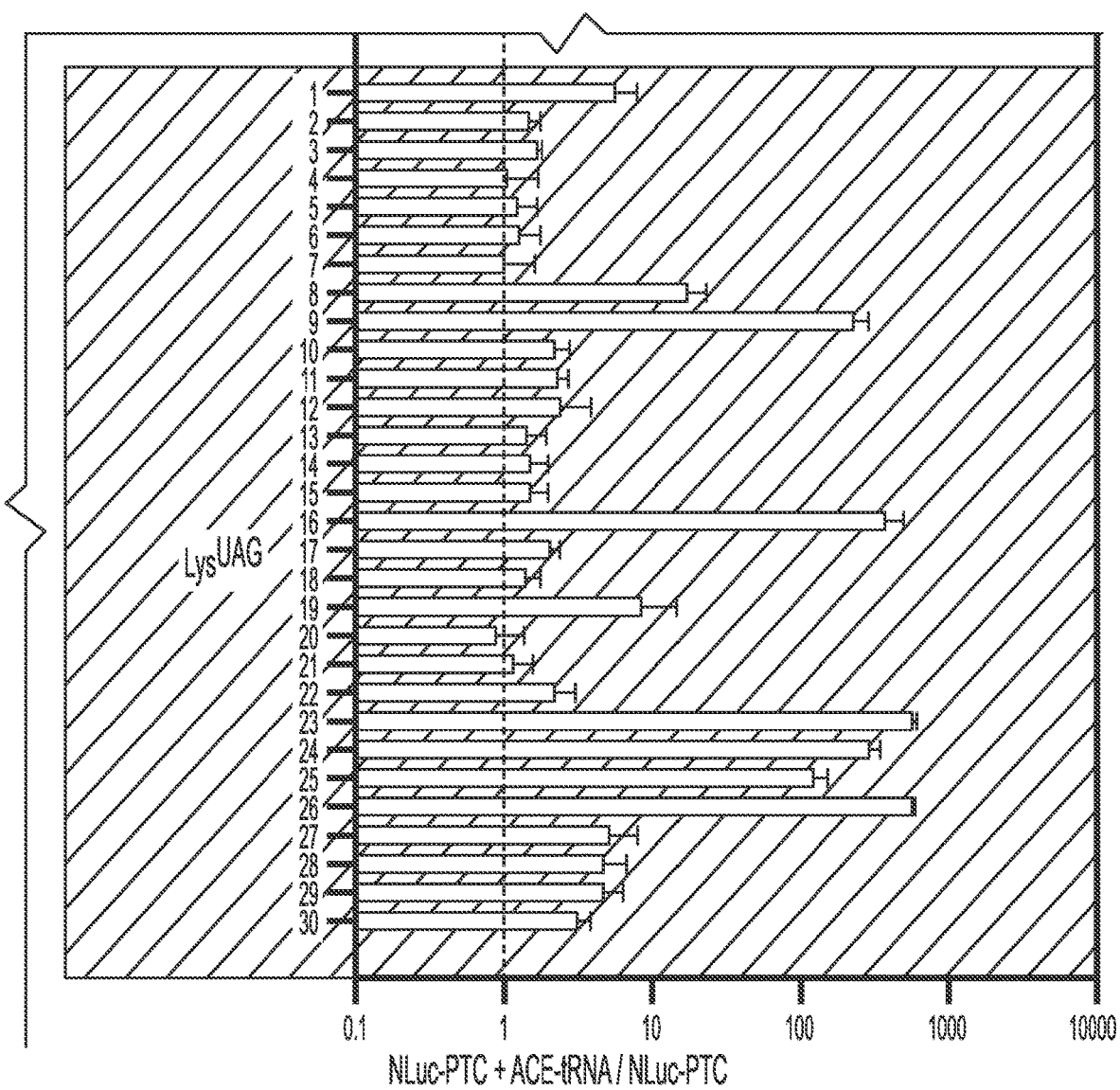

HTC of ACE-tRNA Library tRNA gene sequences were obtained from the tRNA database tRNAscan-SE (http://gtrnadb.ucsc.edu/index.html; PMID: 26673694). Sequences of all tRNA genes used in this study are numbered in FIG. 26 and Table 9. tRNA sequences were synthesized as complementary Ultramers from Integrated DNA Technologies (IDT, USA) in 96 well format at 200 pmol scale with their corresponding anticodons mutated appropriately (UAG, UGA or UAA). All tRNA sequences were synthesized with CGAC and GGAC overhangs (annotated 5'→3') on forward and reverse oligos, respectively. Ultramers were annealed by resuspending in annealing buffer (100 mM Potassium Acetate; 30 mM HEPES, pH 7.5) to 100 ng/ul, heated to 96° C. for 2 mins and cooled at 1° C./min in a thermocyler to 4° C. In 96 well PCR plates, each well contained 10 ng of HTC plasmid with appropriate PTC codon, 2 ng ACE-tRNA duplex, 1 mM ATP, 10 mM DTT, 400 Units T4 DNA Ligase, and 10 Units BbsI-HF, queued to 10 ul with ddH$_2$O. The 96 well plates were cycled as follows ([5 min @37° C., 5 min @20° C.]×30 cycles, 10 min @37° C., 10 min @80° C. and cooled to 4° C. in a thermocycler. In a deep welled 96 well plate 1 ul of the Golden Gate reaction was added to 10 ul of DH5α chemically competent cells (ThermoFisher, USA), heat-shocked @42° C. for 30 sec and resuspended in 100 ul of Super Optimal Broth (S.O.C.; Thermofisher, USA). Transformations were outgrown at 37° C. for 1 hr, 250 rpm and then added to 2 ml of Luria-Bertani-liquid media (LB) supplemented with 100 ug/ml Carbenicillin and grown in covered deep 48 well plates @37° C. for 20 hrs, 300 rpm. *E. coli* outgrowth was performed in deep well plates and clamps from Enzyscreen (http://www.enzyscreen.com). *E. coli* suspension cultures were spun down (10 min, 4,000 g at RI) and plasmid DNA was prepared and diluted to 125 ng/μl (IBI scientific, USA). All clones were sequence verified. Using this method, 100% cloning efficiency was achieved.

HTS of ACE-tRNA Library

The day before transfection, HEK293 cells (<40 passages) were plated at 1.4×10$^4$ cells/well in 96 well cell culture treated plates in Dulbecco's Modified Essential Medium (DMEM) supplemented with 10% FBS, 1% Pen/Step and 2 mM L-Glutamine (Thermofisher, USA). The all-in-one nonsense reporter with ACE-tRNA genes were transfected in triplicate/plate using Calfectin (Signagen, USA). 16 hrs post-transfection, the media was aspirated and 20 ul of PBS was added to each well. 15 ul of lytic Nano-Glo® Luciferase Assay Reagent was added to each well (1:50 reagent to buffer; Promega, USA). The plates were incubated for 2 min after rotational shaking and read using a SpectraMax i3 plate reader (Molecular Devices, USA; integration time, 200 ms; All wavelengths collected in endpoint mode). Luminescence was averaged across three wells for each experiment and all ACE-tRNAs were repeated >3 times in this fashion. Each plate also contained in triplicate wells transfected with the all-in-one nonsense reporter with no ACE-tRNA to server as control for transfection efficiency and baseline PTC readthrough. All values are reported as ratios of ACE-tRNA luminescence over baseline PTC readthrough luminescence±SEM. One-way ANOVAs were performed with Tukey's post-hoc analysis across all ACE-tRNAs in a given amino acid family.

CFTR, HDH-His-Strep and 4×ACE-tRNA Expression Plasmids

For expression in mammalian cells, the cDNA for the coding region and 200 base-pair of the 3' untranslated region (UTR) of human CFTR was ligated into pcDNA3.1(+) (Promega, USA) using the KpnI and XbaI restriction enzymes. The G542tga and W1282tga mutations were introduced using QuickChange XL II (Stratagene, USA). For expression in *Xenopus laevis* oocytes, the cDNA for the coding region and 140 base-pair of the 5' and 244 base-pair 3' UTR of human CFTR was ligated into pGEM-HE (Promega, USA). Bothe the G542tga and W1282tga mutations were introduced using QuickChange XL II. The cDNA encoding the *E. coli* histidinol dehydrogenase was codon optimized for *Mus musculus* and synthesized (BioBasic Inc, Canada) with a c-terminal 8×His-Strep-tag ("8×His" disclosed as SEQ ID NO: 647) for protein purification from mammalian cells. The synthesized cDNA was ligated into pcDNA3.1(+) using EcoRI and XhoI restriction sites. The nonsense mutations tag, taa and tga were introduced using QuickChange XL II. To generate multiplexed ACE-tRNA expression plasmids, a novel parent Golden Gate pUC57 (amp) plasmid was generated by inserting a BbsI "multiple cloning site" (5'-GAATTCTTCCCGAGACGTTC-CAAGTCTTCATGAAGACTACAGGCGTCTCCCAG-GAAG CT-3' (SEQ ID NO: 653); directional BbsI recognition sequences are italicized and unique four base-pair overhangs for ligation are bolded) between the EcoRI and HindIII restriction sites. pUC57(amp) was chosen as a parent plasmid because it is relatively small in size and lacks backbone BbsI restriction sites and T7 and T3 promoter sequence. A feature included in the HTS plasmid is T7 and T3 promoter sequence flanking the ACE-tRNA cassette, giving universal primer binding sequences with comparable melting temperatures ($T_m$), ideal for per amplification. Using the NEB Golden Gate Assembly Tool (https://gold-engate.neb.com/editor) per primers were generated that annealed to the T7 and T3 flanking sequence and created unique four base-pair overhangs following cleavage of distal BbsI recognition sequence. The end result was the generation of four ACE-tRNA per products using universal per primers that could be "daisy-chained" through complementary four base-pair overhangs and ligated into the puc57 Golden Gate plasmid using a one-pot Golden Gate reaction. All clones were sequence verified.

Cell Culture, Protein Expression and Western Blot

HEK293T cells (ATCC, USA) were grown in standard grown media containing (% in v/v) 10% FBS (HiClone, USA), 1% Pen Strep, 1% L-Glut in high glucose DMEM (Gibco, USA) at 37° C., 5% CO2. cDNA was transfected at 75% confluency using Calfectin according to standard protocols (SignaGen Laboratories, USA). Following 36 hrs the cells were scraped and pelleted at 7,000 g for 8 min at 4° C. in PBS supplemented with 0.5 μg/ml pepstatin, 2.5 μg/ml aprotinin, 2.5 μg/ml leupeptin, 0.1 mM PMSF, 0.75 mM benzamidine. For CFTR expressing cells, the cell pellet was vigorously dounced in 100 mM sucrose, 150 mM NaCl, 1 mM DTT, 0.5 μg/ml pepstatin, 2.5 μg/ml aprotinin, 2.5 μg/ml leupeptin, 0.1 mM PMSF, 0.75 mM benzamidine, 50 mM Tris-HCL ph 7.4 and centrifuged at 100,000 g to separate total membranes from the soluble cytosolic proteins. Pellets were solubilized in a buffer containing 1% triton, 250 mM NaCl, 50 mM tris-HCl pH 7.4, and 0.5 μg/ml pepstatin, 2.5 μg/ml aprotinin, 2.5 μg/ml leupeptin, 0.1 mM PMSF, 0.75 mM benzamidine. Equal cell-lysate was loaded on a 3-15% separating gradient SDS-page with 4% stacking gel in the presence of 1% 2-mercaptoethanol, separated at 55 V O/N and transferred to 0.45 μM LF PVDF (Bio-Rad, USA). PVDF was immunoblotted using anti-CFTR antibody M3A7(1:1000; Millipore, USA) in 2% non-fat milk and imaged on LI-COR Odyssey Imaging System (LI-COR, USA). For HDH-His-Strep expressing cells, the cell pellet was vigorously dounce homogenized in 100 mM sucrose, 1 mM DTT, 1 mM EDTA, 20 mM tris-HCl pH 8.0, 0.5 μg/ml pepstatin, 2.5 μg/ml aprotinin, 2.5 μg/ml leupeptin, 0.1 mM PMSF and 0.75 mM benzamidine. The lysate was centrifuged at 100,000 g for 30 min at 4° C. The supernatant (soluble cellular protein) was separated on 4-12% Bis-Tris SDS-page acrylamide gels (ThermoFisher, USA) in the presence of 1% 2-mercaptoethanol, transferred to 0.22 μM LF PVDF (Bio-Rad, USA) and immunoblotted using anti-Strep antibody (1:5000; iba, Germany) in 2% non-fat milk and imaged on LI-COR Odyssey Imaging System (LI-COR, USA).

Mass Spectrometry

Fragmentation data on purified HDH-His-Strep protein were obtained at the University of Iowa Proteomics Facility. Briefly, HDH-His-Strep protein from the soluble fraction of the high-speed spin was passed through StrepTrap HP columns (GE Healthcare, Sweden) and washed with 5 column volumes of 100 mM sucrose, 1 mM DTT, 1 mM EDTA, 20 mM tris-HCl pH 8.0, 0.5 µg/ml pepstatin, 2.5 µg/ml aprotinin, 2.5 µg/ml leupeptin, 0.1 mM PMSF and 0.75 mM benzamidine. The protein was eluted in wash buffer supplemented with 10 mM d-desthbiotin and concentrated in 30 kDA cutoff Amicon-Ultra filtration columns (Millipore, USA). The concentrated protein was loaded on NuPage 4-12% Bis-Tris precast gels (Invitrogen, USA) and separated at 150V for 1.5 hrs. The gel was stained using a Pierce mass spec compatible silver stain kit (ThermoFisher Scientific, USA).

In-gel Trypsin Digestion. Briefly, the targeted protein bands from SDS-PAGE gel were manually excised, cut into 1 mm$^3$ pieces, and washed in 100 mM ammonium bicarbonate:acetonitrile (1:1, v/v) and 25 mM ammonium bicarbonate/acetonitrile (1:1, v/v), respectively to achieve complete destaining. The gel pieces were further treated with ACN, and dried via speed vac. After drying, gel pieces were reduced in 50 µl 10 mM DTT at 56° C. for 60 min and then alkylated by 55 mM IAM for 30 min at room temperature. The gel pieces were washed with 25 mM ammonium bicarbonate:acetonitrile (1:1, v/v) twice to removed excess DTT and IAM. After drying, the gel pieces were placed on ice in 50 µL of trypsin solution at 10 ng/µL in 25 mM ammonium bicarbonate and incubated on ice for 60 min. Then, digestion was performed at 37° C. for 16 h. Peptide extraction was performed twice for 0.5 h with 100 µl 50% acetonitrile/0.2% formic acid. The combined extracts were concentrated in a Speed Vac to ~15 µl.

LC-MS/MS. The mass spectrometry data were collected using an Orbitrap Fusion Lumos mass spectrometer (Thermo Fisher Scientific, San Jose, Calif.) coupled to an Eksigent Ekspert™ nanoLC 425 System (Sciex). A Trap-Elute Jumper Chip (P/N:800-00389) and a coupled to a 1/16" 10 port Valco directed loading performed by the gradient 1 pump and final elution (by the gradient 2 pump). The column assembly was designed as two tandem 75 µm×15 cm columns (ChromXP C18-CL, 3 µm 120 A, Eksigent part of AB SCIEX) mounted in the Ekspert™ cHiPLC system. For each injection, an estimated 0.5 µg of total digest was loaded. Peptides were separated in-line with the mass spectrometer using a 120 min gradient composed of linear and static segments wherein Buffer A is 0.1% formic acid and B is 95% ACN, 0.1% Formic acid. The gradient begins first holds at 4% for 3 min then makes the following transitions (% B, min): (26, 48), (35, 58), (35, 64), (50, 72), (50, 78), (94, 84), (94, 96). (4, 100), (4, 120).

Tandem mass spectrometry on the LUMOS Orbitrap. Scan sequences began with a full survey (m/z 350-1500) acquired on an Orbitrap Fusion Lumos mass spectrometer (Thermo) at a resolution of 60,000 in the off axis Orbitrap segment (MS1). Every 3 seconds of the gradient MS1 scans were acquired during the 120 min gradient described above. The most abundant precursors were selected among 2-8 charge state ions at a 2.0E5 threshold. Ions were dynamically excluded for 30 seconds if they were targeted twice in the prior 30 sec. Selected ions were isolated by a multi-segment quadrupole with a mass window on m/z 2, then sequentially subjected to both CID and HCD activation conditions in the IT and the ioin routing multipole respectively. The AGC target for CID was 4.0E04, 35% collision energy, an activation Q of 0.25 and a 100 milliseconds maximum fill time. Targeted precursors were also fragmented by high energy collision-induced dissociation (HCD) at 40% collision energy, and an activation Q of 0.25.

HCD fragment ions were analyzed using the Orbitrap (AGC 1.2E05, maximum injection time 110 ms, and resolution set to 30,000 at 400 Th). Both MS2 channels were recorded as centroid and the MS1 survey scans were recorded in profile mode.

Proteomic Searches. Initial spectral searches were performed with Proteome Discoverer version 2.1.1.21 (ThermoFisher Scientific, USA) using Sequest HT. Spectra were also searched with Byonic search engine (Protein Metrics) ver. 2.8.2. Search databases were composed of the Uniprot KB for species 9606 (Human) downloaded Oct. 24, 2016 containing 92645 sequences and Uniprot KB for taxonomy 562 (E. coli) downloaded on Nov. 8, 2016 containing 10079 sequences. For Byonic searches, these two data bases were directly concatenated. In either search an equal number of decoy entries were created and searched simultaneously by reversing the original entries in the Target databases.

In vitro cRNA transcription. G542X$_{UGA}$, W1282X$_{UGA}$, and WT CFTR pGEMHE (Mense et al., 2006; PMID: 1703051) plasmids were linearized by 10× excess of NheI-HF restriction enzyme (site positioned 3' of coding region) (New England BioLabs, USA) for 3 hrs at 37° C. and purified using standard cDNA precipitation methods. All cRNAs were transcribed using the mMessage mMachine T7 Kit (ThermoFisher Scientific, USA). Purification of the cRNA from the transcription reaction was conducted on columns from the RNeasy Mini Kit (Qiagen, Germany). Concentration was determined by absorbance measurements at 260 nm and quality was confirmed on a 1% agarose gel (RNase-free). All cRNA was queued to 1 µg/ml before use and all results were generated from ≥2 cRNA preparations.

In vitro tRNA transcription. Trpchr17.trna39 and Glychr19.trna2, the top performing Trp and Gly ACE-tRNAs, were transcribed in vitro using CellScript T7-Scribe Standard RNA IVT Kit (CELLSCRIPT, USA). Equimolar concentration of T7 oligo (5'-taatacgactcactata-3') was annealed to ACE-tRNA PAGE-purified Ultramers (2 ug; Integrated DNA Technologies, Coralville, Iowa) coding for the ACE-tRNA and preceded by a T7 promoter (italics). Importantly, the three terminal nucleotides containing CCA were included (bold).

```
Trpchr17.trna39 (3'->5'):
                                        (SEQ ID NO: 654)
TGGTGACCCCGACGTGATTTGAACACGCAACCTTCTGATCTGAAGTCA

GACGCGCTACCGTTGCGCCACGAGGCCTATAGTGAGTCGTATTA

Glychr19.trna2 (3'->5'):
                                        (SEQ ID NO: 655)
TGGTGCGTTGGCCGGGAATCGAACCCGGGTCAATGCTTTGAAGGAGCT

ATGCTAACCATATACCACCAACGCTATAGTGAGTCGTATTA
```

The total reaction volume was adjusted to 100 µl and the kit reagents were added in the following amounts: 10 µl of 10× T7-Scribe transcription buffer, 7.5 µl of each nucleotide (100 mM stocks), 10 µl of 100 mM Dithiothreitol, 2.5 µl ScriptGuard RNase Inhibitor, 10 µl T7-Scribe enzyme solution. After the reaction was incubated for 4-5 hr at 37° C., the DNA template was digested with 5 µl DNase (1 U/µl) provided with the kit for 30-60 min. The ACE-tRNA was extracted from the reaction with acidic phenol chloroform (5:1, pH 4.5) and precipitated with ethanol. The precipitates ACE-tRNA was pelleted, washed, dried and resuspended in 100 µl DEPC-treated water and further purified with Chroma Spin-30 columns (Clontech, USA). The procedure yielded roughly 100 µl of ~5 µg/µl ACE-tRNA, ACE-tRNAs were re-pelleted in 20 ug aliquots, washed, lyophilized and stored at −80° C. until use. All results were generated from ≥20 ACE-tRNA preparations.

Ribosome Footprint Profiling Library preparation. HEK293 cells transiently transfected with ACE-tRNAs and control plasmid (puc57GG) were grown in standard grown media in the absence of Pen-Strep for 48 h. Libraries were prepared as described[55], with a few modifications. Briefly, cells were rapidly cooled by addition of ice-cold PBS, lysed in lysis buffer (20 mM Tris-HCl/pH7.4, 150 mM NaCl, 5 mM $MgCl_2$, 1 mM DTT, 1% (v/v) Triton X-100, and 25 U $ml^{-1}$ Turbo DNase I) for 10 min on ice, and triturated with ten times through a 26-G needle. After clearance by centrifugation at 16,000 g for 10 min at 4° C., the lysates were digested with 100 U RNase I (Ambion, USA) per $A_{260}$ lysate at room temperature for 45 min with gentle agitation prior to adding 200 U RiboLock RNase Inhibitor (Thermo Scientific). Ribosome protected mRNA fragments were then isolated by loading lysates onto a 1M sucrose cushion prepared in modified polysome buffer (20 mM Tris-HCl/ pH7.4, 150 mM NaCl, 8.5 mM $MgCl_2$, 0.5 mM DTT, 20 U $ml^{-1}$ RiboLock RNase Inhibitor) and centrifugated at 70,000 rpm at 4° C. for 2 h using a Beckmen TLA-110 rotor. Ribosome pellets containing mRNA footprints were extracted using TRIzol and separated on a denaturing 12% polyacrylamide gel containing 8M urea. RNA fragments with sizes ranging from 26 to 34 nt were manually excised from the gel stained with SYBR Gold (Invitrogen) and isolated to generate the ribosome-protected fragment library. Contaminating rRNA fragments depleted using a Ribo-Zero kit (Illumina). 3' Oligonucleotide adaptor ligation, reverse transcription, circularization, and secondary rRNA depletion using biotinylated rRNA depletion oligos (Table 9) were performed as described[55]. Libraries were barcoded using indexing primers for each sample during PCR amplification. Barcoded libraries were then pooled with 3% PhiX (Illumina) and sequenced in an Illumina NextSeq 500 as per manufacturer protocol to typically generate 18-27 million reads per sample.

Ribosome Footprint Data analysis. Data files for each barcoded sample (minus adaptor sequence at 3' end) were first mapped to four rRNA sequences (RNA5S1; NR_023363, RNA5-8SN5; NR_003285, RNA18SN5; NR_003286, and RNA28SN5; NR_003287) using HISAT 2.0.3[56] to eliminate rRNA contaminant reads. The remaining reads were aligned to the sense stands of the longest transcript variant of each human gene (UCSC RefSeq GRCh38). Transcripts with 3'UTR length of at least 75 nt (18,101 sequences) were used for subsequence analysis. A maximum of two mismatches at the 5'end of reads was allowed. All multi-mapped reads were discarded. Fragment reads with lengths between 26 to 34 nt were defined as ribosome footprints and used for analysis. The 5' end nucleotide from each footprint was annotated and mapped on each transcript. Position of the ribosome A-site occupying the 16th-18th nucleotides of each footprint[57, 58] was used to infer the position of the ribosome on each transcript. RPKM (footprint Reads Per Kilobase of transcript per total Million-mapped reads) on each individual transcript (18,101 sequences) was calculated. Only transcripts with a minimum threshold of 5 RPKM in the coding sequence and 0.5 RPKM in 3'UTR region in two replicate libraries (254 transcripts in G418 and 495-748 transcripts in ACE-tRNAs) were included for analysis in FIG. 24A. For transcriptome-wide metagene plots in FIG. 2B, footprint counts for each nucleotide within the region from −35 to +65 nt relative to the first nucleotide of stop codon were normalized per total million-mapped reads. All transcripts (18,101 sequences) were used for mapping, and more than 5,200 transcripts were mapped to at least 1 footprint in the region of interest. Next, we examined the in vivo bioactivity of ACE-tRNAs Glychr19.trna2 and Trpchr17.trna39 to rescue PTC. The sequencing data was analyzed using Galaxy platform[59]. Graphs were generated using Prism 7 (GraphPad Software).

Generation of stable NLuc reporter cell lines. The cDNAs encoding pNLuc with tag, taa and tga stop codons at amino acid position 160 were inserted into AgeI and NotI restriction sites within the multiple cloning site of the retroviral vector pQCXIP (Clontech, USA) using Gibson Assembly (New England Biolabs, USA). PhoenixGP cells (PMID: 7690960) were co-transfected with pNLuc-STOP-pQCXIP and cmv-VSV-G (VSV-G envelope pseudotyping) plasmids using Calfectin (SignaGen Laboratories, USA) and placed in a 33° C. $CO_2$-controlled (5%) cell incubator for 48 hr. The culture media (20 mls) containing retroviral particles was chilled to 4° C. and spun at 10,000 g to remove cell debris and filtered through a 0.45 um MCE-membrane syringe filter (Millipore, USA) onto two 10 cm dishes seeded with low-passage HEK293 cells at 30% confluency. Cell culture dishes were sealed with Parafilm and spun for 90 minutes at 3,500 g at 24° C. and placed in a 37° C. $CO_2$ controlled (5%) cell culture incubator. Cells were selected 24 hr later with puromycin (1 ug/ml) until the control dish (no infection) showed complete cell death. Cells were monodispersed into 96-well plates using FACS and clonal populations were subsequently. Puromycin was not used to maintain selected clones during experimentation and standard DMEM media (DMEM—Dulbecco's Modified Eagle Medium-high glucose with L-glutamine supplemented with 10% FBS, 1% Pen/Step and 2 mM L-Glutamine; ThermoFisher, USA) was used in all studies.

RNA transfection, HEK293 cells stably expressing pNLuc-UGA were plated at $1.4\times10^4$ cells/well in 96 well cell culture treated plates in Dulbecco's Modified Essential Medium (DMEM) supplemented with 10% FBS, 1% Pen/ Step and 2 mM L-Glutamine (Thermofisher, USA). 16-24 hr later the cells were transfected with ACE-tRNAs using lipofectamine 2000 (ThermoFisher Scientific, USA). Briefly, 3 µg of ACE-tRNA were suspended in 150 µl of OptiMEM and 12 µl of Lipofectamine 2000 was mixed with 150 ul of OptiMEM. The volumes were combined, thoroughly mixed and incubated for 10 mins at RT. 75 ul of the transfection complex was added to each well. PTC suppression by ACE-tRNA transcripts was quantified as described above.

Expression in *Xenopus laevis* ocytes. *Xenopus laevis* oocytes (stage V and VI) were purchased from Ecocyte (Austin, Tex.). Prior to injection, each ACE-tRNA pellet was resuspended in 2 µl of ddH$_2$O and debris was pelleted at 21,000×g, 4° C. for 25 min. To determine dose response of ACE-tRNAs on CFTR channel rescue, serial dilutions were generated of ACE-tRNA aliquots (200, 100, 50, 25, 12.5, 6.25, 3.125 and 1.562 ng/oocyte) balanced in volume with ddH$_2$O. In all experiments 25 ng of CFTR cRNA was injected per oocyte and injection volumes were 50 nl. ddH$_2$O was used in no ACE-tRNA background control experiments. After injection, oocytes were kept in OR-3 (50% Leibovitz's medium, 250 mg/l gentamycin, 1 mM L-glutamine, 10 mM HEPES (pH 7.6)) at 18° C. for 36 hr.

Two-electrode voltage clamp (TEVC) recordings. CFTR $Cl^-$ currents were recorded in ND96 bath solution that contained (in mM): 96 NaCl, 2 KCl, $MgCl_2$, and 5 HEPES (pH 7.5) in the presence of a maximal CFTR activation cocktail, forskolin (10 µM; adenylate cyclase activator) and 3-isobutyl-1-methylxanthine (1 mM; phosphodiesterase inhibitor). Glass microelectrodes backfilled with 3 M KCl had resistances of 0.5-2 MΩ. Data were filtered at 1 kHz and digitized at 10 kHz using a Digidata 1322A controlled by the pClamp 9.2 software (Molecular Devices, USA). CFTR currents were elicited using 5 mV voltage steps from −60 to +35 mV using an OC-725C voltage clamp amplifier (Warner Instruments, USA). Oocytes where the CFTR Cl⁻ current reversed positive of −20 mV were discarded. Clampfit 9.2 software was used for current analysis. All values are presented as mean±SEM.

Animals and in vivo imaging. Nu/J mice were purchased from Jackson labs. Animal experiments were approved by the Institutional Animal Care and Use Committee at the Wistar Institute (protocol number: 112762). Mice were treated by injecting 10-20 ug of DNA resuspended in 30 ul of water into the tibialis anterior muscle followed by electroporation. 10 ug pNano-TGA+10 ug Arg ACE-tRNA (right tibialis anterior) or 10 ug pNano-TGA+10 ug empty pUC57 (left tibialis anterior) were injected into 3 mice. As controls 3 other mice were injected with 10 ug pNano-WT (right tibialis anterior; positive control) or water (left tibialis anterior; negative control). The DNA was formulated with 3331U/ml of hyaluronidase (Sigma). One minute after DNA injection, electroporation with CELLECTRA 3P device (Inovio Pharmaceuticals) was performed. Nanoluciferase activity was imaged in mice by injecting 100 ul of furimazine (40× dilution of Nano-Glo substrate) intraperitoneally and imaged mice on an IVIS Spectrum (Perkin Elmer) 5 minutes after injection. Imaging was with open filter and images were acquired at 40 seconds. The images were analyzed using Living Image Software (Perkin Elmer).

TABLE 9

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|   | tRNAscan-SE ID | Sequence | SEQ ID NO |
|---|---|---|---|
| 1 | TrpTGAchr17.trna39 | GGCCTCGTGGCGCAACGGTAGCGCGTCTGACT*tca*GA TCAGAAGGtTGCGTGTTCAAATCACGTCGGGGTCA | 56 |
| 2 | TrpTGAchr17.trna10 | GACCTCGTGGCGCAATGGTAGCGCGTCTGACT*tca*GA TCAGAAGGtTGCGTGTTCAAGTCACGTCGGGGTCA | 57 |
| 3 | TrpTGAchr6.trna171 | GACCTCGTGGCGCAACGGTAGCGCGTCTGACT*tca*GA TCAGAAGGtTGCGTGTTCAAATCACGTCGGGGTCA | 58 |
| 4 | TrpTGAchr12.trna6 | GACCTCGTGGCGCAACGGTAGCGCGTCTGACT*tca*GA TCAGAAGGcTGCGTGTTCGAATCACGTCGGGGTCA | 59 |
| 5 | TrpTGAchr7.trna3 | GACCTCGTGGCGCAACGGCAGCGCGTCTGACT*tca*GA TCAGAAGGtTGCGTGTTCAAATCACGTCGGGGTCA | 60 |
| 6 | TrpTGAchr7.trna31 | GGCCTCATGGTGCAACAGTAGTGTGTCTGACT*tca*GA TCAGAAGGtTGTATGTTCAAATCACGTAGGGGTCA | 61 |
| 1 | TrpTAGchr17.trna39 | GGCCTCGTGGCGCAACGGTAGCGCGTCTGACT*cta*GA TCAGAAGGtTGCGTGTTCAAATCACGTCGGGGTCA | 62 |
| 2 | TrpTAGchr17.trna10 | GACCTCGTGGCGCAATGGTAGCGCGTCTGACT*cta*GA TCAGAAGGtTGCGTGTTCAAGTCACGTCGGGGTCA | 63 |
| 3 | TrpTAGchr6.trna171 | GACCTCGTGGCGCAACGGTAGCGCGTCTGACT*cta*GAT CAGAAGGtTGCGTGTTCAAATCACGTCGGGGTCA | 64 |
| 4 | TrpTAGchr12.trna6 | GACCTCGTGGCGCAACGGTAGCGCGTCTGACT*cta*GA TCAGAAGGcTGCGTGTTCGAATCACGTCGGGGTCA | 65 |
| 5 | TrpTAGchr7.trna3 | GACCTCGTGGCGCAACGGCAGCGCGTCTGACT*cta*GA TCAGAAGGtTGCGTGTTCAAATCACGTCGGGGTCA | 66 |
| 6 | TrpTAGchr7.trna31 | GGCCTCATGGTGCAACAGTAGTGTGTCTGACT*cta*GA TCAGAAGGtTGTATGTTCAAATCACGTAGGGGTCA | 67 |
| 1 | GlyTGAchr1.trna122 | GCATTGGTGGTTCAGTGGTAGAATTCTCGCCT*tca*AC GCGGGAGaCCCGGGTTCAATTCCCGGCCAATGCA | 68 |
| 2 | GlyTGAchr2.trna25 | GCGCCGCTGGTGTAGTGGTATCATGCAAGATT*tcaa*A TTCTTGCGaCCCGGGTTCGATTCCCGGGCGGCGCA | 69 |
| 3 | GlyTGAchr17.trna11 | GCATTGGTGGTTCAATGGTAGAATTCTCGCCT*tca*AC GCAGGAGaCCCAGGTTCGATTCCTGGCCAATGCA | 70 |
| 4 | GlyTGAchr1.trna120 | GCGTTGGTGGTTTAGTGGTAGAATTCTCGCCT*tca*AT GCGGGAGaCCCGGGTTCAATTCCCGGCCACTGCA | 71 |
| 5 | GlyTGAchr1.trna2 | GCCTTGGTGGTGCAGTGGTAGAATTCTCGCCT*tca*AC GTGGGAGaCCCGGGTTCAATTCCCGGCCAATGCA | 72 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|  | tRNAscan-SE ID | Sequence | SEQ ID NO |
|---|---|---|---|
| 6 | GlyTGAchr1.trna83 | GGTGGTTCAGTGGTAGAATTCTCGCCT*tca*ACGCGGG AGaCCCGGGTTTAATTCCCGGTCA | 73 |
| 7 | GlyTGAchr2.trna1 | GTGGTCTAGTGGTTAGGATTCAGCGCT*tca*ACCGCCG CAGCCCGGGTTCGATTCCCGGtCA | 74 |
| 8 | GlyTGAchr1.random. trna2 | GCGTCAGTGGTTTAGTGGTGGAATTCCTGCCT*tca*AT GCACGAGATCCGTGTTCAACTCCTGGTTGGTGCA | 75 |
| 9 | GlyTGAchr1.trna102 | GCGTCAGTGgTTTTAGTGGTGGAATTCCTGCCT*tca*A TGCACGAGATCCGTGTTCAACTCCTGGTTGGTGCA | 76 |
| 10 | GlyTGAchr1.trna16 | GCGTTGGCAGTTCAGTGGTAGAATTCTCGCCT*tca*AC CCGGGAGaCCTGGATTCCATTTCCGGCAAATGCA | 77 |
| 11 | GlyTGAchr1.trna34 | GCATGGGTGGTTCAGTGGTAGAATTCTCGCCT*tca*AC GCGGGAGGCCCGGGTTCGATTCCCGGCCCATGCA | 78 |
| 12 | GlyTGAchr1.trna61 | GCATTGGTGGTTCAGTGGTAGAATTCTCGCCT*tca*AC GCGGGAGGCCCGGGTTCGATTCCCGGCCAATGCA | 79 |
| 13 | GlyTGAchr16.trna25 | GCATTGGTGGTTCAGTGGTAGAATTCTCGCCT*tca*AC GCGGGAGGCCCGGGTTTGATTCCCGGCCAGTGCA | 80 |
| 14 | GlyTGAchr1.trna42 | GCATAGGTGGTTCAGTGGTAGAATTCTTGCCT*tca*AC GCAGGAGGCCCAGGTTTGATTCCTGGCCCATGCA | 81 |
| 15 | GlyTGAchr16.trna19 | GCATTGGTGGTTCAGTGGTAGAATTCTCGCCT*tca*AT GCGGGCGGCCGGGCTTCGATTCCTgGCCAATGCA | 82 |
| 16 | GlyTGAchr6.trna80 | GCATGGGTGATTCAGTGGTAGAATTTTCACCT*tca*AT GCAGGAGGTCCAGGTTCATTTCCTGGCCTATGCA | 83 |
| 17 | GlyTGAchr19.trna2 | GCGTTGGTGGTATAGTGGTtAGCATAGCTGCCT*tca*A AGCAGTTGaCCCGGGTTCGATTCCCGGCCAACGCA | 84 |
| 18 | GlyTGAchr1.trna107 | GCGTTGGTGGTATAGTGGTgAGCATAGCTGCCT*tca*A AGCAGTTGaCCCGGGTTCGATTCCCGGCCAACGCA | 85 |
| 19 | GlyTGAchr17.trna9 | GCGTTGGTGGTATAGTGGTaAGCATAGCTGCCT*tca*A AGCAGTTGaCCCGGGTTCGATTCCCGGCCAACGCA | 86 |
| 20 | GlyTGAchr1.trna75 | GCGTTGGTGGTATAGTGGTgAGCATAGTTGCCT*tca*A AGCAGTTGaCCCGGGCTCGATTCCCGCCCAACGCA | 87 |
| 21 | GlyTGAchr1.trna75-mod | GCGTTGGTGGTATAGTGGTgAGCATAGTTGCCT*tca*A AGCAGTTGaCCCGGGCTCGATTCCCGgCCAACGCA | 88 |
| 1 | ArgTGAchr6.trna6 | GGGCCAGTGGCGCAATGGAtAACGCGTCTGACT*tca*G ATCAGAAGAtTCCAGGTTCGACTCCTGGCTGGCTCG | 89 |
| 2 | ArgTGAchr3.trna8 | GGGCCAGTGGCGCAATGGAtAACGCGTCTGACT*tca*G ATCAGAAGAtTCTAGGTTCGACTCCTGGCTGGCTCG | 90 |
| 3 | ArgTGAchr6.trna115 | GGCCGCGTGGCCTAATGGAtAAGGCGTCTGATT*tca*G ATCAGAAGAtTGAGGGTTCGAGTCCCTTCGTGGTCG | 91 |
| 4 | ArgTGAchr17.trna21 | GACCCAGTGGCCTAATGGAtAAGGCATCAGCCT*tca*G AGCTGGGGAtTGTGGGTTCGAGTCCCATCTGGGTCG | 92 |
| 5 | ArgTGAchr17.trna16 | GCCCCAGTGGCCTAATGGAtAAGGCACTGGCCT*tca*A AGCCAGGGAtTGTGGGTTCGAGTCCCACCTGGGGTA | 93 |
| 6 | ArgTGAchr17.trna19 | GCCCCAGTGGCCTAATGGAtAAGGCACTGGCCT*tca*A AGCCAGGGAtTGTGGGTTCGAGTCCCACCTGGGGTG | 94 |
| 7 | ArgTGAchr16.trna3 | GCCCCGGTGGCCTAATGGAtAAGGCATTGGCCT*tca*A AGCCAGGGAtTGTGGGTTCGAGTCCCACCCGGGGTA | 95 |
| 8 | ArgTGAchr7.trna5 | GCCCCAGTGGCCTAATGGAtAAGGCATTGGCCT*tca*A AGCCAGGGAtTGTGGGTTCGAGTCCCATCTGGGGTG | 96 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|  | tRNAscan-SE ID | Sequence | SEQ ID NO |
|---|---|---|---|
| 9 | ArgTGAchr16.trna13 | GCCCCAGTGGCCTGATGGAtAAGGTACTGGCCTt*ca*A AGCCAGGGAtTGTGGGTTCGAGTTCCACCTGGGGTA | 97 |
| 10 | ArgTGAchr15.trna4 | GGCCGCGTGGCCTAATGGAtAAGGCGTCTGACTt*ca*G ATCAGAAGAtTGCAGGTTCGAGTCCTGCCGCGGTCG | 98 |
| 11 | ArgTGAchr6.trna4 | GACCACGTGGCCTAATGGAtAAGGCGTCTGACTt*ca*G ATCAGAAGAtTGAGGGTTCGAATCCCTCCGTGGTTA | 99 |
| 12 | ArgTGAchr17.trna17 | GACCGCGTGGCCTAATGGAtAAGGCGTCTGACTt*ca*G ATCAGAAGAtTGAGGGTTCGAGTCCCTTCGTGGTCG | 100 |
| 13 | ArgTGAchr6.trna3 | GACCACGTGGCCTAATGGAtAAGGCGTCTGACTt*ca*G ATCAGAAGAtTGAGGGTTCGAATCCCTTCGTGGTTA | 101 |
| 14 | ArgTGAchr6.trna125 | GACCACGTGGCCTAATGGAtAAGGCGTCTGACTt*ca*G ATCAGAAGAtTGAGGGTTCGAATCCCTTCGTGGTTG | 102 |
| 15 | ArgTGAchr9.trna5 | GGCCGTGTGGCCTAATGGAtAAGGCGTCTGACTt*ca*G ATCAAAAGAtTGCAGGTTTGAGTTCTGCCACGGTCG | 103 |
| 16 | ArgTGAchr1.trna10 | GGCTCCGTGGCGCAATGGAtAGCGCATTGGACTt*ca*A gaggctgaaggcATTCAAAGGtTCCGGGTTCGAGTCC CGGCGGAGTCG | 104 |
| 17 | ArgTGAchr1.trna10/ nointron | GGCTCCGTGGCGCAATGGAtAGCGCATTGGACTt*ca*A ATTCAAAGGtTCCGGGTTCGAGTCCCGGCGGAGTCG | 105 |
| 18 | ArgTGAchr17.trna3 | GGCTCTGTGGCGCAATGGAtAGCGCATTGGACTt*ca*A gtgacgaatagagcaATTCAAAGGtTGTGGGTTCGAA TCCCACCAGAGTCG | 106 |
| 19 | ArgTGAchr17.trna3/ nointron | GGCTCTGTGGCGCAATGGAtAGCGCATTGGACTt*ca*A ATTCAAAGGtTGTGGGTTCGAATCCCACCAGAGTCG | 107 |
| 20 | ArgTGAchr9.trna6 | GGCTCTGTGGCGCAATGGAtAGCGCATTGGACTt*ca*A gctgagcctagtgtggtcATTCAAAGGtTGTGGGTTC GAGTCCCACCAGAGTCG | 108 |
| 21 | ArgTGAchr9.trna6/ nointron | GGCTCTGTGGCGCAATGGAtAGCGCATTGGACTt*ca*A ATTCAAAGGtTGTGGGTTCGAGTCCCACCAGAGTCG | 109 |
| 22 | ArgTGAchr11.trna3 | GGCTCTGTGGCGCAATGGAtAGCGCATTGGACTt*ca*A gatagttagagaaATTCAAAGGtTGTGGGTTCGAGTC CCACCAGAGTCG | 110 |
| 23 | ArgTGAchr1.trna79 | GTCTCTGTGGCGCAATGGAcgAGCGCGCTGGACTt*ca* AATCCAGAGGtTCCGGGTTCGAGTCCCGGCAGAGATG | 111 |
| 24 | ArgTGAchr6.trna52 | GGCTCTGTGGCGCAATGGAtAGCGCATTGGACTt*ca*A gcctaaatcaagagATTCAAAGGtTGCGGGTTCGAGT CCCTCCAGAGTCG | 112 |
| 25 | ArgTGAchr6.trna52/ nointron | GGCTCTGTGGCGCAATGGAtAGCGCATTGGACTt*ca*A ATTCAAAGGtTGCGGGTTCGAGTCCCTCCAGAGTCG | 113 |
| 26 | ArgTGAchr5.trna4 | GGCAGCATAGCAGAGTGGtTCAGGTTACAGGTt*ca*AG ATGTAAACTGAGTTCAAATCCCAGTTCTGCCA | 114 |
| 1 | GlnTAGnmt-tRNA-Gln chr10.trna6 | TGGTGTAATAGGTAGCACAGAGAATT*cta*GATTCTCA GGGGTAGGTTCAATTCCTAT | 115 |
| 2 | GlnTAGnmt-tRNA-Gln chrX.trna1 | TAGGACATGGTGTGATAGGTAGCATGGAGAATT*cta*G ATTCTCAGGGGTAGGTTCAATTCCTACAGTTCTAG | 116 |
| 3 | GlnTAGnmt-tRNA-Gln chr7.trna32 | TAGGACGTGGTGTGATAGGTAGCATGGGGAATT*cta*G ATTCTCAGGGGTGGGTTCAATTCCTATAGTTCTAG | 117 |
| 4 | GlnTAGnmt-tRNA-Gln chr7.trna7 | TAGGACGTGGTGTAGTAGGTAGCATGGAGAATG*cta*A ATTCTCAGGGGTAGGTTCAATTCCTATAGTTCTAG | 118 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 5 | GlnTAGnmt-tRNA-Gln chr2.trna24 | TAGGACATGGTGTAATAGGTAGAATGGAGAATT*ctaA*ATTCTCAGGGGTAGGTTCAATTCCTATAGTTCTAG | 119 |
| 6 | GlnTAGnmt-tRNA-Gln chr3.trna7 | TAGGATGTGGTGTATTAGGTAGCACAGAGAATT*ctaG*ATTCTCAGGGGTAGGTTCGATTCCTATAATTCTAC | 120 |
| 7 | GlnTAGnmt-tRNA-Gln chr16.trna15 | TAGGACTTGGTGTAATGGGTAGCACAGAGAATT*ctaG*ATTCTCAGGGGTGGGTTCAATTCCTTTCGTCCTAG | 121 |
| 8 | GlnTAGnmt-tRNA-Gln chr12.trna15 | TCTAGGAtgTGGTGTGATAGGTAGCATGGAGAATT*ct*aGATTCTCAGGGGTAGGTTCAATTCCTATaTTCTAGAA | 122 |
| 9 | GlnTAGnmt-tRNA-Gln chr2.trna21 | TAGGACGTGGTGTGATAGGTAGCATGGAGAATT*ctaG*ATTCTCAGGGATGGGTTCAATTCCTATAGTCCTAG | 123 |
| 10 | GlnTAGnmt-tRNA-Gln chr2.trna9 | TAGGACGTGGTGTGATAGGTAGCACGGAGAATT*ctaG*ATTCTCAGGGATGGGTTCAATTCCTGTAGTTCTAG | 124 |
| 11 | GlnTAGchr6.trna1 | GGTTCCATGGTGTAATGGTtAGCACTCTGGACT*ctaA*ATCCAGCGaTCCGAGTTCAAATCTCGGTGGAACCT | 125 |
| 12 | GlnTAGchr1.trna104 | GGTTCCATGGTGTAATGGTgACCACTTTGGACT*ctaA*ATACAGTGATCAGAGTTCAAGTCTCACTGGAACCT | 126 |
| 13 | GlnTAGchr1.trna28 | GGTTCCATGGTGTAATGGTgAGGGCTTTGGACT*ctaA*CTACAGTGaTCAGAGTTCAAGTCTCAGTGGGACCT | 127 |
| 14 | GlnTAGchr12.trna3 | GGTTCCATGGTGTAATGGTaAGCACCCTGGACT*ctaA*ATCCAGCAaCCAGAGTTCCAGTCTCAGCGtGGACCT | 128 |
| 15 | GlnTAGchr5.trna23 | GGTAGTGTAGTCTACTGGTTAAACGCTTGGgCT*ctaA*CATTAAcGtCCTGGGTTCAAATCCCAGCTTTGTCA | 129 |
| 16 | GlnTAGchr6.trna147 | GGTTCCATGGTGTAATGGTtAGCACTCTGGACT*ctaA*ATCCAGCGaTCCGAGTTCAAGTCTCGGTGGAACCT | 130 |
| 17 | GlnTAGchr1.trna17 | GGTTCCATGGTGTAATGGTgAGCACTCTGGACT*ctaA*ATCCAGCGaTCCGAGTTCGAGTCTCGGTGGAACCT | 131 |
| 18 | GlnTAGchr1.trna101 | GGTTCCATGGTGTAATGGTaAGCACTCTGGACT*ctaA*ATCCAGCGaTCCGAGTTCGAGTCTCGGTGGAACCT | 132 |
| 19 | GlnTAGchr6.trna42 | GGTTCCATGGTGTAATGGTtAGCACTCTGGACT*ctaA*ATCCGGTAaTCCGAGTTCAAATCTCGGTGGAACCT | 133 |
| 20 | GlnTAGchr6.trna132 | GGCCCCATGGTGTAATGGTcAGCACTCTGGACT*ctaA*ATCCAGCGaTCCGAGTTCAAATCTCGGTGGGACCC | 134 |
| 21 | GlnTAGchr1.trna23 | GGTTCCATGGTGTAATGGTaAGCACTCTGGACT*ctaA*ATCCAGCCATCTGAGTTCGAGTCTCTGTGGAACCT | 135 |
| 22 | GlnTAGchr1.trna111 | GGTTCCATGGTGTAATGGTgAGCACTTTGGACT*ctaA*ATACAGTGATCAGAGTTCAAGTCTCACTGGGACCT | 136 |
| 23 | GlnTAGchr1.trna24 | GGTTCCATGgGTTAATGGTgAGCACCCTGGACT*ctaA*ATCAAGCGaTCCGAGTTCAAATCTCGGTGGTACCT | 137 |
| 24 | GlnTAGchr19.trna4 | GTTTCCATGGTGTAATGGTgAGCACTCTGGACT*ctaA*ATCCAGAAATACATTCAAAGAATTAAGAACA | 138 |
| 25 | GlnTAGchr17.trna14 | GGTCCCATGGTGTAATGGTtAGCACTCTGGACT*ctaA*ATCCAGCGaTCCGAGTTCAAATCTCGGTGGGACCT | 139 |
| 26 | GlnTAGchr6.trna63 | GGTCCCATGGTGTAATGGTtAGCACTCTGGACT*ctaA*ATCCAGCAaTCCGAGTTCGAATCTCGGTGGGACCT | 140 |
| 27 | GlnTAGchr6.trna175 | GGCCCCATGGTGTAATGGTtAGCACTCTGGACT*ctaA*ATCCAGCGaTCCGAGTTCAAATCTCGGTGGGACCT | 141 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|  | tRNAscan-SE ID | Sequence | SEQ ID NO |
|---|---|---|---|
| 28 | GlnTAGchr6.trna82 | GGTCCCATGGTGTAATGGTtAGCACTCTGGGCT*ctA*ATCCAGCAaTCCGAGTTCGAATCTTGGTGGACCT | 142 |
| 29 | GlnTAGchr2.trna26 | GGCTGTGTACCTCAGTGGGcAAGGGTATGGACT*ctA*AGCCAGACTaTTTGGGTTCAAATCCCAGCTTGGCCT | 143 |
| 30 | GlnTAGchr4.trna4 | GACCATGTGGCCTAAGGGAaAAGACATCTCACT*ctG*GTCAGAAGAtTGAGGGTTCAAGTCCTTTCATGGTCA | 144 |
| 31 | GlnTAGchr8.trna10 | GGTACAGTGTTAAAGGGGagaAAAATTGCTGACT*cta*AATaCAGTAGaCCTAGGTTTGAATCCTGGCTTTACCA | 145 |
| 1 | GlnTAAnmt-tRNA-Gln chr10.trna6 | TGGTGTAATAGGTAGCACAGAGAATT*ttA*GATTCTCAGGGGTAGGTTCAATTCCTAT | 146 |
| 2 | GlnTAAnmt-tRNA-Gln chrX.trna1 | TAGGACATGGTGTGATAGGTAGCATGGAGAATT*ttG*ATTCTCAGGGGTAGGTTCAATTCCTACAGTTCTAG | 147 |
| 3 | GlnTAAnmt-tRNA-Gln chr7.trna32 | TAGGACGTGGTGTGATAGGTAGCATGGGGAATT*ttG*ATTCTCAGGGGTGGGTTCAATTCCTATAGTTCTAG | 148 |
| 4 | GlnTAAnmt-tRNA-Gln chr7.trna7 | TAGGACGTGGTGTAGTAGGTAGCATGGAGAATG*ttA*ATTCTCAGGGGTAGGTTCAATTCCTATAGTTCTAG | 149 |
| 5 | GlnTAAnmt-tRNA-Gln chr2.trna24 | TAGGACATGGTGTAATAGGTAGAATGGAGAATT*ttA*ATTCTCAGGGGTAGGTTCAATTCCTATAGTTCTAG | 150 |
| 6 | GlnTAAnmt-tRNA-Gln chr3.trna7 | TAGGATGTGGTGTATTAGGTAGCACAGAGAATT*ttA*ATTCTCAGGGGTAGGTTCGATTCCTATAATTCTAC | 151 |
| 7 | GlnTAAnmt-tRNA-Gln chr16.trna15 | TAGGACTTGGTGTAATGGGTAGCACAGAGAATT*ttA*ATTCTCAGGGGTGGGTTCAATTCCTTTCGTCCTAG | 152 |
| 8 | GlnTAAnmt-tRNA-Gln chr12.trna15 | TCTAGGAt*gT*GGTGTGATAGGTAGCATGGAGAATT*tta*GATTCTCAGGGGTAGGTTCAATTCCTATaTTCTAGAA | 153 |
| 9 | GlnTAAnmt-tRNA-Gln chr2.trna21 | TAGGACGTGGTGTGATAGGTAGCATGGAGAATT*ttA*ATTCTCAGGGATGGGTTCAATTCCTATAGTCCTAG | 154 |
| 10 | GlnTAAnmt-tRNA-Gln chr2.trna9 | TAGGACGTGGTGTGATAGGTAGCACGGAGAATT*ttA*ATTCTCAGGGATGGGTTCAATTCCTGTAGTTCTAG | 155 |
| 11 | GlnTAAchr6.trna1 | GGTTCCATGGTGTAATGGTtAGCACTCTGGACT*ttA*ATCCAGCGaTCCGAGTTCAAATCTCGGTGGAACCT | 156 |
| 12 | GlnTAAchr1.trna104 | GGTTCCATGGTGTAATGGTgACCACTTTGGACT*ttA*ATACAGTGATCAGAGTTCAAGTCTCACTGGAACCT | 157 |
| 13 | GlnTAAchr1.trna28 | GGTTCCATGGTGTAATGGTgAGGGCTTTGGACT*ttA*CTACAGTGaTCAGAGTTCAAGTCTCAGTGGGACCT | 158 |
| 14 | GlnTAAchr12.trna3 | GGTTCCATGGTGTAATGGTaAGCACCCTGGACT*ttA*ATCCAGCAaCCAGAGTTCCAGTCTCAGCGtGGACCT | 159 |
| 15 | GlnTAAchr5.trna23 | GGTAGTGTAGTCTACTGGTTAAACGCTTGGgCT*ttA*CATTAAcGtCCTGGGTTCAAATCCCAGCTTTGTCA | 160 |
| 16 | GlnTAAchr6.trna147 | GGTTCCATGGTGTAATGGTtAGCACTCTGGACT*ttA*ATCCAGCGaTCCGAGTTCAAGTCTCGGTGGAACCT | 161 |
| 17 | GlnTAAchr1.trna17 | GGTTCCATGGTGTAATGGTgAGCACTCTGGACT*ttA*ATCCAGCGaTCCGAGTTCGAGTCTCGGTGGAACCT | 162 |
| 18 | GlnTAAchr1.trna101 | GGTTCCATGGTGTAATGGTaAGCACTCTGGACT*ttA*ATCCAGCGaTCCGAGTTCGAGTCTCGGTGGAACCT | 163 |
| 19 | GlnTAAchr6.trna42 | GGTTCCATGGTGTAATGGTtAGCACTCTGGACT*ttA*ATCCGGTAaTCCGAGTTCAAATCTCGGTGGAACCT | 164 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|  | tRNAscan-SE ID | Sequence | SEQ ID NO |
|---|---|---|---|
| 20 | GlnTAAchr6.trna132 | GGCCCCATGTGTAATGGTcAGCACTCTGGACT*tta*AATCCAGCGaTCCGAGTTCAAATCTCGGTGGGACCC | 165 |
| 21 | GlnTAAchr1.trna23 | GGTTCCATGGTGTAATGGTaAGCACTCTGGACT*tta*AATCCAGCCATCTGAGTTCGAGTCTCTGTGGAACCT | 166 |
| 22 | GlnTAAchr1.trna111 | GGTTCCATGGTGTAATGGTgAGCACTTTGGACT*tta*AATACAGTGATCAGAGTTCAAGTCTCACTGGGACCT | 167 |
| 23 | GlnTAAchr1.trna24 | GGTTCCATGgGTTAATGGTgAGCACCCTGGACT*tta*AATCAAGCGaTCCGAGTTCAAATCTCGGTGGTACCT | 168 |
| 24 | GlnTAAchr19.trna4 | GTTTCCATGGTGTAATGGTgAGCACTCTGGACT*tta*AATCCAGAAATACATTCAAAGAATTAAGAACA | 169 |
| 25 | GlnTAAchr17.trna14 | GGTCCCATGGTGTAATGGTtAGCACTCTGGACT*tta*AATCCAGCGaTCCGAGTTCAAATCTCGGTGGGACCT | 170 |
| 26 | GlnTAAchr6.trna63 | GGTCCCATGGTGTAATGGTtAGCACTCTGGACT*tta*AATCCAGCAaTCCGAGTTCGAATCTCGGTGGGACCT | 171 |
| 27 | GlnTAAchr6.trna175 | GGCCCCATGGTGTAATGGTtAGCACTCTGGACT*tta*AATCCAGCGaTCCGAGTTCAAATCTCGGTGGGACCT | 172 |
| 28 | GlnTAAchr6.trna82 | GGTCCCATGGTGTAATGGTtAGCACTCTGGGCT*tta*AATCCAGCAaTCCGAGTTCGAATCTTGGTGGGACCT | 173 |
| 29 | GlnTAAchr2.trna26 | GGCTGTGTACCTCAGTGGGcAAGGGTATGGACT*tta*AAGCCAGACTaTTTGGGTTCAAATCCCAGCTTGGCCT | 174 |
| 30 | GlnTAAchr4.trna4 | GACCATGTGGCCTAAGGGAaAAGACATCTCACT*tta*GGTCAGAAGAtTGAGGGTTCAAGTCCTTTCATGGTCA | 175 |
| 31 | GlnTAAchr8.trna10 | GGTACAGTGTTAAAGGGGagaAAAATTGCTGACT*tta*AATaCAGTAGaCCTAGGTTTGAATCCTGGCTTTACCA | 176 |
| 1 | GluTAAchr1.trna106 | TCCCTGGTGGTCTAGTGGTtAGGATTCGGCGCT*tta*ACCGCCGCGGCCCGGGTTCGATTCCCGGTCAGGGAA | 177 |
| 2 | GluTAAchr1.trna55 | TCCCTGGTGGTCTAGTGGTtAGGATTCGGCGCT*tta*ACCGCCGCGGCCCGGGTTCGATTCCCGGTCAGGAAA | 178 |
| 3 | GluTAAchr13.trna3 | CCCCTGGTGGTCTAGTGCTtAGGATTCGGTGCT*tta*ACCGCTGCTGCCTGCGTTCGATTCCCGGTCAGGGAA | 179 |
| 4 | GluTAAchr8.trna1 | TCCTTGATGTCTAGTGGTtAGGATTTGGTGCT*tta*ACTGCAGCAGCCTGGGTTCATTTCTCAGTCAGGGAA | 180 |
| 5 | GluTAAchr2.trna18 | TCCCATATGGTCTAGCGGTtAGGATTCCTGGTT*tta*ACCCAGGTGGCCCGGGTTCGACTCCCGGTATGGGAA | 181 |
| 6 | GluTAAchr1.trna92 | TCCGTGGTGGTCTAGTGGCtAGGATTCGGCGCT*tta*ACCGCCTGCAGCTCGAGTTCGATTCCTGGTCAGGGAA | 182 |
| 7 | GluTAAchr14.trna15 | CCCTGTGGTCTAGTGGCtAAGACTTTGTGCT*tta*ATTGCTGCAtCCTAGGTTCAATTCCCAGTCAGGGA | 183 |
| 8 | GluTAAchr13.trna2 | TCCCACATGGTCTAGCGGTtAGGATTCCTGGTT*tta*ACCCAGGCGGCCCGGGTTCGACTCCCGGTGTGGGAA | 184 |
| 9 | GluTAAchr1.trna5 | TCCCTGGTGGTCTAGTGGCtAGGATTCGGCGCT*tta*ACCGCCGCGGCCCGGGTTCGATTCCCGGCCAGGGAA | 185 |
| 10 | GluTAAchr1.trna123 | TCCCTGGTGGTCTAGTGGCtAGGATTCGGCGCT*tta*ACCGCCGCGGCCCGGGTTCGATTCCCGGTCAGGGAA | 186 |
| 11 | GluTAAchr1.trna45 | GCGTTGGTGGTGTAGTGGTgAGCACAGCTGCCT*tta*AGCAGTTAaCGCGGGTTCGATTCCCGGGTAACGAA | 187 |
| 12 | GluTAAchr1.trna99 | TCCTTGGTGGTCTAGTGGCtAGGATTCGGTGCT*tta*ACCTGTGCGGCCCGGGTTCAATTCCCGATGAAGGAA | 188 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|    | tRNAscan-SE ID | Sequence | SEQ ID NO |
|----|----|----|----|
| 13 | GluTAAchr1.trna95 | TGTCTGGTGGTCAAGTGGCtAGGATTTGGCGCT*tta*A CTGCCGCGGCCCGCGTTCGATTCCCGGTCAGGGAA | 189 |
| 14 | GluTAAchr1.trna86 | TCCCTGGTGGTCTAGTGGCtAGGATTCGGCGCT*tta*A CCGCCTGCAGCTCGAGTTCGATTCCTGGTCAGGGAA | 190 |
| 15 | GluTAAchr2.trna16 | GCAATGGTGGTTCAGTGGTAGAATTCTCGCCT*tta*AC ACAGGAGaCCCGGGTTCAATTCCTGACCCATGTA | 191 |
| 1 | GluTAGchr1.trna106 | TCCCTGGTGGTCTAGTGGTtAGGATTCGGCGCT*cta*A CCGCCGCGGCCCGGGTTCGATTCCCGGTCAGGGAA | 192 |
| 2 | GluTAGchr1.trna55 | TCCCTGGTGGTCTAGTGGTtAGGATTCGGCGCT*cta*A CCGCCGCGGCCCGGGTTCGATTCCCGGTCAGGAAA | 193 |
| 3 | GluTAGchr13.trna3 | CCCCTGGTGGTCTAGTGGCtAGGATTCGGTGCT*cta*A CCGCTGCTGCCTGCGTTCGATTCCCGGTCAGGGAA | 194 |
| 4 | GluTAGchr8.trna1 | TCCTTGATGTCTAGTGGTtAGGATTTGGTGCT*cta*AC TGCAGCAGCCTGGGTTCATTTCTCAGTCAGGGAA | 195 |
| 5 | GluTAGchr2.trna18 | TCCCATATGGTCTAGCGGTtAGGATTCCTGGTT*cta*A CCCAGGTGGCCCGGGTTCGACTCCCGGTATGGGAA | 196 |
| 6 | GluTAGchr1.trna92 | TCCGTGGTGGTCTAGTGGCtAGGATTCGGCGCT*cta*A CCGCCTGCAGCTCGAGTTCGATTCCTGGTCAGGGAA | 197 |
| 7 | GluTAGchr14.trna15 | CCCTGTGGTCTAGTGGCtAAGACTTTGTGCT*cta*ATT GCTGCAtCCTAGGTTCAATTCCCAGTCAGGGA | 198 |
| 8 | GluTAGchr13.trna2 | TCCCACATGGTCTAGCGGTtAGGATTCCTGGTT*cta*A CCCAGGCGGCCCGGGTTCGACTCCCGGTGTGGGAA | 199 |
| 9 | GluTAGchr1.trna5 | TCCCTGGTGGTCTAGTGGCtAGGATTCGGCGCT*cta*A CCGCCGCGGCCCGGGTTCGATTCCCGGCCAGGGAA | 200 |
| 10 | GluTAGchr1.trna123 | TCCCTGGTGGTCTAGTGGCtAGGATTCGGCGCT*cta*A CCGCCGCGGCCCGGGTTCGATTCCCGGTCAGGGAA | 201 |
| 11 | GluTAGchr1.trna45 | GCGTTGGTGGTGTAGTGGTgAGCACAGCTGCCT*cta*A AGCAGTTAaCGCGGGTTCGATTCCCGGGTAACGAA | 202 |
| 12 | GluTAGchr1.trna99 | TCCTTGGTGGTCTAGTGGCtAGGATTCGGTGCT*cta*A CCTGTGCGGCCCGGGTTCAATTCCCGATGAAGGAA | 203 |
| 13 | GluTAGchr1.trna95 | TGTCTGGTGGTCAAGTGGCtAGGATTTGGCGCT*cta*A CTGCCGCGGCCCGCGTTCGATTCCCGGTCAGGGAA | 204 |
| 14 | GluTAGchr1.trna86 | TCCCTGGTGGTCTAGTGGCtAGGATTCGGCGCT*cta*A CCGCCTGCAGCTCGAGTTCGATTCCTGGTCAGGGAA | 205 |
| 15 | GluTAGchr2.trna16 | GCAATGGTGGTTCAGTGGTAGAATTCTCGCCT*ctact* aACACAGGAGaCCCGGGTTCAATTCCTGACCCATGTA | 206 |
| 1 | TyrTAA chr2.trna13 | CCTTCAATAGTTCAGCTGGTAGAGCAGAGGACT*tta*G ctacttcctcagtaggagacGTCCTTAGGtTGCTGGT TCGATTCCAGCTTGAAGGA | 207 |
| 2 | TyrTAAchr2.trna13/ nointron | CCTTCAATAGTTCAGCTGGTAGAGCAGAGGACT*tta*G GTCCTTAGGtTGCTGGTTCGATTCCAGCTTGAAGGA | 208 |
| 3 | TyrTAAchr1.trna11 | GGTAAAATGGCTGAGTAAGCTTTAGACT*ttaa*AATCT AAAGAGAGATTGAGCTCTCTTTTTACCA | 209 |
| 4 | TyrTAAchr1.trna52 | GGTAAAATGACTGAGTAAGCATTAGACT*tta*AATCTA AAGaCAGAGGTCAAGACCTCTTTTTACCA | 210 |
| 5 | TyrTAAchr11.trna9 | GGTAAAATGGCTGAGTAAGCATTAGACT*tta*AATCTA AAGaCAGAGGTCAAGGCCTCTTTTTACCA | 211 |

TABLE 9-continued

Library of annotated sequences of tRNA screened for PTC suppression
activity. Italicized text for each sequence shows the site of anti-codon
editing. Bold text indicates tRNAs with suppression activity 5-fold above
background. Note that in tRNA the thymidines are replaced with uracils.

| | tRNAscan-SE ID | Sequence | SEQ ID NO |
|---|---|---|---|
| 6 | TyrTAAchr9.trna2 | GGTAAAATGGCTGAGTAAGCATTAGACT*tta*AATCTA AAG*a*CAGAGGTCAAGGCCTTTTTACCA | 212 |
| 7 | TyrTAAchr6.trna14 | CCTTCGATAGCTCAGTTGGTAGAGCGGAGGACT*tta*G ttggctgtgtccttagacATCCTTAGG*t*CGCTGGTTC GAATCCGGCTCGAAGGA | 213 |
| 8 | TyrTAAchr6.trna14/ nointron | CCTTCGATAGCTCAGTTGGTAGAGCGGAGGACT*tta*G ATCCTTAGG*t*CGCTGGTTCGAATCCGGCTCGAAGGA | 214 |
| 9 | TyrTAA chr7.trna12 | GGGGGTATAGCTCAGGGC*t*AGAGCT*t*TTTGACT*tta*G AGCAAGAGG*t*CCCTGGTTCAAATCCAGGTTCTCCCT | 215 |
| 10 | TyrTAAchr7.trna28 | TATAGCTCAGTGGTAGAGCATTTAACT*tta*GATCAAG AGG*t*CCCTGGATCAACTCTGGGTG | 216 |
| 11 | TyrTAAchr15.trna6 | GTCAGTGTTGCACAACGG*t*aAGTGAAGAGGCT*tta*A ACCCAGACTGGATGGGTTCAATTCCCATCTCTGCCG | 217 |
| 12 | TyrTAAchr2.trna2 | CCTTCGATAGCTCAGTTGGTAGAGCGGAGGACT*tta*G tggatagggcgtggcaATCCTTAGG*t*CGCTGGTTCGA TTCCGGCTCGAAGGA | 218 |
| 13 | TyrTAAchr2.trna2/ nointron | CCTTCGATAGCTCAGTTGGTAGAGCGGAGGACT*tta*G ATCCTTAGG*t*CGCTGGTTCGATTCCGGCTCGAAGGA | 219 |
| 14 | TyrTAAchr6.trna16 | CCTTCGATAGCTCAGTTGGTAGAGCGGAGGACT*tta*G gctcattaagcaaggtATCCTTAGG*t*CGCTGGTTCGA ATCCGGCTCGGAGGA | 220 |
| 15 | TyrTAAchr6.trna16/ nointron | CCTTCGATAGCTCAGTTGGTAGAGCGGAGGACT*tta*G ATCCTTAGG*t*CGCTGGTTCGAATCCGGCTCGGAGGA | 221 |
| 16 | TyrTAAchr14.trna19 | CCTTCGATAGCTCAGCTGGTAGAGCGGAGGACT*tta*G attgtatagacatttgcggacATCCTTAGG*t*CGCTGG TTCGATTCCAGCTCGAAGGA | 222 |
| 17 | TyrTAAchr14.trna19/ nointron | CCTTCGATAGCTCAGCTGGTAGAGCGGAGGACT*tta*G ATCCTTAGG*t*CGCTGGTTCGATTCCAGCTCGAAGGA | 223 |
| 18 | TyrTAAchr8.trna2 | CCTTCGATAGCTCAGCTGGTAGAGCGGAGGACT*tta*G ctacttcctcagcaggagacATCCTTAGG*t*CGCTGGT TCGATTCCGGCTCGAAGGA | 224 |
| 19 | TyrTAAchr8.trna2/ nointron | CCTTCGATAGCTCAGCTGGTAGAGCGGAGGACT*tta*G ATCCTTAGG*t*CGCTGGTTCGATTCCGGCTCGAAGGA | 225 |
| 20 | TyrTAAchr8.trna3 | CCTTCGATAGCTCAGCTGGTAGAGCGGAGGACT*tta*G gcgcgcgcccgtggccATCCTTAGG*t*CGCTGGTTCGA TTCCGGCTCGAAGGA | 226 |
| 21 | TyrTAAchr8.trna3/ nointron | CCTTCGATAGCTCAGCTGGTAGAGCGGAGGACT*tta*G ATCCTTAGG*t*CGCTGGTTCGATTCCGGCTCGAAGGA | 227 |
| 22 | TyrTAAchr14.trna20 | CCTTCGATAGCTCAGCTGGTAGAGCGGAGGACT*ttaa* Gcctgtagaaacatttgtggac ATCCTTAGG*t*CGCTG GTTCGATTCCGGCTCGAAGGA | 228 |
| 23 | TyrTAAchr14.trna20/ nointron | CCTTCGATAGCTCAGCTGGTAGAGCGGAGGACT*tta*G ATCCTTAGG*t*CGCTGGTTCGATTCCGGCTCGAAGGA | 229 |
| 24 | TyrTAAchr14.trna17 | CCTTCGATAGCTCAGCTGGTAGAGCGGAGGACT*tta*G attgtacagacatttgcggacATCCTTAGG*t*CGCTGG TTCGATTCCGGCTCGAAGGA | 230 |
| 25 | TyrTAAchr14.trna17/ nointron | CCTTCGATAGCTCAGCTGGTAGAGCGGAGGACT*tta*G ATCCTTAGG*t*CGCTGGTTCGATTCCGGCTCGAAGGA | 231 |
| 26 | TyrTAAchr14.trna5 | CCTTCGATAGCTCAGCTGGTAGAGCGGAGGACT*tta*G tacttaatgtgtggcATCCTTAGG*t*CGCTGGTTCGA TTCCGGCTCGAAGGA | 232 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|    | tRNAscan-SE ID | Sequence | SEQ ID NO |
|---|---|---|---|
| 27 | TyrTAAchr14.trna5/ nointron | CCTTCGATAGCTCAGCTGGTAGAGCGGAGGACT*tta*G ATCCTTAGGtCGCTGGTTCGATTCCGGCTCGAAGGA | 233 |
| 28 | TyrTAAchr6.trna17 | CCTTCGATAGCTCAGCTGGTAGAGCGGAGGACT*tta*G gggtttgaatgtggtcATCCTTAGGtCGCTGGTTCGA ATCCGGCTCGGAGGA | 234 |
| 29 | TyrTAAchr6.trna17/ nointron | CCTTCGATAGCTCAGCTGGTAGAGCGGAGGACT*tta*G ATCCTTAGGtCGCTGGTTCGAATCCGGCTCGGAGGA | 235 |
| 30 | TyrTAAchr14.trna18 | CCTTCGATAGCTCAGCTGGTAGAGCGGAGGACT*tta*G actgcggaaacgtttgtggacATCCTTAGGtCGCTGG TTCAATTCCGGCTCGAAGGA | 236 |
| 31 | TyrTAAchr14.trna18/ nointron | CCTTCGATAGCTCAGCTGGTAGAGCGGAGGACT*tta*G ATCCTTAGGtCGCTGGTTCAATTCCGGCTCGAAGGA | 237 |
| 32 | TyrTAAchr6.trna15 | CTTTCGATAGCTCAGTTGGTAGAGCGGAGGACT*tta*G gttcattaaactaaggcATCCTTAGGtCGCTGGTTCG AATCCGGCTCGAAGGA | 238 |
| 33 | TyrTAAchr6.trna15/ nointron | CTTTCGATAGCTCAGTTGGTAGAGCGGAGGACT*tta*G ATCCTTAGGtCGCTGGTTCGAATCCGGCTCGAAGGA | 239 |
| 34 | TyrTAAchr8.trna11 | TCTTCAATAGCTCAGCTGGTAGAGCGGAGGACT*ttaa* GgtgcacgcccgtggccATTCTTAGGTGCTGGTTTGA TTCCGACTTGGAGAG | 240 |
| 35 | TyrTAAchr8.trna11/ nointron | TCTTCAATAGCTCAGCTGGTAGAGCGGAGGACT*tta*G ATTCTTAGGTGCTGGTTTGATTCCGACTTGGAGAG | 241 |
| 36 | TyrTAAchr1.trna127 | GGTAAAATGGCTGAGTGAAGCATTGGACT*tta*AATCT AAAGaCAGGGGTTAAGCCTCTTTTTACCA | 242 |
| 37 | TyrTAAchr10.trna3 | GGTAAAATGGCTGAGCAAGCATTGGACT*tta*AATCTA AAGaCAGATGTTGAGCCATCTTTTTAGCA | 243 |
| 38 | TyrTAAchr14.trna8 | GGTAAAATGGCTGAGTGAAGCATTGGACT*tta*AATCT AAAGaCAGGGGCTAAGCCTCTTTTTACCA | 244 |
| 39 | TyrTAAchr2.trna12 | GGTAAAATGGCTGAGCAAGCATTAGACT*tta*AATCTA AAGaCAGAGGTTAAGGCCTCTTTTTACCA | 245 |
| 40 | TyrTAAchr7.trna1 | GGTAAAATGGCTGAGTAAGCATTAGACT*tta*AATCTA AAGaCAGAGGTCAAGGCCTCTTTTTTCCT | 246 |
| 41 | TyrTAAchr7.trna2 | GGTAAAATGGCTGAGCAAGCATTAGACT*tta*AATCTG AAAaCAGAGGTCAAAGgTCTCTTTTTACCA | 247 |
| 42 | TyrTAAchr7.trna6 | GGTAAAATGGCTGAGTAAGCATTAGACT*tta*AATCTA AAGaCAGAGGTCAAGGCCTCTTTTTACCA | 248 |
| 43 | TyrTAAchr8.trna7 | GGTAAAATGACTGAATAAGCCTTAGACT*tta*AATCTG AAGaCAGAGGTCAAGGCCTCTTTTTACCA | 249 |
| 44 | TyrTAAchr9.trna10 | GGTAAAATGGCTGAGTAAGCATTGGACT*tta*AATCTA AAGaCAGAGGTCAAGACCTCTTTTTACCA | 250 |
| 45 | TyrTAAchr9.trna4 | GGTAAAATGGCTGAGTAAAGCATTAGACT*tta*AATCT AAGGaCAGAGGCTAAACCTCTTTTTACCA | 251 |
| 1 | TyrTAGchr2.trna13 | CCTTCAATAGTTCAGCTGGTAGAGCAGAGGACT*cta*G ctacttcctcagtaggagacGTCCTTAGGtTGCTGGT TCGATTCCAGCTTGAAGGA | 252 |
| 2 | TyrTAGchr2.trna13/ nointron | CCTTCAATAGTTCAGCTGGTAGAGCAGAGGACT*cta*G GTCCTTAGGtTGCTGGTTCGATTCCAGCTTGAAGGA | 253 |
| 3 | TyrTAGchr1.trna11 | GGTAAAATGGCTGAGTAAGCTTTAGACT*ctaa*AATCT AAAGAGAGATTGAGCTCTCTTTTTACCA | 254 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 4 | TyrTAGchr1.trna52 | GGTAAAATGACTGAGTAAGCATTAGACT*cta*AATCTA AAGaCAGAGGTCAAGACCTCTTTTTACCA | 255 |
| 5 | TyrTAGchr11.trna9 | GGTAAAATGGCTGAGTAAGCATTAGACT*cta*AATCTA AAGaCAGAGGTCAAGGCCTCTTTTTACCA | 256 |
| 6 | TyrTAGchr9.trna2 | GGTAAAATGGCTGAGTAAGCATTAGACT*cta*AATCTA AAGaCAGAGGTCAAGGCCTTTTTACCA | 257 |
| 7 | TyrTAGchr6.trna14 | CCTTCGATAGCTCAGTTGGTAGAGCGGAGGACT*cta*G ttggctgtgtccttagacATCCTTAGGtCGCTGGTTC GAATCCGGCTCGAAGGA | 258 |
| 8 | TyrTAGchr6.trna14/ nointron | CCTTCGATAGCTCAGTTGGTAGAGCGGAGGACT*cta*G ATCCTTAGGtCGCTGGTTCGAATCCGGCTCGAAGGA | 259 |
| 9 | TyrTAGchr7.trna12 | GGGGGTATAGCTCAGGGCtAGAGCTtTTTGACT*ctaa* GAGCAAGAGGtCCCTGGTTCAAATCCAGGTTCTCCCT | 260 |
| 10 | TyrTAGchr7.trna28 | TATAGCTCAGTGGTAGAGCATTTAACT*cta*GATCAAG AGGtCCCTGGATCAACTCTGGGTG | 261 |
| 11 | TyrTAGchr15.trna6 | GTCAGTGTTGCACAACGGT*taA*GTGAAGAGGCT*cta*A ACCCAGACTGGATGGGTTCAATTCCCATCTCTGCCG | 262 |
| 12 | TyrTAGchr2.trna2 | CCTTCGATAGCTCAGTTGGTAGAGCGGAGGACT*cta*G tggatagggcgtggcaATCCTTAGGtCGCTGGTTCGA TTCCGGCTCGAAGGA | 263 |
| 13 | TyrTAGchr2.trna2/ nointron | CCTTCGATAGCTCAGTTGGTAGAGCGGAGGACT*cta*G ATCCTTAGGtCGCTGGTTCGATTCCGGCTCGAAGGA | 264 |
| 14 | TyrTAGchr6.trna16 | CCTTCGATAGCTCAGTTGGTAGAGCGGAGGACT*cta*G gctcattaagcaaggtATCCTTAGGtCGCTGGTTCGA ATCCGGCTCGGAGGA | 265 |
| 15 | TyrTAGchr6.trna16/ nointron | CCTTCGATAGCTCAGTTGGTAGAGCGGAGGACT*cta*G ATCCTTAGGtCGCTGGTTCGAATCCGGCTCGGAGGA | 266 |
| 16 | TyrTAGchr14.trna19 | CCTTCGATAGCTCAGCTGGTAGAGCGGAGGACT*cta*G attgtatagacatttgcggacATCCTTAGGtCGCTGG TTCGATTCCAGCTCGAAGGA | 267 |
| 17 | TyrTAGchr14.trna19/ nointron | CCTTCGATAGCTCAGCTGGTAGAGCGGAGGACT*cta*G ATCCTTAGGtCGCTGGTTCGATTCCAGCTCGAAGGA | 268 |
| 18 | TyrTAGchr8.trna2 | CCTTCGATAGCTCAGCTGGTAGAGCGGAGGACT*cta*G ctacttcctcagcaggagacATCCTTAGGtCGCTGGT TCGATTCCGGCTCGAAGGA | 269 |
| 19 | TyrTAGchr8.trna2/ nointron | CCTTCGATAGCTCAGCTGGTAGAGCGGAGGACT*cta*G ATCCTTAGGtCGCTGGTTCGATTCCGGCTCGAAGGA | 270 |
| 20 | TyrTAGchr8.trna3 | CCTTCGATAGCTCAGCTGGTAGAGCGGAGGACT*cta*G gcgcgcgcccgtggccATCCTTAGGtCGCTGGTTCGA TTCCGGCTCGAAGGA | 271 |
| 21 | TyrTAGchr8.trna3/ nointron | CCTTCGATAGCTCAGCTGGTAGAGCGGAGGACT*cta*G ATCCTTAGGtCGCTGGTTCGATTCCGGCTCGAAGGA | 272 |
| 22 | TyrTAGchr14.trna20 | CCTTCGATAGCTCAGCTGGTAGAGCGGAGGACT*cta*G cctgtagaaacatttgtggacATCCTTAGGtCGCTGG TTCGATTCCGGCTCGAAGGA | 273 |
| 23 | TyrTAGchr14.trna20/ nointron | CCTTCGATAGCTCAGCTGGTAGAGCGGAGGACT*cta*G ATCCTTAGGtCGCTGGTTCGATTCCGGCTCGAAGGA | 274 |
| 24 | TyrTAGchr14.trna17 | CCTTCGATAGCTCAGCTGGTAGAGCGGAGGACT*cta*G attgtacagacatttgcggacATCCTTAGGtCGCTGG TTCGATTCCGGCTCGAAGGA | 275 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 25 | TyrTAGchr14.trna17/ nointron | CCTTCGATAGCTCAGCTGGTAGAGCGGAGGACT*cta*G ATCCTTAGGtCGCTGGTTCGATTCCGGCTCGAAGGA | 276 |
| 26 | TyrTAGchr14.trna5 | CCTTCGATAGCTCAGCTGGTAGAGCGGAGGACT*cta*G tacttaatgtgtggtcATCCTTAGGtCGCTGGTTCGA TTCCGGCTCGAAGGA | 277 |
| 27 | TyrTAGchr14.trna5/ nointron | CCTTCGATAGCTCAGCTGGTAGAGCGGAGGACT*cta*G ATCCTTAGGtCGCTGGTTCGATTCCGGCTCGAAGGA | 278 |
| 28 | TyrTAGchr6.trna17 | CCTTCGATAGCTCAGCTGGTAGAGCGGAGGACT*cta*G gggtttgaatgtggtcATCCTTAGGtCGCTGGTTCGA ATCCGGCTCGGAGGA | 279 |
| 29 | TyrTAGchr6.trna17/ nointron | CCTTCGATAGCTCAGCTGGTAGAGCGGAGGACT*cta*G ATCCTTAGGtCGCTGGTTCGAATCCGGCTCGGAGGA | 280 |
| 30 | TyrTAGchr14.trna18 | CCTTCGATAGCTCAGCTGGTAGAGCGGAGGACT*cta*G actgcggaaacgtttgtggacATCCTTAGGtCGCTGG TTCAATTCCGGCTCGAAGGA | 281 |
| 31 | TyrTAGchr14.trna18/ nointron | CCTTCGATAGCTCAGCTGGTAGAGCGGAGGACT*cta*G ATCCTTAGGtCGCTGGTTCAATTCCGGCTCGAAGGA | 282 |
| 32 | TyrTAGchr6.trna15 | CTTTCGATAGCTCAGTTGGTAGAGCGGAGGACT*cta*G gttcattaaactaaggcATCCTTAGGtCGCTGGTTCG AATCCGGCTCGAAGGA | 283 |
| 33 | TyrTAGchr6.trna15/ nointron | CTTTCGATAGCTCAGTTGGTAGAGCGGAGGACT*cta*G ATCCTTAGGtCGCTGGTTCGAATCCGGCTCGAAGGA | 284 |
| 34 | TyrTAGchr8.trna11 | TCTTCAATAGCTCAGCTGGTAGAGCGGAGGACT*cta*G gtgcacgcccgtggccATTCTTAGGTGCTGGTTTGAT TCCGACTTGGAGAG | 285 |
| 35 | TyrTAGchr8.trna11/ nointron | TCTTCAATAGCTCAGCTGGTAGAGCGGAGGACT*cta*G ATTCTTAGGTGCTGGTTTGATTCCGACTTGGAGAG | 286 |
| 36 | TyrTAGchr1.trna127 | GGTAAAATGGCTGAGTGAAGCATTGGACT*cta*AATCT AAAGaCAGGGGTTAAGCCTCTTTTTACCA | 287 |
| 37 | TyrTAGchr10.trna3 | GGTAAAATGGCTGAGCAAGCATTGGACT*cta*AATCTA AAGaCAGATGTTGAGCCATCTTTTTAGCA | 288 |
| 38 | TyrTAGchr14.trna8 | GGTAAAATGGCTGAGTGAAGCATTGGACT*cta*AATCT AAAGaCAGGGGCTAAGCCTCTTTTTACCA | 289 |
| 39 | TyrTAGchr2.trna12 | GGTAAAATGGCTGAGCAAGCATTAGACT*cta*AATCTA AAGaCAGAGGTTAAGGCCTCTTTTTACCA | 290 |
| 40 | TyrTAGchr7.trna1 | GGTAAAATGGCTGAGTAAGCATTAGACT*cta*AATCTA AAGaCAGAGGTCAAGGCCTCTTTTTTCCT | 291 |
| 41 | TyrTAGchr7.trna2 | GGTAAAATGGCTGAGCAAGCATTAGACT*cta*AATCTG AAAaCAGAGGTCAAGgTCTCTTTTTACCA | 292 |
| 42 | TyrTAGchr7.trna6 | GGTAAAATGGCTGAGTAAGCATTAGACT*cta*AATCTA AAGaCAGAGGTCAAGGCCTCTTTTTACCA | 293 |
| 43 | TyrTAGchr8.trna7 | GGTAAAATGACTGAATAAGCCTTAGACT*cta*AATCTG AAGaCAGAGGTCAAGGCCTCTTTTTACCA | 294 |
| 44 | TyrTAGchr9.trna10 | GGTAAAATGGCTGAGTAAGCATTGGACT*cta*AATCTA AAGaCAGAGGTCAAGACCTCTTTTTACCA | 295 |
| 45 | TyrTAGchr9.trna4 | GGTAAAATGGCTGAGTAAAGCATTAGACT*cta*AATCT AAGGaCAGAGGCTAAACCTCTTTTTACCA | 296 |
| 1 | LeuTAAchr4.trna2 | GTTAAGATGGCAGAGCCtGGTaATTGCA*tta*AACTTA AAATTTTATAAtCAGAGGTTCAACTCCTCTTCTTAAC A | 297 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 2 | LeuTAAnmtchrX.trna2 | GTTAAGATGGCAGAGCCcGGCaATTGCA*tta*GACTTAAAACTTTATAAtCAGAGGTTCAACTCCTCTCATTAACA | 298 |
| 3 | LeuTAAchr6.trna77 | GGTAGCGTGGCCGAGCGGTct AAGGCGCTGGATT*tta*GCTCCAGTCTCTTCGGGGGCGTGGGTTCAAATCCCACCGCTGCCA | 299 |
| 4 | LeuTAAchr6.trna127 | GGTAGCGTGGCCGAGTGGTctAAGACGCTGGATT*tta*GCTCCAGTCTCTTCGGGGGCGTGGGTTTGAATCCCACCGCTGCCA | 300 |
| 5 | LeuTAAchr2.trna4 | GGGCCAGTGGCTCAATGGAtAATGCGTCTGACT*tta*AATCAGAAGAtTCCAGCCTTGACTCCTGGCTGGCTCA | 301 |
| 6 | LeuTAAchr20.trna1 | GGTAGGGTGGCCGAGCGGTctAAGGCACTGTATT*tta*ACTCCAGTCTCTTCAGAGGCATGGGTTTGAATCCCACTGCTGCCA | 302 |
| 7 | LeuTAAchr5.trna20 | GCCGAGCGGTctAAGGCTCCGGATT*tta*GCGCCGGTGTCTTCGGAGgCATGGGTTCGAATTCCAC | 303 |
| 8 | LeuTAAchr6.trna100 | GTCAGGATGGCCGAGTGGTctAAGGCGCCAGACT*tta*GctaagcttcctccgcggtggggaTTCTGGTCTCCAATGGAGGCGTGGGTTCGAATCCCACTTCTGACA | 304 |
| 9 | LeuTAAchr6.trna100/nointron | GTCAGGATGGCCGAGTGGTctAAGGCGCCAGACT*tta*GTTCTGGTCTCCAATGGAGGCGTGGGTTCGAATCCCACTTCTGACA | 305 |
| 10 | LeuTAAchr6.trna73 | GTCAGGATGGCCGAGTGGTctAAGGCGCCAGACT*tta*GcttggcttcctcgtgttgaggaTTCTGGTCTCCAATGGAGGCGTGGGTTCGAATCCCACTTCTGACA | 306 |
| 11 | LeuTAAchr6.trna73/nointron | GTCAGGATGGCCGAGTGGTctAAGGCGCCAGACT*tta*GTTCTGGTCTCCAATGGAGGCGTGGGTTCGAATCCCACTTCTGACA | 307 |
| 12 | LeuTAAchr6.trna141 | GTCAGGATGGCCGAGTGGTctAAGGCGCCAGACT*tta*GcttactgcttcctgtgttcgggtcTTCTGGTCTCCGTATGGAGGCGTGGGTTCGAATCCCACTTCTGACA | 308 |
| 13 | LeuTAAchr6.trna141/nointron | GTCAGGATGGCCGAGTGGTctAAGGCGCCAGACT*tta*GTTCTGGTCTCCGTATGGAGGCGTGGGTTCGAATCCCACTTCTGACA | 309 |
| 14 | LeuTAAchr6.trna142 | GTCAGGATGGCCGAGTGGTctAAGGCGCCAGACT*tta*GttgctacttcccaggtttggggcTTCTGGTCTCCGCATGGAGGCGTGGGTTCGAATCCCACTTCTGACA | 310 |
| 15 | LeuTAAchr6.trna142/nointron | GTCAGGATGGCCGAGTGGTctAAGGCGCCAGACT*tta*GTTCTGGTCTCCGCATGGAGGCGTGGGTTCGAATCCCACTTCTGACA | 311 |
| 16 | LeuTAAchr1.trna54 | GTCAGGATGGCCGAGTGGTctAAGGCGCCAGACT*tta*GgtaagcaccttgcctgcgggctTTCTGGTCTCCGGATGGAGGCGTGGGTTCGAATCCCACTTCTGACA | 312 |
| 17 | LeuTAAchr1.trna54/nointron | GTCAGGATGGCCGAGTGGTctAAGGCGCCAGACT*tta*GtTTCTGGTCTCCGGATGGAGGCGTGGGTTCGAATCCCACTTCTGACA | 313 |
| 18 | LeuTAAchr11.trna1 | GCCTCCTTAGTGCAGTAGGTAGCGCATCAGTCT*tta*AATCTGAATGgtCCTGAGTTCAAGCCTCAGAGGGGGCA | 314 |
| 19 | LeuTAAchr1.trna59 | GTCAGGATGGCCGAGCAGTcttAAGGCGCTGCGTT*tta*ATCGCACCCTCCGCTGGAGGCGTGGGTTCGAATCCCACTTTTGACA | 315 |
| 20 | LeuTAAchr9.trna3 | GGTTCCATGGTGTAATGGTgAGCACTCTGGACT*tta*AATCCAGAAGtAGTgCTGGAACAA | 316 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|    | tRNAscan-SE ID      | Sequence                                                                          | SEQ ID NO |
|----|---------------------|-----------------------------------------------------------------------------------|-----------|
| 21 | LeuTAAchr9.trna7    | GTCAGGGTGGCTGAGCAGTctGAGGGGCTGCGTTttaGTCGCAGTCTGCCCTGGAGGCGTGGGTTCGAATCCCACTCCTGAAA | 317       |
| 22 | LeuTAAchr6.trna81   | ACCAGGATGGCCGAGTGGTtAAGGCGTTGGACTttaGATCCAATGGACATATGTCCGCGTGGGTTCGAACCCCACTCCTGGTA | 318       |
| 23 | LeuTAAchr6.trna135  | ACCGGGATGGCCGAGTGGTtAAGGCGTTGGACTttaGATCCAATGGGCTGGTGCCCGCGTGGGTTCGAACCCCACTCTCGGTA | 319       |
| 24 | LeuTAAchr11.trna4   | ACCAGAATGGCCGAGTGGTtAAGGCGTTGGACTttaGATCCAATGGATTCATATCCGCGTGGGTTCGAACCCCACTTCTGGTA | 320       |
| 25 | LeuTAAchr6.trna156  | ACCGGGATGGCTGAGTGGTtAAGGCGTTGGACTttaGATCCAATGGACAGGTGTCCGCGTGGGTTCGAGCCCCACTCCCGGTA | 321       |
| 26 | LeuTAAchr6.trna79   | ACTCATTTGGCTGAGTGGTtAAGGCATTGGACTttaGATCCAATGGAGTAGTGGCTGTGTGGGTTTAAACCCCACTACTGGTA | 322       |
| 27 | LeuTAAchr1.trna9    | GAGAAAGTcATCGTAGTTACGAAGTTGGCTttaACCCAGTTTtGGGAGGTTCAATTCCTTCCTTTCTCT              | 323       |
| 28 | LeuTAAchr11.trna12  | ACCAGGATGGCCAAGTAGTTaAAGGCACTGGACTttaGAGCCAATGGACATATGTCTGTGTGGGTTTGAACCCCACTCCTGGTG | 324       |
| 29 | LeuTAAchr17.trna42  | GGTAGCGTGGCCGAGCGGTctAAGGCGCTGGATTttaGCTCCAGTCTCTTCGGAGGCGTGGGTTCGAATCCCACCGCTGCCA | 325       |
| 30 | LeuTAAchr14.trna2   | GGTAGTGTGGCCGAGCGGTctAAGGCGCTGGATTttaGCTCCAGTCTCTTCGGGGGCGTGGGTTCGAATCCCACCACTGCCA | 326       |
| 31 | LeuTAAchr16.trna27  | GGTAGCGTGGCCGAGTGGTctAAGGCGCTGGATTttaGCTCCAGTCATTTCGATGgCGTGGGTTCGAATCCCACCGCTGCCA | 327       |
| 32 | LeuTAAchr14.trna16  | GGTAGTGTGGTTGAATGGTctAAGGCACTGAATTttaGCTCCAGTCTCTTTGGGGaCGTGGGTTTAAATCCCACTGCTGCAA | 328       |
| 1  | LeuTAGchr4.trna2    | GTTAAGATGGCAGAGCCtGGTaATTGCActaAACTTAAAATTTTATAAtCAGAGGTTCAACTCCTCTTCTTAACA        | 329       |
| 2  | LeuTAGnmtchrX.trna2 | GTTAAGATGGCAGAGCCcGGCaATTGCActaGACTTAAAACTTTATAAtCAGAGGTTCAACTCCTCTCATTAACA        | 330       |
| 3  | LeuTAGchr6.trna77   | GGTAGCGTGGCCGAGCGGTctAAGGCGCTGGATTctaGCTCCAGTCTCTTCGGGGGCGTGGGTTCAAATCCCACCGCTGCCA | 331       |
| 4  | LeuTAGchr6.trna127  | GGTAGCGTGGCCGAGTGGTctAAGACGCTGGATTctaGCTCCAGTCTCTTCGGGGGCGTGGGTTTGAATCCCACCGCTGCCA | 332       |
| 5  | LeuTAGchr2.trna4    | GGGCCAGTGGCTCAATGGAtAATGCGTCTGACTctaAATCAGAAGAtTCCAGCCTTGACTCCTGGCTGGCTCA          | 333       |
| 6  | LeuTAGchr20.trna1   | GGTAGGGTGGCCGAGCGGTctAAGGCACTGTATTctaACTCCAGTCTCTTCAGAGGCATGGGTTTGAATCCCACTGCTGCCA | 334       |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 7 | LeuTAGchr5.trna20 | GCCGAGCGGTct AAGGCTCCGGATT*cta*GCGCCGGTG TCTTCGGAGgCATGGGTTCGAATTCCAC | 335 |
| 8 | LeuTAGchr6.trna100 | GTCAGGATGGCCGAGTGGTctAAGGCGCCAGACT*cta* Gctaagcttcctccgcggtgggga TTCTGGTCTCCAA TGGAGGCGTGGGTTCGAATCCCACTTCTGACA | 336 |
| 9 | LeuTAGchr6.trna100/ nointron | GTCAGGATGGCCGAGTGGTctAAGGCGCCAGACT*cta* GTTCTGGTCTCCAATGGAGGCGTGGGTTCGAATCCCA CTTCTGACA | 337 |
| 10 | LeuTAGchr6.trna73 | GTCAGGATGGCCGAGTGGTctAAGGCGCCAGACT*cta* Gcttggcttcctcgtgttgagga TTCTGGTCTCCAAT GGAGGCGTGGGTTCGAATCCCACTTCTGACA | 338 |
| 11 | LeuTAGchr6.trna73/ nointron | GTCAGGATGGCCGAGTGGTctAAGGCGCCAGACT*cta* GTTCTGGTCTCCAATGGAGGCGTGGGTTCGAATCCCA CTTCTGACA | 339 |
| 12 | LeuTAGchr6.trna141 | GTCAGGATGGCCGAGTGGTctAAGGCGCCAGACT*cta* Gcttactgcttcctgtgttcgggtc TTCTGGTCTCCG TATGGAGGCGTGGGTTCGAATCCCACTTCTGACA | 340 |
| 13 | LeuTAGchr6.trna141/ nointron | GTCAGGATGGCCGAGTGGTctAAGGCGCCAGACT*cta* GTTCTGGTCTCCGTATGGAGGCGTGGGTTCGAATCCC ACTTCTGACA | 341 |
| 14 | LeuTAGchr6.trna142 | GTCAGGATGGCCGAGTGGTctAAGGCGCCAGACT*cta* Gttgctacttcccaggtttggggc TTCTGGTCTCCGC ATGGAGGCGTGGGTTCGAATCCCACTTCTGACA | 342 |
| 15 | LeuTAGchr6.trna142/ nointron | GTCAGGATGGCCGAGTGGTctAAGGCGCCAGACT*cta* GTTCTGGTCTCCGCATGGAGGCGTGGGTTCGAATCCC ACTTCTGACA | 343 |
| 16 | LeuTAGchr1.trna54 | GTCAGGATGGCCGAGTGGTctAAGGCGCCAGACT*cta* Ggtaagcaccttgcctgcgggct TTCTGGTCTCCGGA TGGAGGCGTGGGTTCGAATCCCACTTCTGACA | 344 |
| 17 | LeuTAGchr1.trna54/ nointron | GTCAGGATGGCCGAGTGGTctAAGGCGCCAGACT*cta* GtTTCTGGTCTCCGGATGGAGGCGTGGGTTCGAATCC CACTTCTGACA | 345 |
| 18 | LeuTAGchr11.trna1 | GCCTCCTTAGTGCAGTAGGTAGCGCATCAGTCT*cta*A ATCTGAATGgtCCTGAGTTCAAGCCTCAGAGGGGGCA | 346 |
| 19 | LeuTAGchr1.trna59 | GTCAGGATGGCCGAGCAGTcttAAGGCGCTGCGTT*ct* *a*ATCGCACCCTCCGCTGGAGGCGTGGGTTCGAATCCC ACTTTTGACA | 347 |
| 20 | LeuTAGchr9.trna3 | GGTTCCATGGTGTAATGGTgAGCACTCTGGACT*cta*A ATCCAGAAGtAGTgCTGGAACAA | 348 |
| 21 | LeuTAGchr9.trna7 | GTCAGGGTGGCTGAGCAGTctGAGGGGCTGCGTT*cta* GTCGCAGTCTGCCCTGGAGGCGTGGGTTCGAATCCCA CTCCTGAAA | 349 |
| 22 | LeuTAGchr6.trna81 | ACCAGGATGGCCGAGTGGTtAAGGCGTTGGACT*cta*G ATCCAATGGACATATGTCCGCGTGGGTTCGAACCCCA CTCCTGGTA | 350 |
| 23 | LeuTAGchr6.trna135 | ACCGGGATGGCCGAGTGGTtAAGGCGTTGGACT*cta*G ATCCAATGGGCTGGTGCCCGCGTGGGTTCGAACCCCA CTCTCGGTA | 351 |
| 24 | LeuTAGchr11.trna4 | ACCAGAATGGCCGAGTGGTtAAGGCGTTGGACT*cta*G ATCCAATGGATTCATATCCGCGTGGGTTCGAACCCCA CTTCTGGTA | 352 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 25 | LeuTAGchr6.trna156 | ACCGGGATGGCTGAGTGGTtAAGGCGTTGGACT*ctaG*ATCCAATGGACAGGTGTCCGCGTGGGTTCGAGCCCCACTCCCGGTA | 353 |
| 26 | LeuTAGchr6.trna79 | ACTCATTTGGCTGAGTGGTtAAGGCATTGGACT*ctaa*GATCCAATGGAGTAGTGGCTGTGTGGGTTTAAACCCCACTACTGGTA | 354 |
| 27 | LeuTAGchr1.trna9 | GAGAAAGTcATCGTAGTTACGAAGTTGGCT*cta*ACCCAGTTTtGGGAGGTTCAATTCCTTCCTTTCTCT | 355 |
| 28 | LeuTAGchr11.trna12 | ACCAGGATGGCCAAGTAGTTaAAGGCACTGGACT*cta*GAGCCAATGGACATATGTCTGTGTGGGTTTGAACCCCACTCCTGGTG | 356 |
| 29 | LeuTAGchr17.trna42 | GGTAGCGTGGCCGAGCGGTctAAGGCGCTGGATT*cta*GCTCCAGTCTCTTCGGAGGCGTGGGTTCGAATCCCACCGCTGCCA | 357 |
| 30 | LeuTAGchr14.trna2 | GGTAGTGTGGCCGAGCGGTctAAGGCGCTGGATT*cta*GCTCCAGTCTCTTCGGGGGCGTGGGTTCGAATCCCACCACTGCCA | 358 |
| 31 | LeuTAGchr16.trna27 | GGTAGCGTGGCCGAGTGGTctAAGGCGCTGGATT*cta*GCTCCAGTCATTTCGATGgCGTGGGTTCGAATCCCACCGCTGCCA | 359 |
| 32 | LeuTAGchr14.trna16 | GGTAGTGTGGTTGAATGGTctAAGGCACTGAATT*cta*GCTCCAGTCTCTTTGGGGaCGTGGGTTTAAATCCCACTGCTGCAA | 360 |
| 1 | LeuTGAchr4.trna2 | GTTAAGATGGCAGAGCCtGGTaATTGCA*tca*AACTTAAAATTTTATAAtCAGAGGTTCAACTCCTCTTCTTAACA | 523 |
| 2 | LeuTGAnmtchrX.trna2 | GTTAAGATGGCAGAGCCcGGCaATTGCA*tca*GACTTAAAACTTTATAAtCAGAGGTTCAACTCCTCTCATTAACA | 524 |
| 3 | LeuTGAchr6.trna77 | GGTAGCGTGGCCGAGCGGTctAAGGCGCTGGATT*tca*GCTCCAGTCTCTTCGGGGGCGTGGGTTCAAATCCCACCGCTGCCA | 525 |
| 4 | LeuTGAchr6.trna127 | GGTAGCGTGGCCGAGTGGTctAAGACGCTGGATT*tca*GCTCCAGTCTCTTCGGGGGCGTGGGTTTGAATCCCACCGCTGCCA | 526 |
| 5 | LeuTGAchr2.trna4 | GGGCCAGTGGCTCAATGGAtAATGCGTCTGACT*tca*AATCAGAAGAtTCCAGCCTTGACTCCTGGCTGGCTCA | 527 |
| 6 | LeuTGAchr20.trna1 | GGTAGGGTGGCCGAGCGGTctAAGGCACTGTATT*tca*ACTCCAGTCTCTTCAGAGGCATGGGTTTGAATCCCACTGCTGCCA | 528 |
| 7 | LeuTGAchr5.trna20 | GCCGAGCGGTctAAGGCTCCGGATT*tca*GCGCCGGTGTCTTCGGAGgCATGGGTTCGAATTCCAC | 529 |
| 8 | LeuTGAchr6.trna100 | GTCAGGATGGCCGAGTGGTctAAGGCGCCAGACT*tca*GctaagcttcctccgcggtggggaTTCTGGTCTCCAATGGAGGCGTGGGTTCGAATCCCACTTCTGACA | 530 |
| 9 | LeuTGAchr6.trna100/nointron | GTCAGGATGGCCGAGTGGTctAAGGCGCCAGACT*tca*GTTCTGGTCTCCAATGGAGGCGTGGGTTCGAATCCCACTTCTGACA | 532 |
| 10 | LeuTGAchr6.trna73 | GTCAGGATGGCCGAGTGGTctAAGGCGCCAGACT*tca*GcttggcttcctcgtgttgaggaTTCTGGTCTCCAATGGAGGCGTGGGTTCGAATCCCACTTCTGACA | 533 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 11 | LeuTGAchr6.trna73/ nointron | GTCAGGATGGCCGAGTGGTctAAGGCGCCAGACT*tca*GTTCTGGTCTCCAATGGAGGCGTGGGTTCGAATCCCACTTCTGACA | 534 |
| 12 | LeuTGAchr6.trna141 | GTCAGGATGGCCGAGTGGTctAAGGCGCCAGACT*tca*GcttactgcttcctgtgttcgggtcTTCTGGTCTCCGTATGGAGGCGTGGGTTCGAATCCCACTTCTGACA | 535 |
| 13 | LeuTGAchr6.trna141/ nointron | GTCAGGATGGCCGAGTGGTctAAGGCGCCAGACT*tca*GTTCTGGTCTCCGTATGGAGGCGTGGGTTCGAATCCCACTTCTGACA | 536 |
| 14 | LeuTGAchr6.trna142 | GTCAGGATGGCCGAGTGGTctAAGGCGCCAGACT*tca*GttgctacttcccaggtttggggcTTCTGGTCTCCGCATGGAGGCGTGGGTTCGAATCCCACTTCTGACA | 537 |
| 15 | LeuTGAchr6.trna142/ nointron | GTCAGGATGGCCGAGTGGTctAAGGCGCCAGACT*tca*GTTCTGGTCTCCGCATGGAGGCGTGGGTTCGAATCCCACTTCTGACA | 538 |
| 16 | LeuTGAchr1.trna54 | GTCAGGATGGCCGAGTGGTctAAGGCGCCAGACT*tca*GgtaagcaccttgcctgcgggctTTCTGGTCTCCGGATGGAGGCGTGGGTTCGAATCCCACTTCTGACA | 539 |
| 17 | LeuTGAchr1.trna54/ nointron | GTCAGGATGGCCGAGTGGTctAAGGCGCCAGACT*tca*GtTTCTGGTCTCCGGATGGAGGCGTGGGTTCGAATCCCACTTCTGACA | 540 |
| 18 | LeuTGAchr11.trna1 | GCCTCCTTAGTGCAGTAGGTAGCGCATCAGTCT*tca*AATCTGAATGgtCCTGAGTTCAAGCCTCAGAGGGGGCA | 541 |
| 19 | LeuTGAchr1.trna59 | GTCAGGATGGCCGAGCAGTCttAAGGCGCTGCGTT*tca*ATCGCACCCTCCGCTGGAGGCGTGGGTTCGAATCCCACTTTTGACA | 542 |
| 20 | LeuTGAchr9.trna3 | GGTTCCATGGTGTAATGGTgAGCACTCTGGACT*tca*AATCCAGAAGtAGTgCTGGAACAA | 543 |
| 21 | LeuTGAchr9.trna7 | GTCAGGGTGGCTGAGCAGTctGAGGGGCTGCGTT*tca*GTCGCAGTCTGCCCTGGAGGCGTGGGTTCGAATCCCACTCCTGAAA | 544 |
| 22 | LeuTGAchr6.trna81 | ACCAGGATGGCCGAGTGGTtAAGGCGTTGGACT*tca*GATCCAATGGACATATGTCCGCGTGGGTTCGAACCCCACTCCTGGTA | 545 |
| 23 | LeuTGAchr6.trna135 | ACCGGGATGGCCGAGTGGTtAAGGCGTTGGACT*tca*GATCCAATGGGCTGGTGCCCGCGTGGGTTCGAACCCCACTCTCGGTA | 546 |
| 24 | LeuTGAchr11.trna4 | ACCAGAATGGCCGAGTGGTtAAGGCGTTGGACT*tca*GATCCAATGGATTCATATCCGCGTGGGTTCGAACCCCACTTCTGGTA | 548 |
| 25 | LeuTGAchr6.trna156 | ACCGGGATGGCTGAGTGGTtAAGGCGTTGGACT*tca*GATCCAATGGACAGGTGTCCGCGTGGGTTCGAGCCCCACTCCCGGTA | 549 |
| 26 | LeuTGAchr6.trna79 | ACTCATTTGGCTGAGTGGTtAAGGCATTGGACT*tca*GATCCAATGGAGTAGTGGCTGTGTGGGTTTAAACCCCACTACTGGTA | 550 |
| 27 | LeuTGAchr1.trna9 | GAGAAAGTcATCGTAGTTACGAAGTTGGCTT*tca*ACCCAGTTTtGGGAGGTTCAATTCCTTCCTTTCTCT | 551 |
| 28 | LeuTGAchr11.trna12 | ACCAGGATGGCCAAGTAGTTaAAGGCACTGGACT*tca*GAGCCAATGGACATATGTCTGTGTGGGTTTGAACCCCACTCCTGGTG | 552 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 29 | LeuTGAchr17.trna42 | GGTAGCGTGGCCGAGCGGTctAAGGCGCTGGATT*tca*GCTCCAGTCTCTTCGGAGGCGTGGGTTCGAATCCCACCGCTGCCA | 553 |
| 30 | LeuTGAchr14.trna2 | GGTAGTGTGGCCGAGCGGTctAAGGCGCTGGATT*tca*GCTCCAGTCTCTTCGGGGGCGTGGGTTCGAATCCCACCACTGCCA | 554 |
| 31 | LeuTGAchr16.trna27 | GGTAGCGTGGCCGAGTGGTctAAGGCGCTGGATT*tca*GCTCCAGTCATTTCGATGgCGTGGGTTCGAATCCCACCGCTGCCA | 555 |
| 32 | LeuTGAchr14.trna16 | GGTAGTGTGGTTGAATGGTctAAGGCACTGAATT*tca*GCTCCAGTCTCTTTGGGGaCGTGGGTTTAAATCCCACTGCTGCAA | 556 |
| 1 | SerTAGnmtchr2.trna19 | GAGAAGGTcACAGAGGTtATGGGATTGGCT*cta*AACCAGTCTGtGGGGGGTTCGATTCCCTCCTTTTTCA | 361 |
| 2 | SerTAGnmtchr2.trna7 | GAGAAGGTcATAGAGGTtATGGGATTGGCT*cta*AACCAGTCTCTGGGGGGTTCGATTCCCTCCTTTTTCA | 362 |
| 3 | SerTAGnmtchr17.trna31 | GAAAAAGTCATAGGGGTTATGAGGCTGGCT*cta*AACCAGCCTtAGGAGGTTCAATTCCTTCCTTTTTTG | 363 |
| 4 | SerTAGchr6.trna41 | GGCCGGTTAGCTCAGTTGGTtAGAGCGTGCTGCT*cta*AATGCCAGGGtCGAGGTTTCGATCCCCGTACGGGCCT | 364 |
| 5 | SerTAGchr6.trna148 | GTAGTCGTGGCCGAGTGGTtAAGGCGATGGACT*cta*AATCCATTGGGGTTTCCCCGCGCAGGTTCGAATCCTGCCGACTACG | 365 |
| 6 | SerTAGchr6.trna50 | GTAGTCGTGGCCGAGTGGTtAAGGCGATGGACT*cta*AATCCATTGGGGTTTCCCCACGCAGGTTCGAATCCTGCCGACTACG | 366 |
| 7 | SerTAGchr6.trna146 | GTAGTCGTGGCCGAGTGGTtAAGGTGATGGACT*cta*aAACCCATTGGGGTCTCCCCGCGCAGGTTCGAATCCTGCCGACTACG | 367 |
| 8 | SerTAGchr7.trna15 | GGGTGTATGGCTCAGGGGTAGAGAATTTGACT*cta*GATCAAGAGGtCCCTGGTTCAAATCCAGGTGCCCCCT | 368 |
| 9 | SerTAGchr11.trna10 | AGTTGTAGCTGAGTGGTtAAGGCAACGAGCT*cta*AATTCGTTGGTTTCTCTCTgTGCAGGTTTGAATCCTGCTAATTA | 369 |
| 10 | SerTAGchr11.trna8 | CAAGAAATTCATAGAGGTTATGGGATTGGCT*cta*AACCAGTTTcAGGAGGTTCGATTCCTTCCTTTTTGG | 370 |
| 11 | SerTAGchr17.trna41 | GCTGTGATGGCCGAGTGGTtAAGGCGTTGGACT*cta*AATCCAATGGGGTCTCCCCGCGCAGGTTCGAATCCTGCTCACAGCG | 371 |
| 12 | SerTAGchr6.trna34 | GCTGTGATGGCCGAGTGGTtAAGGCGTTGGACT*cta*AATCCAATGGGGTCTCCCCGCGCAGGTTCAAATCCTGCTCACAGCG | 372 |
| 13 | SerTAGchr6.trna138 | GCTGTGATGGCCGAGTGGTtAAGGTGTTGGACT*cta*AATCCAATGGGGGTTCCCCGCGCAGGTTCAAATCCTGCTCACAGCG | 373 |
| 14 | SerTAGchr12.trna2 | GTCACGGTGGCCGAGTGGTtAAGGCGTTGGACT*cta*AATCCAATGGGGTTTCCCCGCACAGGTTCGAATCCTGTTCGTGACG | 374 |
| 15 | SerTAGchr6.trna30 | GACGAGGTGGCCGAGTGGTtAAGGCGATGGACT*cta*AATCCATTGTGCTCTGCACGCGTGGGTTCGAATCCCACCCTCGTCG | 375 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|  | tRNAscan-SE ID | Sequence | SEQ ID NO |
|---|---|---|---|
| 16 | SerTAGchr6.trna43 | GACGAGGTGGCCGAGTGGTtAAGGCGATGGACT*cta*A ATCCATTGTGCTCTGCACGCGTGGGTTCGAATCCCAC CTTCGTCG | 376 |
| 17 | SerTAGchr11.trna6 | GGCCGGTTAGCTCAGTTGGTtAGAGCGTGCT*cta*ACT AATGCCAGGGtCGAGGTTTCGATCCCCGTACGGGCCT | 377 |
| 18 | SerTAGchr6.trna61 | GACGAGGTGGCCGAGTGGTtAAGGCGATGGACT*cta*A ATCCATTGTGCTCTGCACACGTGGGTTCGAATCCCAT CCTCGTCG | 378 |
| 19 | SerTAGchr6.trna176 | GAGGCCTGGCCGAGTGGTtAAGGCGATGGACT*cta*AA TCCATTGTGCTCTGCACGCGTGGGTTCGAATCCCATC CTCG | 379 |
| 20 | SerTAGchr10.trna2 | GCAGCGATGGCCGAGTGGTtAAGGCGTTGGACT*cta* ATCCAATGGGGTCTCCCCGCGCAGGTTCGAACCCTGC TCGCTGCG | 380 |
| 21 | SerTAGchr6.trna51 | GTAGTCGTGGCCGAGTGGTtAAGGCGATGGACT*cta*A ATCCATTGGGGTTTCCCCGCGCAGGTTCGAATCCTGC CGACTACG | 381 |
| 22 | SerTAGchr6.trna173 | GTAGTCGTGGCCGAGTGGTtAAGGCGATGGACT*cta*A ATCCATTGGGGTCTCCCCGCGCAGGTTCGAATCCTGC CGACTACG | 382 |
| 23 | SerTAGchr6.trna149 | GTAGTCGTGGCCGAGTGGTtAAGGCGATGGACT*cta*A ATCCATTGGGGTTTCCCCGCGCAGGTTCGAATCCTGT CGGCTACG | 383 |
| 1 | SerTGAnmtchr2.trna19 | GAGAAGGTcACAGAGGTtATGGGATTGGCT*tca*AACC AGTCTGtGGGGGGTTCGATTCCCTCCTTTTTCA | 384 |
| 2 | SerTGAnmt-chr2.trna7 | GAGAAGGTcATAGAGGTtATGGGATTGGCT*tca*AACC AGTCTCTGGGGGGTTCGATTCCCTCCTTTTTCA | 385 |
| 3 | SerTGAnmtchr17.trna31 | GAAAAAGTCATAGGGGTTATGAGGCTGGCT*tca*AACC AGCCTtAGGAGGTTCAATTCCTTCCTTTTTTG | 386 |
| 4 | SerTGAchr6.trna41 | GGCCGGTTAGCTCAGTTGGTtAGAGCGTGCTGCT*tca* AATGCCAGGGtCGAGGTTTCGATCCCCGTACGGGCCT | 387 |
| 5 | SerTGAchr6.trna148 | GTAGTCGTGGCCGAGTGGTtAAGGCGATGGACT*tca*A ATCCATTGGGGTTTCCCCGCGCAGGTTCGAATCCTGC CGACTACG | 388 |
| 6 | SerTGAchr6.trna50 | GTAGTCGTGGCCGAGTGGTtAAGGCGATGGACT*tca*A ATCCATTGGGGTTTCCCACGCGCAGGTTCGAATCCTGC CGACTACG | 389 |
| 7 | SerTGAchr6.trna146 | GTAGTCGTGGCCGAGTGGTtAAGGTGATGGACT*tca*A ACCCATTGGGGTCTCCCCGCGCAGGTTCGAATCCTGC CGACTACG | 390 |
| 8 | SerTGAchr7.trna15 | GGGTGTATGGCTCAGGGGTAGAGAATTTGACT*tca*GA TCAAGAGGtCCCTGGTTCAAATCCAGGTGCCCCCT | 391 |
| 9 | SerTGAchr11.trna10 | AGTTGTAGCTGAGTGGTtAAGGCAACGAGCT*tca*AAT TCGTTGGTTTCTCTCTgTGCAGGTTTGAATCCTGCTA ATTA | 392 |
| 10 | SerTGAchr11.trna8 | CAAGAAATTCATAGAGGTTATGGGATTGGCT*tca*AAC CAGTTTcAGGAGGTTCGATTCCTTCCTTTTTGG | 393 |
| 11 | SerTGAchr17.trna41 | GCTGTGATGGCCGAGTGGTtAAGGCGTTGGACT*tca*A ATCCAATGGGGTCTCCCCGCGCAGGTTCGAATCCTGC TCACAGCG | 394 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|    | tRNAscan-SE ID | Sequence | SEQ ID NO |
|---|---|---|---|
| 12 | SerTGAchr6.trna34 | GCTGTGATGGCCGAGTGGTtAAGGCGTTGGACT*tca*A ATCCAATGGGGTCTCCCCGCGCAGGTTCAAATCCTGC TCACAGCG | 395 |
| 13 | SerTGAchr6.trna138 | GCTGTGATGGCCGAGTGGTtAAGGTGTTGGACT*tca*A ATCCAATGGGGGTTCCCCGCGCAGGTTCAAATCCTGC TCACAGCG | 396 |
| 14 | SerTGAchr12.trna2 | GTCACGGTGGCCGAGTGGTtAAGGCGTTGGACT*tca*A ATCCAATGGGGTTTCCCCGCACAGGTTCGAATCCTGT TCGTGACG | 397 |
| 15 | SerTGAchr6.trna30 | GACGAGGTGGCCGAGTGGTtAAGGCGATGGACT*tca*A ATCCATTGTGCTCTGCACGCGTGGGTTCGAATCCCAC CCTCGTCG | 398 |
| 16 | SerTGAchr6.trna43 | GACGAGGTGGCCGAGTGGTtAAGGCGATGGACT*tca*A ATCCATTGTGCTCTGCACGCGTGGGTTCGAATCCCAC CTTCGTCG | 399 |
| 17 | SerTGAchr11.trna6 | GGCCGGTTAGCTCAGTTGGTtAGAGCGTGCT*tca*ACT AATGCCAGGGtCGAGGTTTCGATCCCCGTACGGGCCT | 400 |
| 18 | SerTGAchr6.trna61 | GACGAGGTGGCCGAGTGGTtAAGGCGATGGACT*tca*A ATCCATTGTGCTCTGCACACGTGGGTTCGAATCCCAT CCTCGTCG | 401 |
| 19 | SerTGAchr6.trna176 | GAGGCCTGGCCGAGTGGTtAAGGCGATGGACT*tca*AA TCCATTGTGCTCTGCACGCGTGGGTTCGAATCCCATC CTCG | 402 |
| 20 | SerTGAchr10.trna2 | GCAGCGATGGCCGAGTGGTtAAGGCGTTGGACT*tca*A ATCCAATGGGGTCTCCCCGCGCAGGTTCGAACCCTGC TCGCTGCG | 403 |
| 21 | SerTGAchr6.trna51 | GTAGTCGTGGCCGAGTGGTtAAGGCGATGGACT*tca*A ATCCATTGGGGTTTCCCCGCGCAGGTTCGAATCCTGC CGACTACG | 404 |
| 22 | SerTGAchr6.trna173 | GTAGTCGTGGCCGAGTGGTtAAGGCGATGGACT*tca*A ATCCATTGGGGTCTCCCCGCGCAGGTTCGAATCCTGC CGACTACG | 405 |
| 23 | SerTGAchr6.trna149 | GTAGTCGTGGCCGAGTGGTtAAGGCGATGGACT*tca*A ATCCATTGGGGTTTCCCCGCGCAGGTTCGAATCCTGT CGGCTACG | 406 |
| 1 | SerTAAnmtchr2.trna19 | GAGAAGGTcACAGAGGTtATGGGATTGGCT*tta*AACC AGTCTGtGGGGGGTTCGATTCCCTCCTTTTTCA | 557 |
| 2 | SerTAAnmtchr2.trna7 | GAGAAGGTcATAGAGGTtATGGGATTGGCT*tta*AACC AGTCTCTGGGGGGTTCGATTCCCTCCTTTTTCA | 558 |
| 3 | SerTAAnmtchr17.trna31 | GAAAAAGTCATAGGGGTtATGAGGCTGGCT*tta*AACC AGCCTtAGGAGGTTCAATTCCTTCCTTTTTTG | 559 |
| 4 | SerTAAchr6.trna41 | GGCCGGTTAGCTCAGTTGGTtAGAGCGTGCTGCT*tta* AATGCCAGGGtCGAGGTTTCGATCCCCGTACGGGCCT | 560 |
| 5 | SerTAAchr6.trna148 | GTAGTCGTGGCCGAGTGGTtAAGGCGATGGACT*tta*A ATCCATTGGGGTTTCCCCGCGCAGGTTCGAATCCTGC CGACTACG | 561 |
| 6 | SerTAAchr6.trna50 | GTAGTCGTGGCCGAGTGGTtAAGGCGATGGACT*tta*A ATCCATTGGGGTTTCCCCACGCAGGTTCGAATCCTGC CGACTACG | 562 |
| 7 | SerTAAchr6.trna146 | GTAGTCGTGGCCGAGTGGTtAAGGTGATGGACT*tta*A ACCCATTGGGGTCTCCCCGCGCAGGTTCGAATCCTGC CGACTACG | 563 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|  | tRNAscan-SE ID | Sequence | SEQ ID NO |
|---|---|---|---|
| 8 | SerTAAchr7.trna15 | GGGTGTATGGCTCAGGGGTAGAGAATTTGACT*tta*GATCAAGAGG*t*CCCTGGTTCAAATCCAGGTGCCCCCT | 564 |
| 9 | SerTAAchr11.trna10 | AGTTGTAGCTGAGTGGT*t*AAGGCAACGAGCT*tta*AATTCGTTGGTTTCTCTC*t*G*t*GCAGGTTTGAATCCTGCTAATTA | 565 |
| 10 | SerTAAchr11.trna8 | CAAGAAATTCATAGAGGTTATGGGATTGGCT*tta*AACCAGTTT*c*AGGAGGTTCGATTCCTTCCTTTTTGG | 566 |
| 11 | SerTAAchr17.trna41 | GCTGTGATGGCCGAGTGGT*t*AAGGCGTTGGACT*tta*AATCCAATGGGGTCTCCCCGCGCAGGTTCGAATCCTGCTCACAGCG | 567 |
| 12 | SerTAAchr6.trna34 | GCTGTGATGGCCGAGTGGT*t*AAGGCGTTGGACT*tta*AATCCAATGGGGTCTCCCCGCGCAGGTTCAAATCCTGCTCACAGCG | 568 |
| 13 | SerTAAchr6.trna138 | GCTGTGATGGCCGAGTGGT*t*AAGGTGTTGGACT*tta*AATCCAATGGGGGTTCCCCGCGCAGGTTCAAATCCTGCTCACAGCG | 569 |
| 14 | SerTAAchr12.trna2 | GTCACGGTGGCCGAGTGGT*t*AAGGCGTTGGACT*tta*AATCCAATGGGGTTTCCCCGCACAGGTTCGAATCCTGTTCGTGACG | 570 |
| 15 | SerTAAchr6.trna30 | GACGAGGTGGCCGAGTGGT*t*AAGGCGATGGACT*tta*AATCCATTGTGCTCTGCACGCGTGGGTTCGAATCCCACCCTCGTCG | 571 |
| 16 | SerTAAchr6.trna43 | GACGAGGTGGCCGAGTGGT*t*AAGGCGATGGACT*tta*AATCCATTGTGCTCTGCACGCGTGGGTTCGAATCCCACCTTCGTCG | 572 |
| 17 | SerTAAchr11.trna6 | GGCCGGTTAGCTCAGTTGGT*t*AGAGCGTGCT*tta*ACTAATGCCAGGG*t*CGAGGTTTCGATCCCCGTACGGGCCT | 573 |
| 18 | SerTAAchr6.trna61 | GACGAGGTGGCCGAGTGGT*t*AAGGCGATGGACT*tta*AATCCATTGTGCTCTGCACACGTGGGTTCGAATCCCATCCTCGTCG | 574 |
| 19 | SerTAAchr6.trna176 | GAGGCCTGGCCGAGTGGT*t*AAGGCGATGGACT*tta*AATCCATTGTGCTCTGCACGCGTGGGTTCGAATCCCATCCTCG | 575 |
| 20 | SerTAAchr10.trna2 | GCAGCGATGGCCGAGTGGT*t*AAGGCGTTGGACT*tta*AATCCAATGGGGTCTCCCCGCGCAGGTTCGAACCCTGCTCGCTGCG | 576 |
| 21 | SerTAAchr6.trna51 | GTAGTCGTGGCCGAGTGGT*t*AAGGCGATGGACT*tta*AATCCATTGGGGTTTCCCCGCGCAGGTTCGAATCCTGCCGACTACG | 577 |
| 22 | SerTAAchr6.trna173 | GTAGTCGTGGCCGAGTGGT*t*AAGGCGATGGACT*tta*AATCCATTGGGGTCTCCCCGCGCAGGTTCGAATCCTGCCGACTACG | 578 |
| 23 | SerTAAchr6.trna149 | GTAGTCGTGGCCGAGTGGT*t*AAGGCGATGGACT*tta*AATCCATTGGGGTTTCCCCGCGCAGGTTCGAATCCTGTCGGCTACG | 579 |
| 1 | LysTAAchr19.trna6 | GCCCAGCTAGCTCAGTCGGTAGAGCATAAGACT*tta*AATCTCAGGG*t*TGTGGATTCGTGCCCCATGCTGGGTG | 407 |
| 2 | LysTAAchr19.trna7 | CTGCAGCTAGCTCAGTCGGTAGAGCATGAGACT*tta*AATCTCAGGG*t*CATGGGTTCGTGCCCCATGTTGGG | 408 |
| 3 | LysTAAchr1.trna8 | CCAGCATGTCTCAGTCGGTATAGTGTGAGACT*tta*AATCTCAGGG*t*CGTGGGTTCAAGCCCCACATTGGG | 409 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|  | tRNAscan-SE ID | Sequence | SEQ ID NO |
|---|---|---|---|
| 4 | LysTAAchr1.trna47 | GTCTAGCTAGATCAGTTGGTAGAGCATAAGACT*tta*A ATCTCAGGG*t*CATGGGTTTGAGCCCTACGTTGGGCG | 410 |
| 5 | LysTAAchr16.trna14 | GCCCAGCTAGCTCAGCCGGTAGAGCACAAGACT*tta*A ATCTCAGGG*t*CGTGGGTTTGAGCCCTGTGTTGAGCA | 411 |
| 6 | LysTAAchr11.trna2 | CCGAATAGCTTAGTTGAT*g*AAGCGTGAGACT*tta*AAT CTCAGGG*t*AGTGGGTTCAAGCCCCACATTGGA | 412 |
| 7 | LysTAAchr15.trna7 | GCCTGGCTACCTCAGTTGGTAGAGCATGGGACT*tta*A ATCCCAGAG*t*cAGTGGGTTCAAGCCTCACATTGAGTG | 413 |
| 8 | LysTAAchr16.trna31 | GCCCGGCTAGCTCAGTCGGTAGAGCATGAGACC*tta*A ATCTCAGGG*t*CGTGGGTTCGAGCCCACGTTGGGCG | 414 |
| 9 | LysTAAchr16.trna11 | GCCCGGCTAGCTCAGTCGGTAGAGCATGGGACT*tta*A ATCTCAGGG*t*CGTGGGTTCGAGCCCCACGTTGGGCG | 415 |
| 10 | LysTAAchr16.trna30 | GCCCGGCTAGCTCAGTCGATAGAGCATGAGACT*tta*A ATCTCAGGG*t*CGTGGGTTCGAGCCGCACGTTGGGCG | 416 |
| 11 | LysTAAchr1.trna117 | GCCCAGCTAGCTCAGTCGGTAGAGCATGAGACT*tta*A ATCTCAGGG*t*CATGGGTTTGAGCCCCACGTTTGGTG | 417 |
| 12 | LysTAAchr16.trna6 | GCCTGGCTAGCTCAGTCGGCAAAGCATGAGACT*tta*A ATCTCAGGG*t*CGTGGGCTCGAGCTCCATGTTGGGCG | 418 |
| 13 | LysTAAchr5.trna25 | GCCGACTACCTCAGTCGGT*g*GAGCATGGGACT*tta*C ATCCCAGGG*t*TGTGGGTTCGAGCCCCACATTGGGCA | 419 |
| 14 | LysTAAchr16.trna1 | CCCCGGCTGGCTCAGTCAGTAGATCATGAGACT*tta*A ATCTCAGGG*t*CGTGGGTTCACGCCCCACACTGGGCG | 420 |
| 15 | LysTAAchr7.trna30 | GCGCTAGTCAGTAGAGCATGAGACT*tta*AATCTCAGG G*t*CGTGGGTTCGAGCCCCACATCGGGCG | 421 |
| 16 | LysTAAchr16.trna23 | GCCTGGATAGCTCAGTTGGTAGAGCATCAGACT*tta*A ATCTGAGGG*t*CCAGGGTTCAAGTCCCTGTTCAGGCA | 422 |
| 17 | LysTAAchr19.trna10 | GCCAGGATAGTTCAGGTGGTAGAGCATCAGACT*tta*a AACCTGAGGG*t*TCAGGGTTCAAGTCTCTGTTTGGGCG | 423 |
| 18 | LysTAAchr12.trna1 | ACCCAGATAGCTCAGTCAGTAGAGCATCAGACT*tta*A ATCTGAGGG*t*CCAAGGTTCATGTCCCTTTTTGGGTG | 424 |
| 19 | LysTAAchr19.trna8 | ACCTGGGTAGCTTAGTTGGTAGAGCATTGGACT*tta*A ATTTGAGGG*c*CCAGGTTTCAAGTCCCTGTTTGGGTG | 425 |
| 20 | LysTAAchr6.trna119 | GCCTGGGTAGCTCAGTCGGTAGAGCTaTCAGACT*tta* AGCCTGAGGA*t*TCAGGGTTCAATCCCTTGCTGGGCG | 426 |
| 21 | LysTAAchr14.trna13 | GATAGCTCAGTTGATAGAGCATCAGACT*tta*AATCTG AGGG*t*CCAGGGTTCATGTCCCTGTT | 427 |
| 22 | LysTAAchr2.trna15 | GTTGGGGTAACTCAGTTGGTAGAGTAGCAGACT*tta*C ATCTGAGGG*t*CCAGGGTTTAAGTCCATGTCCAGGCA | 428 |
| 23 | LysTAAchr11.trna11 | GCCTGGATAGCTCAGTTGGTAGAGCATCAGACT*tta*A ATCTGAGGG*t*CCAGGGTTCAAGTCCCTGTTCAGGCG | 429 |
| 24 | LysTAAchr6.trna144 | GCCTGGATAGCTCAGTCGGTAGAGCATCAGACT*tta*A ATCTGAGGG*t*CCAGGGTTCAAGTCCCTGTTCAGGCG | 430 |
| 25 | LysTAAchr11.trna5 | GCCCGATAGCTCAGTCGGTAGAGCATCAGACT*tta*A ATCTGAGGG*t*CCGGGGTTCAAGTCCCTGTTCGGGCG | 431 |
| 26 | LysTAAchr6.trna150 | GCCTGGGTAGCTCAGTCGGTAGAGCATCAGACT*tta*A ATCTGAGGG*t*CCAGGGTTCAAGTCCCTGTCCAGGCG | 432 |
| 27 | LysTAAchr6.trna70 | GCCTGGATAGCTCAGTTGGTAGAACATCAGACT*tta*A ATCTGACGG*t*GCAGGGTTCAAGTCCCTGTTCAGGCG | 433 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 28 | LysTAAchr1.trna50 | GCCCGGAGAGCTCAGTGGGTAGAGCATCAGACT*tta*A ATCTGAGGGtCCAGGGTTCAAGTCCTCGTTCGGGCA | 434 |
| 29 | LysTAAchr6.trna53 | ACCTGGGTAGCTCAGTAGGTAGAACATCAGACT*tta*A ATCTGAGGGtCTAGGGTTCAAGTCCCTGTCCAGGCG | 435 |
| 30 | LysTAAchr3.trna2 | GCCTGGATAGCTCCTTCGGTAGAGCATCAT*cag*ACT*t ta*AATGTGAGGGtCCAGGGTTCAAGTTCCTGTTTGGG CG | 436 |
| 1 | LysTAGchr19.trna6 | GCCCAGCTAGCTCAGTCGGTAGAGCATAAGACT*cta*A ATCTCAGGGtTGTGGATTCGTGCCCCATGCTGGGTG | 437 |
| 2 | LysTAGchr19.trna7 | CTGCAGCTAGCTCAGTCGGTAGAGCATGAGACT*cta*A ATCTCAGGGtCATGGGTTCGTGCCCCATGTTGGG | 438 |
| 3 | LysTAGchr1.trna8 | CCAGCATGTCTCAGTCGGTATAGTGTGAGACT*cta*AA TCTCAGGGtCGTGGGTTCAAGCCCCACATTGGG | 439 |
| 4 | LysTAGchr1.trna47 | GTCTAGCTAGATCAGTTGGTAGAGCATAAGACT*cta*A ATCTCAGGGtCATGGGTTTGAGCCCTACGTTGGGCG | 440 |
| 5 | LysTAGchr16.trna14 | GCCCAGCTAGCTCAGCCGGTAGAGCACAAGACT*cta*A ATCTCAGGGtCGTGGGTTTGAGCCCTGTGTTGAGCA | 441 |
| 6 | LysTAGchr11.trna2 | CCGAATAGCTTAGTTGAT*g*AAGCGTGAGACT*cta*AAT CTCAGGGtAGTGGGTTCAAGCCCCACATTGGA | 442 |
| 7 | LysTAGchr15.trna7 | GCCTGGCTACCTCAGTTGGTAGAGCATGGGACT*cta*A ATCCCAGAGt*c*AGTGGGTTCAAGCCTCACATTGAGTG | 443 |
| 8 | LysTAGchr16.trna31 | GCCCGGCTAGCTCAGTCGGTAGAGCATGAGACC*cta*A ATCTCAGGGtCGTGGGTTCGAGCCCCACGTTGGGCG | 444 |
| 9 | LysTAGchr16.trna11 | GCCCGGCTAGCTCAGTCGGTAGAGCATGGGACT*cta*A ATCTCAGGGtCGTGGGTTCGAGCCCCACGTTGGGCG | 445 |
| 10 | LysTAGchr16.trna30 | GCCCGGCTAGCTCAGTCGATAGAGCATGAGACT*cta*A ATCTCAGGGtCGTGGGTTCGAGCCGCACGTTGGGCG | 446 |
| 11 | LysTAGchr1.trna117 | GCCCAGCTAGCTCAGTCGGTAGAGCATGAGACT*cta*A ATCTCAGGGtCATGGGTTTGAGCCCCACGTTTGGTG | 447 |
| 12 | LysTAGchr16.trna6 | GCCTGGCTAGCTCAGTCGGCAAAGCATGAGACT*cta*A ATCTCAGGGtCGTGGGCTCGAGCTCCATGTTGGGCG | 448 |
| 13 | LysTAGchr5.trna25 | GCCCGACTACCTCAGTCGGT*g*GAGCATGGGACT*cta*C ATCCCAGGGtTGTGGGTTCGAGCCCCACATTGGGCA | 449 |
| 14 | LysTAGchr16.trna1 | CCCCGGCTGGCTCAGTCAGTAGATCATGAGACT*cta*A ATCTCAGGGtCGTGGGTTCACGCCCCACACTGGGCG | 450 |
| 15 | LysTAGchr7.trna30 | GCGCTAGTCAGTAGAGCATGAGACT*cta*AATCTCAGG GtCGTGGGTTCGAGCCCCACATCGGGCG | 451 |
| 16 | LysTAGchr16.trna23 | GCCTGGATAGCTCAGTTGGTAGAGCATCAGACT*cta*A ATCTGAGGGtCCAGGGTTCAAGTCCCTGTTCAGGCA | 452 |
| 17 | LysTAGchr19.trna10 | GCCAGGATAGTTCAGGTGGTAGAGCATCAGACT*cta*A ACCTGAGGGtTCAGGGTTCAAGTCTCTGTTTGGGCG | 453 |
| 18 | LysTAGchr12.trna1 | ACCCAGATAGCTCAGTCAGTAGAGCATCAGACT*cta*A ATCTGAGGGtCCAAGGTTCATGTCCCTTTTTGGGTG | 454 |
| 19 | LysTAGchr19.trna8 | ACCTGGGTAGCTTAGTTGGTAGAGCATTGGACT*cta*A ATTTGAGGGcCCAGGGTTCAAGTCCCTGTTTGGGTG | 455 |
| 20 | LysTAGchr6.trna119 | GCCTGGGTAGCTCAGTCGGTAGAGCTaTCAGACT*cta a*AGCCTGAGGAtTCAGGGTTCAATCCCTTGCTGGGGC G | 456 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

|  | tRNAscan-SE ID | Sequence | SEQ ID NO |
|---|---|---|---|
| 21 | LysTAGchr14.trna13 | GATAGCTCAGTTGATAGAGCATCAGACT*cta*AATCTGAGGGtCCAGGGTTCATGTCCCTGTT | 457 |
| 22 | LysTAGchr2.trna15 | GTTGGGGTAACTCAGTTGGTAGAGTAGCAGACT*cta*CATCTGAGGGtCCAGGGTTTAAGTCCATGTCCAGGCA | 458 |
| 23 | LysTAGchr11.trna11 | GCCTGGATAGCTCAGTTGGTAGAGCATCAGACT*cta*AATCTGAGGGtCCAGGGTTCAAGTCCCTGTTCAGGCG | 459 |
| 24 | LysTAGchr6.trna144 | GCCTGGATAGCTCAGTCGGTAGAGCATCAGACT*cta*AATCTGAGGGtCCAGGGTTCAAGTCCCTGTTCAGGCG | 460 |
| 25 | LysTAGchr11.trna5 | GCCCGGATAGCTCAGTCGGTAGAGCATCAGACT*cta*AATCTGAGGGtCCGGGGTTCAAGTCCCTGTTCGGGCG | 461 |
| 26 | LysTAGchr6.trna150 | GCCTGGGTAGCTCAGTCGGTAGAGCATCAGACT*cta*AATCTGAGGGtCCAGGGTTCAAGTCCCTGTCCAGGCG | 462 |
| 27 | LysTAGchr6.trna70 | GCCTGGATAGCTCAGTTGGTAGAACATCAGACT*cta*AATCTGACGGtGCAGGGTTCAAGTCCCTGTTCAGGCG | 463 |
| 28 | LysTAGchr1.trna50 | GCCCGGAGAGCTCAGTGGGTAGAGCATCAGACT*cta*AATCTGAGGGtCCAGGGTTCAAGTCCTCGTTCGGGCA | 464 |
| 29 | LysTAGchr6.trna53 | ACCTGGGTAGCTCAGTAGGTAGAACATCAGACT*cta*AATCTGAGGGtCTAGGGTTCAAGTCCCTGTCCAGGCG | 465 |
| 30 | LysTAGchr3.trna2 | GCCTGGATAGCTCCTTCGGTAGAGCATCATcagACT*cta*AATGTGAGGGtCCAGGGTTCAAGTTCCTGTTTGGGCG | 466 |
| 1 | CysTGAUndchr17.trna20 | GGCAGAATGGTGCAGCGGTt*c*AGCACCCAGgCTCT*tc aGc*CAGCTGTTGCCTGGGCTCAAATCCCAGCTCTGCCA | 467 |
| 2 | CysTGAchr5.trna30 | GGCTGTATAGCTCAGTGGTAGAGCATTTGACT*tca*GaatcctatactcaggggaaggagaactgggggtttctcagtgggtcaaaggacttgtagtggtaaatcaaaagcaactctataagctatgtaacaaaCTTTAAAGTCATAtGTAGcTGGGTTCAAATCCTGTTTCTGCCA | 468 |
| 3 | CysTGAchr5.trna3/nointron | GGCTGTATAGCTCAGTGGTAGAGCATTTGACT*tca*GCTTTAAAGTCATAtGTAGcTGGGTTCAAATCCTGTTTCTGCCA | 469 |
| 4 | CysTGAchr7.trna8 | GGGGGCATAGCTCAGTGGTAGAGCATTTGACT*tca*GATCAAGAGGtCCCTGGTTCAAATCCAGGTGCCCCCT | 470 |
| 5 | CysTGAchr7.trna26 | GGGGGTATAGCTCAGGGGTAGAGCATTTGACT*tca*GATCAAGAGGtCCCTGGTTCAAATCCAGGTGCCCCCC | 471 |
| 6 | CysTGAchr7.trna24 | GGGGGTATAGCTTAGCGGTAGAGCATTTGACT*tca*GATCAAGAGGtCCCCGGTTCAAATCCGGGTGCCCCCT | 472 |
| 7 | CysTGAchr7.trna20 | GGGGGTATAGCTTAGGGGTAGAGCATTTGACT*tca*GATCAAAAGGtCCCTGGTTCAAATCCAGGTGCCCCTT | 473 |
| 8 | CysTGAchr7.trna29 | GGGGGTATAGCTCAGGGGTAGAGCATTTGACT*tca*GATCAAGAGGtCCCCAGTTCAAATCTGGGTGCCCCCT | 474 |
| 9 | CysTGAchr17.trna28 | GGGGGTATAGCTCAGGGGTAGAGCATTTGACT*tca*GATCAAGAAGtCCCCGGTTCAAATCCGGGTGCCCCCT | 475 |
| 10 | CysTGAchr7.trna13 | GGGGGTATAGCTCAGGGGTAGAGCATTTGACT*tca*GATCAAGAGGtCTCTGGTTCAAATCCAGGTGCCCCCT | 476 |
| 11 | CysTGAchr7.trna10 | GGGGGTATAGCTCAGGGGTAGAGCACTTGACT*tca*GATCAAGAAGtCCTTGGTTCAAATCCAGGTGCCCCCT | 477 |
| 12 | CysTGAchr7.trna19 | GGGGATATAGCTCAGGGGTAGAGCATTTGACT*tca*GATCAAGAGGtCCCCGGTTCAAATCCGGGTGCCCCCC | 478 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| | tRNAscan-SE ID | Sequence | SEQ ID NO |
|---|---|---|---|
| 13 | CysTGAchr7.trna27 | GGGGGTATAGTTCAGGGGTAGAGCATTTGACT*tca*GA TCAAGAGGtCCCTGGTTCAAATCCAGGTGCCCCCT | 479 |
| 14 | CysTGAchr7.trna21 | GGGGGTATAGCTCAGGGGTAGAGCATTTGACT*tca*AA TCAAGAGGtCCCTGATTCAAATCCAGGTGCCCCCT | 480 |
| 15 | CysTGAchr7.trna14 | GGGCGTATAGCTCAGGGGTAGAGCATTTGACT*tca*GA TCAAGAGGtCCCCAGTTCAAATCTGGGTGCCCCCT | 481 |
| 16 | CysTGAchr7.trna17 | GGGGGTATAGCTCACAGGTAGAGCATTTGACT*tca*GA TCAAGAGGtCCCCGGTTCAAATCTGGGTGCCCCCT | 482 |
| 17 | CysTGAchr7.trna11 | GGGCGTATAGCTCAGGGGTAGAGCATTTGACT*tca*GA TCAAGAGGtCCCCAGTTCAAATCTGGGTGCCCA | 483 |
| 18 | CysTGAchr7.trna22 | GGGGGTATAGCTCACAGGTAGAGCATTTGACT*tca*GA TCAAGAGGtCCCCGGTTCAAATCCGGTTACTCCCT | 484 |
| 19 | CysTGAchr17.trna29 | GGGGGTAGGGCTCAGGGAtAGAGCATTTGACT*tca*GA TCAAGAGGtCCCCGGTTCGAATCTAGGTGCCCCCT | 485 |
| 20 | CysTGAchr3.trna9 | GGTATATCTCAGGGGGcAGAGCATTTGACT*tca*GATC AAGAGGtCCCCGGTTGAAATCCGGGTGCT | 486 |
| 21 | CysTGAchr7.trna23 | GGGGGTATAGCTCAGGGGTAGAGCACTTGACT*tca*GA TCAAGAGGtCCCTGGTTCAAATCCAGGTGCCCCCT | 487 |
| 22 | CysTGAchr17.trna27 | GGGGGTATAGCTCAGTGGTAGAGCATTTGACT*tca*GA TCAAGAGGtCCCTGGTTCAAATCCGGGTGCCCCCT | 488 |
| 23 | CysTGAchr15.trna3 | GGGGGTATAGCTCAGTGGGTAGAGCATTTGACT*tca*G ATCAAGAGGtCCCCGGTTCAAATCCGGGTGCCCCCT | 489 |
| 24 | CysTGAchr3.trna6 | GGGGGTGTAGCTCAGTGGTAGAGCATTTGACT*tca*GA TCAAGAGGtCCCTGGTTCAAATCCAGGTGCCCCCT | 490 |
| 25 | CysTGAchr14.trna9 | GGGGGTATAGCTCAGGGGTAGAGCATTTGACT*tca*GA TCAAGAGGtCCCCGGTTCAAATCCGGGTGCCCCCT | 491 |
| 26 | CysTGAchr3.trna5 | GGGGGTATAGCTCAGGGGTAGAGCATTTGACT*tca*GA TCAAGAGGtCCCTGGTTCAAATCCAGGTGCCCCCT | 492 |
| | *Mus_musculus*chr11.trna817-Trp | GACCTCGTGGCGCAATGGTAGCGCGTCTGACT*tca*GA TCAGAAGGtTGCGTGTTCAAATCACGTCGGGGTCA | 493 |
| | *Mus_musculus*chr10.trna567 | GACCTCGTGGCACAATGGTAGCACGTCTGACT*tca*GA TCAGAAGGtTGCGTGTTCAAATCACGTCGGGGTCA | 494 |
| | *Saccharomyces_cerevisiae*chrVII.trna33 | GAAGCGGTGGCTCAATGGTAGAGCTTTCGACT*tca*At taaatcttggaaattccacggaataagattgcaATCG AAGGGtTGCAGGTTCAATTCCTGTCCGTTTCA | 495 |
| | *Saccharomyces_cerevisiae*chrVII.trna33 | GAAGCGGTGGCTCAATGGTAGAGCTTTCGACT*tca*AA TCGAAGGGtTGCAGGTTCAATTCCTGTCCGTTTCA | 496 |
| | *Pan_troglodytes*chr7.trna28 | GGCCTCATGGTGCAACAGTAGTGTGTCTGACT*tca*GA TCAGAAGGtTGTATGTTCAAATCACATAGGGGTCA | 497 |
| | *Oryctolagus_cuniculus*chrUn0422.trna1 | GACCTCGTGGTGAAATGGTAGCATGTTTGACT*tca*AA TCAGGAGGTTGTGTGTTCAAGTCACATCAGGGTCA | 498 |
| | *Oryctolagus_cuniculus_*chrUn0563.trna1 | GACCTTGTGGCGCAATGGTAGCATGTTTGACT*tca*AA TCAGGAGGTTGTGTGTTCAAGTCACATCAGGGTCA | 499 |
| | *Oryctolagus_cuniculus_*chrUn0062.trna12 | GACCTCGTGGCGCAACGGTAGCGCGTCTGACT*tca*GA TCAGAAGGCTGCGTGTTCGAATCACGCCGGGGTCA | 500 |

TABLE 9-continued

Library of annotated sequences of tRNA screened for PTC suppression activity. Italicized text for each sequence shows the site of anti-codon editing. Bold text indicates tRNAs with suppression activity 5-fold above background. Note that in tRNA the thymidines are replaced with uracils.

| tRNAscan-SE ID | Sequence | SEQ ID NO |
|---|---|---|
| *Rattus_norvegicus_*chr13.trna4571 | GACCTTGTGGCTCAATGGTAGCGCATCTGACT*tca*GATCAGGAGGTTGCACGTTCAAATCATGCCGGGGTCA | 501 |
| *Rattus_norvegicus_*chr17.trna3948 | GACCTTGTGGCGCAACGGTAGCGCGTCTGACT*tca*GATCAGAAGGTTGCGTGTTCAAATCACGTCGGGGTCA | 502 |
| *Xenopus_tropicalis_*tRNA-Trp-CCA-10-1 | GACCTCGTGGCGCAACGGTAGCGCGTCTGACT*tca*GATCAGAAGGtTGCGTATTCAAATCACGTCGGGGTCA | 503 |
| *Xenopus_tropicalis_*tRNA-Trp-CCA-11-1 | GACCTCGTGGCGCAACGGCAGCGCGTCTGACT*tca*CATTAGAAGGtTGCGTGTTCAAATCACGTCGGGGTCA | 504 |
| *Xenopus_tropicalis_*tRNA-Trp-CCA-12-1 | GACCTCATGGCGCAACGGTAGCGCGTCTGACT*tca*GATCAGAAGGtTGCGTGTTCAAATCACATCGGGGTCA | 505 |
| *Xenopus_tropicalis_*tRNA-Trp-CCA-13-1 | GACCTCGTGGTGCAACGGTAGCGCGTATGATT*tca*GATCAGAAGGtTGCGTGTTCAAATCACGTCGGGGTCA | 506 |
| *Xenopus_tropicalis_*tRNA-Trp-CCA-3-1 | GACCTCGTAGCGCAACGGTAGCGCGTCTGACT*tca*GATCAGAAGGtTGCGTGTTCAAATCACGTCGGGGTCA | 507 |
| *Xenopus_tropicalis_*tRNA-Trp-CCA-5-1 | AGGGGTATAGCTCAATTGGCAGAGCGTCGGTCT*tca*AAACCGAAGGtTGTAGGTTCGATTCCTACTGCCCCTGCCA | 508 |
| *Xenopus_tropicalis_*tRNA-Trp-CCA-6-1 | GACCTCATGGCGCAACGGTAGCGCGTCTGACT*tca*GATCAGAAGGtTGCGTGTTCAAATCACGTCGGGGTCA | 509 |
| *Xenopus_tropicalis_*tRNA-Trp-CCA-7-1 | GACCTCGTGGCGCAACGGTAGCGCGTCTAACT*tca*GATCAGAAGGtTGCGTGTTCAAATCACGTCGGGGTCA | 510 |
| *Xenopus_tropicalis_*tRNA-Trp-CCA-8-1 | ACGGGAGTAGCTCAGTTGGTAGAGCACCGGTCT*tca*AAACCGGGTGtCGGGAGTTCGAGCCTCTCCTCCCGTG | 511 |
| *Xenopus_tropicalis_*tRNA-Trp-CCA-9-1 | GACCTCGTGGCGCAACGGTAGCGCGTCTGACT*tca*GATCAGAAGGtTGCATGTTCAAATCACGTCGGGGTCA | 512 |
| *Drosophila_melanogaster_*tRNA-Trp-CCA-2-1 | GACTCCGTGGCGCAACGGTAGCGCGTCCGACT*tca*GATCGGAAGGtTGCGTGTTCAAATCACGTCGGGGTCA | 513 |
| *Drosophila_melanogaster_*tRNA-Trp-CCA-1-1 | GACTCCGTGGCGCAACGGTAGCGCGTCTGACT*tca*GATCAGAAGGtTGCGTGTTCAAATCACGTCGGGGTCA | 514 |
| TrpWT-chr17.trna39 | GGCCTCGTGGCGCAACGGTAGCGCGTCTGACT*cca*GATCAGAAGGtTGCGTGTTCAAATCACGTCGGGGTCA | 515 |
| HirshWT | GGCCTCGTGGCGCAACGGTAGCaCGTCTGACT*cca*GATCAGAAGGtTGCGTGTTCAAATCACGTCGGGGTCA | 516 |
| HirshACE-tRNA | CGGCCTCGTGGCGCAACGGTAGCaCGTCTGACT*tca*GATCAGAAGGtTGCGTGTTCAAATCACGTCGGGGTCA | 517 |
| G9CWT | GGCCTCGTcGCGCAACGGTAGCGCGTCTGACT*cca*GATCAGAAGGtTGCGTGTTCAAATCACGTCGGGGTCA | 518 |
| G9CACE-tRNA | GGCCTCGTcGCGCAACGGTAGCGCGTCTGACT*tca*GATCAGAAGGtTGCGTGTTCAAATCACGTCGGGGTCA | 519 |
| G9C + HirshWT | GGCCTCGTcGCGCAACGGTAGCaCGTCTGACT*cca*GATCAGAAGGtTGCGTGTTCAAATCACGTCGGGGTCA | 520 |
| G9C + HirshACE-tRNA | GGCCTCGTcGCGCAACGGTAGCaCGTCTGACT*tca*GATCAGAAGGtTGCGTGTTCAAATCACGTCGGGGTCA | 521 |

EXAMPLE 5

References

1. Maquat, L. E., Kinniburgh, A. J., Rachmilewitz, E. A. & Ross, J. Unstable beta-globin mRNA in mRNA-deficient beta o thalassemia. *Cell* 27, 543-553 (1981).

2. Popp, M. W. & Maquat, L. E. Organizing principles of mammalian nonsense-mediated mRNA decay. *Annu Rev Genet* 47, 139-165 (2013).

3. Chang, Y. F., Imam, J. S. & Wilkinson, M. F. The nonsense-mediated decay RNA surveillance pathway. *Annu Rev Biochem* 76, 51-74 (2007).

4. Cheng, S. H. et al. Defective intracellular transport and processing of CFTR is the molecular basis of most cystic fibrosis. *Cell* 63, 827-834 (1990).

5. Lefebvre, S. et al. Identification and characterization of a spinal muscular atrophy-determining gene. *Cell* 80, 155-165 (1995).

6. Das, A. K. et al. Molecular genetics of palmitoyl-protein thioesterase deficiency in the U.S. *J. Chin Invest* 102, 361-370 (1998).

7. Chang, J. C. & Kan, Y. W. beta 0 thalassemia, a nonsense mutation in man. *Proc Natl Acad Sci USA* 76, 2886-2889 (1979).

8. Kalatzis, V. et al. Identification of 14 novel CTNS mutations and characterization of seven splice site mutations associated with cystinosis. *Hum Mutat* 20, 439-446 (2002).

9. Pan, Y., Metzenberg, A., Das, S., Jing, B. & Gitschier, J. Mutations in the V2 vasopressin receptor gene are associated with X-linked nephrogenic diabetes insipidus. *Nat Genet* 2, 103-106 (1992).

10. Ballabio, A. & Gieselmann, V. Lysosomal disorders: from storage to cellular damage. *Biochim Biophys Acta* 1793, 684-696 (2009).

11. Reiners, J., Nagel-Wolfrum, K., Jurgens, K., Marker, T. & Wolfrum, U. Molecular basis of human Usher syndrome: deciphering the meshes of the Usher protein network provides insights into the pathomechanisms of the Usher disease. *Exp Eye Res* 83, 97-119 (2006).

12. Gilad, S. et al. Ataxia-telangiectasia: founder effect among north African Jews. *Hum Mol Genet* 5, 2033-2037 (1996).

13. Krawczak, M. et al. Human gene mutation database-a biomedical information and research resource. *Hum Mutat* 15, 45-51 (2000).

14. Howard, M., Frizzell, R. A. & Bedwell, D. M. Aminoglycoside antibiotics restore CFTR function by overcoming premature stop mutations. *Nat Med* 2, 467-469 (1996).

15. Arakawa, M. et al. Negamycin restores dystrophin expression in skeletal and cardiac muscles of mdx mice. *J. Biochem* 134, 751-758 (2003).

16. Welch, E. M. et al. PTC124 targets genetic disorders caused by nonsense mutations. *Nature* 447, 87-91 (2007).

17. Singh, A., Ursic, D. & Davies, J. Phenotypic suppression and misreading *Saccharomyces cerevisiae*. *Nature* 277, 146-148 (1979).

18. Palmer, E., Wilhelm, J. M. & Sherman, F. Phenotypic suppression of nonsense mutants in yeast by aminoglycoside antibiotics. *Nature* 277, 148-150 (1979).

19. Burke, J. F. & Mogg, A. E. Suppression of a nonsense mutation in mammalian cells in vivo by the aminoglycoside antibiotics G-418 and paromomycin. *Nucleic Acids Res* 13, 6265-6272 (1985).

20. Du, M. et al. PTC124 is an orally bioavailable compound that promotes suppression of the human CFTR-G542X nonsense allele in a CF mouse model. *Proc Natl Acad Sci USA* 105, 2064-2069 (2008).

21. Roy, B. et al. Ataluren stimulates ribosomal selection of near-cognate tRNAs to promote nonsense suppression. *Proc Natl Acad Sci USA* 113, 12508-12513 (2016).

22. Kotecha, B. & Richardson, G. P. Ototoxicity in vitro: effects of neomycin, gentamicin, dihydrostreptomycin, amikacin, spectinomycin, neamine, spermine and poly-L-lysine. *Hear Res* 73, 173-184 (1994).

23. Dai, W. J. et al. CRISPR-Cas9 for in vivo Gene Therapy: Promise and Hurdles. *Mol Ther Nucleic Acids* 5, e349 (2016).

24. Peng, R., Lin, G. & Li, J. Potential pitfalls of CRISPR/Cas9-mediated genome editing. *FEBS J* 283, 1218-1231 (2016).

25. Temple, G. F., Dozy, A. M., Roy, K. L. & Kan, Y. W. Construction of a functional human suppressor tRNA gene: an approach to gene therapy for beta-thalassaemia. *Nature* 296, 537-540 (1982).

26. Panchal, R. G., Wang, S., McDermott, J. & Link, C. J., Jr. Partial functional correction of xeroderma pigmentosum group A cells by suppressor tRNA. *Hum Gene Ther* 10, 2209-2219 (1999).

27. Buvoli, M., Buvoli, A. & Leinwand, L. A. Suppression of nonsense mutations in cell culture and mice by multimerized suppressor tRNA genes. *Mol Cell Biol* 20, 3116-3124 (2000).

28. Lowe, T. M. & Chan, P. P. tRNAscan-SE On-line: integrating search and context for analysis of transfer RNA genes. *Nucleic Acids Res* 44, W54-57 (2016).

29. Lowe, T. M. & Eddy, S. R. tRNAscan-SE: a program for improved detection of transfer RNA genes in genomic sequence. *Nucleic Acids Res* 25, 955-964 (1997).

30. Lee, J. H., Skowron, P. M., Rutkowska, S. M., Hong, S. S. & Kim, S. C. Sequential amplification of cloned DNA as tandem multimers using class-IIS restriction enzymes. *Genetic analysis: biomolecular engineering* 13, 139-145 (1996).

31. Wang, H. et al. Improved seamless mutagenesis by recombineering using ccdB for counterselection. *Nucleic Acids Res* 42, e37 (2014).

32. Dixon, A. S. et al. NanoLuc Complementation Reporter Optimized for Accurate Measurement of Protein Interactions in Cells. *ACS chemical biology* 11, 400-408 (2016).

33. Pang, Y. L., Poruri, K. & Martinis, S. A. tRNA synthetase: tRNA aminoacylation and beyond. *Wiley Interdiscip Rev RNA* 5, 461-480 (2014).

34. Hirsh, D. Tryptophan transfer RNA as the UGA suppressor. *J Mol Biol* 58, 439-458 (1971).

35. Smith, D. & Yarus, M. Transfer RNA structure and coding specificity. I. Evidence that a D-arm mutation reduces tRNA dissociation from the ribosome. *J Mol Biol* 206, 489-501 (1989).

36. Smith, D. & Yarus, M. Transfer RNA structure and coding specificity. II. A D-arm tertiary interaction that restricts coding range. *J Mol Biol* 206, 503-511 (1989).

37. Dalphin, M. E., Brown, C. M., Stockwell, P. A. & Tate, W. P. The translational signal database, TransTerm, is now a relational database. *Nucleic Acids Res* 26, 335-337 (1998).

38. Brown, C. M., Dalphin, M. E., Stockwell, P. A. & Tate, W. P. The translational termination signal database. *Nucleic Acids Res* 21, 3119-3123 (1993).

39. Major, L. L., Edgar, T. D., Yee Yip, P., Isaksson, L. A. & Tate, W. P. Tandem termination signals: myth or reality? *FEBS Lett* 514, 84-89 (2002).

40. Wheeler, T. M. et al. Reversal of RNA dominance by displacement of protein sequestered on triplet repeat RNA. *Science* 325, 336-339 (2009).

41. Wheeler, T. M., Lueck, J. D., Swanson, M. S., Dirksen, R. T. & Thornton, C. A. Correction of ClC-1 splicing eliminates chloride channelopathy and myotonia in mouse models of myotonic dystrophy. *J Clin Invest* 117, 3952-3957 (2007).

42. Muthumani, K. et al. Novel prostate cancer immunotherapy with a DNA-encoded anti-prostate-specific membrane antigen monoclonal antibody. *Cancer Immunol Immunother* 66, 1577-1588 (2017).

43. Bladen, C. L. et al. The TREAT-NMD DMD Global Database: analysis of more than 7,000 Duchenne muscular dystrophy mutations. *Hum Mutat* 36, 395-402 (2015).

44. Brown, C. M., Stockwell, P. A., Trotman, C. N. & Tate, W. P. Sequence analysis suggests that tetra-nucleotides signal the termination of protein synthesis in eukaryotes. *Nucleic Acids Res* 18, 6339-6345 (1990).

45. Sachs, M. S. et al. Toeprint analysis of the positioning of translation apparatus components at initiation and termination codons of fungal mRNAs. *Methods* 26, 105-114 (2002).

46. Amrani, N. et al. A faux 3'-UTR promotes aberrant termination and triggers nonsense-mediated mRNA decay. *Nature* 432, 112-118 (2004).

47. Bengtson, M. H. & Joazeiro, C. A. Role of a ribosome-associated E3 ubiquitin ligase in protein quality control. *Nature* 467, 470-473 (2010).

48. Crowder, J. J. et al. Rkr1/Ltn1 Ubiquitin Ligase-mediated Degradation of Translationally Stalled Endoplasmic Reticulum Proteins. *J Biol Chem* 290, 18454-18466 (2015).

49. Rowe, S. M., Miller, S. & Sorscher, E. J. Cystic fibrosis. *The New England journal of medicine* 352, 1992-2001 (2005).

50. Manuvakhova, M., Keeling, K. & Bedwell, D. M. Aminoglycoside antibiotics mediate context-dependent suppression of termination codons in a mammalian translation system. *RNA* 6, 1044-1055 (2000).

51. Bonetti, B., Fu, L., Moon, J. & Bedwell, D. M. The efficiency of translation termination is determined by a synergistic interplay between upstream and downstream sequences in *Saccharomyces cerevisiae*. *J Mol Biol* 251, 334-345 (1995).

52. Xue, X. et al. Synthetic aminoglycosides efficiently suppress cystic fibrosis transmembrane conductance regulator nonsense mutations and are enhanced by ivacaftor. *American journal of respiratory cell and molecular biology* 50, 805-816 (2014).

53. Gogakos, T. et al. Characterizing Expression and Processing of Precursor and Mature Human tRNAs by Hydro-tRNAseq and PAR-CLIP. *Cell Rep* 20, 1463-1475 (2017).

54. Geslain, R. & Pan, T. Functional analysis of human tRNA isodecoders. *J Mol Biol* 396, 821-831 (2010).

55. Ingolia, N. T., Brar, G. A., Rouskin, S., McGeachy, A. M. & Weissman, J. S. The ribosome profiling strategy for monitoring translation in vivo by deep sequencing of ribosome-protected mRNA fragments. *Nat Protoc* 7, 1534-1550 (2012).

56. Kim, D., Langmead, B. & Salzberg, S. L. HISAT: a fast spliced aligner with low memory requirements. *Nat Methods* 12, 357-360 (2015).

57. Ingolia, N. T., Ghaemmaghami, S., Newman, J. R. & Weissman, J. S. Genome-wide analysis in vivo of translation with nucleotide resolution using ribosome profiling. *Science* 324, 218-223 (2009).

58. Guydosh, N. R. & Green, R. Dom34 rescues ribosomes in 3' untranslated regions. *Cell* 156, 950-962 (2014).

59. Afgan, E. et al. The Galaxy platform for accessible, reproducible and collaborative biomedical analyses: 2016 update. *Nucleic Acids Res* 44, W3-W10 (2016).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A modified transfer RNA (tRNA) comprising a T-arm, a D-arm, an anticodon-arm and an acceptor arm, wherein the anticodon-arm comprises a tri-nucleotide anticodon, wherein the anticodon is 5'-UCA-3' and recognizes TGA stop codons, and wherein the acceptor arm is operably linked to an arginine, wherein the modified tRNA is encoded by a sequence comprising a sequence selected from the group consisting of: SEQ ID NOs: 90-97, 99-100, 102-111, and 113.

2. The modified tRNA of claim 1, wherein the T-arm comprises rational nucleotide replacement that enhances or tunes the interaction with Elongation Factor 1-alpha 1 (EF1alpha).

3. The modified tRNA of claim 1, wherein the modified tRNA is encoded by a sequence that comprises the sequence as set forth in SEQ ID NO: 90.

4. The modified tRNA of claim 1, wherein the modified tRNA is encoded by a sequence that comprises the sequence as set forth in SEQ ID NO: 91.

5. The modified tRNA of claim 1, wherein the modified tRNA is encoded by a sequence that comprises the sequence as set forth in SEQ ID NO: 92.

6. The modified tRNA of claim 1, wherein the modified tRNA is encoded by a sequence that comprises the sequence as set forth in SEQ ID NO: 93.

7. The modified tRNA of claim 1, wherein the modified tRNA is encoded by a sequence that comprises the sequence as set forth in SEQ ID NO: 94.

8. The modified tRNA of claim 1, wherein the modified tRNA is encoded by a sequence that comprises the sequence as set forth in SEQ ID NO: 95.

9. The modified tRNA of claim 1, wherein the modified tRNA is encoded by a sequence that comprises the sequence as set forth in SEQ ID NO: 96.

10. The modified tRNA of claim 1, wherein the modified tRNA is encoded by a sequence that comprises the sequence as set forth in SEQ ID NO: 97.

11. The modified tRNA of claim 1, wherein the modified tRNA is encoded by a sequence that comprises the sequence as set forth in SEQ ID NO: 99.

12. The modified tRNA of claim 1, wherein the modified tRNA is encoded by a sequence that comprises the sequence as set forth in SEQ ID NO: 100.

13. The modified tRNA of claim 1, wherein the modified tRNA is encoded by a sequence that comprises the sequence as set forth in SEQ ID NO: 102.

14. The modified tRNA of claim 1, wherein the modified tRNA is encoded by a sequence that comprises the sequence as set forth in SEQ ID NO: 103.

15. The modified tRNA of claim 1, wherein the modified tRNA is encoded by a sequence that comprises the sequence as set forth in SEQ ID NO: 104.

16. The modified tRNA of claim 1, wherein the modified tRNA is encoded by a sequence that comprises the sequence as set forth in SEQ ID NO: 105.

17. The modified tRNA of claim 1, wherein the modified tRNA is encoded by a sequence that comprises the sequence as set forth in SEQ ID NO: 106.

18. The modified tRNA of claim 1, wherein the modified tRNA is encoded by a sequence that comprises the sequence as set forth in SEQ ID NO: 107.

19. The modified tRNA of claim 1, wherein the modified tRNA is encoded by a sequence that comprises the sequence as set forth in SEQ ID NO: 108.

20. The modified tRNA of claim 1, wherein the modified tRNA is encoded by a sequence that comprises the sequence as set forth in SEQ ID NO: 109.

21. The modified tRNA of claim 1, wherein the modified tRNA is encoded by a sequence that comprises the sequence as set forth in SEQ ID NO: 110.

22. The modified tRNA of claim 1, wherein the modified tRNA is encoded by a sequence that comprises the sequence as set forth in SEQ ID NO: 111.

23. The modified tRNA of claim 1, wherein the modified tRNA is encoded by a sequence that comprises the sequence as set forth in SEQ ID NO: 113.

24. A method of restoring translation to a nucleotide sequence that includes a nonsense mutation in a cell, comprising introducing to the cell the modified tRNA of claim 1, wherein modified tRNA restores translation to the nucleotide sequence that includes a nonsense mutation.

* * * * *